(12) United States Patent
McGuire

(10) Patent No.: US 11,116,835 B2
(45) Date of Patent: Sep. 14, 2021

(54) EPSTEIN BARR VIRUS ANTIBODIES, VACCINES, AND USES OF THE SAME

(71) Applicant: Fred Hutchinson Cancer Research Center, Seattle, WA (US)

(72) Inventor: Andrew McGuire, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 24 days.

(21) Appl. No.: 16/612,265

(22) PCT Filed: May 10, 2018

(86) PCT No.: PCT/US2018/032127
§ 371 (c)(1),
(2) Date: Nov. 8, 2019

(87) PCT Pub. No.: WO2018/209125
PCT Pub. Date: Nov. 15, 2018

(65) Prior Publication Data
US 2020/0164059 A1   May 28, 2020

Related U.S. Application Data

(60) Provisional application No. 62/560,061, filed on Sep. 18, 2017, provisional application No. 62/504,447, filed on May 10, 2017.

(51) Int. Cl.
| | | |
|---|---|---|
| *A61K 39/245* | (2006.01) | |
| *A61P 31/00* | (2006.01) | |
| *A61K 39/39* | (2006.01) | |
| *C07K 16/08* | (2006.01) | |
| *C12N 15/113* | (2010.01) | |
| *A61K 39/00* | (2006.01) | |

(52) U.S. Cl.
CPC .......... *A61K 39/245* (2013.01); *A61K 39/39* (2013.01); *A61P 31/00* (2018.01); *C07K 16/085* (2013.01); *C12N 15/1133* (2013.01); *A61K 2039/5156* (2013.01)

(58) Field of Classification Search
CPC .............. A61K 39/245; A61K 39/39; A61K 2039/5156; A61K 39/12; A61P 31/00; C07K 16/085; C12N 15/1133; C12N 2710/16211
See application file for complete search history.

(56) References Cited

U.S. PATENT DOCUMENTS

| | | |
|---|---|---|
| 6,194,551 B1 | 2/2001 | Idusogie et al. |
| 7,521,541 B2 | 4/2009 | Eigenbrot et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2011/0033389 A1* | 2/2011 | Chen .................... C07K 16/087 424/9.6 |
| 2011/0142859 A1* | 6/2011 | Ebens, Jr. .......... C07K 16/2896 424/178.1 |
| 2016/0303224 A1* | 10/2016 | Kanekiyo .............. C07K 14/00 |

FOREIGN PATENT DOCUMENTS

| | | |
|---|---|---|
| WO | WO1992016221 A1 | 10/1992 |
| WO | WO1999051642 A1 | 10/1999 |
| WO | WO2000061739 A1 | 10/2000 |
| WO | WO200129246 A1 | 4/2001 |
| WO | WO2002031140 A1 | 4/2002 |
| WO | WO2003084570 A1 | 10/2003 |
| WO | WO2003085107 A1 | 10/2003 |
| WO | WO2003085119 A1 | 10/2003 |
| WO | WO2005035586 A1 | 4/2005 |
| WO | WO2005035778 A1 | 4/2005 |
| WO | WO2005053742 A1 | 6/2005 |
| WO | WO2016145102 A1 | 9/2016 |

OTHER PUBLICATIONS

Kask, et al., "Structural requirements for the intracellular subunit polymerization of the complement inhibitor C4b-binding protein," Biochemistry, vol. 41, No. 30, 2002, pp. 9349-9357.

Kimanius, et al., "Accelerated cryo-EM Structure Determination With Parallelisation Using GPUs in RELION-2," Elife, vol. 5, 2016, 21 pages.

Kirchner, et al., "Binding-site Interactions Between Epstein-Barr Virus Fusion Proteins gp42 and gH/gL Reveal a Peptide That Inhibits Both Epithelial and B-cell Membrane Fusion," J. Virol., vol. 81, No. 17, 2007, pp. 9216-9229.

Kirschner, et al., "Soluble Epstein-Barr Virus Glycoproteins gH, gL, and gp42 Form a 1:1:1 Stable Complex That Acts Like Soluble gp42 in B-cell Fusion but Not in Epithelial Cell Fusion," J. Virol., vol. 80, No. 19, 2006, pp. 9444-9454.

Krissinel and Henrick, "Inference of Macromolecular Assemblies from Crystalline State," J. Mol. Biol., vol. 372, No. 3 2007, pp. 774-797.

Li, et al., "Chaperone Functions Common to Nonhomologous Epstein-Barr Virus gL and Varicella-Zoster Virus gL Proteins," J. Virol., vol. 71, No. 2, 1997, pp. 1667-1670.

Li, et al., "Epstein-Barr Virus Infection and Replication in a Human Epithelial Cell System," Nature, vol. 356, No. 6367, 1992, pp. 347-350.

Li, et al., "The Epstein-Barr Virus (EBV) BZLF2 Gene Product Associates with the gH and gL Homologs of EBV and Carries an Epitope Critical to Infection of B Cells but Not of Epithelial Cells," J. Virol., vol. 69, No. 7, 1995, pp. 3987-3994.

(Continued)

*Primary Examiner* — Rachel B Gill
(74) *Attorney, Agent, or Firm* — Lee & Hayes PC; C. Rachal Winger; Thu Nguyen

(57) ABSTRACT

Anti-Epstein Barr Virus (EBV) antibodies and vaccines are described herein. The antibodies and vaccines can be used to treat and/or reduce the risk of EBV infection and to treat and/or reduce the risk of complications associated with EBV infection, such as infectious mononucleosis, lymphoproliferative disorders, carcinomas, and smooth muscle tumors.

20 Claims, 55 Drawing Sheets

Specification includes a Sequence Listing.

(56) References Cited

OTHER PUBLICATIONS

Macagno, et al., "Isolation of Human Monoclonal Antibodies That Potently Neutralize Human Cytomegalovirus Infection by Targeting Different Epitopes on the gH/gL/UL128-131A Complex," J. Virol., vol. 84, No. 2, 2010, pp. 1005-1013.
Magro, et al., "Neutralizing Antibodies Against the Preactive Form of Respiratory Syncytial Virus Fusion Protein Offer Unique Possibilities for Clinical Intervention," PNAS, vol. 109, No. 8, 2012, pp. 3089-3094.
Matsuura, et al., "Crystal Structure of the Epstein-Barr Virus (EBV) Glycoprotein H/glycoprotein L (gH/gL) Complex," PNAS, vol. 107, No. 52, 2010, pp. 22641-22646.
McGuire, et al., "Specifically Modified Env Immunogens Activate B-cell Precursors of Broadly Neutralizing HIV-1 Antibodies in Transgenic Mice," Nat. Commun., vol. 7, 2016, 10 pages.
McLellan, et al., "Structure of RSV Fusion Glycoprotein Trimer Bound to a Prefusion-Specific Neutralizing Antibody," Science, vol. 340, No. 6136, pp. 1113-1117.
McShane and Longnecker, "Analysis of Fusion Using a Virus-Free Cell Fusion Assay," Methods Mol. Biol., vol. 292, 2005, pp. 187-196.
Meyers, et al., "A Phase I Study Including Pharmacokinetics of Polyethylene Glycol Conjugated interleukin-2," Clin. Pharmacol. Ther., vol. 49, No. 3, 1991, pp. 307-313.
Miller and Hutt-Fletcher, "Epstein-Barr Virus Enters B Cells and Epithelial Cells by Different Routes," J. Virol., vol. 6, No. 6, 1992, pp. 3409-3414.
Miller, et al., "Infectious Mononucleosis: Appearance of Neutralizing Antibody to Epstein-Barr Virus Measured by Inhibition of Formation of Lymphoblastoid Cell Lines," J. Infect. Dis., vol. 125, No. 4, 1972, pp. 403-406.
Mohl, et al., "Structural and Mechanistic Insights Into the Tropism of Epstein-Barr Virus," Mol. Cells, vol. 39, No. 4, 2016, pp. 286-291.
Mohl, et al., "The Conserved Disulfide Bond Within Domain II of Epstein-Barr Virus gH Has Divergent Roles in Membrane Fusion With Epithelial Cells and B Cells," J. Virol., vol. 88, No. 23, 2014, pp. 13570-13579.
Molesworth, et al., "Epstein-Barr Virus gH is Essential for Penetration of B Cells but Also Plays a Role in Attachment of Virus to Epithelial Cells," J. Virol., vol. 74, No. 14, 2000, pp. 6324-6332.
Moody, et al., "H3N2 Influenza Infection Elicits More Cross-Reactive and Less Clonally Expanded Anti-Hemagglutinin Antibodies Than Influenza Vaccination," PLoS One, vol. 6, No. 10, 2011, 14 pages.
Moss and Pope, "Assay of the Infectivity of Epstein-Barr Virus by Transformation of Human Leucocytes in Vitro," J. Gen. Virol., vol. 17, No. 2, 1972, pp. 233-236.
Moutschen, et al., "Phase I/II Studies to Evaluate Safety and Immunogenicity of a Recombinant gp350 Epstein-Barr Virus Vaccine in Healthy Adults," Vaccine, vol. 25, No. 24, 2007, pp. 4697-4705.
Neuhierl, et al., "Glycoprotein gp110 of Epstein-Barr Virus Determines Viral Tropism and Efficiency of Infection," PNAS., vol. 99, No. 23, 2002, pp. 15036-15041.
Oda, et al., "Epstein-Barr Virus Lacking Glycoprotein gp85 Cannot Infect B Cells and Epithelial Cells," Virology, vol. 276, No. 1, 2000, pp. 52-58.
Ogembo, et al., "Human Complement Receptor Type 1/CD35 is an Epstein-Barr Virus Receptor," Cell Rep., vol. 3, No. 2, 2013, pp. 371-385.
Okazaki, et al., "Fucose Depletion From Human IgG1 Oligosaccharide Enhances Binding Enthalpy and Association Rate Between IgG1 and FcgammaRIIIa," J. Mol. Biol., vol. 336, No. 5, 2004, pp. 1239-1249.
Okuma, et al., "Host Range of Human T-cell Leukemia Virus Type I Analyzed by a Cell Fusion-Dependent Reporter Gene Activation Assay," Virology, vol. 254, No. 2, 1999, pp. 235-244.
Omerovic, et al., "The Amino Terminus of Epstein-Barr Virus Glycoprotein gH is Important for Fusion With Epithelial and B Cells," J. Virol., vol. 79, No. 19, 2005, pp. 12408-12415.
Otwinowski and Minor, "Processing of X-ray Diffraction Data Collected in Oscillation Mode," Methods Enzymol., vol. 276, 1997, pp. 307-326.
Pechman, et al., "Immune suppression blocks sodium-sensitive hypertension following recovery from ischemic acute renal failure," Am. J. Physiol., vol. 294, 2008, pp. R1234-R1239.
Pettersen, et al., "UCSF Chimera-a Visualization System for Exploratory Research and Analysis," J. Comput. Chem., vol. 25, No. 13, 2004, pp. 1605-1612.
Plate, et al., "Mapping Regions of Epstein-Barr Virus (EBV) Glycoprotein B (gB) Important for Fusion Function With gH/gL," Virology, vol. 413, 2011, pp. 26-38.
Rappouli, et al., "Reverse Vaccinology 2.0: Human Immunology Instructs Vaccine Antigen Design," J. Exp. Med., vol. 213, No. 4, 2016, pp. 469-481.
Rickinson, et al., "Cellular Immune Controls Over Epstein-Barr Virus Infection: New Lessons From the Clinic and the Laboratory," Trends Immunol., vol. 35, No. 4, 2014, pp. 159-169.
Ripka, et al., "Two Chinese Hamster Ovary Glycosylation Mutants Affected in the Conversion of GDP-mannose to GDP-fucose," Arch. Biochem. Biophys., vol. 249, No. 2, 1986, pp. 533-545.
Rosenthal and Henderson, "Optimal Determination of Particle Orientation, Absolute Hand, and Contrast Loss in Single-Particle Electron Cryomicroscopy," J. Mole. Bio., vol. 333, 2003, pp. 721-745.
Sashihara, et al., "Human Antibody Titers to Epstein-Barr Virus (EBV) gp350 Correlate With Neutralization of Infectivity Better Than Antibody Titers to EBV gp42 Using a Rapid Flow Cytometry-Based EBV Neutralization Assay," Virology, vol. 391, No. 2, 2009, pp. 249-256.
Sathiyamoorthy, et al., "Assembly and Architecture of the EBV B Cell Entry Triggering Complex," PLoS Pathog., vol. 10, No. 8, 2014, 16 pages.
Sathiyamoorthy, et al., "Inhibition of EBV-mediated Membrane Fusion by anti-gHgL Antibodies," PNAS., vol. 114, No. 41, 2017, pp. E8703-E8710.
Sathiyamoorthy, et al., "Structural Basis for Epstein-Barr Virus Host Cell Tropism Mediated by gp42 and gHgL Entry Glycoproteins," Nat. Commun., vol. 7, 2016, 14 pages.
Scheres and Chen, "Prevention of Overfitting in cryo-EM Structure Determination," Nat. Methods., vol. 9, No. 9, 2012, pp. 853-854.
Smith, et al., "Mouse Model Recapitulating Human Fcγ Receptor Structural and Functional Diversity," PNAS, vol. 109, No. 16, 2012, pp. 6181-6186.
Snijder, et al., "Vitrification After Multiple Rounds of Sample Application and Blotting Improves Particle Density on Cryo-Electron Microscopy Grids," J. Struct. Biol., vol. 198, No. 1, 2017, pp. 38-42.
Sokal, et al., "Recombinant gp350 Vaccine for Infectious Mononucleosis: A Phase 2, Randomized, Double-Blind, Placebo-Controlled Trial to Evaluate the Safety, Immunogenicity, and Efficacy of an Epstein-Barr Virus Vaccine in Healthy Young Adults," J. Infect. Dis., vol. 196, No. 12, 2007, pp. 1749-1753.
Spriggs, et al., "The Extracellular Domain of the Epstein-Barr Virus BZLF2 Protein Binds the HLA-DR Beta Chain and Inhibits Antigen Presentation," J. Virol., vol. 70, No. 8, 1996, pp. 5557-5563.
Strnad, et al., "Production and Characterization of Monoclonal Antibodies Against the Epstein-Barr Virus Membrane Antigen," J. Virol., vol. 41, No. 1, 1982, pp. 258-264.
Suloway, et al., "Automated Molecular Microscopy: The New Leginon System," vol. 151, No. 1, 2005, pp. 41-60.
Suzuki, et al., "Physicochemical and Biological Properties of Poly-(ethylene Glycol)-Coupled Immunoglobulin G," Biochim. Biophys. Acta., vol. 788, No. 2, 1984, pp. 248-255.
Tang, et al., "EMAN2: An Extensible Image Processing Suite for Electron Microscopy," J. Struct. Biol., vol. 157, No. 1, 2007, pp. 38-46.

(56) References Cited

OTHER PUBLICATIONS

Abuchowski, et al., "Cancer Therapy With Chemically Modified Enzymes. I. Antitumor Properties of Polyethylene Glycol-Asparaginase Conjugates," Cancer Biochem. Biophys., vol. 7, No. 2, 1984, pp. 175-186.
Abuchowski, et al., "Effect of Covalent Attachment of Polyethylene Glycol on Immunogenicity and Circulating Life of Bovine Liver Catalase," J. Biol. Chem., vol. 252, No. 11, 1977, pp. 3582-3586.
Adams, et al., "PHENIX: a comprehensive Python-based system for macromolecular structure solution," Acta. Crystallogr. D. Biol. Crystallogr., vol. 66, No. 2, 2010, pp. 213-221.
Agirre, et al., "Privateer: Software for the Conformational Validation of Carbohydrate Structures," Nat. Struct. Mol. Biol., vol. 22, No. 11, 2015, pp. 833-834.
Backovic, et al., "Hydrophobic Residues That Form Putative Fusion Loops of Epstein-Barr Virus Glycoprotein B are Critical for Fusion Activity," J. Virol., vol. 81, No. 17, 2007, pp. 9596-9600.
Backovic, et al., "Structure of a Trimeric Variant of the Epstein-Barr Virus Glycoprotein B," PNAS, vol. 106, No. 8, 2009, pp. 2880-2885.
Balachandran, et al., "Antigenic Cross-Reactions Among Herpes Simplex Virus Types 1 and 2, Epstein-Barr Virus, and Cytomegalovirus," J. Virol., vol. 61, No. 4, 1987, pp. 1125-1135.
Bandaranayake, et al., "Daedalus: A Robust, Turnkey Platform for Rapid Production of Decigram Quantities of Active Recombinant Proteins in Human Cell Lines Using Novel Lentiviral Vectors," Nucleic. Acids Res., vol. 39, No. 21, 2011, 11 pages.
Bern, et al., "Byonic: Advanced Peptide and Protein Identification Software," Curr. Protoc. Bioinformatics., vol. 13, No. 13.20, 2012, 17 pages.
Blom, et al., "Complement inhibitor C4b-binding protein-friend or foe in the innate immune system," Mol. Immunol., vol. 40, No. 18, 2004, pp. 1333-1346.
Borza and Hutt-Fletcher, "Alternate Replication in B Cells and Epithelial Cells Switches Tropism of Epstein-Barr Virus," Nat. Med., vol. 8, No. 6, 2002, pp. 594-599.
Borza, et al., "Use of gHgL for Attachment of Epstein-Barr Virus to Epithelial Cells Compromises Infection," J. Virol., vol. 78, No. 10, 2004, pp. 5007-5014.
Brochet, et al., "IMGT/V-QUEST: The Highly Customized and Integrated System for IG and TR Standardized V-J and V-D-J Sequence Analysis," Nucleic Acids Res., vol. 36, 2008, pp. W503-W508.
Brown, et al., "Tools for Macromolecular Model Building and Refinement Into Electron Cryo-Microscopy Reconstructions," Acta Crystallogr. D. Biol. Crystallogr., vol. 71, No. 1, 2015, pp. 136-153.
Chandramouli and Malito, "Structural Basis for Potent Antibody-Mediated Neutralization of Human Cytomegalovirus," Sci. Immunol., vol. 2, No. 12, 2017, 10 pages.
Chen, et al., "Ephrin Receptor A2 is a Functional Entry Receptor for Epstein-Barr Virus," Nat. Microbiol., vol. 3, No. 2, 2018, pp. 172-180.
Chen, et al., "High-resolution Noise Substitution to Measure Overfitting and Validate Resolution in 3D Structure Determination by Single Particle Electron Cryomicroscopy," Ultramicroscopy, vol. 135, pp. 24-35.
Chen, et al., "MolProbity: All-Atom Structure Validation for Macromolecular Crystallography," Acta Crystallogr. D. Biol. Crystallogr., vol. 66, No. 1, 2010, pp. 12-22.
Chen, et al., "The KGD Motif of Epstein-Barr Virus gH/gL Is Bifunctional, Orchestrating Infection of B Cells and Epithelial Cells," mBio., vol. 3, No. 1, 2012, 9 pages.
Chen, et al., "The Large Groove Found in the gH/gL Structure is an Important Functional Domain for Epstein-Barr Virus Fusion," J. Virol., vol. 87, No. 7, 2013, pp. 3620-3627.
Chesnokova, et al., "Fusion of Epstein-Barr Virus With Epithelial Cells Can Be Triggered by alphavbeta5 in Addition to alphavbeta6 and alphavbeta8, and Integrin Binding Triggers a Conformational Change in Glycoproteins gHgL," J. Virol., vol. 85, No. 24, 2011, pp. 13214-13223.
Chesnokova, et al., "Fusion of Epithelial Cells by Epstein-Barr Virus Proteins is Triggered by Binding of Viral Glycoproteins gHgL to Integrins alphavbeta6 or alphavbeta8," PNAS, vol. 106, No. 48, 2009, pp. 20464-20469.
Chowdary, et al., "Crystal Structure of the Conserved Herpesvirus Fusion Regulator Complex gH-gL," Nat. Struct. Mol. Biol., vol. 17, No. 7, 2010, pp. 882-888.
Ciferri et al., "Antigenic Characterization of the HCMV gH/gL/gO and Pentamer Cell Entry Complexes Reveals Binding Sites for Potently Neutralizing Human Antibodies," PLoS Pathog., vol. 11, No. 10, 2015, 20 pages.
Cohen, et al., "Epstein-Barr Virus: An Important Vaccine Target for Cancer Prevention," Sci. Transl. Med., vol. 3, No. 107, 2011, 6 pages.
Cohen, et al., "The Need and Challenges for Development of an Epstein-Barr Virus Vaccine," Vaccine, vol. 31, No. 2, 2013, pp. B194-B196.
Connolly, et al., "Fusing Structure and Function: A Structural View of the Herpesvirus Entry Machinery," Nat. Rev. Microbiol., vol. 9, No. 5, 2011, pp. 369-381.
Cui, et al., "Rabbits Immunized With Epstein-Barr Virus gH/gL or gB Recombinant Proteins Elicit Higher Serum Virus Neutralizing Activity Than gp350," Vaccine, vol. 34, No. 34, 2016, pp. 4050-4055.
DeLano, "PyMOL: An Open-Source Molecular Graphics Tool," DeLano Scientific, 2002, 9 pages.
Delecluse, et al., "Propagation and Recovery of Intact, Infectious Epstein-Barr Virus From Prokaryotic to Human Cells," PNAS, vol. 95, No. 14, 1998, pp. 8245-8250.
DiMaio, et al., "Atomic-accuracy Models From 4.5-A Cryo-Electron Microscopy Data With Density-Guided Iterative Local Refinement," Nat. Methods, vol. 12, No. 4, 2015, pp. 361-365.
DiMaio, et al., "Refinement of Protein Structures Into Low-Resolution Density Maps Using Rosetta," J. Mol. Biol., vol. 392, No. 1, 2009, pp. 181-190.
Doria-Rose, et al., "New Member of the V1V2-Directed CAP256-VRC26 Lineage That Shows Increased Breadth and Exceptional Potency," J. Virol., vol. 90, No. 1, 2015, pp. 76-91.
Easterhoff, et al., "Boosting of HIV Envelope CD4 Binding Site Antibodies With Long Variable Heavy Third Complementarity Determining Region in the Randomized Double Blind RV305 HIV-1 Vaccine Trial," PLoS Pathog., vol. 13, No. 2, 2017, 21 pages.
Emsley, et al., "Features and Development of Coot," Acta Crystallogr. D. Biol. Crystallogr., vol. 66, No. 4, 2010, pp. 486-501.
Forbes, et al., "T Cell Responses Induced by Adenoviral Vectored Vaccines Can Be Adjuvanted by Fusion of Antigen to the Oligomerization Domain of C4b-binding Protein," PLoS One, vol. 7, No. 9, 2012, 12 pages.
Frese, et al., "Unambiguous Phosphosite Localization Using Electron-Transfer/Higher-Energy Collision Dissociation (EThcD)," J. Proteome. Res., vol. 12, No. 3, 2013, pp. 1520-1525.
Goddard, et al., "Visualizing Density Maps With UCSF Chimera," J. Struct. Biol., vol. 157, No. 1, 2007, pp. 281-287.
Haan, et al., "Different Functional Domains in the Cytoplasmic Tail of Glycoprotein B Are Involved in Epstein-Barr Virus-Induced Membrane Fusionv," Virology, vol. 290, No. 1, 2001, pp. 106-114.
Haan, et al., "Epstein-Barr Virus Entry Utilizing HLA-DP or HLA-DQ as a Coreceptor," J. Virol., vol. 74, No. 5, 2000, pp. 2451-2454.
Haque, et al., "A Mouse Monoclonal Antibody Against Epstein-Barr Virus Envelope Glycoprotein 350 Prevents Infection Both in Vitro and in Vivo," J. Infect. Dis., vol. 194, No. 5, 2006, pp. 584-587.
Heikkinen, et al., "Safety of MF59-adjuvanted A/H1N1 Influenza Vaccine in Pregnancy: A Comparative Cohort Study," Am. J. Obstet. Gynecol., vol. 207, No. 3, pp. 177.e1-177.e8.
Herrman, et al., "Epstein-Barr Virus gp350 Can Functionally Replace the Rhesus Lymphocryptovirus Major Membrane Glycoprotein and Does Not Restrict Infection of Rhesus Macaques," J. Virol., vol. 90, No. 3, 2015, pp. 1222-1230.
Hershfield, et al., "Treatment of Adenosine Deaminase Deficiency With Polyethylene Glycol-Modified Adenosine Deaminase," N. Engl. J. Med., vol. 316, No. 10, 1987, pp. 589-596.

(56) References Cited

OTHER PUBLICATIONS

Hoffman, et al., "Monoclonal Antibody Against a 250,000-dalton Glycoprotein of Epstein-Barr Virus Identifies a Membrane Antigen and a Neutralizing Antigen," PNAS, vol. 77, No. 5, 1980, pp. 2979-2983.
Hofmeyer, et al., "Arranged Sevenfold: Structural Insights Into the C-terminal Oligomerization Domain of Human C4b-binding Protein," J. Mol. Biol., vol. 425, No. 8, 2013, pp. 1302-1317.
Hutchinson, et al., "A Novel Herpes Simplex Virus Glycoprotein, gL, Forms a Complex With Glycoprotein H (gH) and Affects Normal Folding and Surface Expression of gH," J. Virol., vol. 66, No. 4, 1992, pp. 2240-2250.
Idusogie, et al., "Mapping of the C1q Binding Site on Rituxan, a Chimeric Antibody with a Human IgG1 Fc," J. Immunol., vol. 164, No. 8, 2000, pp. 4178-4184.
Joyce, et al., "Vaccine-Induced Antibodies that Neutralize Group 1 and Group 2 Influenza A Viruses," Cell, vol. 166, No. 3, 2016, pp. 609-623.
Kanda, et al., "Comparison of Cell Lines for Stable Production of Fucose-Negative Antibodies With Enhanced ADCC," Biotechnol. Bioeng., vol. 94, No. 4, 2006, pp. 680-688.
Invitation to Pay Additional Fees Dated Jul. 23, 2018, for International Application No. PCT/US2018/032127, 3 pages.
Search Report dated Oct. 1, 2018, for International Application No. PCT/US2018/032127, 13 pages.
PDBePISA, "Structure of AMM01 FAN ANTI EBV GH/GL Neutralizing Antibody", Retrieved on Jul. 16, 2018, from: <https://www.ebi.ac.uk/msd-srv/pisa/cgi-bin/piserver?qi=6bla>, dated Oct. 20, 2014, 3 pages.
Perez, et. al., "Novel Epstein-Barr virus-like particles incororating gH/gL-EBNA1 or gB-LMP2 induce high neutralizing antibody titers and EBV-specific T-cell responses in immunized mice," Oncotarget, vol. 8, No. 12, 2017, pp. 19255-19273.
Saxena, et al, "Advances in Therapeautic Fc Engineering—Modulation of IgG-Associated Effector Functions and Serum Half-life," Frontiers in Immunology, vol. 7, No. 580, 2016, pp. 1-11.
Sochaj, "Current methods for the synthesis of homogeneous antibody-drug conjugates", Biotechnology Advances, vol. 33, 2015, pp. 775-784.
Tangye, et al., "Human Immunity Against EBV-lessons From the Clinic," J. Exp. Med., vol. 214, No. 2, 2017, pp. 269-283.
Tanner, et al., "Epstein-Barr Virus gp350/220 Binding to the B Lymphocyte C3d Receptor Mediates Adsorption, Capping, and Endocytosis," Cell, vol. 50, No. 2, 1987, pp. 203-213.
Taylor, et al., "Deletion and Anergy of Polyclonal B Cells Specific for Ubiquitous Membrane-Bound Self-Antigen," J. Exp. Med., vol. 209, No. 11, 2012, pp. 2065-2077.
Taylor, et al., "The Immunology of Epstein-Barr Virus-Induced Disease," Ann. Rev. Immunol., vol. 33, 2015, pp. 787-821.
Thorley-Lawson and Geilinger, "Monoclonal Antibodies Against the Major Glycoprotein (gp350/220) of Epstein-Barr Virus Neutralize Infectivity," PNAS, vol. 77, No. 9, 1980, pp. 5307-5311.
Tsai, et al., "Exposure to MF59-adjuvanted Influenza Vaccines During Pregnancy—A Retrospective Analysis," Vaccine, vol. 28, No. 7, 2010, pp. 1877-1880.
Tugizov, et al., "Epstein-Barr Virus Infection of Polarized Tongue and Nasopharyngeal Epithelial Cells," Nat. Med., vol. 9, No. 3, 2003, pp. 307-314.
Turk, et al., "Antibodies to gp350/220 Enhance the Ability of Epstein-Barr Virus to Infect Epithelial Cells," J. Viol., vol. 80, No. 19, 2006, pp. 9628-9633.
Voss, et al., "DoG Picker and TiltPicker: Software Tools to Facilitate Particle Selection in Single Particle Electron Microscopy," J. Struct. Biol., vol. 166, No. 2, 2009, pp. 205-213.
Wang, et al., "Epstein-Barr Virus Uses Different Complexes of Glycoproteins gH and gL to Infect B Lymphocytes and Epithelial Cells," J. Virol., vol. 72, No. 7, 1998, pp. 5552-5558.
Wrammert, et al., "Rapid Cloning of High-Affinity Human Monoclonal Antibodies Against Influenza Virus," Nature, vol. 453, No. 7195, 2008, pp. 667-671.
Wu, et al., "Mutations of Epstein-Barr Virus gH That Are Differentially Able to Support Fusion With B Cells or Epithelial Cells," J. Virol., vol. 79, No. 17, 2005, pp. 10923-10930.
Xing, et al., "A Site of Varicella-Zoster Virus Vulnerability Identified by Structural Studies of Neutralizing Antibodies Bound to the Glycoprotein Complex gHgL," PNAS., vol. 112, No. 19, 2015, pp. 6056-5061.
Yamane-Ohnuki, et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnol. Bioeng., vol. 87, No. 5, 2004, pp. 614-622.
Young and Rickinson, "Epstein-Barr Virus: 40 Years on," Nat. Rev. Cancer, vol. 4, No. 10, 2004, pp. 757-768.
Zalevsky, et al., "Enhanced Antibody Half-Life Improves in Vivo Activity," Nat. Biotechnol., vol. 28, No. 2, 2010, pp. 157-159.
Zhang, "Gctf: Real-time CTF Determination and Correction," J. Struct. Biol., vol. 193, No. 1, 2016, pp. 1-12.
Zhang, et al., "Ephrin receptor A2 is an epithelial cell receptor for Epstein-Barr virus entry," Nature Microbiology, vol. 3, No. 9, 2018, pp. 1075.
Zheng, et al., "MotionCor2: Anisotropic Correction of Beam-Induced Motion for Improved Cryo-Electron Microscopy," Nat. Methods, vol. 14, No. 4, 2017, pp. 331-332.

\* cited by examiner

FIG. 1

|  | AMMO1 Fab |
|---|---|
| Data collection | |
| Space group | $P2_12_12_1$ |
| Cell dimensions | |
| $\quad a, b, c$ (Å) | 49.9, 69.9, 136.3 |
| $\quad \alpha, \beta, \gamma$ (°) | 90.0, 90.0, 90.0 |
| Resolution (Å) | 50-1.55 (1.64-1.61, 1.61-1.58, 1.58-1.55) |
| $R_{sym}$ or $R_{merge}$ | 20.9 (44.6, 49, 51) |
| $I/\sigma(I)$ | 9.1 (2.2, 1.5, 1.1) |
| Completeness (%) | 88.3 (58.2, 45.4, 31.6) |
| Redundancy | 5.7 (3.1, 2.6, 1.9) |
| $CC_{1/2}$ | (0.737, 0.670, 0.630) |
| | |
| Refinement | |
| Resolution (Å) | 48.81-1.55 (1.58-1.55) |
| No. reflections | 61,842 |
| $R_{work} / R_{free}$ | 0.1660/0.1937 (0.2756/0.3216) |
| No. atoms | 3,754 |
| $\quad$ Protein | 3,310 |
| $\quad$ Ligand/ion | 99 |
| $\quad$ Water | 345 |
| B-factors | 37.2 |
| $\quad$ Protein | 35.9 |
| $\quad$ Ligand/ion | 69.5 |
| $\quad$ Water | 40.8 |
| R.m.s. deviations | |
| $\quad$ Bond lengths (Å) | 0.009 |
| $\quad$ Bond angles (°) | 1.006 |

Statistics for the highest-resolution shell are shown in parentheses.

FIG. 2

|  | gH/gL/gp42/AMMO1 Fab |
|---|---|
| Data collection | |
| Number of particles | 72,000 |
| Pixel size (Å) | 1.36 |
| Defocus range (μm) | 2-4 |
| Accelration voltage (kV) | 300 |
| Electron dose (e-/Å$^2$) | 65 |
| | |
| Refinement | |
| Resolution (Å) | 4.8 |
| Map sharpening B factor (Å$^2$) | -400 |
| | |
| Model Validation | |
| Favored rotamers (%) | 98.62 |
| Poor rotamers (%) | 0.34 |
| Ramachandran allowed (%) | 99.78 |
| Ramachandran favored (%) | 97.01 |
| Ramachandran outliers (%) | 0.22 |
| *Clash score* | 1.05 |
| Molprobity score | 0.98 |

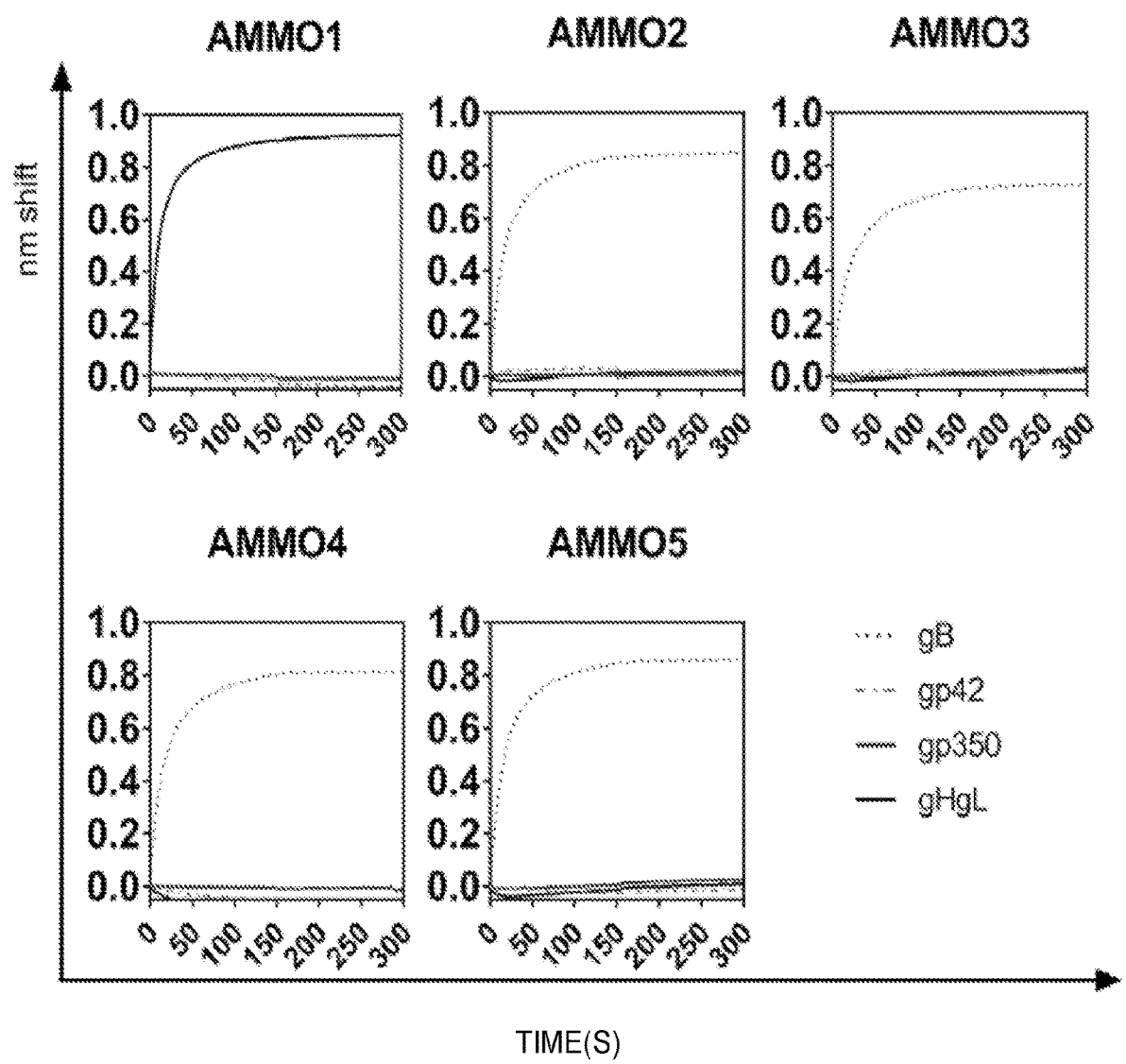

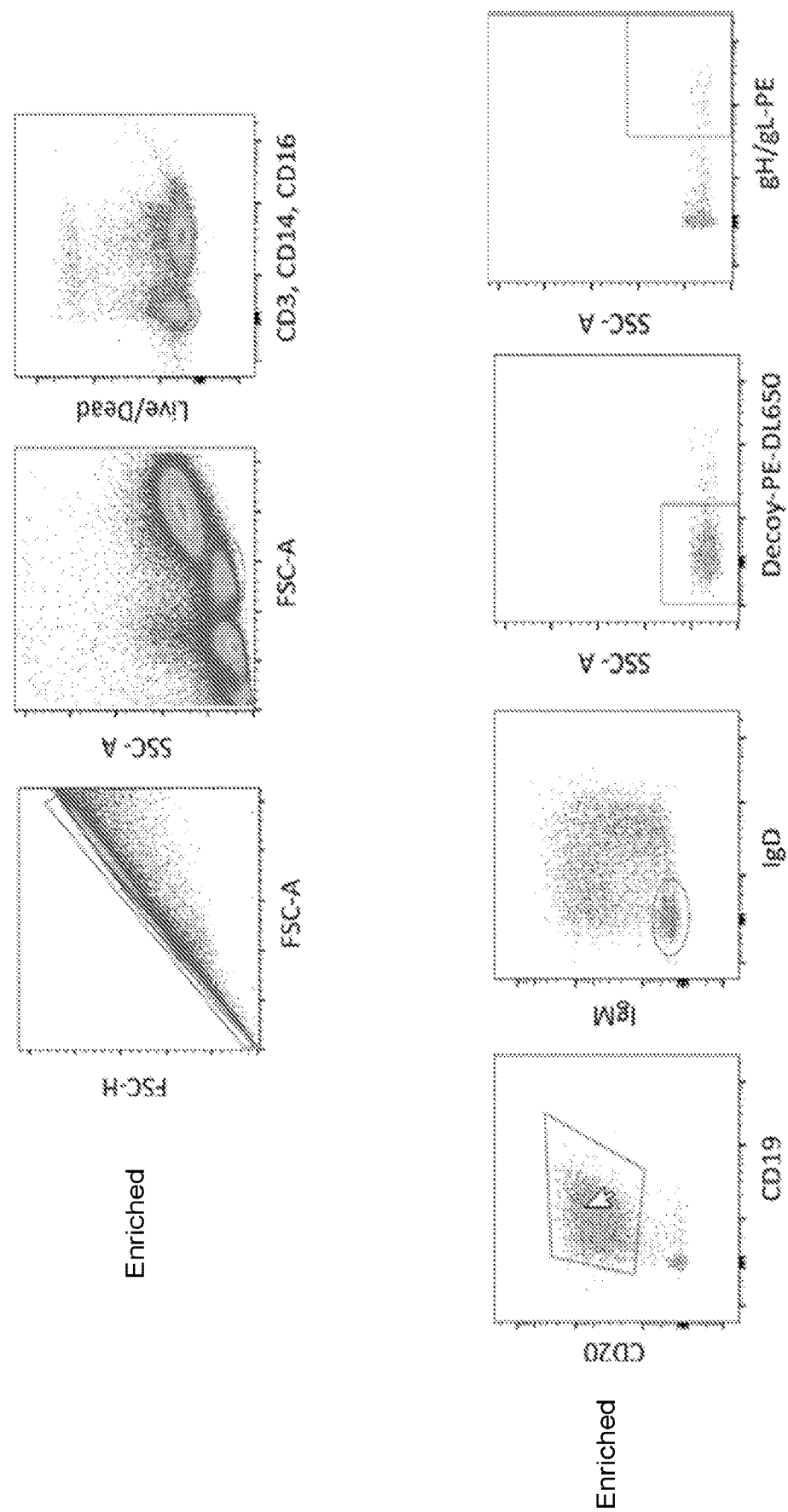

Summary of antigen-specific B cell sorting and VH/VL recovery.

| Donor | Donor F | | Donor N | | Donor D |
|---|---|---|---|---|---|
| # of PBMC | 100M | 100M | 100M | 100M | 400M |
| bait | gB | gH/gL | gB | gH/gL | gH/gL and gB |
| Sorted Cells | 35 | 10 | 22 | 44 | 83 |
| IgG+ ELISA* | 17 | 9 | 17 | 20 | Not Done |
| Ag+ ELISA* | 1 | 0 | 2 | 2 | 4, all against gB |
| H+L pair | 0 | 0 | 2 (AMMO2, AMMO3) | 1 (AMMO1) | 2 (AMMO4, AMMO5) |

*positive if >mean + 3× standard deviation of control wells

FIG. 7

AMMO1 HC: 8%VH mutated (KY631779)

VH1-18*01 — D6-19*01 — HJ4*02

QVQLVQSGAEVKKPGASVKVSCKASGYTFTSYGISWVRQAPGQGLEWMGWISAYNGNTNYAQKLQGRVTMTTDTSTSTAYMELRSLRSD
..........D............................................................DTN.......S...........G...........ST.
DTAVYYCARALEMGYSSGTFEDYWGQGTLVTVSS  (SEQ ID NO: 41)
.....F..............H.............V....P

AMMO1 LC: 6.8% VL mutated (KY631780)

LV3-21*01 — LJ1*01

SYVLTQPPSVSVAPGKTARITCGGNNIGSKSVHWYQQKPGQAPVLVIYYDSDRPSGIPERFSGSNSGNTATLTISRVEAGDEADYC
......E...........QR.T....H..A..N.....................Q..........................S..............
QVWDSSSDHPIYVFGTGTKVTVL  (SEQ ID NO: 42)
............GRG.........G........

FIG. 7 cont'd

AMMO2 HC: 10% VH mutated (KY631781)

VH1-69*01-D4-23*01-HJ6*02

QVQLVQSGAEVKKPGSSVKVSCKASGGTFSSYAISWVRQAPGQGLEWMGGIIPIFGTANYAQKFQGRVTITADESTSTAYMELSSLRSE
..........I....T...P..T.G.N..................W...V.D.SSF..R..D.LS....A.........R........

DTAVYYCAR<u>DRVLGAH</u>GGNPLNGH<u>YYGMD</u>WGQGTTVTVSS   (SEQ ID NO:43)
..............A........H.....................

AMMO2 LC: 5.7% VK mutated (KY631782)

KV1-12*01-KJ4*01

DIQMTQSPSSVSASVGDRVTITCRASQGISSWLAWYQQKPGKAPKLLIYAASSLQSGVPSRFSGSGSGTDFTLTISSLQPEDFATYYC
..I.....................................NL....D...............R...........E.........IY.................V...F.

<u>QQANSFPLIT</u>FGGGTKVEIK  (SEQ ID NO:44)
........S......R.D.A

FIG. 7 cont'd

AMMO3 HC: 8.3% mutated (KY631783)

<u>VH2-5*09</u> – <u>D5-12*01</u> – <u>J4*01</u>
QVTLKESGPTLVKPTQTLTLTCTFSGFSLSTSGVGVGWIRQPPGKALEWLALIYWDDDKRYGPSLKSRLTITKDTSKNQVLTMTNMDP
E.Q.V..........................A....................H.AA..S...RN.F..........................
VDTATYYCAHRDKLYSGYKFDYWGQGTLVTVSS (SEQ ID NO:45)
.......F..FA.....GDS..........

AMMO3 LC: 7.9% VL mutated (KY631784)

<u>LV3-1*01</u> <u>LJ2*01</u>
SYELTQPPSVSVSPGQTASITCSGDKLGDKYACWYQQKPGQSPVLVIYQDSKRPSGIPERFSGSNSGNTATLTISGTQAMDEADYYC
QSA...................................EE.V.....................RN.P.................A.........
QAMDSSTVVFGGGTKLTVL (SEQ ID NO:46)
..........

FIG. 7 cont'd

AMMO4 HC: 9.4% VH mutated (KY631785)

VH1-69*06-*D2-2*01*-HJ4*02

QVQLVQSGAEVKKPGSSVKVSCKASGGTFSSYAISWVRQAPGQGLEWMGGIIPIFGIANYAQKFQGRVTITADKSTSTAYMELSSLRSE
................T.........R.........AS..NHG.V............I..V..V.G......N..........N..L..R....D

DTAVYYCARDVPGQCTRTSCINFSSQWGQGTLVTVSS (SEQ ID NO: 47)
....................T.F.........

AMMO4 LC: 5.4VK mutated (KY631786)

KV2-30*01 – KJ2*01

DVVMTQSPLSLPVTLGQPASISCRSSQSLVYSDGNTYLNWFQQRPGQSPRRLIYKVSNRDSGVPDRFSGSGSGTDFTLKISRVEAEDVG
....................T......T....N......SF.S......H.............N........

VYYCMQGTHWPPMYTFGQGTKLEIK (SEQ ID NO: 48)
.........Y......F........

FIG. 7 cont'd

AMMO5 HC: 6.9% VH mutated (KY631788)

VH3-23*01 D4-17*01-J5*02

EVQLLESGGGLVQPGGSLRLSCAASGFTFSSYAMSWVRQAPGKGLEWVSAISGSGGSTYYADSVKGRFTISRDNSKNTLYLQMNSLRAE
................F.....................N.............P....S..ATD...........E..L..........V.

DTAVYYCAKDGAGDYLGWFDPWGQGTLVTVSS (SEQ ID NO:49)
....L.....................L...H.....I..L

AMMO5 LC: 5.3% VK mutated (KY631787)

VK3-20*01-KJ1*01

EIVLTQSPGTLSLSPGERATLSCRASQSVSSSYLAWYQQKPGQAPRLLIYGASSRATGIPDRFSGSGSGTDFTLTISRLEPEDFAVYYC
.................G....................NN.E...................I.K................D........

QQYGSSPPRTFGQGTKVEIK (SEQ ID NO:50)
......N.S..........

FIG. 7 cont'd

>glAMMO1_LC
SYVLTQPPSVSVAPGKTARITCGGNNIGSKSVHWYQQKPGQAPVLVIYYDSDRPSGIPERFSGSNSGNTATLTISRVEAGDEADYYCQVWDSSSDHPLYVFGTGTKVTVL (SEQ ID NO: 65)

>glAMMO1_HC
QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARALEMGYRSGFPFDYWGQGTLVTVSS (SEQ ID NO: 66)

>glAMMO2_LC
DIQMTQSPSSVSASVGDRVTITCRASQGISSWLAWYQQKPGKAPKLLIYAASSLQSGVPSRFSGSGSGTDFTLTISSLQPEDFATYYCQQANSFPLTFGGGTKVEIK (SEQ ID NO: 67)

>glAMMO2_HC
QVQLVQSGAEVKKPGSSVKVSCKASGGTFSSYAISWVRQAPGQGLEWMGGIIPIFGTANYAQKFQGRVTITADESTSTAYMELSLRSEDTAVYYCARDRVLGAHGGNPLNGHYYGMDVWGQGTTVTVSS (SEQ ID NO: 68)

>glAMMO3_LC
SYELTQPPSVSVSPGQTASITCSGDKLGDKYACWYQQKPGQSPVLVIYQDSKRPSGIPERFSGSNSGNTATLTISGTQAMDEADYYCQAWDSSTVVFGGGTKLTVL (SEQ ID NO: 69)

>glAMMO3_HC
QVTLKESGPTLVKPTQTLTLTCTFSGFSLSTSGVGVGWIRQPPGKALEWLALIYWDDDKRYGPSLKSRLTITKDTSKNQVVLTMTNMDPVDTATYYCAHRDKLYSGYVKFDYWGQGTLVTVSS (SEQ ID NO: 70)

>gl_AMMO4_LC
DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPPMYTFGQGTKLEIK (SEQ ID NO: 71)

FIG. 7 cont'd

>gl_AMMO4_HC
QVQLVQSGAEVKKPGSSVKVSCKASGGTFSSYAISWVRQAPGQGLEWMGGIIPILGIANYAQKFQGRVTITADKSTSTAYMELSSLRSEDTAVYYCARDVPGQCTRTSC
YNFSSQWGQGTLVTVSS (SEQ ID NO: 72)

>gl_AMMO5_LC
EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPPRTFGQGTKVEIK (SEQ
ID NO: 73)

>glAMMO5HC
EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKDGAGDYLGWF
DPWGQGTLVTVSS (SEQ ID NO: 74)

FIG. 9

Kinetic Analysis of Antibodies, or gp42 binding to gH/gL measured by BLI

| Ligand | pH | Analyte | $K_A M^{-1}$ $\times 10^7$ | $K_D M$ $\times 10^{-9}$ | $k_{on}$ (1/Ms) $\times 10^5$ | $k_{on}$ Error $\times 10^3$ | $k_{off}$ (1/s) $\times 10^{-3}$ | $k_{off}$ Error $\times 10^{-6}$ |
|---|---|---|---|---|---|---|---|---|
| AMMO1 Mab | 7.4 | gH/gL | 863 | 0.12 | 3.34 | 2.76 | 0.0387 | 2.05 |
| AMMO1 Mab | 5.0 | gH/gL | 784 | 0.13 | 5.73 | 3.22 | 0.0731 | 1.16 |
| AMMO1Q1N$_{HC}$ Mab | 7.4 | gH/gL | 634 | 0.16 | 2.44 | 0.87 | 0.0385 | 0.75 |
| AMMO1 Mab | 7.4 | gH/gL T62A | 585 | 0.17 | 7.89 | 6.08 | 0.135 | 2.50 |
| gH/gL | 7.4 | AMMO1 Fab | 812 | 0.12 | 4.09 | 1.35 | 0.0503 | 0.934 |
| gH T62A/gL | 7.4 | AMMO1 Fab | 523 | 0.19 | 5.64 | 1.73 | 0.108 | 0.938 |
| CL40 Mab | 7.4 | gH/gL | 14.8 | 6.77 | 4.69 | 4.71 | 3.18 | 8.99 |
| CL40 Mab | 5.0 | gH/gL | 16.7 | 5.99 | 5.94 | 9.37 | 3.56 | 1.61 |
| CL59 Mab | 7.4 | gH/gL | 15.7 | 6.39 | 4.38 | 8.24 | 2.80 | 11.9 |
| CL59 Mab | 5.0 | gH/gL | 18.1 | 5.52 | 3.37 | 4.83 | 1.86 | 8.67 |
| E1D1 Mab | 7.4 | gH/gL | 7.70 | 12.98 | 1.53 | 1.94 | 1.99 | 4.72 |
| gH/gL | 7.4 | gp42 | 78.4 | 1.28 | 2.24 | 2.42 | 0.286 | 3.06 |
| gH/gL | 7.4 | gp42 T175A | 48.5 | 2.06 | 1.45 | 2.39 | 0.299 | 3.63 |

FIG. 10

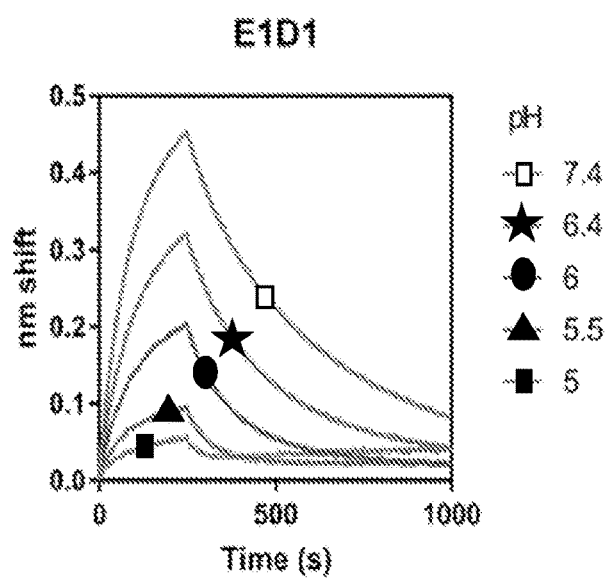

Ligand: AMMO1

Ligand: CL40

Ligand: CL59

Ligand: E1D1 time (s)

△ — gH/gL
□ — gH/gL + AMMO1
▲ — gH/gL + CL40
■ — gH/gL + CL59
○ — gH/gL + E1D1
● --- gH/gL + gIFl6

FIG. 18C
FIG. 18D
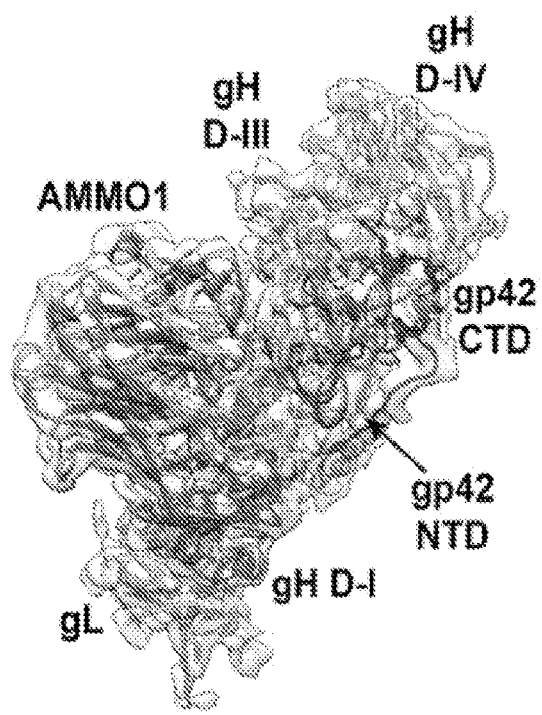
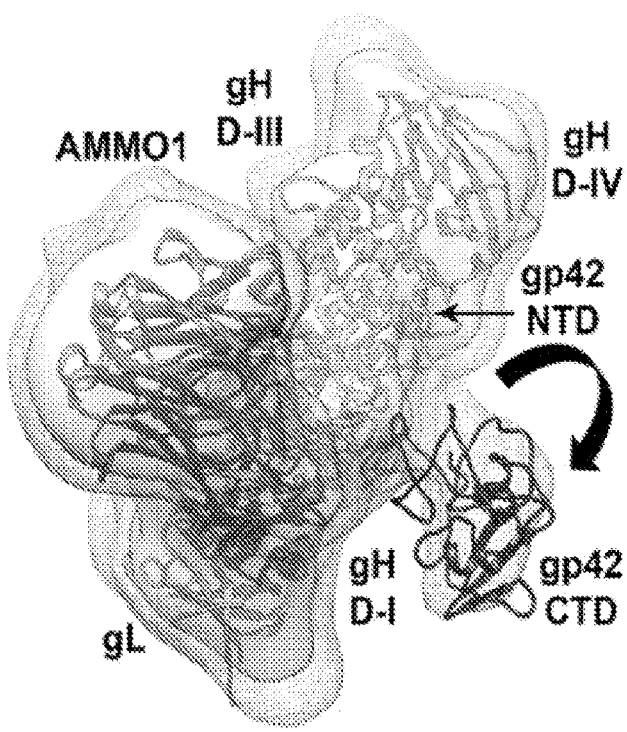
FIG. 18E
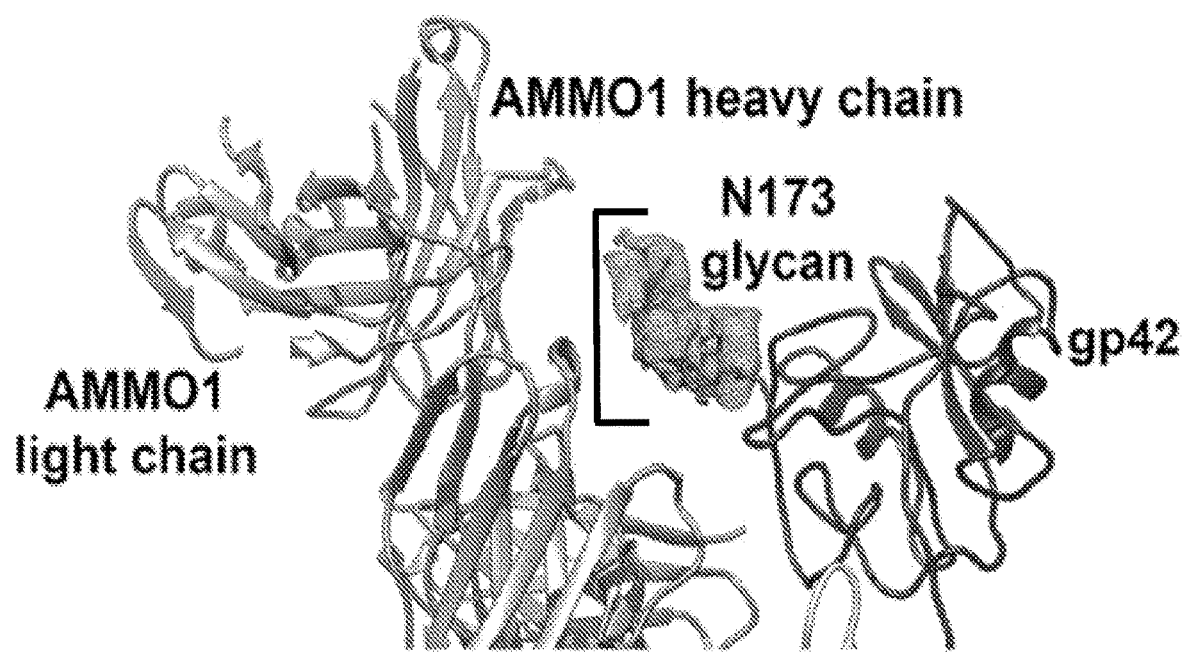

FIG. 19A
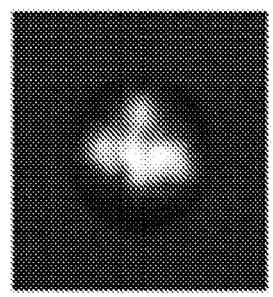 
FIG. 19B
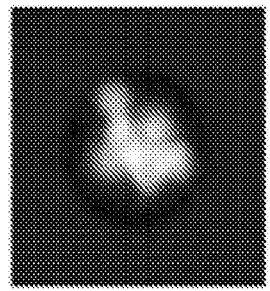 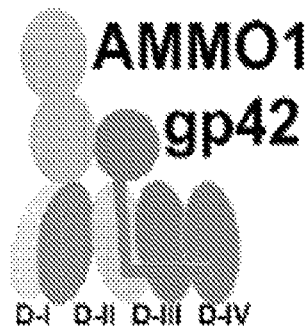
FIG. 19C
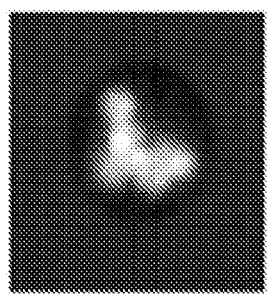 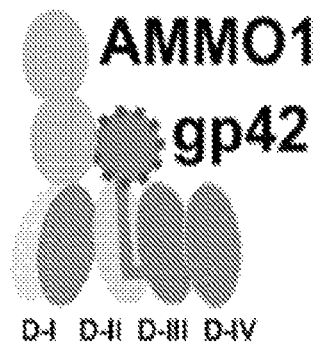
FIG. 19D
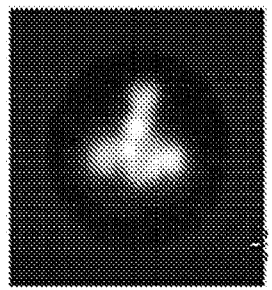 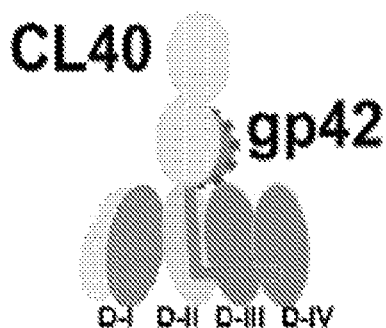

FIG. 24

>AMMO1 heavy chain variable region (SEQ ID NO: 1)

QVQLVQSGADVKKPGASVKVSCKASGYTFIHFGISWVRQAPGQGLEWMGWIDTNNGNTNYA
QSLQGRVTMTTDTSTGTAYMELRSLSTDDTAVYFCARALEMGHRSGFPFDYWGQGVLVTVSP

>AMMO1 light chain variable region (SEQ ID NO: 2)

SYELTQPPSVSVAPGQRATITCGGHNIGAKNVHWYQQKPGQAPVLVIQYDSDRPSGIPERFSG
SNSGSTATLTISRVEAGDEADYYCQVWDSGRGHPLYVFGGGTKVTVL

>AMMO2 heavy chain variable region (SEQ ID NO: 3)

QVQLVQSGAEVKKPGSSIKVSCKTSGGPFSTYGINWVRQAPGQGLEWMGWIPVFDTSSFAQ
RFQDRLSITADASTSTAYMELRSLRSEDTAVYYCARDRVLGAHGANPLNGHHYGMDVWGQGT
TVTVSS

>AMMO2 light chain variable region (SEQ ID NO: 4)

DIQITQSPSSVSASVGDRVTITCRANLGISDWLAWYQQKPGRAPKLLIYAASSLESGVPSRFSG
SGSGIYFTLTISSLQPEDVATYFCQQANSFPLSFGGGTRVDIA

>AMMO3 heavy chain variable region (SEQ ID NO: 5)

EVQLVESGPTLVKPTQTLTLTCTFSGFSLSTSGVGVGWIRQPPAKALEWLALIYWHDAARYSPS
LRNRFTITKDTSKNQVVLTMTNMDPVDTATYFCAFADKLYGDSVKFDYWGQGTLVTVSS

>AMMO3 light chain variable region (SEQ ID NO: 6)

QSALTQPPSVSVSPGQTASITCSGDKLGEEYVCWYQQKPGQSPVLVIYQDRNRPPGIPERFSG
SNAGNTATLTISGTQAMDEADYYCQAWDSSTVVFGGGTKLTVL

>AMMO4 heavy chain variable region (SEQ ID NO: 7)

QVQLVQSGTEVKKPGSSVRVSCKASGASFSNHGIVWVRQAPGQGLEWIGGIVPIVGGANYAQ
NFQGRVTITADKSTNTAYLELRSLRSDDTAVYYCARDVPGQCTRTTCFNFSSQWGQGTLVTVS
S

>AMMO4 light chain variable region (SEQ ID NO: 8)

DVVMTQSPLSLPVTLGQTASISCTSSQSLVNSDGNSFLSWFHQRPGQSPRRLIYKVSHRDSGV
PDRFSGSGSGTDFTLKINRVEAEDVGVYYCMQGTYWPPMFTFGQGTKLEIK

>AMMO5 heavy chain variable region (SEQ ID NO: 9)

EVQLLESGGGFVQPGGSLRLSCAASGFTFSNYAMSWVRQAPGKGPEWVSSISATDGSTYYA
DSVEGRLTISRDNSKNTLYLQMNSLRVEDTALYYCAKDGAGDYLGWFDLWGHGTLVIVSL

>AMMO5 light chain variable region (SEQ ID NO: 10)

EIVLTQSPGTLSLSPGEGATLSCRASQSVSNNYFAWYQQKPGQAPRLLIYGISKRATGIPDRFS
GSGSGTDFTLTISRLEPDDFAVYYCQQYGNSSPRTFGQGTKVEIK

FIG. 24 cont'd

EBV Envelope glycoprotein H (gH)

MQLLCVFCLVLLWEVGAASLSEVKLHLDIEGHASHYTIPWTELMAKVPGLSPEALWREAN
VTEDLASMLNRYKLIYKTSGTLGIALAEPVDIPAVSEGSMQVDASKVHPGVISGLNSPACML
SAPLEKQLFYYIGTMLPNTRPHSYVFYQLRCHLSYVALSINGDKFQYTGAMTSKFLMGTYK
RVTEKGDEHVLSLVFGKTKDLPDLRGPFSYPSLTSAQSGDYSLVIVTTFVHYANFHNYFVP
NLKDMFSRAVTMTAASYARYVLQKLVLLEMKGGCREPELDTETLTTMFEVSVAFFKVGHA
VGETGNGCVDLRWLAKSFFELTVLKDIIGICYGATVKGMQSYGLERLAAMLMATVKMEEL
GHLTTEKQEYALRLATVGYPKAGVYSGLIGGATSVLLSAYNRHPLFQPLHTVMRETLFIGS
HVVLRELRLNVTTQGPNLALYQLLSTALCSALEIGEVLRGLALGTESGLFSPCYLSLRFDLT
RDKLLSMAPQEATLDQAAVSNAVDGFLGRLSLEREDRDAWHLPAYKCVDRLDKVLMIIPLI
NVTFIISSDREVRGSALYEASTTYLSSSLFLSPVIMNKCSQGAVAGEPRQIPKIQNFTRTQK
SCIFCGFALLSYDEKEGLETTTYITSQEVQNSILSSNYFDFDNLHVHYLLLTTNGTVMEIAGL
YEERAHVVLAIILYFIAFALGIFLVHKIVMFFL (SEQ ID NO: 51)

EBV Envelope glycoprotein L (gL)

MRAVGVFLAICLVTIFVLPTWGNWAYPCCHVTQLRAQHLLALENISDIYLVSNQTCDGFSL
ASLNSPKNGSNQLVISRCANGLNVVSFFISILKRSSSALTGHLRELLTTLETLYGSFSVEDLF
GANLNRYAWHRGG (SEQ ID NO: 52)

EBV Glycoprotein B (gB)

MESRIWCLVVCVNLCIVCLGAAVSSSSTSHATSSTHNGSHTSRTTSAQTRSVYSQHVTSS
EAVSHRANETIYNTTLKYGDVVGVNTTKYPYRVCSMAQGTDLIRFERNIICTSMKPINEDLD
EGIMVVYKRNIVAHTFKVRVYQKVLTFRRSYAYIYTTYLLGSNTEYVAPPMWEIHHINKFAQ
CYSSYSRVIGGTVFVAYHRDSYENKTMQLIPDDYSNTHSTRYVTVKDQWHSRGSTWLYR
ETCNLNCMLTITTARSKYPYHFFATSTGDVVYISPFYNGTNRNASYFGENADKFFIFPNYTI
VSDFGRPNAAPETHRLVAFLERADSVISWDIQDEKNVTCQLTFWEASERTIRSEAEDSYHF
SSAKMTATFLSKKQEVNMSDSALDCVRDEAINKLQQIFNTSYNQTYEKYGNVSVFETSGG
LVVFWQGIKQKSLVELERLANRSSLNITHRTRRSTSDNNTTHLSSMESVHNLVYAQLQFTY
DTLRGYINRALAQIAEAWCVDQRRTLEVFKELSKINPSAILSAIYNKPIAARFMGDVLGLASC
VTINQTSVKVLRDMNVKESPGRCYSRPVVIFNFANSSYVQYGQLGEDNEILLGNHRTEEC
QLPSLKIFIAGNSAYEYVDYLFKRMIDLSSISTVDSMIALDIDPLENTDFRVLELYSQKELRSS
NVFDLEEIMREFNSYKQRVKYVEDKVVDPLPPYLKGLDDLMSGLGAAGKAVGVAIGAVGG
AVASVVEGVATFLKNPFGAFTIILVAIAVVIITYLIYTRQRRLCTQPLQNLFPYLVSADGTTVT
SGSTKDTSLQAPPSYEESVYNSGRKGPGPPSSDASTAAPPYTNEQAYQMLLALARLDAE
QRAQQNGTDSLDGQTGTQDKGQKPNLLDRLRHRKNGYRHLKDSDEEENV (SEQ ID NO: 53)

EBV Glycoprotein 42 (gp42)

MVSFKQVRVPLFTAIALVIVLLLAYFLPPRVRGGGRVAAAAITWVPKPNVEVWPVDPPPPV
NFNKTAEQEYGDKEVKLPHWTPTLHTFQVPQNYTKANCTYCNTREYTFSYKGCCFYTK
KKHTWNGCFQACAELYPCTYFYGPTPDILPVVTRNLNAIESLWWGVYRVGEGNWTSLDG
GTFKVYQIFGSHCTYVSKFSTVPVSHHECSFLKPCLCVSQRSNS (SEQ ID NO: 54)

```
SEQUENCE LISTING

<160> NUMBER OF SEQ ID NOS: 74

<210> SEQ ID NO 1
<211> LENGTH: 123
<212> TYPE: PRT
<213> ORGANISM: Artificial Sequence
<220> FEATURE:
<223> OTHER INFORMATION: AMMO1 heavy chain variable region

<400> SEQUENCE: 1

Gln Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Ile His Phe
            20                  25                  30

Gly Ile Ser Trp Val Arg Gln Ala Pro Gly Gln Gly Leu Glu Trp Met
        35                  40                  45

Gly Trp Ile Asp Thr Asn Asn Gly Asn Thr Asn Tyr Ala Gln Ser Leu
    50                  55                  60

Gln Gly Arg Val Thr Met Thr Thr Asp Thr Ser Thr Gly Thr Ala Tyr
65                  70                  75                  80

Met Glu Leu Arg Ser Leu Ser Thr Asp Asp Thr Ala Val Tyr Phe Cys
                85                  90                  95

Ala Arg Ala Leu Glu Met Gly His Arg Ser Gly Phe Pro Phe Asp Tyr
            100                 105                 110

Trp Gly Gln Gly Val Leu Val Thr Val Ser Pro
        115                 120

<210> SEQ ID NO 2
<211> LENGTH: 110
<212> TYPE: PRT
<213> ORGANISM: Artificial Sequence
<220> FEATURE:
<223> OTHER INFORMATION: AMMO1 light chain variable region

<400> SEQUENCE: 2

Ser Tyr Glu Leu Thr Gln Pro Pro Ser Val Ser Val Ala Pro Gly Gln
1               5                   10                  15

Arg Ala Thr Ile Thr Cys Gly Gly His Asn Ile Gly Ala Lys Asn Val
            20                  25                  30

His Trp Tyr Gln Gln Lys Pro Gly Gln Ala Pro Val Leu Val Ile Gln
        35                  40                  45

Tyr Asp Ser Asp Arg Pro Ser Gly Ile Pro Glu Arg Phe Ser Gly Ser
    50                  55                  60

Asn Ser Gly Ser Thr Ala Thr Leu Thr Ile Ser Arg Val Glu Ala Gly
65                  70                  75                  80
```

```
Asp Glu Ala Asp Tyr Tyr Cys Gln Val Trp Asp Ser Gly Arg Gly His
                85                  90                  95

Pro Leu Tyr Val Phe Gly Gly Gly Thr Lys Val Thr Val Leu
            100                 105                 110

<210> SEQ ID NO 3
<211> LENGTH: 130
<212> TYPE: PRT
<213> ORGANISM: Artificial Sequence
<220> FEATURE:
<223> OTHER INFORMATION: AMMO2 heavy chain variable region

<400> SEQUENCE: 3

Gln Val Gln Leu Val Gln Ser Gly Ala Glu Val Lys Lys Pro Gly Ser
1               5                   10                  15

Ser Ile Lys Val Ser Cys Lys Thr Ser Gly Gly Pro Phe Ser Thr Tyr
                20                  25                  30

Gly Ile Asn Trp Val Arg Gln Ala Pro Gly Gln Gly Leu Glu Trp Met
            35                  40                  45

Gly Trp Ile Ile Pro Val Phe Asp Thr Ser Ser Phe Ala Gln Arg Phe
    50                  55                  60

Gln Asp Arg Leu Ser Ile Thr Ala Asp Ala Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Asp Arg Val Leu Gly Ala His Gly Ala Asn Pro Leu Asn Gly
            100                 105                 110

His His Tyr Gly Met Asp Val Trp Gly Gln Gly Thr Thr Val Thr Val
        115                 120                 125

Ser Ser
    130

<210> SEQ ID NO 4
<211> LENGTH: 107
<212> TYPE: PRT
<213> ORGANISM: Artificial Sequence
<220> FEATURE:
<223> OTHER INFORMATION: AMMO2 light chain variable region

<400> SEQUENCE: 4

Asp Ile Gln Ile Thr Gln Ser Pro Ser Ser Val Ser Ala Ser Val Gly
1               5                   10                  15

Asp Arg Val Thr Ile Thr Cys Arg Ala Asn Leu Gly Ile Ser Asp Trp
                20                  25                  30

Leu Ala Trp Tyr Gln Gln Lys Pro Gly Arg Ala Pro Lys Leu Leu Ile
            35                  40                  45

Tyr Ala Ala Ser Ser Leu Glu Ser Gly Val Pro Ser Arg Phe Ser Gly
    50                  55                  60

Ser Gly Ser Gly Ile Tyr Phe Thr Leu Thr Ile Ser Ser Leu Gln Pro
65                  70                  75                  80

Glu Asp Val Ala Thr Tyr Phe Cys Gln Gln Ala Asn Ser Phe Pro Leu
                85                  90                  95

Ser Phe Gly Gly Gly Thr Arg Val Asp Ile Ala
            100                 105

<210> SEQ ID NO 5
<211> LENGTH: 123
<212> TYPE: PRT
<213> ORGANISM: Artificial Sequence
```

<220> FEATURE:
<223> OTHER INFORMATION: AMMO3 heavy chain variable region

<400> SEQUENCE: 5

Glu Val Gln Leu Val Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Ala Lys Ala Leu Glu
        35                  40                  45

Trp Leu Ala Leu Ile Tyr Trp His Asp Ala Ala Arg Tyr Ser Pro Ser
    50                  55                  60

Leu Arg Asn Arg Phe Thr Ile Thr Lys Asp Thr Ser Lys Asn Gln Val
65                  70                  75                  80

Val Leu Thr Met Thr Asn Met Asp Pro Val Asp Thr Ala Thr Tyr Phe
                85                  90                  95

Cys Ala Phe Ala Asp Lys Leu Tyr Gly Asp Ser Val Lys Phe Asp Tyr
            100                 105                 110

Trp Gly Gln Gly Thr Leu Val Thr Val Ser Ser
        115                 120

<210> SEQ ID NO 6
<211> LENGTH: 106
<212> TYPE: PRT
<213> ORGANISM: Artificial Sequence
<220> FEATURE:
<223> OTHER INFORMATION: AMMO3 light chain variable region

<400> SEQUENCE: 6

Gln Ser Ala Leu Thr Gln Pro Pro Ser Val Ser Val Ser Pro Gly Gln
1               5                   10                  15

Thr Ala Ser Ile Thr Cys Ser Gly Asp Lys Leu Gly Glu Glu Tyr Val
            20                  25                  30

Cys Trp Tyr Gln Gln Lys Pro Gly Gln Ser Pro Val Leu Val Ile Tyr
        35                  40                  45

Gln Asp Arg Asn Arg Pro Pro Gly Ile Pro Glu Arg Phe Ser Gly Ser
    50                  55                  60

Asn Ala Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 7
<211> LENGTH: 126
<212> TYPE: PRT
<213> ORGANISM: Artificial Sequence
<220> FEATURE:
<223> OTHER INFORMATION: AMMO4 heavy chain variable region

<400> SEQUENCE: 7

Gln Val Gln Leu Val Gln Ser Gly Thr Glu Val Lys Lys Pro Gly Ser
1               5                   10                  15

Ser Val Arg Val Ser Cys Lys Ala Ser Gly Ala Ser Phe Ser Asn His
            20                  25                  30

Gly Ile Val Trp Val Arg Gln Ala Pro Gly Gln Gly Leu Glu Trp Ile
        35                  40                  45

Gly Gly Ile Val Pro Ile Val Gly Gly Ala Asn Tyr Ala Gln Asn Phe
    50                  55                  60

Gln Gly Arg Val Thr Ile Thr Ala Asp Lys Ser Thr Asn Thr Ala Tyr
65                  70                  75                  80

Leu Glu Leu Arg Ser Leu Arg Ser Asp Asp Thr Ala Val Tyr Tyr Cys
                85                  90                  95

Ala Arg Asp Val Pro Gly Gln Cys Thr Arg Thr Thr Cys Phe Asn Phe
            100                 105                 110

Ser Ser Gln Trp Gly Gln Gly Thr Leu Val Thr Val Ser Ser
        115                 120                 125

<210> SEQ ID NO 8
<211> LENGTH: 114
<212> TYPE: PRT
<213> ORGANISM: Artificial Sequence
<220> FEATURE:
<223> OTHER INFORMATION: AMM04 light chain variable region

<400> SEQUENCE: 8

Asp Val Val Met Thr Gln Ser Pro Leu Ser Leu Pro Val Thr Leu Gly
1               5                   10                  15

Gln Thr Ala Ser Ile Ser Cys Thr Ser Ser Gln Ser Leu Val Asn Ser
            20                  25                  30

Asp Gly Asn Ser Phe Leu Ser Trp Phe His Gln Arg Pro Gly Gln Ser
        35                  40                  45

Pro Arg Arg Leu Ile Tyr Lys Val Ser His Arg Asp Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Val Gly Val Tyr Tyr Cys Met Gln Gly
                85                  90                  95

Thr Tyr Trp Pro Pro Met Phe Thr Phe Gly Gln Gly Thr Lys Leu Glu
            100                 105                 110

Ile Lys

<210> SEQ ID NO 9
<211> LENGTH: 121
<212> TYPE: PRT
<213> ORGANISM: Artificial Sequence
<220> FEATURE:
<223> OTHER INFORMATION: AMM05 heavy chain variable region

<400> SEQUENCE: 9

Glu Val Gln Leu Leu Glu Ser Gly Gly Gly Phe Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Pro Glu Trp Val
        35                  40                  45

Ser Ser Ile Ser Ala Thr Asp Gly Ser Thr Tyr Tyr Ala Asp Ser Val
    50                  55                  60

Glu Gly Arg Leu Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asp Gly Ala Gly Asp Tyr Leu Gly Trp Phe Asp Leu Trp Gly
            100                 105                 110

His Gly Thr Leu Val Ile Val Ser Leu
        115                 120

<210> SEQ ID NO 10
<211> LENGTH: 109
<212> TYPE: PRT
<213> ORGANISM: Artificial Sequence
<220> FEATURE:
<223> OTHER INFORMATION: AMMO5 light chain variable region

<400> SEQUENCE: 10

Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Ser Val Ser Asn Asn
            20                  25                  30

Tyr Phe Ala Trp Tyr Gln Gln Lys Pro Gly Gln Ala Pro Arg Leu Leu
        35                  40                  45

Ile Tyr Gly Ile Ser Lys Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Asp Asp Phe Ala Val Tyr Tyr Cys Gln Gln Tyr Gly Asn Ser Ser
                85                  90                  95

Pro Arg Thr Phe Gly Gln Gly Thr Lys Val Glu Ile Lys
            100                 105

<210> SEQ ID NO 11
<211> LENGTH: 11
<212> TYPE: PRT
<213> ORGANISM: Artificial Sequence
<220> FEATURE:
<223> OTHER INFORMATION: AMMO1 CDRL1

<400> SEQUENCE: 11

Gly Gly His Asn Ile Gly Ala Lys Asn Val His
1               5                   10

<210> SEQ ID NO 12
<211> LENGTH: 7
<212> TYPE: PRT
<213> ORGANISM: Artificial Sequence
<220> FEATURE:
<223> OTHER INFORMATION: AMMO1 CDRL2

<400> SEQUENCE: 12

Tyr Asp Ser Asp Arg Pro Ser
1               5

<210> SEQ ID NO 13
<211> LENGTH: 14
<212> TYPE: PRT
<213> ORGANISM: Artificial Sequence
<220> FEATURE:
<223> OTHER INFORMATION: AMMO1 CDRL3

<400> SEQUENCE: 13

Cys Gln Val Trp Asp Ser Gly Arg Gly His Pro Leu Tyr Val
1               5                   10

```
<210> SEQ ID NO 14
<211> LENGTH: 10
<212> TYPE: PRT
<213> ORGANISM: Artificial Sequence
<220> FEATURE:
<223> OTHER INFORMATION: AMMO1 CDRH1

<400> SEQUENCE: 14

Tyr Thr Phe Ile His Phe Gly Ile Ser Trp
1               5                   10

<210> SEQ ID NO 15
<211> LENGTH: 16
<212> TYPE: PRT
<213> ORGANISM: Artificial Sequence
<220> FEATURE:
<223> OTHER INFORMATION: AMMO1 CDRH2

<400> SEQUENCE: 15

Ile Asp Thr Asn Asn Gly Asn Thr Asn Tyr Ala Gln Ser Leu Gln Gly
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: AMMO1 CDRH3

<400> SEQUENCE: 16

Arg Ala Leu Glu Met Gly His Arg Ser Gly Phe Pro Phe Asp Tyr
1               5                   10                  15

<210> SEQ ID NO 17
<211> LENGTH: 11
<212> TYPE: PRT
<213> ORGANISM: Artificial Sequence
<220> FEATURE:
<223> OTHER INFORMATION: AMMO2 CDRL1

<400> SEQUENCE: 17

Arg Ala Asn Leu Gly Ile Ser Asp Trp Leu Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: AMMO2 CDRL2

<400> SEQUENCE: 18

Ala Ala Ser Ser Leu Glu Ser
1               5

<210> SEQ ID NO 19
<211> LENGTH: 9
<212> TYPE: PRT
<213> ORGANISM: Artificial Sequence
<220> FEATURE:
<223> OTHER INFORMATION: AMMO2 CDRL3

<400> SEQUENCE: 19

Gln Gln Ala Asn Ser Phe Pro Leu Ser
1               5
```

```
<210> SEQ ID NO 20
<211> LENGTH: 9
<212> TYPE: PRT
<213> ORGANISM: Artificial Sequence
<220> FEATURE:
<223> OTHER INFORMATION: AMMO2 CDRH1

<400> SEQUENCE: 20

Gly Pro Phe Ser Thr Tyr Gly Ile Asn
1               5

<210> SEQ ID NO 21
<211> LENGTH: 13
<212> TYPE: PRT
<213> ORGANISM: Artificial Sequence
<220> FEATURE:
<223> OTHER INFORMATION: AMMO2 CDRH2

<400> SEQUENCE: 21

Trp Ile Ile Pro Val Phe Asp Thr Ser Ser Phe Ala Gln
1               5                   10

<210> SEQ ID NO 22
<211> LENGTH: 22
<212> TYPE: PRT
<213> ORGANISM: Artificial Sequence
<220> FEATURE:
<223> OTHER INFORMATION: AMMO2 CDRH3

<400> SEQUENCE: 22

Arg Asp Arg Val Leu Gly Ala His Gly Ala Asn Pro Leu Asn Gly His
1               5                   10                  15

His Tyr Gly Met Asp Val
            20

<210> SEQ ID NO 23
<211> LENGTH: 12
<212> TYPE: PRT
<213> ORGANISM: Artificial Sequence
<220> FEATURE:
<223> OTHER INFORMATION: AMMO3 CDRL1

<400> SEQUENCE: 23

Ser Gly Asp Lys Leu Gly Glu Glu Tyr Val Cys Trp
1               5                   10

<210> SEQ ID NO 24
<211> LENGTH: 7
<212> TYPE: PRT
<213> ORGANISM: Artificial Sequence
<220> FEATURE:
<223> OTHER INFORMATION: AMMO3 CDRL2

<400> SEQUENCE: 24

Gln Asp Arg Asn Arg Pro Pro
1               5

<210> SEQ ID NO 25
<211> LENGTH: 9
<212> TYPE: PRT
<213> ORGANISM: Artificial Sequence
<220> FEATURE:
<223> OTHER INFORMATION: AMMO3 CDRL3

<400> SEQUENCE: 25

Gln Ala Trp Asp Ser Ser Thr Val Val
1               5
```

```
<210> SEQ ID NO 26
<211> LENGTH: 11
<212> TYPE: PRT
<213> ORGANISM: Artificial Sequence
<220> FEATURE:
<223> OTHER INFORMATION: AMMO3 CDRH1

<400> SEQUENCE: 26

Phe Ser Leu Ser Thr Ser Gly Val Gly Val Gly
1               5                   10

<210> SEQ ID NO 27
<211> LENGTH: 16
<212> TYPE: PRT
<213> ORGANISM: Artificial Sequence
<220> FEATURE:
<223> OTHER INFORMATION: AMMO3 CDRH2

<400> SEQUENCE: 27

Leu Ile Tyr Trp His Asp Ala Ala Arg Tyr Ser Pro Ser Leu Arg Asn
1               5                   10                  15

<210> SEQ ID NO 28
<211> LENGTH: 13
<212> TYPE: PRT
<213> ORGANISM: Artificial Sequence
<220> FEATURE:
<223> OTHER INFORMATION: AMMO3 CDRH3

<400> SEQUENCE: 28

Ala Asp Lys Leu Tyr Gly Asp Ser Val Lys Phe Asp Tyr
1               5                   10

<210> SEQ ID NO 29
<211> LENGTH: 16
<212> TYPE: PRT
<213> ORGANISM: Artificial Sequence
<220> FEATURE:
<223> OTHER INFORMATION: AMMO4 CDRL1

<400> SEQUENCE: 29

Thr Ser Ser Gln Ser Leu Val Asn Ser Asp Gly Asn Ser Phe Leu Ser
1               5                   10                  15

<210> SEQ ID NO 30
<211> LENGTH: 6
<212> TYPE: PRT
<213> ORGANISM: Artificial Sequence
<220> FEATURE:
<223> OTHER INFORMATION: AMMO4 CDRL2

<400> SEQUENCE: 30

Val Ser His Arg Asp Ser
1               5

<210> SEQ ID NO 31
<211> LENGTH: 12
<212> TYPE: PRT
<213> ORGANISM: Artificial Sequence
<220> FEATURE:
<223> OTHER INFORMATION: AMMO4 CDRL3

<400> SEQUENCE: 31

Met Gln Gly Thr Tyr Trp Pro Pro Met Phe Thr Phe
1               5                   10
```

```
<210> SEQ ID NO 32
<211> LENGTH: 9
<212> TYPE: PRT
<213> ORGANISM: Artificial Sequence
<220> FEATURE:
<223> OTHER INFORMATION: AMMO4 CDRH1

<400> SEQUENCE: 32

Ala Ser Phe Ser Asn His Gly Ile Val
1               5

<210> SEQ ID NO 33
<211> LENGTH: 17
<212> TYPE: PRT
<213> ORGANISM: Artificial Sequence
<220> FEATURE:
<223> OTHER INFORMATION: AMMO4 CDRH2

<400> SEQUENCE: 33

Gly Ile Val Pro Ile Val Gly Gly Ala Asn Tyr Ala Gln Asn Phe Gln
1               5                   10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: AMMO4 CDRH3

<400> SEQUENCE: 34

Asp Val Pro Gly Gln Cys Thr Arg Thr Thr Cys Phe Asn Phe Ser Ser
1               5                   10                  15

Gln

<210> SEQ ID NO 35
<211> LENGTH: 11
<212> TYPE: PRT
<213> ORGANISM: Artificial Sequence
<220> FEATURE:
<223> OTHER INFORMATION: AMMO5 CDRL1

<400> SEQUENCE: 35

Arg Ala Ser Gln Ser Val Ser Asn Asn Tyr Phe
1               5                   10

<210> SEQ ID NO 36
<211> LENGTH: 8
<212> TYPE: PRT
<213> ORGANISM: Artificial Sequence
<220> FEATURE:
<223> OTHER INFORMATION: AMMO5 CDRL2

<400> SEQUENCE: 36

Gly Ile Ser Lys Arg Ala Thr Gly
1               5

<210> SEQ ID NO 37
<211> LENGTH: 10
<212> TYPE: PRT
<213> ORGANISM: Artificial Sequence
<220> FEATURE:
<223> OTHER INFORMATION: AMMO5 CDRL3
```

```
<400> SEQUENCE: 37

Gln Gln Tyr Gly Asn Ser Ser Pro Arg Thr
1               5                   10

<210> SEQ ID NO 38
<211> LENGTH: 9
<212> TYPE: PRT
<213> ORGANISM: Artificial Sequence
<220> FEATURE:
<223> OTHER INFORMATION: AMMO5 CDRH1

<400> SEQUENCE: 38

Phe Thr Phe Ser Asn Tyr Ala Met Ser
1               5

<210> SEQ ID NO 39
<211> LENGTH: 17
<212> TYPE: PRT
<213> ORGANISM: Artificial Sequence
<220> FEATURE:
<223> OTHER INFORMATION: AMMO5 CDRH2

<400> SEQUENCE: 39

Ser Ile Ser Ala Thr Asp Gly Ser Thr Tyr Tyr Ala Asp Ser Val Glu
1               5                   10                  15

Gly

<210> SEQ ID NO 40
<211> LENGTH: 8
<212> TYPE: PRT
<213> ORGANISM: Artificial Sequence
<220> FEATURE:
<223> OTHER INFORMATION: AMMO5 CDRH3

<400> SEQUENCE: 40

Lys Asp Gly Ala Gly Asp Tyr Leu
1               5

<210> SEQ ID NO 41
<211> LENGTH: 123
<212> TYPE: PRT
<213> ORGANISM: Artificial Sequence
<220> FEATURE:
<223> OTHER INFORMATION: AMMO1 heavy chain variable region without
      mutations

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Ala Leu Glu Met Gly Tyr Ser Ser Gly Phe Pro Phe Asp Tyr
            100                 105                 110

Trp Gly Gln Gly Thr Leu Val Thr Val Ser Ser
        115                 120

<210> SEQ ID NO 42
<211> LENGTH: 110
<212> TYPE: PRT
<213> ORGANISM: Artificial Sequence
<220> FEATURE:
<223> OTHER INFORMATION: AMMO1 light chain variable region without
      mutations

<400> SEQUENCE: 42

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Leu Tyr Val Phe Gly Thr Gly Thr Lys Val Thr Val Leu
            100                 105                 110

<210> SEQ ID NO 43
<211> LENGTH: 130
<212> TYPE: PRT
<213> ORGANISM: Artificial Sequence
<220> FEATURE:
<223> OTHER INFORMATION: AMMO2 heavy chain variable region without
      mutations

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Val Leu Gly Ala His Gly Gly Asn Pro Leu Asn Gly
            100                 105                 110

His Tyr Tyr Gly Met Asp Val Trp Gly Gln Gly Thr Thr Val Thr Val
        115                 120                 125

Ser Ser
130
```

-continued

<210> SEQ ID NO 44
<211> LENGTH: 107
<212> TYPE: PRT
<213> ORGANISM: Artificial Sequence
<220> FEATURE:
<223> OTHER INFORMATION: AMMO2 light chain variable region without
      mutations

<400> SEQUENCE: 44

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 45
<211> LENGTH: 123
<212> TYPE: PRT
<213> ORGANISM: Artificial Sequence
<220> FEATURE:
<223> OTHER INFORMATION: AMMO3 heavy chain variable region without
      mutations

<400> SEQUENCE: 45

Gln Val Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Gly Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Asp Lys Leu Tyr Ser Gly Tyr Val Lys Phe Asp Tyr
            100                 105                 110

Trp Gly Gln Gly Thr Leu Val Thr Val Ser Ser
        115                 120

<210> SEQ ID NO 46
<211> LENGTH: 106
<212> TYPE: PRT
<213> ORGANISM: Artificial Sequence
<220> FEATURE:
<223> OTHER INFORMATION: AMMO3 light chain variable region without
      mutations

<400> SEQUENCE: 46

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 47
<211> LENGTH: 126
<212> TYPE: PRT
<213> ORGANISM: Artificial Sequence
<220> FEATURE:
<223> OTHER INFORMATION: AMMO4 heavy chain variable region without
      mutations

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Pro Gly Gln Cys Thr Arg Thr Ser Cys Tyr Asn Phe
            100                 105                 110

Ser Ser Gln Trp Gly Gln Gly Thr Leu Val Thr Val Ser Ser
        115                 120                 125

<210> SEQ ID NO 48
<211> LENGTH: 114
<212> TYPE: PRT
<213> ORGANISM: Artificial Sequence
<220> FEATURE:
<223> OTHER INFORMATION: AMMO4 light chain variable region without
      mutations

<400> SEQUENCE: 48

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

```
Pro Arg Leu Ile Tyr Lys Val Ser Asn Arg Asp Ser Gly Val Pro
    50              55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Gly
                85                  90                  95

Thr His Trp Pro Pro Met Tyr Thr Phe Gly Gln Gly Thr Lys Leu Glu
            100                 105                 110

Ile Lys

<210> SEQ ID NO 49
<211> LENGTH: 121
<212> TYPE: PRT
<213> ORGANISM: Artificial Sequence
<220> FEATURE:
<223> OTHER INFORMATION: AMMO5 heavy chain variable region without
      mutations

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Gly Asp Tyr Leu Gly Trp Phe Asp Pro Trp Gly
            100                 105                 110

Gln Gly Thr Leu Val Thr Val Ser Ser
        115                 120

<210> SEQ ID NO 50
<211> LENGTH: 109
<212> TYPE: PRT
<213> ORGANISM: Artificial Sequence
<220> FEATURE:
<223> OTHER INFORMATION: AMMO5 light chain variable region

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Arg Thr Phe Gly Gln Gly Thr Lys Val Glu Ile Lys
            100                 105
```

<210> SEQ ID NO 51
<211> LENGTH: 706
<212> TYPE: PRT
<213> ORGANISM: Epstein Barr virus

<400> SEQUENCE: 51

Met Gln Leu Leu Cys Val Phe Cys Leu Val Leu Trp Glu Val Gly
1               5                   10                  15

Ala Ala Ser Leu Ser Glu Val Lys Leu His Leu Asp Ile Glu Gly His
            20                  25                  30

Ala Ser His Tyr Thr Ile Pro Trp Thr Glu Leu Met Ala Lys Val Pro
        35                  40                  45

Gly Leu Ser Pro Glu Ala Leu Trp Arg Glu Ala Asn Val Thr Glu Asp
    50                  55                  60

Leu Ala Ser Met Leu Asn Arg Tyr Lys Leu Ile Tyr Lys Thr Ser Gly
65                  70                  75                  80

Thr Leu Gly Ile Ala Leu Ala Glu Pro Val Asp Ile Pro Ala Val Ser
                85                  90                  95

Glu Gly Ser Met Gln Val Asp Ala Ser Lys Val His Pro Gly Val Ile
            100                 105                 110

Ser Gly Leu Asn Ser Pro Ala Cys Met Leu Ser Ala Pro Leu Glu Lys
        115                 120                 125

Gln Leu Phe Tyr Tyr Ile Gly Thr Met Leu Pro Asn Thr Arg Pro His
    130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
            180                 185                 190

Val Leu Ser Leu Val Phe Gly Lys Thr Lys Asp Leu Pro Asp Leu Arg
        195                 200                 205

Gly Pro Phe Ser Tyr Pro Ser Leu Thr Ser Ala Gln Ser Gly Asp Tyr
    210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
            260                 265                 270

Glu Met Lys Gly Gly Cys Arg Glu Pro Glu Leu Asp Thr Glu Thr Leu
        275                 280                 285

Thr Thr Met Phe Glu Val Ser Val Ala Phe Phe Lys Val Gly His Ala
    290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
            340                 345                 350

Ala Met Leu Met Ala Thr Val Lys Met Glu Glu Leu Gly His Leu Thr
        355                 360                 365

Thr Glu Lys Gln Glu Tyr Ala Leu Arg Leu Ala Thr Val Gly Tyr Pro
    370                 375                 380

```
Lys Ala Gly Val Tyr Ser Gly Leu Ile Gly Ala Thr Ser Val Leu
385                 390                 395                 400

Leu Ser Ala Tyr Asn Arg His Pro Leu Phe Gln Pro Leu His Thr Val
        405                 410                 415

Met Arg Glu Thr Leu Phe Ile Gly Ser His Val Val Leu Arg Glu Leu
        420                 425                 430

Arg Leu Asn Val Thr Thr Gln Gly Pro Asn Leu Ala Leu Tyr Gln Leu
        435                 440                 445

Leu Ser Thr Ala Leu Cys Ser Ala Leu Glu Ile Gly Glu Val Leu Arg
    450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495

Gln Glu Ala Thr Leu Asp Gln Ala Ala Val Ser Asn Ala Val Asp Gly
                500                 505                 510

Phe Leu Gly Arg Leu Ser Leu Glu Arg Glu Asp Arg Asp Ala Trp His
                515                 520                 525

Leu Pro Ala Tyr Lys Cys Val Asp Arg Leu Asp Lys Val Leu Met Ile
    530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
                580                 585                 590

Ala Gly Glu Pro Arg Gln Ile Pro Lys Ile Gln Asn Phe Thr Arg Thr
                595                 600                 605

Gln Lys Ser Cys Ile Phe Cys Gly Phe Ala Leu Leu Ser Tyr Asp Glu
    610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
                660                 665                 670

Leu Tyr Glu Glu Arg Ala His Val Val Leu Ala Ile Ile Leu Tyr Phe
                675                 680                 685

Ile Ala Phe Ala Leu Gly Ile Phe Leu Val His Lys Ile Val Met Phe
    690                 695                 700

Phe Leu
705

<210> SEQ ID NO 52
<211> LENGTH: 137
<212> TYPE: PRT
<213> ORGANISM: Epstein Barr virus

<400> SEQUENCE: 52

Met Arg Ala Val Gly Val Phe Leu Ala Ile Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45
```

```
Tyr Leu Val Ser Asn Gln Thr Cys Asp Gly Phe Ser Leu Ala Ser Leu
         50                  55                  60

Asn Ser Pro Lys Asn Gly Ser Asn Gln Leu Val Ile Ser Arg Cys Ala
 65                  70                  75                  80

Asn Gly Leu Asn Val Val Ser Phe Phe Ile Ser Ile Leu Lys Arg Ser
                 85                  90                  95

Ser Ser Ala Leu Thr Gly His Leu Arg Glu Leu Leu Thr Thr Leu Glu
                100                 105                 110

Thr Leu Tyr Gly Ser Phe Ser Val Glu Asp Leu Phe Gly Ala Asn Leu
                115                 120                 125

Asn Arg Tyr Ala Trp His Arg Gly Gly
            130                 135

<210> SEQ ID NO 53
<211> LENGTH: 906
<212> TYPE: PRT
<213> ORGANISM: Epstein Barr virus

<400> SEQUENCE: 53

Met Glu Ser Arg Ile Trp Cys Leu Val Val Cys Val Asn Leu Cys Ile
 1               5                  10                  15

Val Cys Leu Gly Ala Ala Val Ser Ser Ser Thr Ser His Ala Thr
                 20                  25                  30

Ser Ser Thr His Asn Gly Ser His Thr Ser Arg Thr Thr Ser Ala Gln
                 35                  40                  45

Thr Arg Ser Val Tyr Ser Gln His Val Thr Ser Ser Glu Ala Val Ser
         50                  55                  60

His Arg Ala Asn Glu Thr Ile Tyr Asn Thr Thr Leu Lys Tyr Gly Asp
 65                  70                  75                  80

Val Val Gly Val Asn Thr Thr Lys Tyr Pro Tyr Arg Val Cys Ser Met
                 85                  90                  95

Ala Gln Gly Thr Asp Leu Ile Arg Phe Glu Arg Asn Ile Ile Cys Thr
                100                 105                 110

Ser Met Lys Pro Ile Asn Glu Asp Leu Asp Glu Gly Ile Met Val Val
                115                 120                 125

Tyr Lys Arg Asn Ile Val Ala His Thr Phe Lys Val Arg Val Tyr Gln
                130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
                180                 185                 190

Ile Gly Gly Thr Val Phe Val Ala Tyr His Arg Asp Ser Tyr Glu Asn
                195                 200                 205

Lys Thr Met Gln Leu Ile Pro Asp Asp Tyr Ser Asn Thr His Ser Thr
                210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
                260                 265                 270

Val Val Tyr Ile Ser Pro Phe Tyr Asn Gly Thr Asn Arg Asn Ala Ser
                275                 280                 285
```

```
Tyr Phe Gly Glu Asn Ala Asp Lys Phe Phe Ile Phe Pro Asn Tyr Thr
    290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
                340                 345                 350

Glu Arg Thr Ile Arg Ser Glu Ala Asp Ser Tyr His Phe Ser Ser
            355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
                420                 425                 430

Gly Ile Lys Gln Lys Ser Leu Val Glu Leu Glu Arg Leu Ala Asn Arg
            435                 440                 445

Ser Ser Leu Asn Ile Thr His Arg Thr Arg Arg Ser Thr Ser Asp Asn
450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
            515                 520                 525

Ser Ala Ile Tyr Asn Lys Pro Ile Ala Ala Arg Phe Met Gly Asp Val
530                 535                 540

Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
                580                 585                 590

Gln Leu Gly Glu Asp Asn Glu Ile Leu Leu Gly Asn His Arg Thr Glu
            595                 600                 605

Glu Cys Gln Leu Pro Ser Leu Lys Ile Phe Ile Ala Gly Asn Ser Ala
    610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
                660                 665                 670

Ser Ser Asn Val Phe Asp Leu Glu Glu Ile Met Arg Glu Phe Asn Ser
            675                 680                 685

Tyr Lys Gln Arg Val Lys Tyr Val Glu Asp Lys Val Val Asp Pro Leu
    690                 695                 700
```

```
Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
            725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
            755                 760                 765

Leu Ile Tyr Thr Arg Gln Arg Arg Leu Cys Thr Gln Pro Leu Gln Asn
            770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
            805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
            835                 840                 845

Leu Ala Leu Ala Arg Leu Asp Ala Glu Gln Arg Ala Gln Gln Asn Gly
            850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                    885                 890                 895

Leu Lys Asp Ser Asp Glu Glu Asn Val
            900                 905

<210> SEQ ID NO 54
<211> LENGTH: 223
<212> TYPE: PRT
<213> ORGANISM: Epstein Barr virus

<400> SEQUENCE: 54

Met Val Ser Phe Lys Gln Val Arg Val Pro Leu Phe Thr Ala Ile Ala
1               5                   10                  15

Leu Val Ile Val Leu Leu Ala Tyr Phe Leu Pro Pro Arg Val Arg
            20                  25                  30

Gly Gly Gly Arg Val Ala Ala Ala Ile Thr Trp Val Pro Lys Pro
            35                  40                  45

Asn Val Glu Val Trp Pro Val Asp Pro Pro Pro Val Asn Phe Asn
    50                  55                  60

Lys Thr Ala Glu Gln Glu Tyr Gly Asp Lys Glu Val Lys Leu Pro His
65                  70                  75                  80

Trp Thr Pro Thr Leu His Thr Phe Gln Val Pro Gln Asn Tyr Thr Lys
                85                  90                  95

Ala Asn Cys Thr Tyr Cys Asn Thr Arg Glu Tyr Thr Phe Ser Tyr Lys
            100                 105                 110

Gly Cys Cys Phe Tyr Phe Thr Lys Lys His Thr Trp Asn Gly Cys
            115                 120                 125

Phe Gln Ala Cys Ala Glu Leu Tyr Pro Cys Thr Tyr Phe Tyr Gly Pro
130                 135                 140

Thr Pro Asp Ile Leu Pro Val Val Thr Arg Asn Leu Asn Ala Ile Glu
145                 150                 155                 160

Ser Leu Trp Val Gly Val Tyr Arg Val Gly Glu Gly Asn Trp Thr Ser
                165                 170                 175
```

Leu Asp Gly Gly Thr Phe Lys Val Tyr Gln Ile Phe Gly Ser His Cys
            180                 185                 190

Thr Tyr Val Ser Lys Phe Ser Thr Val Pro Val Ser His His Glu Cys
        195                 200                 205

Ser Phe Leu Lys Pro Cys Leu Cys Val Ser Gln Arg Ser Asn Ser
    210                 215                 220

<210> SEQ ID NO 55
<211> LENGTH: 68
<212> TYPE: PRT
<213> ORGANISM: Artificial Sequence
<220> FEATURE:
<223> OTHER INFORMATION: C4b multimerization domain

<400> SEQUENCE: 55

Ser Gly Arg Ala His Ala Gly Trp Glu Thr Pro Glu Gly Cys Glu Gln
1               5                   10                  15

Val Leu Thr Gly Lys Arg Leu Met Gln Cys Leu Pro Asn Pro Glu Asp
            20                  25                  30

Val Lys Met Ala Leu Glu Val Tyr Lys Leu Ser Leu Glu Ile Glu Gln
        35                  40                  45

Leu Glu Leu Gln Arg Asp Ser Ala Arg Gln Ser Thr Leu Asp Lys Glu
    50                  55                  60

Leu Val Pro Arg
65

<210> SEQ ID NO 56
<211> LENGTH: 55
<212> TYPE: PRT
<213> ORGANISM: Artificial Sequence
<220> FEATURE:
<223> OTHER INFORMATION: C4b multimerization domain

<400> SEQUENCE: 56

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Leu Gln Gly Leu Ser Lys Glu
    50                  55

<210> SEQ ID NO 57
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 57

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Ser Ala
        35                  40                  45

Arg Gln Ser Thr Leu Asp Lys Glu Leu
    50                  55

```
<210> SEQ ID NO 58
<211> LENGTH: 58
<212> TYPE: PRT
<213> ORGANISM: Artificial Sequence
<220> FEATURE:
<223> OTHER INFORMATION: C4b multimerization domain

<400> SEQUENCE: 58

Trp Glu Thr Pro Glu Gly Cys Glu Gln Val Leu Thr Gly Lys Arg Leu
1               5                   10                  15

Met Gln Cys Leu Pro Asn Pro Glu Asp Val Lys Met Ala Leu Glu Val
            20                  25                  30

Tyr Lys Leu Ser Leu Glu Ile Glu Gln Leu Glu Leu Gln Arg Asp Ser
        35                  40                  45

Ala Arg Gln Ser Thr Leu Asp Lys Glu Leu
    50                  55

<210> SEQ ID NO 59
<211> LENGTH: 52
<212> TYPE: PRT
<213> ORGANISM: Artificial Sequence
<220> FEATURE:
<223> OTHER INFORMATION: C4b multimerization domains

<400> SEQUENCE: 59

Cys Glu Gln Val Leu Thr Gly Lys Arg Leu Met Gln Cys Leu Pro Asn
1               5                   10                  15

Pro Glu Asp Val Lys Met Ala Leu Glu Val Tyr Lys Leu Ser Leu Glu
            20                  25                  30

Ile Glu Gln Leu Glu Leu Gln Arg Asp Ser Ala Arg Gln Ser Thr Leu
        35                  40                  45

Asp Lys Glu Leu
    50

<210> SEQ ID NO 60
<211> LENGTH: 15
<212> TYPE: PRT
<213> ORGANISM: Artificial Sequence
<220> FEATURE:
<223> OTHER INFORMATION: Avitag amino acid sequence

<400> SEQUENCE: 60

Gly Leu Asn Asp Ile Phe Glu Ala Gln Lys Ile Glu Trp His Glu
1               5                   10                  15

<210> SEQ ID NO 61
<211> LENGTH: 6
<212> TYPE: PRT
<213> ORGANISM: Artificial Sequence
<220> FEATURE:
<223> OTHER INFORMATION: 6xhistidine tag

<400> SEQUENCE: 61

His His His His His His
1               5

<210> SEQ ID NO 62
<211> LENGTH: 25
<212> TYPE: PRT
<213> ORGANISM: Artificial Sequence
<220> FEATURE:
<223> OTHER INFORMATION: TPA leader peptide
```

```
<400> SEQUENCE: 62

Met Asp Ala Met Lys Arg Gly Leu Cys Cys Val Leu Leu Cys Gly
1               5                   10                  15

Ala Val Phe Val Ser Pro Ser Ala Ser
            20                  25

<210> SEQ ID NO 63
<211> LENGTH: 26
<212> TYPE: PRT
<213> ORGANISM: Artificial Sequence
<220> FEATURE:
<223> OTHER INFORMATION: HIS-Avi Tag

<400> SEQUENCE: 63

Gly Ser Gly Ser Gly His His His His His Gly Leu Asn Asp Ile
1               5                   10                  15

Phe Glu Ala Gln Lys Ile Glu Trp His Glu
            20                  25

<210> SEQ ID NO 64
<211> LENGTH: 19
<212> TYPE: PRT
<213> ORGANISM: Artificial Sequence
<220> FEATURE:
<223> OTHER INFORMATION: murine leader sequence

<400> SEQUENCE: 64

Met Gly Trp Ser Cys Ile Ile Leu Phe Leu Val Ala Thr Ala Thr Gly
1               5                   10                  15

Val His Ser

<210> SEQ ID NO 65
<211> LENGTH: 110
<212> TYPE: PRT
<213> ORGANISM: Artificial Sequence
<220> FEATURE:
<223> OTHER INFORMATION: glAMMO1_LC

<400> SEQUENCE: 65

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Leu Tyr Val Phe Gly Thr Gly Thr Lys Val Thr Val Leu
            100                 105                 110

<210> SEQ ID NO 66
<211> LENGTH: 123
<212> TYPE: PRT
<213> ORGANISM: Artificial Sequence
<220> FEATURE:
<223> OTHER INFORMATION: glAMMO1_HC
```

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Leu Glu Met Gly Tyr Arg Ser Gly Phe Pro Phe Asp Tyr
            100                 105                 110

Trp Gly Gln Gly Thr Leu Val Thr Val Ser Ser
        115                 120

<210> SEQ ID NO 67
<211> LENGTH: 107
<212> TYPE: PRT
<213> ORGANISM: Artificial Sequence
<220> FEATURE:
<223> OTHER INFORMATION: g1AMMO2_LC

<400> SEQUENCE: 67

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 68
<211> LENGTH: 130
<212> TYPE: PRT
<213> ORGANISM: Artificial Sequence
<220> FEATURE:
<223> OTHER INFORMATION: g1AMMO2_HC

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Val Leu Gly Ala His Gly Gly Asn Pro Leu Asn Gly
            100                 105                 110

His Tyr Tyr Gly Met Asp Val Trp Gly Gln Gly Thr Thr Val Thr Val
        115                 120                 125

Ser Ser
    130

<210> SEQ ID NO 69
<211> LENGTH: 106
<212> TYPE: PRT
<213> ORGANISM: Artificial Sequence
<220> FEATURE:
<223> OTHER INFORMATION: g1AMMO3_LC

<400> SEQUENCE: 69

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 70
<211> LENGTH: 123
<212> TYPE: PRT
<213> ORGANISM: Artificial Sequence
<220> FEATURE:
<223> OTHER INFORMATION: g1AMMO3_HC

<400> SEQUENCE: 70

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Gly Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Asp Lys Leu Tyr Ser Gly Tyr Val Lys Phe Asp Tyr
            100                 105                 110

Trp Gly Gln Gly Thr Leu Val Thr Val Ser Ser
        115                 120

<210> SEQ ID NO 71
<211> LENGTH: 114
<212> TYPE: PRT
<213> ORGANISM: Artificial Sequence
<220> FEATURE:
<223> OTHER INFORMATION: gl_AMMO4_LC

<400> SEQUENCE: 71

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Met Tyr Thr Phe Gly Gln Gly Thr Lys Leu Glu
            100                 105                 110

Ile Lys

<210> SEQ ID NO 72
<211> LENGTH: 126
<212> TYPE: PRT
<213> ORGANISM: Artificial Sequence
<220> FEATURE:
<223> OTHER INFORMATION: gl_AMMO4_HC

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Val Pro Gly Gln Cys Thr Arg Thr Ser Cys Tyr Asn Phe
            100                 105                 110

Ser Ser Gln Trp Gly Gln Gly Thr Leu Val Thr Val Ser Ser
        115                 120                 125

<210> SEQ ID NO 73
<211> LENGTH: 109
<212> TYPE: PRT
<213> ORGANISM: Artificial Sequence
<220> FEATURE:
<223> OTHER INFORMATION: gl_AMMO5_LC

```
<400> SEQUENCE: 73

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Arg Thr Phe Gly Gln Gly Thr Lys Val Glu Ile Lys
                100                 105

<210> SEQ ID NO 74
<211> LENGTH: 121
<212> TYPE: PRT
<213> ORGANISM: Artificial Sequence
<220> FEATURE:
<223> OTHER INFORMATION: g1AMMO5HC

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Gly Asp Tyr Leu Gly Trp Phe Asp Pro Trp Gly
                100                 105                 110

Gln Gly Thr Leu Val Thr Val Ser Ser
            115                 120
```

EPSTEIN BARR VIRUS ANTIBODIES, VACCINES, AND USES OF THE SAME

CROSS REFERENCE TO RELATED APPLICATIONS

This application is a U.S. National Phase Application of International Patent Application No. PCT/US2018/032127, filed May 10, 2018, which claims priority to U.S. Provisional Patent Application No. 62/504,447 filed May 10, 2017 and to U.S. Provisional Patent Application No. 62/560,061 filed Sep. 18, 2017, the entire contents of each of which are incorporated by reference herein in their entirety.

REFERENCE TO SEQUENCE LISTING

The Sequence Listing associated with this application is provided in text format in lieu of a paper copy and is hereby incorporated by reference into the specification. The name of the text file containing the Sequence Listing is 2730328 ST25.txt. The text file is 60.4 KB, was created on Nov. 7, 2019, and is being submitted electronically via EFS-Web.

FIELD OF THE DISCLOSURE

Anti-Epstein Barr Virus (EBV) antibodies, vaccines, and uses of the same are described. The antibodies and vaccines can be used to treat and/or reduce the risk of EBV infection and also to treat and/or reduce the risk of complications associated with EBV infection, such as infectious mononucleosis, lymphoproliferative disorders, carcinomas, and smooth muscle tumors. Cells can be genetically engineered to express the antibodies, vaccines, or fragments thereof, for example, in vivo.

BACKGROUND OF THE DISCLOSURE

Epstein Barr virus (EBV) is an orally transmitted gamma herpesvirus that infects B cells and epithelial cells in the majority of adults worldwide. Most primary infections are asymptomatic, however, EBV is a causative agent of infectious mononucleosis (IM) in children and young adults. Following primary infection, infected individuals become lifelong carriers of EBV, which can lie dormant (i.e., latent) in cells. However, in certain individuals the latent virus can begin to express genes that alter cellular replication, leading to cancer or cancer-like diseases. EBV is also associated with nasopharyngeal carcinoma and lymphoproliferative disorders in immunocompromised patients such as those with HIV/AIDS or in patients undergoing immune suppression for organ transplantation. Thus, antibodies or vaccines that treat, reduce, or prevent EBV infection of cells or treat EBV-associated diseases would be a major benefit to public health.

A primary goal of most vaccine design strategies is to elicit production of neutralizing antibodies, which are a type of antibody that can inhibit the biological function of its target. Neutralizing antibodies are also useful as protein therapeutics to treat viral infection. Neutralizing antibodies against viruses such as EBV typically function by blocking a virus from entering a cell.

To enter a cell, EBV, like other herpesviruses, first attaches to the cell surface through an interaction between a protein on the surface of the virus and a receptor binding site of a cell surface protein. Following this attachment, the virus membrane can fuse with the cell membrane, allowing the contents of the virus to be inserted into the cell. Viral fusion also occurs through interaction of a viral protein with an epitope on an antigen of a cell protein. The interactions resulting in viral attachment to a cell and the interactions resulting in viral fusion to a cell are distinct, each involving different viral proteins and different cellular proteins. Thus, neutralizing antibodies could block EBV entry into cells by preventing virus/cell protein interactions leading to attachment and/or fusion.

Previous efforts to design EBV vaccines have included vaccines that target the EBV protein gp350, which is involved in EBV attachment to cells. However, while a phase 2 trial showed that the vaccine could reduce the incidence of IM, it did not protect from EBV infection. Furthermore, EBV vaccine research to-date has not led to the development of an effective human neutralizing antibody against EBV.

SUMMARY OF THE DISCLOSURE

The current disclosure provides anti-Epstein Barr virus (EBV) antibodies, EBV vaccines, and uses of the same. In particular embodiments, the anti-EBV antibodies are effective human neutralizing antibodies. In particular embodiments the anti-EBV antibodies neutralize EBV infection of B cells and epithelial cells. In particular embodiments, the disclosed anti-EBV antibodies are referred to herein as AMMO1, AMMO2, AMMO3, AMMO4 and AMMO5.

In particular embodiments the anti-EBV antibodies bind the EBV core fusion machinery: heterodimer envelope glycoprotein H/envelope glycoprotein L (gH/gL) and/or glycoprotein B (gB). In particular embodiments, the anti-EBV antibodies bind across the D-I/D-II groove of the gH/gL heterodimer complex. In particular embodiments, the anti-EBV antibodies bind at least one of residues 60, 70-81, 211-216, and 234-239 of gH; and/or at least one of residues 123-128 of gL. In particular embodiments, the anti-EBV antibodies bind residues 60, 70-81, 211-216, and 234-239 of gH; and residues 123-128 of gL. In particular embodiments, the anti-EBV antibodies bind residues 73 and 76 of gH wherein residue 73 is lysine and residue 76 is tyrosine. These epitopes bound by the antibodies of the disclosure can be used as vaccine antigen epitopes to produce EBV vaccines.

In particular embodiments the anti-EBV antibodies include a human antibody, or an antigen-binding portion thereof (including scFv) that dissociates from EBV gH/gL with a $K_D$ of $1\times1^{-10}$ or less and a $k_{off}$ rate constant of $3\times 10^{-5\ s-1}$ or less, both determined by surface plasmon resonance or biolayer interferometry. In particular embodiments, the anti-EBV antibodies neutralize EBV infection of B cells and/or epithelial cells with an $IC_{50}$ of $3\times10^{-9}M$ or less.

In particular embodiments, the anti-EBV antibodies include SEQ ID NO: 41 and SEQ ID NO: 42 with mutations selected from one or more heavy chain mutations selected from D10E; G76S; S83R; T84S; F91Y; V107T; and P113S and/or one or more light chain mutations selected from E3V; Q17K; R18T; T20R; Q49Y; S69N; and G100T.

In particular embodiments, the anti-EBV antibodies include SEQ ID NO: 41 and SEQ ID NO: 42 with heavy chain mutations D10E; G76S; S83R; T84S; F91Y; V107T; and P113S and light chain mutations E3V; Q17K; R18T; T20R; Q49Y; S69N; and G100T.

In particular embodiments, the anti-EBV antibodies include SEQ ID NO: 1 and SEQ ID NO: 2. In particular embodiments, SEQ ID NO: 1 includes mutation Q1N.

In particular embodiments, the anti-EBV antibodies include SEQ ID NO: 3 and SEQ ID NO: 4. In particular embodiments, SEQ ID NO: 3 includes mutation Q1N.

In particular embodiments, the anti-EBV antibodies include SEQ ID NO: 5 and SEQ ID NO: 6. In particular embodiments, SEQ ID NO: 5 includes mutation E1N. In particular embodiments, SEQ ID NO: 6 includes mutation Q1N. In particular embodiments, SEQ ID NO: 5 includes mutation E1N and SEQ ID NO: 6 includes mutation Q1N.

In particular embodiments, the anti-EBV antibodies include SEQ ID NO: 7 and SEQ ID NO: 8. In particular embodiments, SEQ ID NO: 7 includes mutation Q1N.

In particular embodiments, the anti-EBV antibodies include SEQ ID NO: 9 and SEQ ID NO: 10. In particular embodiments, SEQ ID NO: 9 includes mutation E1N. In particular embodiments, SEQ ID NO: 10 includes mutation E1N. In particular embodiments, SEQ ID NO: 9 includes mutation E1N and SEQ ID NO: 10 includes mutation E1N.

In particular embodiments, the anti-EBV antibodies include the complementary determining regions (CDRs): SEQ ID NO: 11, SEQ ID NO: 12, SEQ ID NO: 13, SEQ ID NO: 14, SEQ ID NO: 15, and SEQ ID NO: 16; SEQ ID NO: 17, SEQ ID NO: 18, SEQ ID NO: 19, SEQ ID NO: 20, SEQ ID NO: 21, and SEQ ID NO: 22; SEQ ID NO: 23, SEQ ID NO: 24, SEQ ID NO: 25, SEQ ID NO: 26, SEQ ID NO: 27, and SEQ ID NO: 28; SEQ ID NO: 29, SEQ ID NO: 30, SEQ ID NO: 31, SEQ ID NO: 32, SEQ ID NO: 33, and SEQ ID NO: 34; or SEQ ID NO: 35, SEQ ID NO: 36, SEQ ID NO: 37, SEQ ID NO: 38, SEQ ID NO: 39, and SEQ ID NO: 40.

In particular embodiments the EBV antibodies and/or vaccine antigen epitopes can be formulated to treat an EBV-infected subject or a subject at risk of EBV infection. In particular embodiments, cells, such as B cells, can be genetically modified to express one or more EBV antibodies and/or vaccine antigen epitopes described herein. Genetic modification can be in vivo or in vitro. Treating EBV can reduce EBV infection and/or treat a condition associated with EBV infection, such as infectious mononucleosis or lymphoproliferative disorder. Moreover, high levels of antibodies that neutralize EBV B-cell infection are associated with lowered risks for nasopharyngeal carcinoma.

BRIEF DESCRIPTION OF THE SEVERAL VIEWS OF THE DRAWINGS

FIG. 1. X-ray data collection and refinement statistics.

FIG. 2. CryoEM data collection and refinement statistics.

(FIG. 3A) Purified EBV ectodomain proteins were separated by reducing and non-reducing SDS-PAGE and stained with Coomassie Brilliant Blue as indicated. gH/gL formed a heterodimer. Under non-reducing conditions, gB ran as a single band of 120 kDa. Under reducing conditions, the majority of gB runs as 2 bands corresponding to 80 and 40 kDa, consistent with efficient furin-mediated proteolytic cleavage and disulfide bond formation. (FIG. 3B) Anti-EBV antibodies were captured from hybridoma supernatants using anti-mouse Fc capture biosensors and binding to a 0.5 μM solution of purified EBV ectodomain proteins was evaluated as indicated. The antibody is indicated at the top of each panel and its antigenic target is included in parentheses. (FIG. 3C) $EC_{50}$ of serum binding responses to gp42, gH/gL, gp350 and gp42 from 16 donors were measured by ELISA. Symbols and error bars present the mean and standard deviation of two independent measurements performed in duplicate. Symbols on the dashed line represent a seropositive response that did not saturate at the highest concentration tested. Symbols on the abscissa represent undetectable serum responses at the highest concentration tested.

FIGS. 4A-4C. Isolation of anti-EBV antibodies from antigen specific B cells. (FIG. 4A) Class switched B cells (live, single, CD14−, CD16−, CD3−, CD19+, CD20+, IgM−, IgD−) were stained with streptavidin-PE, or streptavidin-PE conjugated to gH/gL, gB, gp350, or gp42 as indicated. (FIG. 4B) Peripheral blood mononuclear cells were stained with a decoy protein conjugated to streptavidin-PE-DL650 and streptavidin-PE alone, or streptavidin-PE conjugated to gH/gL or gB as indicated. A positive magnetic enrichment using anti-PE microbeads was performed and then cells were stained as in FIG. (4A). PE-DL650−/PE+ B cells (live, single, CD14−, CD16−, CD3−, CD19+, CD20+, IgM−, IgD−) are shown. Numbers indicate the % of PE+ class switched B cells in each panel in FIGS. 4A and 4B. (FIG. 4C) AMMO1, AMMO2, AMMO3, AMMO4, and AMMO5, antibodies cloned from B cells sorted using the approach in (FIG. 4B) were loaded onto anti-human Fc capture biosensors. Binding to 0.5 μM solutions of gB, gp42, gp350 and gH/gL was measured by BLI as indicated. PE: phycoerythrin SSA: side-scatter area in (FIG. 4A) and (FIG. 4B).

FIGS. 5A-5C. Example of gating strategy for sorting antigen positive B cells. (FIG. 5A) PBMC from an EBV-seropositive donor were stained with gH/gL conjugated to streptavidin-PE, viability dye, and antibodies specific for CD3, CD14, CD16, CD19, CD20, IgM, and IgD. (FIG. 5B) PBMC were stained with gH/gL-PE and a decoy protein conjugated to PE-DL650. PE+ and PE− DL650+ cells were enriched using magnetic beads conjugated to an anti-PE antibody. The cells were stained as in (FIG. 5A). Cells in the pink gate on the right-most panel were sorted using FACS. (FIG. 5C) The bottom right panel in (FIG. 5B) is shown in black. There are 45 cells PE+/PE-DL650 (black cells) in the gate, with cells excluded from previous gate (PE-DL650+) overlaid in gray (n=70). $4.2 \times 10^6$ events are shown in (5 FIG. A) and $3.2 \times 10^5$ events are shown in (FIG. 5B) and FIG. (5C).

FIG. 6. Summary of antigen-specific B cell sorting and VHNL recovery.

FIG. 7. Sequences of isolated anti-EBV MAbs. The amino acid sequence of the isolated antibodies is shown as an alignment to the closest chromosomally encoded V- D- and J-gene segments shown in underlining, bold italics, and bold underlining, respectively. "." indicates identity to chromosomally encoded amino acid. The complementary determining regions (Kabat definition) are highlighted in gray. The percentage of VH or VL mutation based on the nucleotide sequence is provided for each antibody chain, and the Genbank accession number is provided in brackets. The gene usage, and mutation percentages were determined using the IMGT/V-Quest tool (Brochet et al., 2008, Nucleic Acids Research doi: 10.1093/nar/gkn316. PubMed PMID: 18503082).

FIG. 9. Kinetic analysis of antibodies, or gp42 binding to gH/gL measured by BLI.

FIG. 10. E1D1 binding to gH/gL is pH-dependent. Biotinylated E1D1 was immobilized on streptavidin biosensors.

After obtaining a baseline reading in KB, the biosensors were immersed into 50 nM solutions of gH/gL in KB at the indicated pH for 250 s, and then immersed into kinetics buffer at the indicated pH for 750 s.

Figure 11:
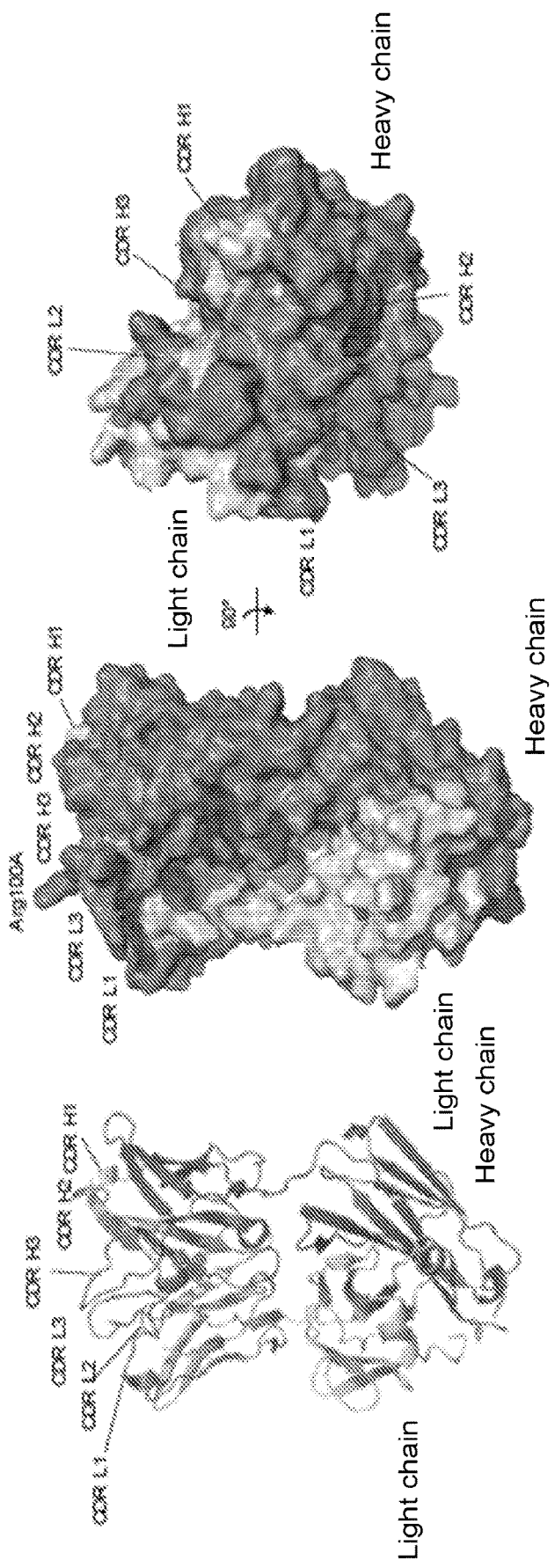

FIG. 11. Crystal structure of the free AMMO1 Fab. (Left) AMMO1 Fab shown as ribbon representation with light chain shown in light and heavy chain in dark. CDRs are marked. (Middle) Surface representation of AMMO1 Fab with Arg100A of heavy chain protruding towards the solvent. No clear electron density was observed for Arg100A and the most favorable rotamer was chosen. However, Arg100A appears to interact with DII of gH in the cryo-EM model. (Right) 900 rotation, view down the combining site with CDRs labeled.

Figure 12A:
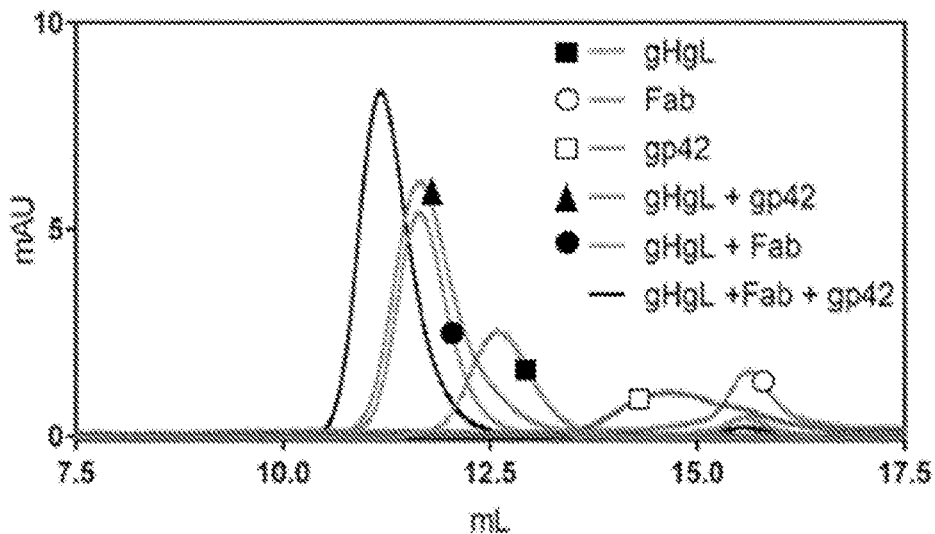
Figure 12B:
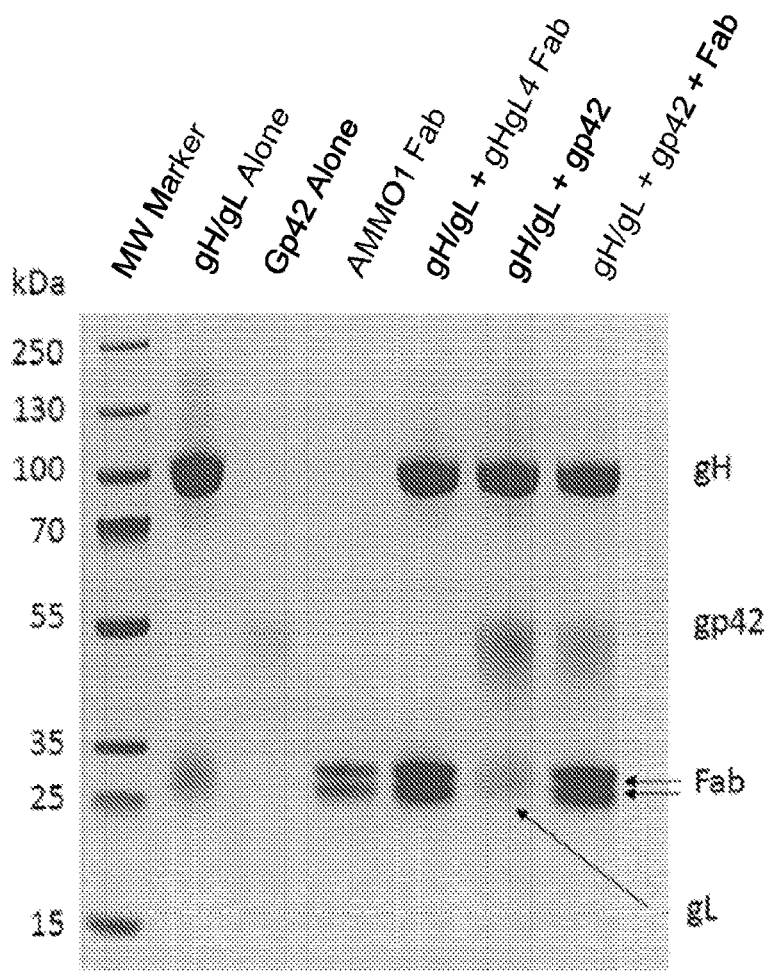

FIGS. 12A, 12B. AMMO1 forms a 1:1:1 complex with gH/gL and gp42. (12A) Equimolar amounts of gH/gL, gp42, and the AMMO1 FAb were passed over a 10/300 S200 superdex column alone, or pre-incubated together as indicated. The absorbance was measured at 280 nM and the peaks from each run were overlaid. (12B) Fractions corresponding to the peak in (12A) were collected, concentrated and separated by reducing SDS-PAGE, and stained with Coomassie Brilliant Blue.

FIGS. 13A-13G. (FIG. 13A) CryoEM reconstruction of gH/gL-gp42-AMMO1 complex at 4.8 Å resolution. (FIG. 13B) 90° rotation from (FIG. 13A): AMMO1 heavy chain is marked, AMMO1 light chain is marked, gL is marked, gH D-I is marked, gH D-II is marked, gH D-III is marked, gH D-IV is marked, and gp42 is marked. (FIGS. 13C, 13D) Ribbon diagram of the gH/gL/gp42-AMMO1 atomic model rendered with the same colors as panels FIG. 13A and FIG. 13B. (FIG. 13E) Zoomed-in view of the AMMO1 epitope with regions of interest labeled. (FIG. 13F) AMMO1 footprint on the gH/gL/gp42 complex. For clarity, only the AMMO1 CDR loops are shown interacting with gH/gL/gp42 rendered in surface representation. Residues that have been identified as being important for AMMO1 binding (K73 and Y76) are marked with an asterisk. (FIG. 13G) The gH N60 glycan is shown in stick representation in the corresponding region of cryoEM density to highlight the putative contacts made with AMMO1. The black dot shows the position of the gH KGD motif FIGS. 14A-14H. Overview of cryo electron microscopy and glycan analysis of gH/gL-gp42-AMMO1 complex (FIG. 14A) Representative micrograph of frozen-hydrated gH/gL-gp42-AMMO1 complex. Scale bar: 200 nm. (FIG. 14B) Selected 2D class averages. (FIG. 14C) Schematic workflow for 3D reconstruction of gH/gL-gp42-AMMO1 complex in RELION 2.0. (FIG. 14D) FSC curve for final reconstruction of gH/gL/gp42 complex. Resolution at FSC=0.143 is 4.8 Å. (FIG. 14E) Angular distribution of particle images in the final reconstruction. (FIG. 14F) ResMap-based estimate of local resolution (in A) of the final reconstruction. (FIG. 14G) FSC curve for final reconstruction of gH/gL/gp42 complex in which the gp42 C terminal domain is displaced. (FIG. 14H) Characterization of the gH/gL/gp42 glycans by mass spectrometry. The predominant type of identified N-linked glycan is represented at each site. Glycans are shown with parentheses to highlight their variability and the unresolved branching structure.

FIGS. 15A-15E. Binding of AMMO1 to cell-surface expressed gH/gL mutants. gH/gL with the indicated mutations were expressed on the surface of 293F cells and stained with the CL59 MAb followed by an anti-mouse PE secondary Ab and serially-diluted AMMO1 conjugated directly to DL650. Cells expressing gH/gL variants were identified by PE (CL59) staining. (FIG. 15A) Mean-fluorescence intensity (MFI) of PE positive cells expressing WT gH/gL or gH with mutated gL variants. The PE-MFI of mock transfected cells is shown as a control. (FIG. 15B) The DL650 MFI for each gH/gL variant was normalized to the PE-MFI of the gH/gLN127A mutant (shown in A) and plotted as a function of AMMO1 concentration. (FIG. 15C) The mean-fluorescence intensity (MFI) of PE positive cells expressing WT gH/gL or mutant gH variants paired with WT gL. The PE-MFI of mock transfected cells is shown as a control. (FIGS. 15D, 15E) The DL650 MFI for each gH/gL variant was normalized to the PE-MFI of the gHS79R/gL mutant (shown in FIG. 15C) and plotted as a function of AMMO1 concentration. gH/gL variants with mutations in the $2\alpha1$ and $2\alpha4$ helices of gH along with WT gH/gL are shown in 15D and 15E respectively.

Figure 16:
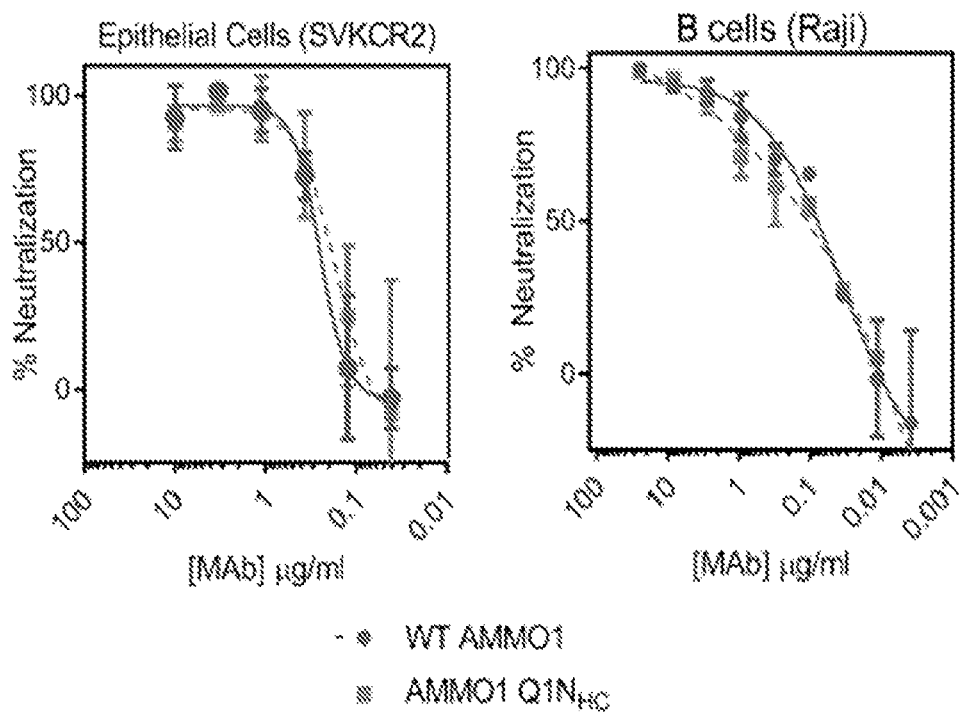

FIG. 16. A heavy chain Q1N mutation does not affect AMMO1 neutralization potency. Serial dilutions of wildtype AMMO1 (WT AMMO1) or AMMO1 containing a Q1N heavy chain mutation (AMMO1 Q1NHC) antibodies were evaluated for their ability to neutralize AKTA-GFP EBV infection of epithelial (SVKCR2) cells or B95.8/F EBV infection of B (Raji) cells as indicated.

Figure 17A:
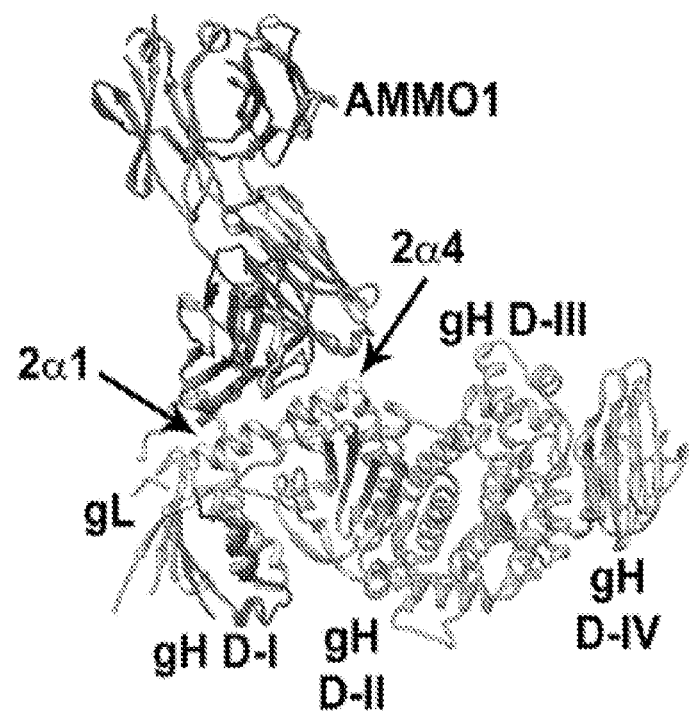
Figure 17B:
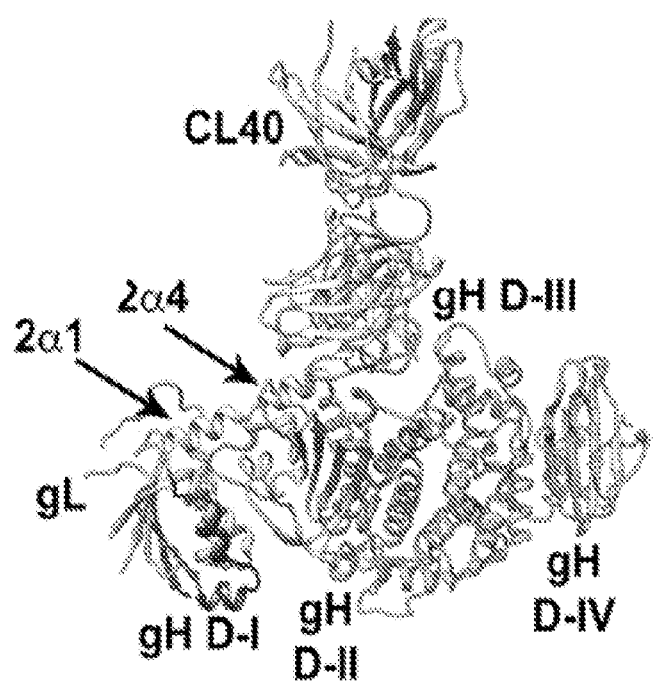
Figure 17C:
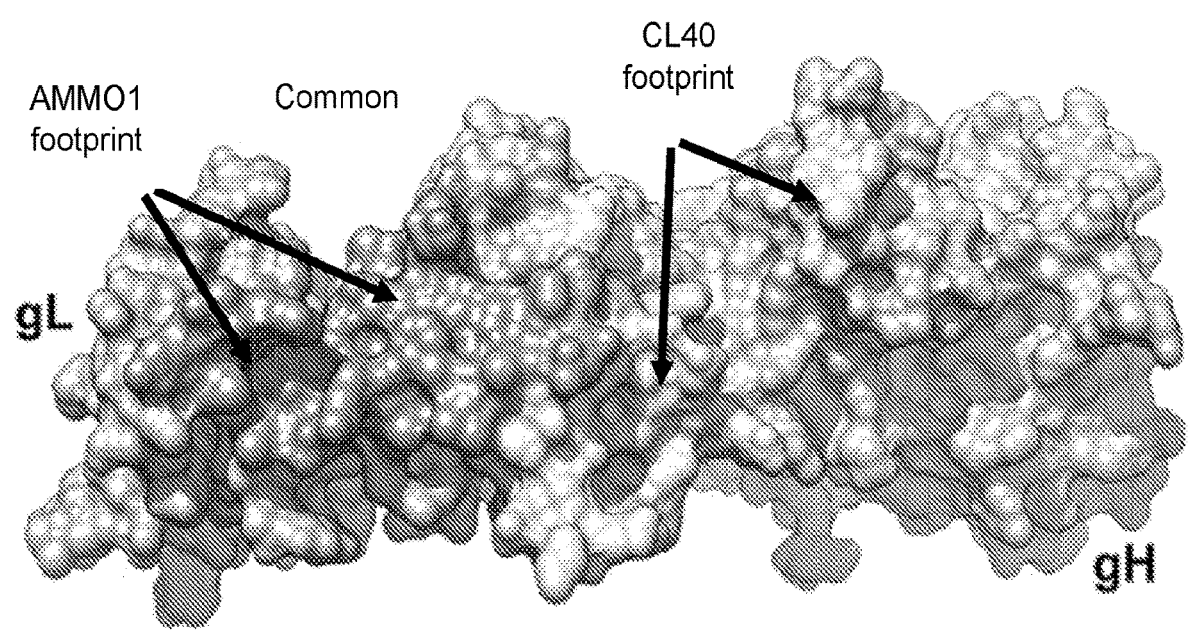
Figure 17D:
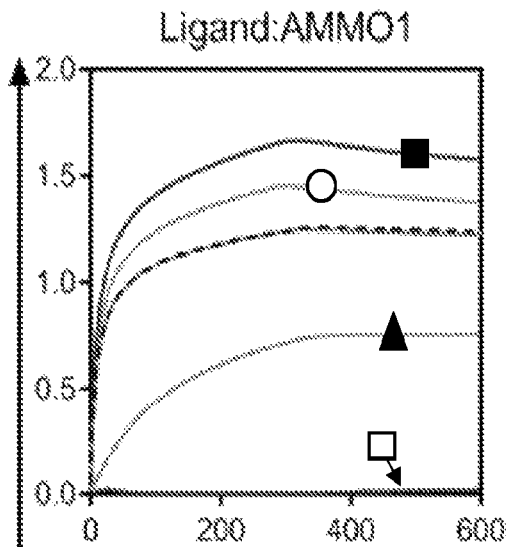

FIGS. 17A-17G. AMMO1 and CL40 share partially overlapping epitopes. Ribbon diagrams of the gH/gL/gp42-AMMO1 (FIG. 17A) and gH/gL/gp42-CL40 complexes (FIG. 17B, PDB 5WOK). AMMO1 heavy chain, AMMO1 light chain, CL40, gL, gH D-I, gH D-II, gH D-III and gH D-IV are indicated. gp42 is omitted from FIG. 17A and FIG. 17B for clarity. (FIG. 17C) gH/gL residues experiencing a change in accessible surface area upon antibody binding are indicated and colored medium grey (AMMO1) and dark grey (CL40). Areas that experience a change in accessible surface area upon binding of either AMMO1 or CL40 are shown in dark pink. Biotinylated AMMO1 (FIG. 17D), CL40 (FIG. 17E), CL59 (FIG. 17F), or E1D1 (FIG. 17G) were immobilized on a streptavidin biosensor and used to measure binding a 250 nM solution of gH/gL alone, or pre-complexed with 500 nM of non-biotinylated antibody by BLI as indicated. The unrelated anti-influenza hemagglutinin glFl6 MAb was used as a negative control.

FIGS. 18A-18F. An AMMO1-gp42 N173 glycan clash displaces the gp42 CTD. (FIG. 18A) gH/gL residues that experience a change in accessible surface area upon AMMO1 binding are colored medium grey (indicated by arrows), those that experience a change in accessible surface area upon gp42 binding are colored dark grey (indicated by arrows). Asn 240 (circled) experiences a change in accessible surface area upon binding to AMMO1 and to gp42. (FIG. 18B) Zoomed-in view of the region around gH Asn 240. Ribbons are rendered with the same shading as in FIGS. 13A-13G. (FIG. 18C) CryoEM reconstructions of the gH/gL/gp42-AMMO1 complex show that most particle images harbor the gp42 C-domain bound on top of gH D-III. (FIG. 18D) A small fraction of particle images are characterized by a displacement of the gp42 C-domain. The map is shown at high contour (isosurface) and at low contour (mesh) level to demonstrate that the gp42 CTD is much less well ordered than the rest of the complex. The orientation of the gp42-CTD is approximate due to the limited resolution of this reconstruction. (FIG. 18E) The 4.8 Å resolution reconstruction shown in (FIG. 18C) reveals that the gp42 N173 glycan points toward the AMMO1 framework region. The glycan is rendered in stick representation with the corresponding region of cryoEM density (bracket). (FIG. 18F) Biolayer interferometry traces showing that gp42 partially competes for gH/gL binding to immobilized AMMO1.

The competition is abrogated when the gp42 N173 glycan is removed by introduction of a T175A mutation disrupting the glycosylation sequon.

FIGS. 19A-19D. Selected 2D class averages of negatively stained gH/gL/gp42 (FIG. 19A) and gH/gL/gp42/AMMO1 (FIGS. 19B, 19C) and gH/gL/CL40 (FIG. 19D) along with the corresponding density assignments in cartoon form (right). The AMMO1 or CL40-mediated displacement of gp42 is emphasized with a dashed outline surrounding gp42. The box size of the 2D class averages is 29.4 nm.

FIGS. 20A-20F. AMMO1 interferes with cell fusion. (FIG. 20A) Biotinylated gH/gL/gp42, or gH/gL/gp42/AMMO1 complexes were assembled on immobilized on streptavidin biosensors and used to measure binding to a 500 nM solution of HLA-DR using BLI as indicated. (FIG. 20B) B cell surface staining with streptavidin-PE alone, or streptavidin-PE conjugated to biotinylated gH/gL, biotinylated gB, or biotinylated gH/gL bound to gp42+/− an excess of the indicated MAbs. * indicates that the mean fluorescence intensity (MFI) of PE of n=4 wells is significantly different (p<0.05) from the gH/gL/gp42 only control using a two-tailed, unpaired t-test. (FIG. 20C) Epithelial cell surface staining with streptavidin-PE alone, or streptavidin-PE conjugated to biotinylated gH/gL+/− an excess of the indicated MAbs. * indicates that the mean fluorescence intensity (MFI) of PE of n=4 wells is significantly different (p<0.05) from the gH/gL only control using a two-tailed, unpaired t-test. (FIG. 20D) Biotinylated gH/gL was immobilized on streptavidin biosensors, and then used to measure binding to a 1 µM solution of αvβ5, αvβ6, αvβ8, gp42, or an HIV-1 Envelope protein as indicated. (FIG. 20E) Biotinylated gH/gL or gH/gL/AMMO1 was immobilized on streptavidin biosensors, and used to measure binding to a 3.5 µM solution of EphA2 by BLI as indicated. (FIG. 20F) CHO-K1 cells were transfected with expression plasmids encoding gH, gL, gB and luciferase under the control of a T7 promoter, and then overlaid on HEK293 cells stably expressing T7 polymerase, +/−the indicated MAbs. As a control, CHO KI cells were transfected as above except the gL plasmid was omitted. * indicates that the mean RLU of n=5 wells are significantly different (p<0.05) from the No Ab control using a two-tailed, unpaired t-test.

Figure 21A:
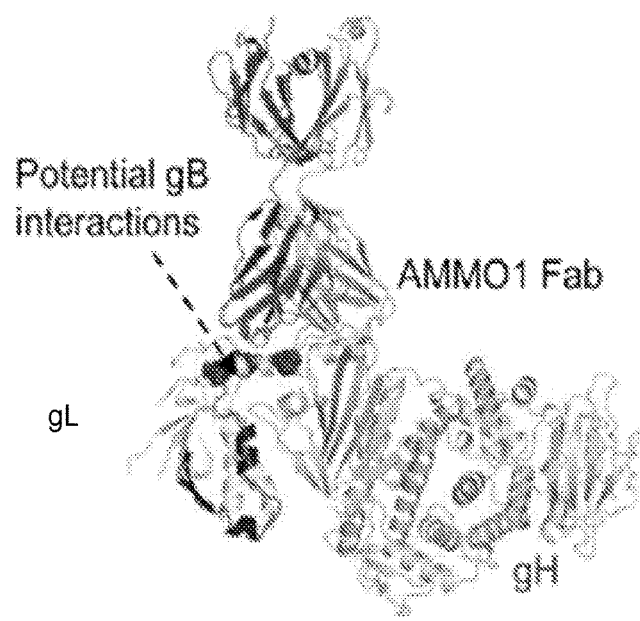
Figure 21B:
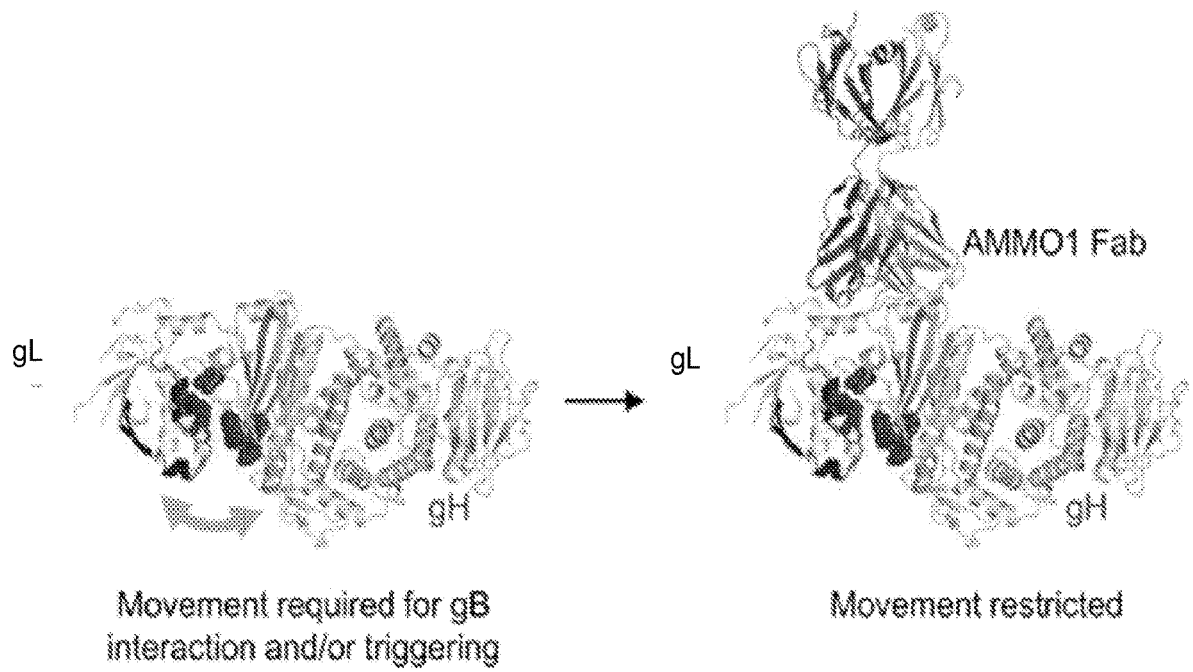
Figure 21C:
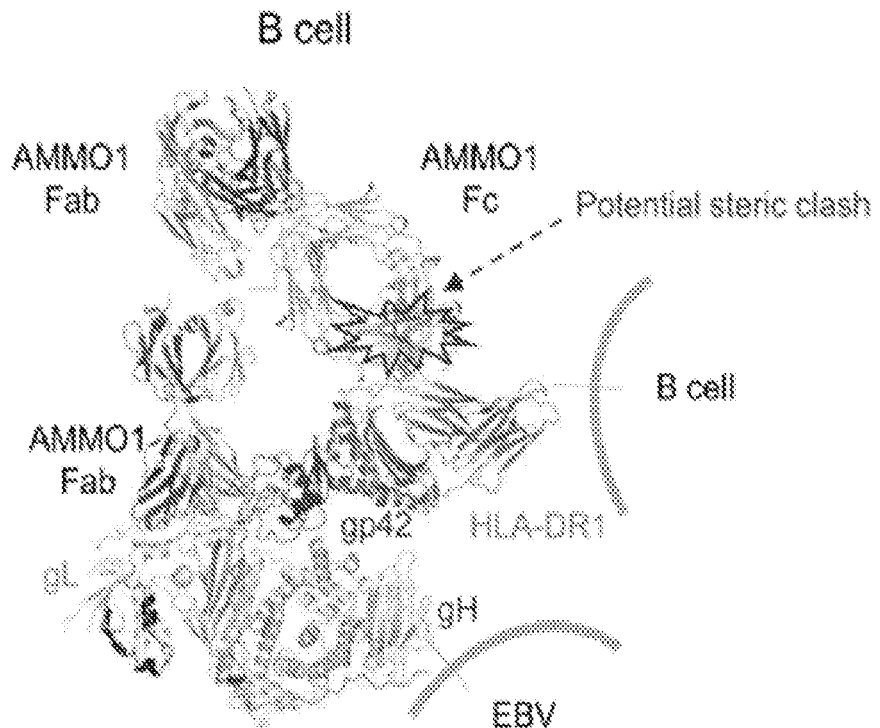
Figure 21D:
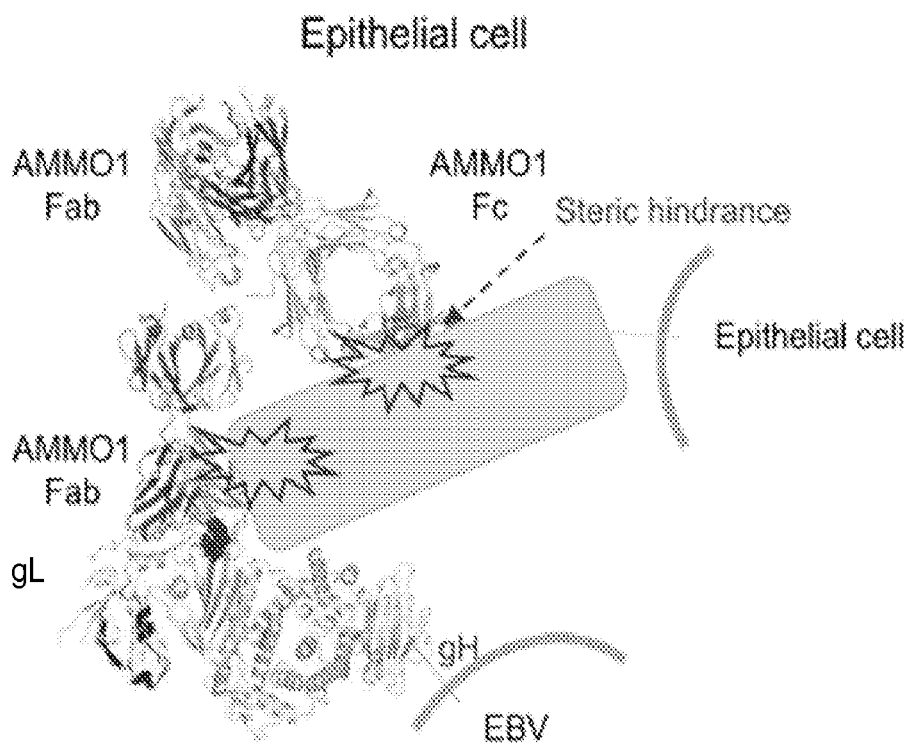

FIGS. 21A-21D. Possible mechanisms of AMMO1-mediated neutralization. (FIG. 21A) Direct inhibition of gB binding. AMMO1 heavy chain, AMMO1 light chain, gL, gH D-I, gH D-III, gH D-III, and gH D-IV are shown. Residues in the linker helix which have been previously shown to affect cell fusion (L65, L69 and L74) when mutated are shown in black. AMMO1 binding to gH/gL could prevent subsequent interaction with gB and fusion activation. (FIG. 21B) Molecular clamp preventing gB triggering. gH, gL and AMMO1 are colored as in (FIG. 21A). Residues within the D-I/D-II groove (L55, L207, R152, H154, T174, K94) that have been shown to affect membrane fusion when mutated are shown in black. By binding across D-I and D-III, AMMO1 could restrict movements across the D-I/D-II groove that are required for gB interaction and/or triggering. (FIG. 21C) Restriction of B cell receptor interactions. Although AMMO1 binds away from the HLA-II binding site on the gH/gL/gp42 complex, it could restrain access to membrane anchored receptors through the second FAb arm or the Fc region (modelled using PDB ID 1HZH) of the antibody. gH, gL and AMMO1 are as in (FIG. 21A) and gp42 is also indicated. HLA-DR1 is indicated and positioned to bind its predicted binding site of gp42 (PDB ID 1KG0). (FIG. 21D) Restriction of epithelial cell receptor interactions. AMMO1 could inhibit binding to one or more epithelial cell receptors by directly restricting access to the interacting site (e.g. reduction of KGD motif accessibility) or by indirect steric hindrance mediated through the second FAb arm or the Fc region of the antibody. The KGD motif which has been implicated in gH/gL binding to integrins is shown in red. The gray rectangle could represent αvβ5, αvβ6, αvβ8, integrins, EphA2 or another unidentified receptor.

Figure 22A:
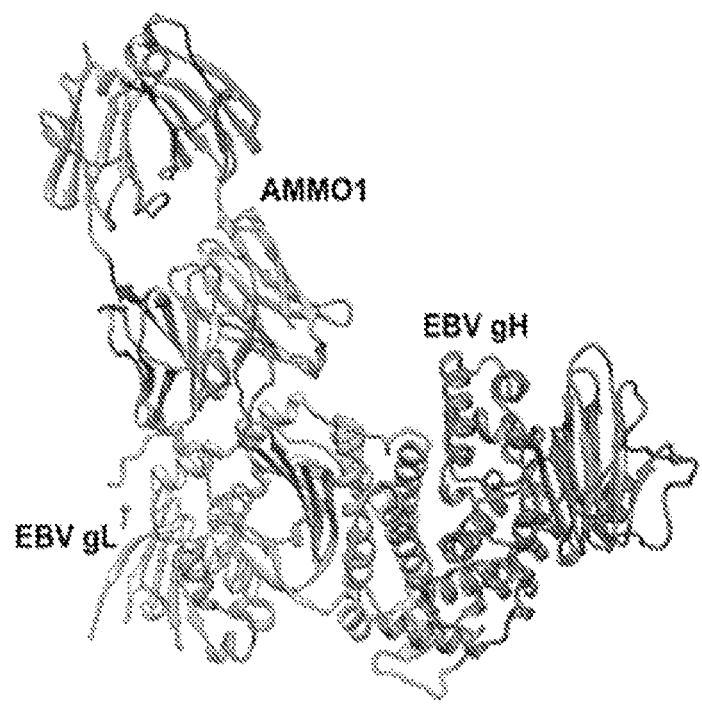
Figure 22B:
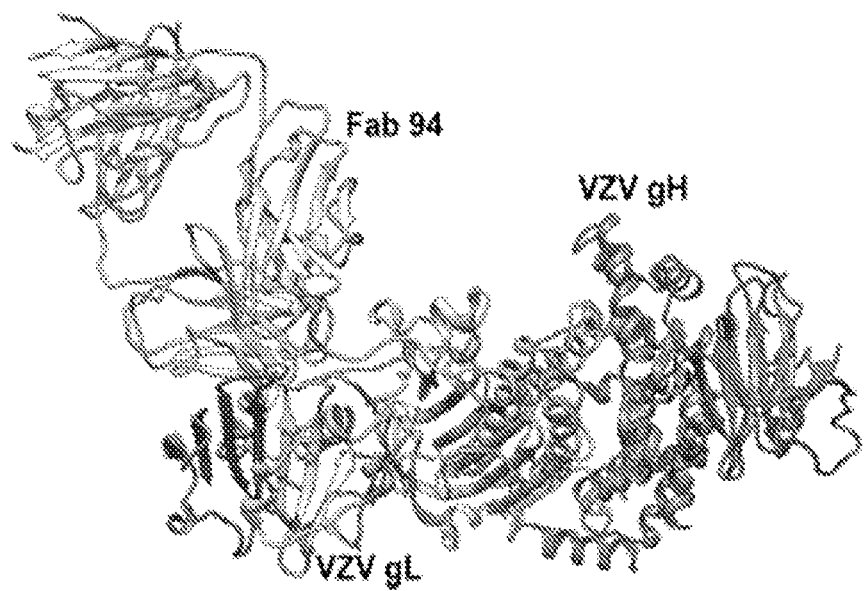

FIGS. 22A, 22B. Comparison of (FIG. 22A) the AMMO1 epitope on EBV gH/GI and (FIG. 22B) the epitope of Fab 94 on varicella zoster virus (VZV) gH/GI (PDB ID: 4X15). Fab RC (PBD ID: 4XHJ) binds to a similar epitope on VZV gH/GI (not shown). Both antibodies bridge D-I/D-II (H1A/H1B in VZV gH/gL) and bind to the gH/gL interface, suggesting a common mechanism of neutralization of these two herpes viruses.

Figure 23A:
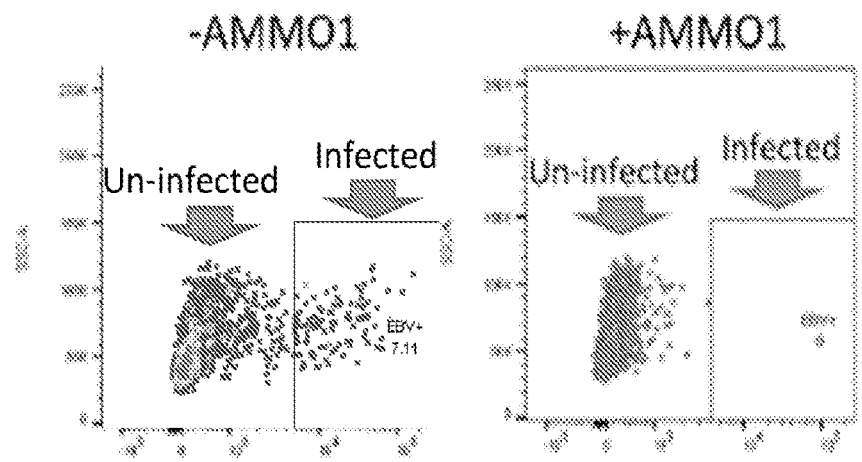
Figure 23B:
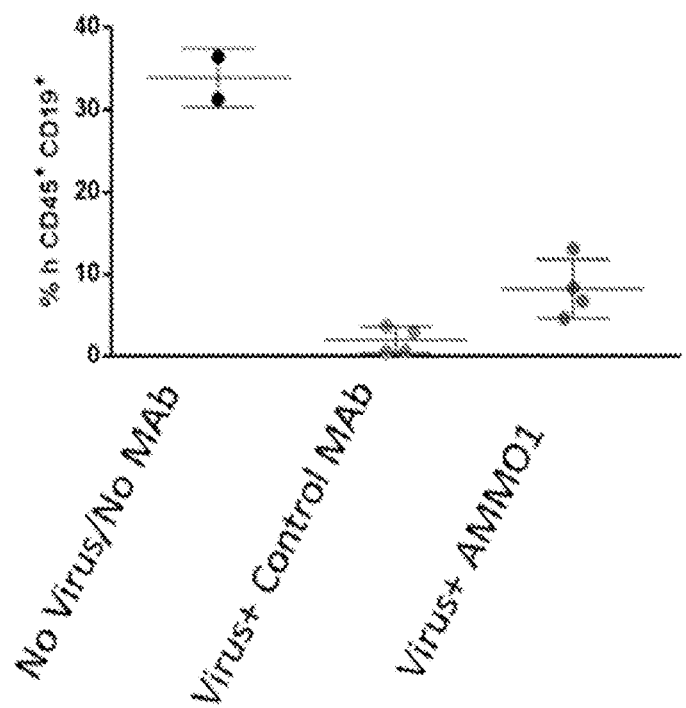
Figure 23C:
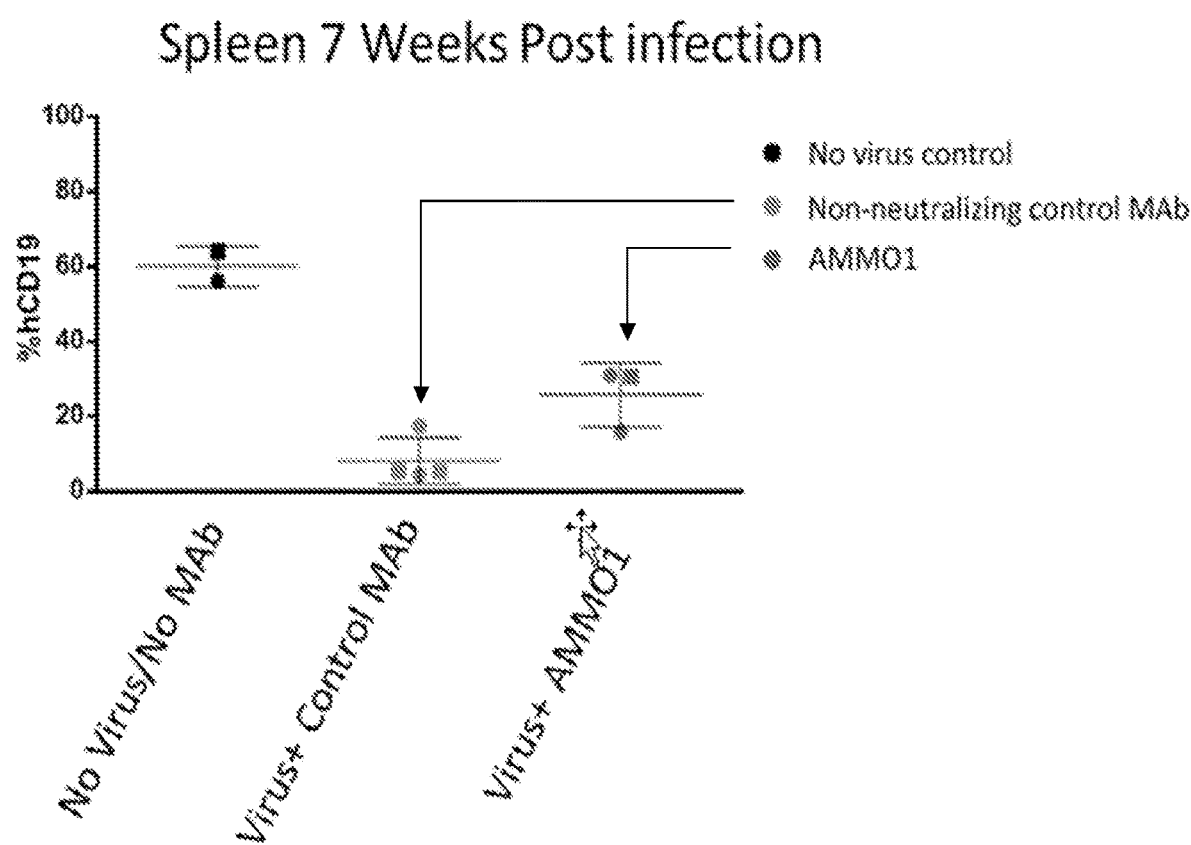

FIGS. 23A-23C. B cells were harvested from mice and challenged with a low-dose EBV reporter virus that induces GFP expression upon infection. The absence of antibody could readily be detected (FIG. 23A, left), yet there was no evidence of infection in the presence of AMMO1 (FIG. 23A, right). 0.5 mg AMMO1 or an irrelevant anti-HIV MAb was administered to humanized mice 2 days prior to a high dose ($5 \times IC_{50}$) intravenous EBV challenge. 6 weeks later, nearly all of the human B cells (hCD45+,hCD19+) in the blood had died in mice that received the control antibody (FIG. 23B), while B cells survived in mice that received AMMO1 (FIG. 23B). Similar results were observed in the spleen at week 7 (FIG. 23C).

FIG. 24. Sequences supporting the disclosure.

DETAILED DESCRIPTION

Epstein Barr virus (EBV) is an orally transmitted gamma herpesvirus that infects B cells and epithelial cells. Most primary infections are asymptomatic, however, EBV is a causative agent of infectious mononucleosis (IM) in children and young adults. Following primary infection, infected individuals become lifelong carriers of EBV, which can lie dormant (i.e., latent) in cells. However, in certain individuals the latent virus can begin to express genes that alter cellular replication, leading to cancer or cancer-like diseases. EBV is also associated with nasopharyngeal carcinoma and lymphoproliferative disorders in immunocompromised patients such as those with HIV/AIDS or in patients undergoing immune suppression for organ transplantation. Thus, antibodies or vaccines that treat, reduce, or prevent EBV infection of cells or treat EBV-associated diseases would be a major benefit to public health.

A primary goal of most vaccine design strategies is to elicit production of neutralizing antibodies, which are a type of antibody that can inhibit the biological function of its target. Neutralizing antibodies are also useful as protein therapeutics to treat viral infection. Neutralizing antibodies against viruses such as EBV typically function by blocking a virus from entering a cell.

Previous efforts to design EBV vaccines have included vaccines that target the EBV protein gp350, which is involved in EBV attachment to cells. However, while a phase 2 trial showed that the vaccine could reduce the incidence of IM, it did not protect from EBV infection. Furthermore, EBV vaccine research to-date has not led to the development of an effective human neutralizing antibody against EBV.

In particular embodiments the current disclosure provides EBV therapeutics, which can be formulated to treat an EBV-infected subject or a subject at risk of EBV infection.

In particular embodiments, EBV therapeutics refer to agents that treat EBV infection, reduce the risk or severity of EBV infection, and/or induce an immune response against EBV. Treating EBV can reduce EBV infection and/or treat a condition associated with EBV infection, such as infectious mononucleosis or lymphoproliferative disorder. In particular embodiments, use of EBV therapeutics disclosed herein lower the risk for nasopharyngeal carcinoma in a subject.

In particular embodiments, EBV therapeutics can be used to reduce the risk of infection when, for example, an EBV positive person donates solid organ or tissue to an EBV negative person who is immunosuppressed. In this context, the antibody can be transferred to prevent or reduce the risk of infection. EBV therapeutics can also be used to recognize tumor cells expressing EBV antigens for diagnosis or treatment (such as antibody-drug conjugates).

In particular embodiments, cells, such as B cells, can be genetically modified to express one or more EBV antibodies and/or vaccine antigen epitopes described herein. Genetic modification can be in vivo or in vitro.

Examples of EBV therapeutics include anti-EBV antibodies, EBV vaccines, and cells genetically modified to express anti-EBV antibodies, EBV vaccines, and/or fragments thereof. In particular embodiments, the EBV therapeutics include anti-gH/gL or anti-gB antibodies, and/or EBV vaccines designed to elicit anti-gH/gL or anti-gB antibodies.

In particular embodiments, anti-EBV antibodies are effective human neutralizing antibodies. In particular embodiments the anti-EBV antibodies neutralize EBV infection of B cells and epithelial cells. In particular embodiments, the anti-EBV antibodies neutralize EBV infection of B cells and/or epithelial cells with an $IC_{50}$ of $3 \times 10^{-9}$ M or less.

Particular antibodies disclosed herein do not bind to gp350, but instead bind the EBV fusion machinery (gH/gL and gB). One antibody disclosed herein, referred to as AMMO1, is an anti-gH/gL antibody. AMMO1, is uniquely able to potently neutralize infection of B cells and epithelial cells, the two major cell types that EBV infects. Cryoelectron microscopy reconstructions of the gH/gL/gp42/AMMO1 complex demonstrated that AMMO1 binds to a discontinuous epitope formed by both gH and gL at the Domain-I/Domain-II interface.

In particular embodiments, the anti-EBV antibodies bind at least one of residues 60, 70-81, 211-216, and 234-239 of gH; and/or at least one of residues 123-128 of gL. In particular embodiments, the anti-EBV antibodies bind at least one of residues 60, 70-81, 211-216, and 234-239 of gH; and at least one of residues 123-128 of gL. In particular embodiments, the anti-EBV antibodies bind residues 73 and 76 of gH wherein residue 73 is lysine and residue 76 is tyrosine. These epitopes bound by the antibodies of the disclosure can be used as vaccine antigen epitopes to produce EBV vaccines.

In particular embodiments, "bind" refers to an interaction between a molecule (e.g., antibody) and its binding partner (e.g., antigen and/or target epitope) with a binding affinity represented by a dissociation constant ($K_D$) of $10^{-8}$ M or less, in particular embodiments of from $10^{-5}$ M to $10^{-13}$ M, in particular embodiments of from $10^{-5}$ M to $10^{-10}$ M, in particular embodiments of from $10^{-5}$ M to $10^{-7}$ M, in particular embodiments of from $10^{-8}$ M to $10^{-13}$ M, or in particular embodiments of from $10^{-9}$ M to $10^{-13}$ M. The term can be further used to indicate that the binding domain does not bind to other biomolecules present, (e.g., it binds to other biomolecules with a dissociation constant ($K_D$) of $10^{-4}$ M or more, in particular embodiments of from $10^{-4}$ M to 1 M).

In particular embodiments the anti-EBV antibodies include a human antibody, or an antigen-binding portion thereof (including scFv) that dissociates from EBV gH/gL with a $K_D$ of $1 \times 10^{-10}$ or less and a $k_{off}$ rate constant of $3 \times 10^{-5}$ $s^{-1}$ or less, both determined by surface plasmon resonance or biolayer interferometry.

Without being bound by theory, and integrating structural, biochemical and infectivity data, AMMO1 inhibits fusion of the viral and cellular membranes. This work delineates a critical epitope for the design of next-generation subunit vaccines against this major public health burden.

The following sections describe in additional supporting detail: (I) Antibody Structures; (II) Antibody Epitopes; (III) Vaccines; (IV) Recombinant Production; (V) Modifications to Produce Administration Benefits; (VI) Genetically-Modified Therapeutic Cells; (VII) Therapeutic Compositions; (IX) Kits; (IX) Methods of Use; (X) Exemplary Embodiments; and (XI) Examples.

(I) Antibody Structures. Naturally occurring antibody structural units include a tetramer. Each tetramer includes two pairs of polypeptide chains, each pair having one light chain and one heavy chain.

The amino-terminal portion of each chain includes a variable region that is responsible for antigen recognition and epitope binding. The variable regions exhibit the same general structure of relatively conserved framework regions (FR) joined by three hyper variable regions, also called complementarity determining regions (CDRs). The CDRs from the two chains of each pair are aligned by the framework regions, which enables binding to a specific epitope. From N-terminal to C-terminal, both light and heavy chain variable regions include the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, J. Mol. Biol., 196:901-917 (1987); Chothia et al., Nature, 342:878-883 (1989). Kabat numbering is used herein unless specifically noted otherwise.

The carboxy-terminal portion of each chain defines a constant region that can be responsible for effector function. Examples of effector functions include: C1q binding and complement dependent cytotoxicity (CDC); antibody-dependent cell-mediated cytotoxicity (ADCC); antibody-dependent phagocytosis (ADCP); down regulation of cell surface receptors (e.g. B cell receptors); and B cell activation.

Within full-length light and heavy chains, the variable and constant regions are joined by a "J" region of amino acids, with the heavy chain also including a "D" region of amino acids. See, e.g., Fundamental Immunology, Ch. 7 (Paul, W., ed., 2nd ed. Raven Press, N.Y. (1989).

Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, IgG1, IgG2, IgG3, and IgG4. IgM has subclasses including IgM1 and IgM2. IgA is similarly subdivided into subclasses including IgA1 and IgA2.

Unless otherwise indicated, the term "antibody" includes, in addition to antibodies including two full-length heavy chains and two full-length light chains as described above, variants, derivatives, and fragments thereof, examples of which are described below. Furthermore, unless explicitly excluded, antibodies can include monoclonal antibodies, human antibodies, bispecific antibodies, polyclonal antibodies, linear antibodies, minibodies, domain antibodies, synthetic antibodies, chimeric antibodies, antibody fusions, and fragments thereof, respectively. In particular embodiments, antibodies (e.g., full length antibodies) can be produced in human suspension cells.

In particular embodiments, monoclonal antibodies refer to antibodies produced by a clone of B cells or hybridoma cells. In particular embodiments, monoclonal antibodies are identical to each other and/or bind the same epitope, except for possible antibodies containing naturally occurring mutations or mutations arising during production of a monoclonal antibody. In particular embodiments, in contrast to polyclonal antibody preparations, which include different antibodies directed against different epitopes, each monoclonal antibody of a monoclonal antibody preparation is directed against a single epitope on an antigen.

A "human antibody" is one which includes an amino acid sequence which corresponds to that of an antibody produced by a human or a human cell or derived from a non-human source that utilizes human antibody repertoires or other human antibody-encoding sequences.

A "human consensus framework" is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. The subgroup of sequences can be a subgroup as in Kabat et al., Sequences of Proteins of Immunological Interest, Fifth Edition, NIH Publication 91-3242, Bethesda Md. (1991), vols. 1-3. In particular embodiments, for the $V_L$, the subgroup is subgroup kappa I as in Kabat et al., supra. In particular embodiments, for the $V_H$, the subgroup is subgroup III as in Kabat et al., supra.

In particular embodiments, an antibody fragment is used. An "antibody fragment" denotes a portion of a complete or full length antibody that retains the ability to bind to an epitope. Examples of antibody fragments include Fv, single chain Fv fragments (scFvs), Fab, Fab', Fab'-SH, F(ab')$_2$, diabodies, linear antibodies, Fc, and/or any biologically effective fragments of an immunoglobulin that bind specifically to an epitope described herein. Antibodies or antibody fragments include all or a portion of polyclonal antibodies, monoclonal antibodies, human antibodies, humanized antibodies, synthetic antibodies, chimeric antibodies, bispecific antibodies, mini bodies, and linear antibodies.

Binding domains from human origin or humanized antibodies have lowered immunogenicity in humans and have a lower number of non-immunogenic epitopes compared to non-human antibodies. Binding domains will generally be selected to have reduced antigenicity in human subjects. Binding domains can particularly include any peptide that specifically binds a selected epitope.

A single chain variable fragment (scFv) is a fusion protein of the variable regions of the heavy and light chains of immunoglobulins connected with a short linker peptide. Fv fragments include the VL and VH domains of a single arm of an antibody. Although the two domains of the Fv fragment, VL and VH, are coded by separate genes, they can be joined, using, for example, recombinant methods, by a synthetic linker that enables them to be made as a single protein chain in which the VL and VH regions pair to form monovalent molecules (single chain Fv (scFv)). For additional information regarding Fv and scFv, see e.g., Bird, et al., Science 242 (1988) 423-426; Huston, et al., Proc. Natl. Acad. Sci. USA 85 (1988) 5879-5883; Plueckthun, in The Pharmacology of Monoclonal Antibodies, vol. 113, Rosenburg and Moore (eds.), Springer-Verlag, New York), (1994) 269-315; WO1993/16185; U.S. Pat. Nos. 5,571,894; and 5,587,458.

A Fab fragment is a monovalent antibody fragment including $V_L$, $V_H$, $C_L$ and $C_{H1}$ domains. A F(ab')$_2$ fragment is a bivalent fragment including two Fab fragments linked by a disulfide bridge at the hinge region. For discussion of Fab and F(ab')$_2$ fragments having increased in vivo half-life, see U.S. Pat. No. 5,869,046. Diabodies include two epitope-binding sites that may be bivalent. See, for example, EP 0404097; WO1993/01161; and Holliger, et al., Proc. Natl. Acad. Sci. USA 90 (1993) 6444-6448. Dual affinity retargeting antibodies (DART™; based on the diabody format but featuring a C-terminal disulfide bridge for additional stabilization (Moore et al., Blood 117, 4542-51 (2011)) can also be used. Antibody fragments can also include isolated CDRs. For a review of antibody fragments, see Hudson, et al., Nat. Med. 9 (2003) 129-134.

Antibody fragments can be made by various techniques, including proteolytic digestion of an intact antibody as well as production by recombinant host-cells (e.g., human suspension cell lines, E. coli or phage), as described herein. Antibody fragments can be screened for their binding properties in the same manner as intact antibodies.

In particular embodiments, the anti-EBV antibodies are neutralizing antibodies. A neutralizing antibody can refer to an antibody that, upon epitope binding, can reduce biological function of its target antigen. In particular embodiments neutralizing antibodies can reduce (i.e., neutralize) EBV infection of cells. In particular embodiments, neutralizing antibodies can block or neutralize EBV infection of B cells and/or epithelial cells. In particular embodiments percent neutralization can refer to a percent decrease in EBV infectivity in the presence of the antibody, as compared to EBV infectivity in the absence of the antibody. For example, if half as many cells in a sample become infected in the presence of an antibody, as compared to in the absence of the antibody, this can be calculated as 50% neutralization. In particular embodiments "neutralize EBV infection" can refer to at least 40% neutralization, at least 50% neutralization, at least 60% neutralization, at least 70% neutralization, at least 80% neutralization, or at least 90% neutralization of EBV infection. In particular embodiments, the antibodies disclosed herein can block EBV infection (i.e., 100% neutralization). In particular embodiments, the anti-EBV antibodies can inhibit EBV envelope fusion with target cells (e.g., epithelial cells and/or B cells), which can result in neutralization of EBV infection. Inhibition of EBV envelope fusion to target cells can be at least 40%, inhibition, at least 50%, inhibition, at least 60%, inhibition, at least 70%, inhibition, at least 80%, inhibition, or at least 90%, inhibition, as compared to EBV envelope fusion in the absence of the anti-EBV antibody. In particular embodiments, the target cells are epithelial cells and/or B cells. In particular embodiments, the neutralizing antibodies are AMMO1 and AMMO5.

In particular embodiments, anti-EBV antibodies include CDRs of the light chains and/or heavy chains of one or more of AMMO1, AMMO2, AMMO3, AMMO4, or AMMO5 (see, e.g., FIG. 24 and SEQ ID NOs: 1-10). In particular embodiments the anti-EBV antibodies include the CDRs from the light chain and heavy chain of AMMO1 (SEQ ID NOs: 1 and 2) or AMMO5 (SEQ ID NOs: 9 and 10).

In particular embodiments, an anti-EBV antibody (e.g., scFv) includes a variable light chain including an AMMO1 CDRL1 sequence including GGHNIGAKNVH (SEQ ID NO: 11), an AMMO1 CDRL2 sequence including YDS- DRPS (SEQ ID NO: 12), and an AMMO1 CDRL3 sequence including CQVWDSGRGHPLYV (SEQ ID NO: 13). In particular embodiments an anti-EBV antibody (e.g., scFv) includes a variable heavy chain including an AMMO1 CDRH1 sequence including YTFIHFGISW (SEQ ID NO: 14), an AMMO1 CDRH2 sequence including IDTNNG-NTNYAQSLQG (SEQ ID NO: 15), and an AMMO1 CDRH3 sequence including RALEMGHRSGFPFDY (SEQ ID NO: 16).

In particular embodiments, an anti-EBV antibody (e.g., scFv) includes a variable light chain including an AMMO2 CDRL1 sequence including RANLGISDWLA (SEQ ID NO: 17), an AMMO2 CDRL2 sequence including AASSLES (SEQ ID NO: 18), and an AMMO2 CDRL3 sequence including QQANSFPLS (SEQ ID NO: 19). In particular embodiments an anti-EBV antibody (e.g., scFv) includes a variable heavy chain including an AMMO2 CDRH1 sequence including GPFSTYGIN (SEQ ID NO: 20), an AMMO2 CDRH2 sequence including WIIPVFDTSSFAQ (SEQ ID NO: 21), and an AMMO2 CDRH3 sequence including RDRVLGAHGAN-PLNGHHYGMDV (SEQ ID NO: 22).

In particular embodiments, an anti-EBV antibody (e.g., scFv) includes a variable light chain including an AMMO3 CDRL1 sequence including SGDKLGEEYVCW (SEQ ID NO: 23), an AMMO3 CDRL2 sequence including QDRNRPP (SEQ ID NO: 24), and an AMMO3 CDRL3 sequence including QAWDSSTVV (SEQ ID NO: 25). In particular embodiments an anti-EBV antibody (e.g., scFv) includes a variable heavy chain including an AMMO3 CDRH1 sequence including FSLSTSGVGVG (SEQ ID NO: 26), an AMMO3 CDRH2 sequence including LIY-WHDAARYSPSLRN (SEQ ID NO: 27), and an AMMO3 CDRH3 sequence including ADKLYGDSVKFDY (SEQ ID NO: 28).

In particular embodiments, an anti-EBV antibody (e.g., scFv) includes a variable light chain including an AMMO4 CDRL1 sequence including TSSQSLVNSDGNSFLS (SEQ ID NO: 29), an AMMO4 CDRL2 sequence including VSHRDS (SEQ ID NO: 30), and an AMMO4 CDRL3 sequence including MQGTYWPPMFTF (SEQ ID NO: 31). In particular embodiments an anti-EBV antibody (e.g., scFv) includes a variable heavy chain including an AMMO4 CDRH1 sequence including ASFSNHGIV (SEQ ID NO: 32), an AMMO4 CDRH2 sequence including GIVPIVGG-ANYAQNFQG (SEQ ID NO: 33), and an AMMO4 CDRH3 sequence including DVPGQCTRTTCFNFSSQ (SEQ ID NO: 34).

In particular embodiments, an anti-EBV antibody (e.g., scFv) includes a variable light chain including an AMMO5 CDRL1 sequence including RASQSVSNNYF (SEQ ID NO: 35), an AMMO5 CDRL2 sequence including GISK-RATG (SEQ ID NO: 36), and an AMMO5 CDRL3 sequence including QQYGNSSPRT (SEQ ID NO: 37). In particular embodiments an anti-EBV antibody (e.g., scFv) includes a variable heavy chain including an AMMO5 CDRH1 sequence including FTFSNYAMS (SEQ ID NO: 38), an AMMO5 CDRH2 sequence including SISATDGSTYY-ADSVEG (SEQ ID NO: 39), and an AMMO5 CDRH3 sequence including KDGAGDYL (SEQ ID NO: 40).

In particular embodiments, the anti-EBV antibodies include a heavy chain including SEQ ID NO: 1 and a light chain including SEQ ID NO: 2. In particular embodiments, SEQ ID NO: 1 includes mutation Q1N.

In particular embodiments, the anti-EBV antibodies include a heavy chain including SEQ ID NO: 3 and a light chain including SEQ ID NO: 4. In particular embodiments, SEQ ID NO: 3 includes mutation Q1N.

In particular embodiments, the anti-EBV antibodies include a heavy chain including SEQ ID NO: 5 and a light chain including SEQ ID NO: 6. In particular embodiments, SEQ ID NO: 5 includes mutation E1N. In particular embodiments, SEQ ID NO: 6 includes mutation Q1N. In particular embodiments, SEQ ID NO: 5 includes mutation E1N and SEQ ID NO: 6 includes mutation Q1N.

In particular embodiments, the anti-EBV antibodies include a heavy chain including SEQ ID NO: 7 and a light chain including SEQ ID NO: 8. In particular embodiments, SEQ ID NO: 7 includes mutation Q1N.

In particular embodiments, the anti-EBV antibodies include a heavy chain including SEQ ID NO: 9 and a light chain including SEQ ID NO: 10. In particular embodiments, SEQ ID NO: 9 includes mutation E1N. In particular embodiments, SEQ ID NO: 10 includes mutation E1N. In particular embodiments, SEQ ID NO: 9 includes mutation E1N and SEQ ID NO: 10 includes mutation E1N.

In particular embodiments, the anti-EBV antibodies include a heavy chain including SEQ ID NO: 41 and a light chain including SEQ ID NO: 42 with mutations selected from one or more heavy chain mutations selected from D10E; G76S; S83R; T84S; F91Y; V107T; and P113S and/or one or more light chain mutations selected from E3V; Q17K; R18T; T20R; Q49Y; S69N; and G100T.

In particular embodiments, the anti-EBV antibodies include a heavy chain including SEQ ID NO: 41 and a light chain including SEQ ID NO: 42 with heavy chain mutations D10E; G76S; S83R; T84S; F91Y; V107T; and P113S and light chain mutations E3V; Q17K; R18T; T20R; Q49Y; S69N; and G100T.

As indicated, in particular embodiments, a $V_H$ region of the present disclosure can be derived from or based on a $V_H$ of an AMMO antibody and can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_H$ of an AMMO antibody. An insertion, deletion or substitution may be anywhere in the $V_H$ region, including at the amino- or carboxy-terminus or both ends of this region, provided that each CDR includes zero changes or at most one, two, or three changes and provided a modified $V_H$ can still specifically bind its target epitope with an affinity similar to the wild type AMMO VH.

In particular embodiments, a $V_L$ region of the present disclosure can be derived from or based on a $V_L$ of an AMMO antibody and can include one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the $V_L$ of an AMMO antibody. An insertion, deletion or substitution may be anywhere in the $V_L$ region, including at the amino- or carboxy-terminus or both ends of this region, provided that each CDR includes zero changes or at most one, two, or three changes and provided a modified $V_L$ can still specifically bind its target epitope with an affinity similar to the wild type AMMO $V_L$.

In particular embodiments, an antibody variant includes or is a sequence that has at least 90%, at least 91%, at least 92%, at least 93%, at least 94%, at least 95%, at least 96%, at least 97%, at least 98%, at least 99%, or at least 99.5% sequence identity to an antibody sequence disclosed herein. In particular embodiments, an antibody variant includes or is a sequence that has at least 90%, at least 91%, at least 92%, at least 93%, at least 94%, at least 95%, at least 96%, at least 97%, at least 98%, at least 99%, or at least 99.5% sequence identity to a light chain variable region ($V_L$) and/or to a heavy chain variable region ($V_H$), or both, wherein each CDR includes zero changes or at most one, two, or three changes, from the reference antibody disclosed herein or fragment thereof that binds to a targeted EBV epitope. In particular embodiments, an antibody variant includes or is a sequence that has at least 90%, at least 91%, at least 92%, at least 93%, at least 94%, at least 95%, at least 96%, at least 97%, at least 98%, at least 99%, or at least 99.5% sequence identity to the CDRs of an antibody disclosed herein (AMMO1-AMMO5).

(II) Antibody Epitopes. As indicated, antibodies bind epitopes on antigens. An antigen refers to a molecule or a portion of a molecule capable of being bound by an antibody. An epitope is a region of an antigen that is bound by the variable region of an antibody. An epitope includes specific amino acids that contact the variable region of an antibody. Epitope determinants can include chemically active surface groupings of molecules such as amino acids, sugar side chains, phosphoryl or sulfonyl groups, and can have specific three dimensional structural characteristics, and/or specific charge characteristics.

An "epitope" includes any determinant capable of being bound by an antigen-binding protein, such as an antibody. An epitope is a region of molecule that is bound by a binding protein that targets that region of molecule, and when that region of molecule is a protein, includes specific residues that directly contact the binding protein. In particular embodiments, an "epitope" denotes the binding site on a protein target bound by a corresponding binding domain. The binding domain either binds to a linear epitope, (e.g., an epitope including a stretch of 5 to 12 consecutive amino acids), or the binding domain binds to a three-dimensional structure formed by the spatial arrangement of several short stretches of the protein target. Three-dimensional epitopes recognized by a binding domain, e.g., by the epitope recognition site or paratope of an antibody or antibody fragment, can be thought of as three-dimensional surface features of an epitope molecule. These features fit precisely (in)to the corresponding binding site of the binding domain and thereby binding between the binding domain and its target protein is facilitated. In particular embodiments, an epitope can be considered to have two levels: (i) the "covered patch" which can be thought of as the shadow an antibody or binding domain would cast; and (ii) the individual participating side chains and backbone residues. Binding is then due to the aggregate of ionic interactions, hydrogen bonds, and hydrophobic interactions.

In particular embodiments, the EBV epitopes targeted by the antibodies disclosed herein are present on envelope glycoprotein H (gH, see, e.g., SEQ ID NO: 51), envelope glycoprotein L (gL, see, e.g., SEQ ID NO: 52), and/or glycoprotein B (gB, see, e.g., SEQ ID NO: 53). gH, gL, and gB are glycoproteins expressed by EBV that can form complexes together and are important for virus entry into cells. In particular embodiments, the EBV epitope includes gH/gL, which is a heterodimer of gH and gL that binds to glycoprotein 42 (gp42, SEQ ID NO: 54) to form a trimer on the surface of EBV virions. In particular embodiments the EBV epitope bridges the D-I/D-II groove, and encompasses the linker helix of the gH/gL complex. Description of the D-I and D-II domains can be found in Matsuura, et al., Proc. Natl. Acad. Sci. USA 107 (2010) 22641-22646. In particular embodiments, the EBV antibody binds to an epitope on gH/gL that includes one or more of amino acids 60, 70-81, 211-216, and 234-239 of gH; and/or one or more of amino acids 123-128 of gL. In particular embodiments, the anti-EBV antibody binds residues 73 and 76 of gH wherein residue 73 is lysine and residue 76 is tyrosine.

When an antibody disclosed herein binds to a gH/gL epitope, it competes for binding with CL40. CL40 is a neutralizing anti-EBV antibody that binds to an epitope of gH/gL. In particular embodiments, an anti-EBV antibody (e.g., AMMO1) can reduce CL40 binding to EBV or a gH/gL complex (see FIG. 17E).

(III) Vaccines. In particular embodiments the EBV therapeutics include EBV vaccines. The EBV vaccines can include an EBV antigen with a vulnerable EBV epitope such as those described herein. In particular embodiments, the EBV vaccines include an EBV antigen that includes a gH/gL complex, and/or a D-I/D-II groove and the DI/DII linker helix of a gH/gL complex. In particular embodiments, the EBV vaccines include an AMMO1 epitope. An AMMO1 epitope can refer to the gH/gL residues that are bound by the antibody AMMO1. Examples of AMMO1 epitope residues include: gH residues 60, 70-81, 211-216, and 234-239; and gL residues 123-128. In particular embodiments, examples of AMMO1 epitopes include residues 73 and 76 of gH wherein residue 73 is lysine and residue 76 is tyrosine. In particular embodiments, the EBV vaccines include an AMMO5 epitope. An AMMO5 epitope is a region of gB that is capable of binding to AMMO5.

In particular embodiments, the EBV vaccine can include a subunit vaccine. A subunit vaccine can refer to a vaccine that does not contain a whole live or killed pathogen, but only a subunit (e.g., a single protein or protein fragment) of the pathogen that stimulates an immune response against the pathogen. In particular embodiments, the EBV subunits vaccines can include vaccine proteins including (i) gH/gL or a fragment of gH/gL that binds to AMMO1; and/or (ii) gB or a fragment of gB that binds to AMMO5.

In particular embodiments, the EBV therapeutics include immunogenic proteins. An immunogenic protein can, for example, be used to elicit an antibody response in a subject. In particular embodiments, the immunogenic proteins include one or more AMMO epitopes. An AMMO epitope is an epitope bound by an AMMO antibody described herein. In particular embodiments, an immunogenic protein includes one or more of: an AMMO1 epitope, an AMMO2 epitope, an AMMO3 epitope, an AMMO4 epitope, and/or an AMMO5 epitope.

In particular embodiments, EBV therapeutics (e.g., EBV vaccines, immunogenic proteins) can include multimerization domains. Multimerization domains can allow for multimerization of the EBV vaccine proteins and/or immunogenic proteins, which can enhance their immunogenicity. In particular embodiments, the multimerization domain is C4b multimerization domain. C4 binding protein (C4b) is the major inhibitor of the classical complement and lectin pathway. The complement system is a major part of innate immunity and is the first line of defense against invading microorganisms. Orchestrated by more than 60 proteins, its major task is to discriminate between host cells and pathogens and to initiate immune responses when necessary. It also recognizes necrotic or apoptotic cells. Hofmeyer et al., J Mol Biol. 2013 Apr. 26; 425(8):1302-17.

Full-length native C4b includes seven α-chains linked together by a multimerization (i.e., heptamerization) domain at the C-terminus of the α-chains. Blom et al., (2004) Mol Immunol 40: 1333-1346. One of the α-chains can be replaced by a β-chain in humans. The wild-type C4b multimerization domain is 57 amino acid residues in humans and 54 amino acid residues in mice. Forbes et al., PLoS One. 2012; 7(9): e44943. It contains an amphipathic α-helix region, which is necessary and sufficient for heptamerization, as well as two cysteine residues which stabilize the structure. Kask et al., (2002) Biochemistry 41: 9349-9357.

Examples of C4b multimerization domains that can be used include:

| SEQ ID NO: | Sequence |
|---|---|
| 55 | SGRAHAGWETPEGCEQVLTGKRLMQCLPNPEDVKMALEVYKLSLEIEQLELQRDSARQSTLDKELVPR |
| 56 | KKQGDADVCGEVAYIQSVVSDCHVPTAELRTLLEIRKLFLEIQKLKVELQGLSKE |
| 57 | ETPEGCEQVLTGKRLMQCLPNPEDVKMALEVYKLSLEIEQLELQRDSARQSTLDKEL |
| 58 | WETPEGCEQVLTGKRLMQCLPNPEDVKMALEVYKLSLEIEQLELQRDSARQSTLDKEL |
| 59 | CEQVLTGKRLMQCLPNPEDVKMALEVYKLSLEIEQLELQRDSARQSTLDKEL |

In particular embodiments, the C4b multimerization domain will be a multimerization domain which includes (i) glycine at position 12, (ii) alanine at position 28, (iii) leucines at positions 29, 34, 36, and/or 41; (iv) tyrosine at position 32; (v) lysine at position 33; and/or (vi) cysteine at positions 6 and 18. In particular embodiments, the C4b multimerization domain will be a multimerization domain which includes (i) glycine at position 12, (ii) alanine at position 28, (iii) leucines at positions 29, 34, 36, and 41; (iv) tyrosine at position 32; (v) lysine at position 33; and (vi) cysteine at positions 6 and 18.

C4b multimerization domains can include any of SEQ ID NOs: 55-59 with an N-terminal deletion of at least 1 consecutive amino acid residues (e.g. at least 2, 3, 4, 5, 6, 7, 8, 9, 10 consecutive amino acid residues) in length. Additional embodiments can include a C-terminal deletion of at least 1 consecutive amino acid residues (e.g. at least 2, 3, 4, 5, 6, 7, 8, 9, 10 consecutive amino acid residues) in length.

Particular C4b multimerization domain embodiments will retain or will be modified to include at least 1 of the following residues: A6; E11; A13; D21; C22; P25; A27; E28; L29; R30; T31; L32; L33; E34; I35; K37; L38; L40; E41; I42; Q43; K44; L45; E48; L49; or Q50. Further embodiments will retain or will be modified to include A6; E11; A13; D21; C22; P25; A27; E28; L29; R30; T31; L32; L33; E34; I35; K37; L38; L40; E41; I42; Q43; K44; L45; E48; L49; and Q50. Particular C4b multimerization domain embodiments will include the amino acid sequence "AELR".

(IV) Recombinant Production. In particular embodiments, the anti-EBV antibodies or EBV vaccine proteins are produced from a gene using a protein expression system. Protein expression systems can utilize DNA constructs (e.g., chimeric genes, expression cassettes, expression vectors, recombination vectors) including a nucleic acid sequence encoding the protein or proteins of interest operatively linked to appropriate regulatory sequences. In particular embodiments, such DNA constructs are not naturally-occurring DNA molecules and are useful for introducing DNA into host-cells to express selected proteins of interest. In particular embodiments, a DNA construct that encodes an anti-EBV antibody or vaccine protein can be inserted into cells (e.g., bacterial, mammalian, insect, etc.), which can produce the anti-EBV antibody or vaccine protein encoded by the DNA construct.

Operatively linked refers to the linking of DNA sequences (including the order of the sequences, the orientation of the sequences, and the relative spacing of the various sequences) in such a manner that the encoded protein is expressed. Methods of operatively linking expression control sequences to coding sequences are well known in the art. See, e.g., Maniatis et al., Molecular Cloning: A Laboratory Manual, Cold Spring Harbor, N.Y., 1982; and Sambrook et al., Molecular Cloning: A Laboratory Manual, Cold Spring Harbor, N. Y., 1989.

Expression control sequences are DNA sequences involved in any way in the control of transcription or translation. Suitable expression control sequences and methods of making and using them are well known in the art. Expression control sequences generally include a promoter. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, Nucleic Acids Res., 15, 2343-2361, 1987. Also, the location of the promoter relative to the transcription start may be optimized. See, e.g., Roberts et al., Proc. Natl. Acad. Sci. USA, 76:760-764, 1979.

The promoter may include, or be modified to include, one or more enhancer elements. In particular embodiments, the promoter will include a plurality of enhancer elements. Promoters including enhancer elements can provide for higher levels of transcription as compared to promoters that do not include them.

For efficient expression, the coding sequences can be operatively linked to a 3' untranslated sequence. In particular embodiments, the 3' untranslated sequence can include a transcription termination sequence and a polyadenylation sequence. The 3' untranslated region can be obtained, for example, from the flanking regions of genes.

In particular embodiments, a 5' untranslated leader sequence can also be employed. The 5' untranslated leader sequence is the portion of an mRNA that extends from the 5' CAP site to the translation initiation codon.

In particular embodiments, a "hisavi" tag can be added to the N-terminus or C-terminus of a gene by the addition of nucleotides coding for the Avitag amino acid sequence, "GLNDIFEAQKIEWHE" (SEQ ID NO: 60), as well as the 6× histidine tag "HHHHHH" (SEQ ID NO: 61). The Avitag avidity tag can be biotinylated by a biotin ligase to allow for biotin-avidin or biotin-streptavidin based interactions for protein purification, as well as for immunobiology (such as immunoblotting or immunofluorescence) using anti-biotin antibodies. The 6× histidine tag allows for protein purification using $Ni^{-2+}$ affinity chromatography.

In particular embodiments, anti-EBV antibodies and/or EBV therapeutics disclosed herein can be produced using, for example, human suspension cells and/or the Daedalus expression system as described in Pechman et al., Am J Physiol 294: R1234-R1239, 2008. The Daedalus system utilizes inclusion of minimized ubiquitous chromatin opening elements in transduction vectors to reduce or prevent genomic silencing and to help maintain the stability of decigram levels of expression. This system can bypass tedious and time-consuming steps of other protein production methods by employing the secretion pathway of serum-free adapted human suspension cell lines, such as 293

Freestyle. Using optimized lentiviral vectors, yields of 20-100 mg/l of correctly folded and post-translationally modified, endotoxin-free protein of up to 70 kDa in size, can be achieved in conventional, small-scale (100 ml) culture. At these yields, most proteins can be purified using a single size-exclusion chromatography step, immediately appropriate for use in structural, biophysical or therapeutic applications. Bandaranayake et al., Nucleic Acids Res., 2011 (November); 39(21). In some instances, purification by chromatography may not be needed due to the purity of manufacture according the methods described herein.

In particular embodiments, the DNA constructs can be introduced by transfection, a technique that involves introduction of foreign DNA into the nucleus of eukaryotic cells. In particular embodiments, the proteins can be synthesized by transient transfection (DNA does not integrate with the genome of the eukaryotic cells, but the genes are expressed for 24-96 hours). Various methods can be used to introduce the foreign DNA into the host-cells, and transfection can be achieved by chemical-based means including by the calcium phosphate, by dendrimers, by liposomes, and by the use of cationic polymers. Non-chemical methods of transfection include electroporation, sono-poration, optical transfection, protoplast fusion, impalefection, and hydrodynamic delivery. In particular embodiments, transfection can be achieved by particle-based methods including gene gun where the DNA construct is coupled to a nanoparticle of an inert solid which is then "shot" directly into the target-cell's nucleus. Other particle-based transfection methods include magnet assisted transfection and impalefection.

Nucleic acid sequences encoding proteins disclosed herein can be derived by those of ordinary skill in the art. Nucleic acid sequences can also include one or more of various sequence polymorphisms, mutations, and/or sequence variants (e.g., splice variants or codon optimized variants). In particular embodiments, the sequence polymorphisms, mutations, and/or sequence variants do not affect the function of the encoded protein.

Sequence information provided by public databases can be used to identify additional gene and protein sequences that can be used with the systems and methods disclosed.

(V) Modifications to Produce Administration Benefits. In particular embodiments, variants or proteins disclosed herein can be modified to produce an administration benefit. Exemplary administration benefits can include (1) reduced susceptibility to proteolysis, (2) reduced susceptibility to oxidation, (3) altered binding affinity for forming protein complexes, (4) altered binding affinities, (5) reduced immunogenicity; and/or (6) extended half-life.

In particular embodiments, one or more amino acid modifications may be introduced into the Fc region of an antibody, thereby generating an Fc region variant. The Fc region variant may include a human Fc region sequence (e.g., a human IgG1, IgG2, IgG3 or IgG4 Fc region) including an amino acid modification (e.g. a substitution) at one or more amino acid positions. In particular embodiments the antibodies can be mutated to increase their binding to Fc receptors. Antibodies can contain Fc regions that, upon epitope-engagement, can bind to Fc Receptors that are expressed, for example, by phagocytes. Exemplary mutations that increase the binding to Fc receptors include: G236A/S239D/A330L/I332E (GASDALIE). Smith et al., Proceedings of the National Academy of Sciences of the United States of America, 109(16), 6181-6186 (2012). In particular embodiments, an antibody variant includes an Fc region with one or more amino acid substitutions which improve ADCC, e.g., substitutions at positions 298, 333, and/or 334 of the Fc region (EU numbering of residues). In particular embodiments, alterations are made in the Fc region that result in altered C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

In particular embodiments the anti-EBV antibodies or vaccine proteins can include amino acid mutations that increase the half-life of the antibodies in serum. M428L/N434S is a pair of mutations that increase the half-life of antibodies in serum, as described in Zalevsky et al., Nature Biotechnology 28, 157-159 (2010).

In particular embodiments, anti-EBV antibodies can be mutated to lower the immunogenicity of the antibody. For example, human antibodies can have somatic mutations in the framework region that induce immunogenicity, and these mutations can be reverted back to the germline sequence to decrease the immunogenicity of the antibody.

In particular embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further below. In particular embodiments, residue S400 (EU numbering) of the heavy chain Fc region is selected. Cysteine engineered antibodies may be generated as described, e.g., in U.S. Pat. No. 7,521,541.

In particular embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at position 297 in the Fc region (Eu numbering of Fc region residues); however, Asn297 may also be located ±3 amino acids upstream or downstream of position 297, i.e., between positions 294 and 300, due to minor sequence variations in antibodies. Such fucosylation variants may have improved ADCC function. See, e.g., WO2000/61739; WO 2001/29246; WO2002/031140; US2002/0164328; WO2003/085119; WO2003/084570; US2003/0115614; US2003/0157108; US2004/0093621; US2004/0110704; US2004/0132140; US2004/0110282; US2004/0109865; WO2005/035586; WO2005/035778; WO2005/053742; Okazaki et al. J. Mol. Biol. 336:1239-1249 (2004); and Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986)), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4): 680-688 (2006); and WO2003/085107).

In particular embodiments, modified anti-EBV antibodies or EBV vaccine proteins include those wherein one or more amino acids have been replaced with a non-amino acid component, or where the amino acid has been conjugated to a functional group or a functional group has been otherwise associated with an amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. Amino acid(s) can be modified, for example, co-translationally or post-translationally during recombinant production (e.g., N-linked glycosylation at N-X-S/T motifs during expression in mammalian cells) or modified by synthetic means. The modified amino acid can be within the sequence or at the terminal end of a sequence. Modifications also include nitrited proteins.

PEGylation particularly is a process by which polyethylene glycol (PEG) polymer chains are covalently conjugated to other molecules such as proteins. Several methods of PEGylating proteins have been reported in the literature. For example, N-hydroxy succinimide (NHS)-PEG was used to PEGylate the free amine groups of lysine residues and N-terminus of proteins; PEGs bearing aldehyde groups have been used to PEGylate the amino-termini of proteins in the presence of a reducing reagent; PEGs with maleimide functional groups have been used for selectively PEGylating the free thiol groups of cysteine residues in proteins; and site-specific PEGylation of acetyl-phenylalanine residues can be performed.

Covalent attachment of proteins to PEG has proven to be a useful method to increase the half-lives of proteins in the body (Abuchowski, A. et al., Cancer Biochem. Biophys., 1984, 7:175-186; Hershfield, M. S. et al., N. Engl. J. Medicine, 1987, 316:589-596; and Meyers, F. J. et al., Clin. Pharmacol. Ther., 1991, 49:307-313). The attachment of PEG to proteins not only protects the molecules against enzymatic degradation, but also reduces their clearance rate from the body. The size of PEG attached to a protein has significant impact on the half-life of the protein. The ability of PEGylation to decrease clearance is generally not a function of how many PEG groups are attached to the protein, but the overall molecular weight of the altered protein. Usually the larger the PEG is, the longer the in vivo half-life of the attached protein. In addition, PEGylation can also decrease protein aggregation (Suzuki et al., Biochem. Bioph. Acta vol. 788, pg. 248 (1984)), alter protein immunogenicity (Abuchowski et al.; J. Biol. Chem. vol. 252 pg. 3582 (1977)), and increase protein solubility as described, for example, in PCT Publication No. WO 92/16221).

Several sizes of PEGs are commercially available (Nektar Advanced PEGylation Catalog 2005-2006; and NOF DDS Catalogue Ver 7.1), which are suitable for producing proteins with targeted circulating half-lives. A variety of active PEGs have been used including mPEG succinimidyl succinate, mPEG succinimidyl carbonate, and PEG aldehydes, such as mPEG-propionaldehyde.

In particular embodiments, the anti-EBV antibodies or EBV vaccine proteins can be linked to human serum albumin (HSA). Linkage to HSA can increase the size of the protein and can increase serum half-life. An HSA-linkage can increase antibody or vaccine protein half-life without altering the binding and/or activity of the antibody or vaccine protein.

In particular embodiments, anti-EBV antibodies bind tumor cells expressing EBV antigens for diagnosis (e.g., imaging) or treatment. For example, EBV antibodies can be conjugated to an enzyme label, a colored label, a cytostatic agent, a label that can be photoactivated and which is suitable for use in photodynamic therapy, haptens, digoxigenin, biotin, or a chemotherapeutic agent. Exemplary conjugation partners include enzyme labels such as alkaline phosphatase, horseradish peroxidase, and β-galactosidase; therapeutically active agents such as radionuclides, toxins, small organic molecules, and therapeutic peptides; toxins such as pertussis-toxin, diphtheria toxin, ricin, saporin, pseudomonas exotoxin, calicheamicin, taxoids, maytansinoids, tubulysins and dolastatin or dolastatin analogues (e.g., auristatin E, monomethylauristatin E, auristatin PYE and auristatin PHE); cytostatic or chemotherapeutic agents such as Abiraterone, Adriamycine, Anthracycline (Doxorubicin), Azacitidine, Azathioprine, Beuacizumab, Bortezomib, Bleomycin, Capecitabine, Camptotecine, Carboplatin, Cetuximab, Chlorambucil, Cisplatin, curacin, Cyclophosphamide, Cyclophosphoramide, Cytarabine, Dacarbazine, Daunorubicin, Doxifluridine, Epirubicin, Epothilone, Etoposide, 5-Fluorouracil, Gemeitabine, hydroxyurea, Idarubicin, Irinotecan, Imatinib, Lenalidomide, Leucovorin, Leuprorelin, Mechlorethamine, Mercaptopurine, Methotrexate, Mitoxantrone, oxadiazolines, Oxaliplatin, Paclitaxel, Pemetrexed, retinoic acid, Rituximab, sulfonamides, Taxotere (Docetaxel), Teniposide, Tioguanine, Topotecan, Trastuzumab, Valrubicin, Vinblastin, Vincristine, Vindesine, and Vinorelbine; and therapeutically active nucleic acids such as antisense nucleic acid molecules, small interfering RNAs, micro RNAs and ribozymes. Such conjugations can be carried out using any conventional coupling method known in the art. Depending on intended use to visualize tumor cells or target cancer cells for destruction, compounds within this paragraph can be referred to as "imaging agents" or "drugs".

(VI) Genetically-Modified Therapeutic Cells. In particular embodiments, nucleic acids encoding antibodies disclosed herein can be delivered into cells for therapeutic expression, for example, within a subject. These embodiments may be referred to as "gene editing or vectored immunoprophylaxis". Nucleic acids can be delivered into, for example, B cells using gene editing systems and/or viral vector systems.

Gene editing systems include typically include a targeting molecule for precise targeting of a portion of a genome to be edited and a cutting molecule for cutting the targeted genetic site. Guide RNA is one example of a targeting molecule while various nucleases provide examples of cutting molecules. When insertion of a nucleic acid encoding an antibody or vaccine antigen (or fragment thereof) is intended, the systems can also include a homology-directed repair template (which can include homology arms) associated with the nucleic acid encoding the antibody or vaccine antigen (or fragment thereof). As detailed further below, however, different gene editing systems can adopt different components and configurations while maintaining the ability to precisely target, cut, and modify selected genomic sites.

Particular embodiments utilize zinc finger nucleases (ZFNs) as gene editing agents. ZFNs are a class of site-specific nucleases engineered to bind and cleave DNA at specific positions. ZFNs are used to introduce double strand breaks (DSBs) at a specific site in a DNA sequence which enables the ZFNs to target unique sequences within a genome in a variety of different cells. Moreover, subsequent to double-stranded breakage, homology-directed repair (HDR) can take place to repair the DSB, thus enabling genome editing.

ZFNs are synthesized by fusing a zinc finger DNA-binding domain to a DNA cleavage domain. The DNA-binding domain includes three to six zinc finger proteins which are transcription factors. The DNA cleavage domain includes the catalytic domain of, for example, FokI endonuclease. The FokI domain functions as a dimer requiring two constructs with unique DNA binding domains for sites on the target sequence. The FokI cleavage domain cleaves within a five or six base pair spacer sequence separating the two inverted half-sites.

For additional information regarding ZFNs, see Kim, et al. Proceedings of the National Academy of Sciences of the United States of America 93, 1156-1160 (1996); Wolfe, et al. Annual review of biophysics and biomolecular structure 29, 183-212 (2000); Bibikova, et al. Science 300, 764 (2003); Bibikova, et al. Genetics 161, 1169-1175 (2002); Miller, et al. The EMBO journal 4, 1609-1614 (1985); and Miller, et al. Nature biotechnology 25, 778-785 (2007)].

Particular embodiments can use transcription activator like effector nucleases (TALENs) as gene editing agents. TALENs refer to fusion proteins including a transcription activator-like effector (TALE) DNA binding protein and a DNA cleavage domain. TALENs are used to edit genes and genomes by inducing DSBs in the DNA, which induce repair mechanisms in cells. Generally, two TALENs must bind and flank each side of the target DNA site for the DNA cleavage domain to dimerize and induce a DSB. The DSB can then be repaired in the cell by HDR with an exogenous double-stranded donor DNA fragment.

As indicated, TALENs have been engineered to bind a target sequence of, for example, an endogenous genome, and cut DNA at the location of the target sequence. The TALEs of TALENs are DNA binding proteins secreted by *Xanthomonas* bacteria. The DNA binding domain of TALEs include a highly conserved 33 or 34 amino acid repeat, with divergent residues at the $12^{th}$ and $13^{th}$ positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant FokI endonucleases. For additional information regarding TALENs, see Boch, et al. Science 326, 1509-1512 (2009); Moscou, & Bogdanove, Science 326, 1501 (2009); Christian, et al. Genetics 186, 757-761 (2010); and Miller, et al. Nature biotechnology 29, 143-148 (2011).

Particular embodiments utilize MegaTALs as gene editing agents. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

In particular embodiments, CRISPR gene editing systems may be used. The CRISPR nuclease system is a prokaryotic immune system that confers resistance to foreign genetic elements such as plasmids and phages and provides a form of acquired immunity. CRISPRs are DNA loci containing short repetitions of base sequences. In the context of a prokaryotic immune system, each repetition is followed by short segments of spacer DNA belonging to foreign genetic elements that the prokaryote was exposed to. This CRISPR array of repeats interspersed with spacers can be transcribed into RNA. The RNA can be processed to a mature form and associate with a cas (CRISPR-associated) nuclease. A CRISPR-Cas system including an RNA having a sequence that can hybridize to the foreign genetic elements and Cas nuclease can then recognize and cut these exogenous genetic elements in the genome.

A CRISPR-Cas system does not require the generation of customized proteins to target specific sequences, but rather a single Cas enzyme can be programmed by a short guide RNA molecule to recognize a specific DNA target (crRNA). A classification of CRISPR-Cas systems is proposed in which these systems are broadly divided into two classes, Class 1 with multi-subunit effector complexes and Class 2 with single-subunit effector modules exemplified by the Cas9 protein. In addition to the Class 1 and Class 2 CRISPR-Cas systems, more recently a putative Class 2, Type V CRISPR-Cas class exemplified by Cpf1 has been identified.

The Cpf1 nuclease particularly can provide added flexibility in target site selection by means of a short, three base pair recognition sequence (TTN), known as the protospacer-adjacent motif or PAM. Cpf1's cut site is at least 18 bp away from the PAM sequence, thus the enzyme can repeatedly cut a specified locus after indel (insertion and deletion) formation, increasing the efficiency of HDR. Moreover, staggered DSBs with sticky ends permit orientation-specific donor template insertion, which is advantageous in non-dividing cells.

Additional information regarding CRISPR-Cas systems and components thereof are described in, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Nucleic acids encoding antibodies or vaccine antigens (or fragments thereof) can also be delivered into, for example, B cells using viral vector systems. The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors include cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

(VII) Therapeutic Compositions. EBV therapeutics (antibodies, vaccines, gene editing systems, viral vectors, or cells modified by gene editing system or viral vectors) can be formulated alone or in combination into compositions for administration to subjects. In particular embodiments, the EBV therapeutics (e.g., anti-EBV antibodies (whether in single or conjugated form) or EBV vaccines) include immunogenic compositions. An immunogenic composition refers to an agent that stimulates an innate and/or an adaptive immune response in a subject.

Salts and/or pro-drugs of EBV therapeutics can also be used.

A pharmaceutically acceptable salt includes any salt that retains the activity of the EBV therapeutic and is acceptable for pharmaceutical use. A pharmaceutically acceptable salt also refers to any salt which may form in vivo as a result of administration of an acid, another salt, or a prodrug which is converted into an acid or salt.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable pharmaceutically acceptable base addition salts include metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine.

A prodrug includes an active ingredient which is converted to a therapeutically active compound after administration, such as by cleavage of an EBV therapeutic or by hydrolysis of a biologically labile group.

In particular embodiments, compositions disclosed herein include an EBV therapeutic of at least 0.1% w/v or w/w of the composition; at least 1% w/v or w/w of composition; at least 10% w/v or w/w of composition; at least 20% w/v or w/w of composition; at least 30% w/v or w/w of composition; at least 40% w/v or w/w of composition; at least 50% w/v or w/w of composition; at least 60% w/v or w/w of composition; at least 70% w/v or w/w of composition; at least 80% w/v or w/w of composition; at least 90% w/v or w/w of composition; at least 95% w/v or w/w of composition; or at least 99% w/v or w/w of composition.

The amount of genetically modified cells within a composition can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

Exemplary carriers for compositions, including cell-based formulations, include saline, buffered saline, physiological saline, water, Hanks' solution, Ringer's solution, Nonnosol-R (Abbott Labs), Plasma-Lyte A® (Baxter Laboratories, Inc., Morton Grove, Ill.), glycerol, ethanol, and combinations thereof.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and/or trimethylamine salts.

An exemplary chelating agent is EDTA.

Exemplary isotonic agents include polyhydric sugar alcohols including trihydric or higher sugar alcohols, such as glycerin, erythritol, arabitol, xylitol, sorbitol, or mannitol.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Stabilizers refer to a broad category of excipients which can range in function from a bulking agent to an additive which solubilizes the EBV therapeutic or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, α-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on therapeutic weight.

The compositions disclosed herein can be formulated for administration by, for example, injection, inhalation, infusion, perfusion, lavage, or ingestion. The compositions disclosed herein can further be formulated for intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, intrathecal, intratumoral, intramuscular, intravesicular, and/or subcutaneous injection.

For injection, compositions can be formulated as aqueous solutions, such as in buffers including Hanks' solution, Ringer's solution, or physiological saline. The aqueous solutions can include formulatory agents such as suspending, stabilizing, and/or dispersing agents.

Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as powders, capsules and tablets, suitable excipients include binders (gum tragacanth, acacia, cornstarch, gelatin), fillers such as sugars, e.g., lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

Compositions can be formulated as an aerosol. In particular embodiments, the aerosol is provided as part of an anhydrous, liquid or dry powder inhaler. Aerosol sprays from pressurized packs or nebulizers can also be used with a suitable propellant, e.g., dichlorodifluoromethane, trichlorofluoromethane, dichlorotetrafluoroethane, carbon dioxide or other suitable gas. In the case of a pressurized aerosol, a dosage unit may be determined by providing a valve to deliver a metered amount. Capsules and cartridges of gelatin for use in an inhaler or insufflator may also be formulated including a powder mix of EBV therapeutic composition and a suitable powder base such as lactose or starch.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts.

Additionally, compositions can be formulated as sustained-release systems utilizing semipermeable matrices of solid polymers including at least one EBV therapeutic. Various sustained-release materials have been established and are well known by those of ordinary skill in the art. Sustained-release systems may, depending on their chemical nature, release one or more EBV therapeutics following administration for a few weeks up to over 100 days. Depot preparations can be administered by injection; parenteral injection; instillation; or implantation into soft tissues, a body cavity, or occasionally into a blood vessel with injection through fine needles.

Depot formulations can include a variety of bioerodible polymers including poly(lactide), poly(glycolide), poly(caprolactone) and poly(lactide)-co(glycolide) (PLG) of desirable lactide:glycolide ratios, average molecular weights, polydispersities, and terminal group chemistries. Blending different polymer types in different ratios using various grades can result in characteristics that borrow from each of the contributing polymers.

The use of different solvents (for example, dichloromethane, chloroform, ethyl acetate, triacetin, N-methyl pyrrolidone, tetrahydrofuran, phenol, or combinations thereof) can alter microparticle size and structure in order to modulate release characteristics. Other useful solvents include water, ethanol, dimethyl sulfoxide (DMSO), N-methyl-2-pyrrolidone (NMP), acetone, methanol, isopropyl alcohol (IPA), ethyl benzoate, and benzyl benzoate.

Exemplary release modifiers can include surfactants, detergents, internal phase viscosity enhancers, complexing agents, surface active molecules, co-solvents, chelators, stabilizers, derivatives of cellulose, (hydroxypropyl)methyl cellulose (HPMC), HPMC acetate, cellulose acetate, pluronics (e.g., F68/F127), polysorbates, Span® (Croda Americas, Wilmington, Del.), poly(vinyl alcohol) (PVA), Brij® (Croda Americas, Wilmington, Del.), sucrose acetate isobutyrate (SAIB), salts, and buffers.

Excipients that partition into the external phase boundary of microparticles such as surfactants including polysorbates, dioctylsulfosuccinates, poloxamers, PVA, can also alter properties including particle stability and erosion rates, hydration and channel structure, interfacial transport, and kinetics in a favorable manner.

Additional processing of the disclosed sustained release depot formulations can utilize stabilizing excipients including mannitol, sucrose, trehalose, and glycine with other components such as polysorbates, PVAs, and dioctylsulfosuccinates in buffers such as Tris, citrate, or histidine. A freeze-dry cycle can also be used to produce very low moisture powders that reconstitute to similar size and performance characteristics of the original suspension.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

(VIII) Kits. Also disclosed herein are kits including one or more containers including one or more of the anti-EBV antibodies, EBV vaccines, modified cells, EBV therapeutics, drug and/or imaging conjugates, and/or compositions and/or adjuvants described herein. Associated with such container(s) can be a notice in the form prescribed by a governmental agency regulating the manufacture, use, or sale of pharmaceuticals or biological products, which notice reflects approval by the agency of manufacture, use, or sale for human administration. Particular embodiments of kits include: AMMO1, and/or AMMO5; AMMO1-5; a vaccine antigen AMMO1 epitope; AMMO1 and a vaccine antigen AMMO1 epitope; a vaccine antigen AMMO5 epitope; AMMO5 and vaccine antigen AMMO5 epitope; and/or AMMO1, AMMO5, a vaccine antigen AMMO1 epitope and a vaccine antigen AMMO5 epitope. In particular embodiments, kits including a vaccine antigen AMMO1 epitope and/or a vaccine antigen AMMO5 epitope further include one or more vaccine adjuvants.

(IX) Methods of Use. Methods disclosed herein include treating subjects (e.g., humans, veterinary animals (dogs, cats, reptiles, birds) livestock (e.g., horses, cattle, goats, pigs, chickens) and research animals (e.g., monkeys, rats, mice, fish) with compositions disclosed herein.

Treating subjects includes delivering therapeutically effective amounts. Therapeutically effective amounts include those that provide effective amounts, prophylactic treatments and/or therapeutic treatments.

An "effective amount" is the amount of a composition necessary to result in a desired physiological change in the subject. For example, an effective amount can provide an immunogenic effect. Effective amounts are often administered for research purposes. Effective amounts disclosed herein can cause a statistically-significant effect in an in vitro assay, an animal model or clinical study relevant to the assessment of an infection's development, progression, and/or resolution, as well as the effects of the infection. An immunogenic composition can be provided in an effective amount, wherein the effective amount stimulates an immune response.

A "prophylactic treatment" includes a treatment administered to a subject who does not display signs or symptoms of an infection or displays only early signs or symptoms of an infection such that treatment is administered for the purpose of diminishing or decreasing the risk of developing the infection further. Thus, a prophylactic treatment functions as a preventative treatment against an infection and/or the potential effects of an infection (e.g., IM, a lymphoproliferative disorder (e.g., Hodgkin lymphoma, non-Hodgkin lymphoma, Burkitt lymphoma, T cell lymphoma, lymphoproliferative disease), a carcinoma (e.g., nasopharyngeal and/or gastric) or a smooth muscle tumor).

In particular embodiments, a prophylactic treatment can prevent, delay, or reduce the risk of primary infection with a virus. In particular embodiments, primary infection can refer to when an EBV seronegative individual first becomes infected by EBV and therefore becomes EBV seropositive. In this context, seropositive requires a subject's serum to include different antibodies that bind with multiple and different EBV proteins. Primary infection can result in IM.

In particular embodiments, a prophylactic treatment can be given prior to treatment with an immunosuppressant (such as prior to an organ or cell-based transplant or before chemotherapy or ionizing radiation). In particular embodiments, a prophylactic treatment can prevent or reduce the severity of a lymphoproliferative disorder that may result from EBV primary infection during immunosuppression.

In particular embodiments, prophylactic treatments reduce, delay, or prevent the worsening of an infection. In particular embodiments, a prophylactic treatment can prevent, delay or reduce the severity of EBV reactivation. In particular embodiments, a prophylactic treatment can prevent or reduce the severity of a lymphoproliferative disorder that may result from EBV reactivation during immunosuppression. In particular embodiments, a prophylactic treatment can prevent or reduce the risk of a carcinoma (e.g., nasopharyngeal and/or gastric) or a smooth muscle tumor.

Particular uses of the compositions include use as prophylactic vaccines. Vaccines increase the immunity of a subject against a particular infection. Therefore, "EBV vaccine" can refer to a treatment that increases the immunity of a subject against EBV. Therefore, in particular embodiments, a vaccine may be administered prophylactically, for example to a subject that is immunologically naive (e.g., no prior exposure or experience with EBV). In particular embodiments, a vaccine may be administered therapeutically to a subject who has been exposed to EBV. Thus, a vaccine can be used to ameliorate a symptom associated with EBV, such as a lymphoproliferative disorder. A vaccine can also reduce the risk of a carcinoma (e.g., nasopharyngeal and/or gastric) or a smooth muscle tumor.

In particular embodiments, an EBV vaccine is a therapeutically effective composition including one or more EBV antigens including an AMMO epitope disclosed herein that induces an immune response in a subject against EBV. The skilled artisan will appreciate that the immune system generally is capable of producing an innate immune response and an adaptive immune response. An innate immune response generally can be characterized as not being substantially antigen specific and/or not generating immune memory. An adaptive immune response can be characterized as being substantially antigen specific, maturing over time (e.g., increasing affinity and/or avidity for antigen), and in general can produce immunologic memory. Even though these and other functional distinctions between innate and adaptive immunity can be discerned, the skilled artisan will appreciate that the innate and adaptive immune systems can be integrated and therefore can act in concert.

In particular embodiments, administration of an EBV vaccine can further include administration of one or more adjuvants. The term "adjuvant" refers to material that enhances the immune response to a vaccine antigen and is used herein in the customary use of the term. The precise mode of action is not understood for all adjuvants, but such lack of understanding does not prevent their clinical use for a wide variety of vaccines.

Exemplary vaccine adjuvants, include any kind of Toll-like receptor ligand or combinations thereof (e.g. CpG, Cpg-28 (a TLR9 agonist), polyriboinosinic polyribocytidylic acid (Poly(I:C)), α-galactoceramide, MPLA, Motolimnod (VTX-2337, a novel TLR8 agonist developed by VentiRx), IMO-2055 (EMD1201081), TMX-101 (imiquimod), MGN 1703 (a TLR9 agonist), G100 (a stabilized emulsion of the TLR4 agonist glucopyranosyl lipid A), Entolimod (a derivative of *Salmonella* flagellin also known as CBLB502), Hiltonol (a TLR3 agonist), and Imiquimod), and/or inhibitors of heat-shock protein 90 (Hsp90), such as 17-DMAG (17-dimethylaminoethylamino-17-demethoxygeldanamycin).

In particular embodiments a squalene-based adjuvant can be used. Squalene is part of the group of molecules known as triterpenes, which are all hydrocarbons with 30 carbon molecules. Squalene can be derived from certain plant sources, such as rice bran, wheat germ, amaranth seeds, and olives, as well as from animal sources, such as shark liver oil. In particular embodiments, the squalene-based adjuvant is MF59® (Novartis, Basel, Switzerland). An example of a squalene-based adjuvant that is similar to MF59® but is designed for preclinical research use is Addavax™ (Invivo-Gen, San Diego, Calif.). MF59 has been FDA approved for use in an influenza vaccine, and studies indicate that it is safe for use during pregnancy (Tsai T, et al. Vaccine. 2010. 17:28(7):1877-80; Heikkinen T, et al. Am J Obstet Gynecol. 2012. 207(3):177). In particular embodiments, squalene based adjuvants can include 0.1%-20% (v/v) squalene oil. In particular embodiments, squalene based adjuvants can include 5% (v/v) squalene oil.

In particular embodiments the adjuvant alum can be used. Alum refers to a family of salts that contain two sulfate groups, a monovalent cation, and a trivalent metal, such as aluminum or chromium. Alum is an FDA approved adjuvant. In particular embodiments, vaccines can include alum in the amounts of 1-1000 μg/dose or 0.1 mg-10 mg/dose.

In particular embodiments, one or more STING agonists are used as a vaccine adjuvant. "STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM 173)".

In particular embodiments, STING agonists include cyclic molecules with one or two phosphodiester linkages, and/or one or two phosphorothioate diester linkages, between two nucleotides. This includes (3',5')-(3',5') nucleotide linkages (abbreviated as (3',3')); (3',5')-(2',5') nucleotide linkages (abbreviated as (3',2')); (2',5')-(3',5') nucleotide linkages (abbreviated as (2',3')); and (2',5')-(2',5') nucleotide linkages (abbreviated as (2',2')). "Nucleotide" refers to any nucleoside linked to a phosphate group at the 5', 3' or 2' position of the sugar moiety.

In particular embodiments, STING agonists include c-AIMP; (3',2')c-AIMP; (2',2')c-AIMP; (2',3')c-AIMP; c-AIMP(S); c-(dAMP-dlMP); c-(dAMP-2'FdlMP); c-(2'FdAMP-2'FdlMP); (2',3')c-(AMP-2'FdlMP); c-[2'FdAMP(S)-2'FdlMP(S)]; c-[2'FdAMP(S)-2'FdlMP(S)] (POM)2; and DMXAA. Additional examples of STING agonists are described in WO2016/145102.

Other immune stimulants can also be used as vaccine adjuvants. Additional exemplary small molecule immune stimulants include TGF-β inhibitors, SHP-inhibitors, STAT-3 inhibitors, and/or STAT-5 inhibitors. Exemplary siRNA capable of down-regulating immune-suppressive signals or oncogenic pathways (such as kras) can be used whereas any plasmid DNA (such as minicircle DNA) encoding immune-stimulatory proteins can also be used.

In particular embodiments, the immune stimulant may be a cytokine and or a combination of cytokines, such as IL-2, IL-12 or IL-15 in combination with IFN-α, IFN-β or IFN-γ, or GM-CSF, or any effective combination thereof, or any other effective combination of cytokines. The above-identified cytokines stimulate $T_H1$ responses, but cytokines that stimulate $T_H2$ responses may also be used, such as IL-4, IL-10, IL-11, or any effective combination thereof. Also, combinations of cytokines that stimulate $T_H1$ responses along with cytokines that stimulate $T_H2$ responses may be used.

"Immune response" refers to a response of the immune system to an EBV antigen disclosed herein. In particular embodiments, an immune response to an EBV antigen can be an innate and/or adaptive response. In particular embodiments, an adaptive immune response can be a "primary immune response" which refers to an immune response occurring on the first exposure of a "naive" subject to an EBV antigen. For example, in the case of a primary antibody response, after a lag or latent period of from 3 to 14 days depending on, for example, the composition, dose, and subject, antibodies to the EBV antigen can be produced. Generally, IgM production lasts for several days followed by IgG production and the IgM response can decrease.

Antibody production can terminate after several weeks but memory cells can be produced. In particular embodiments, an adaptive immune response can be a "secondary immune response", "anamnestic response," or "booster response" which refer to the immune response occurring on a second and subsequent exposure of a subject to an EBV antigen disclosed herein. Generally, in a secondary immune response, memory cells respond to the EBV antigen and therefore the secondary immune response can differ from a primary immune response qualitatively and/or quantitatively. For example, in comparison to a primary antibody response, the lag period of a secondary antibody response can be shorter, the peak antibody titer can be higher, higher affinity antibody can be produced, and/or antibody can persist for a greater period of time.

In particular embodiments, an immune response against EBV will include antibody production against: the D-I/D-II domain of a gH/gL complex, gB, and/or an AMMO epitope.

A "therapeutic treatment" includes a treatment administered to a subject who displays symptoms or signs of an infection and is administered to the subject for the purpose of diminishing or eliminating those signs or symptoms of the infection or effects of the infection (e.g. IM, a lymphoproliferative disorder (e.g., Hodgkin lymphoma, non-Hodgkin lymphoma, Burkitt lymphoma, T cell lymphoma, lymphoproliferative disease), a carcinoma (e.g., nasopharyngeal and/or gastric) or a smooth muscle tumor). The therapeutic treatment can reduce, control, or eliminate the presence or activity of the infection and/or reduce, control or eliminate side effects of the infection.

In particular embodiments a therapeutic treatment can reduce, control, or eliminate EBV reactivation. In particular embodiments, a reduction in EBV reactivation can be determined by measuring expression of EBV latency genes, wherein detection of fewer latency genes or detection of lower expression levels of latency genes can indicate a reduction in EBV reactivation.

In particular embodiments a therapeutic treatment can reduce, control, or eliminate a primary infection with EBV. In particular embodiments a therapeutic treatment can reduce or eliminate the symptoms of IM.

In particular embodiments, a prophylactic and/or therapeutic treatment can reduce the severity of immunosuppression treatment complications resulting from EBV primary infection of an immunosuppressed individual. In particular embodiments a therapeutically effective treatment to reduce the severity of immunosuppression treatment complications can be given to a pediatric patient. A pediatric patient can refer to patient who is 18 years of age or younger. Pediatric patients are more likely to be EBV seronegative and therefore are at an increased risk of immunosuppression treatment complications from EBV primary infection, as compared to adult patients.

In particular embodiments a therapeutic treatment can eliminate or reduce the severity of a lymphoproliferative disorder. Elimination of or reduced severity of a lymphoproliferative disorder can be indicated by a reduction in lymphocyte count in an individual with the lymphoproliferative disorder.

In particular embodiments a therapeutic treatment can eliminate or reduce the risk or severity of a carcinoma (e.g., nasopharyngeal and/or gastric) or a smooth muscle tumor.

Function as an effective amount, prophylactic treatment or therapeutic treatment are not mutually exclusive, and in particular embodiments, administered dosages may accomplish more than one treatment type.

In particular embodiments, therapeutically effective amounts provide anti-infection effects. Anti-infection effects include a decrease in the number of infected cells, a decrease in volume of infected tissue, reduced infection-associated lymphoproliferation, reduced occurrence of infection-associated carcinoma (e.g., nasopharyngeal and/or gastric) or a smooth muscle tumor, and/or reduction or elimination of a symptom associated with the treated infection.

Effects of EBV infection can include infectious mononucleosis (IM), a lymphoproliferative disorder, and/or a carcinoma (e.g., nasopharyngeal and/or gastric) or a smooth muscle tumor. IM is an illness caused by primary infection with EBV and symptoms of IM can include fever, swollen lymph nodes, swollen tonsils, loss of appetite, fatigue, abdominal pain, and/or spleen enlargement. In particular embodiments, therapeutically effective amounts provide anti-IM effects. Anti-IM effects include a reduction or elimination of an IM symptom.

Lymphoproliferative disorders can refer to the uncontrolled division of lymphocytes. Subjects with compromised immune systems are at increased risk of developing a lymphoproliferative disorder. Examples of lymphoproliferative disorders include Hodgkin lymphoma, non-Hodgkin lymphoma, Burkitt lymphoma, T cell lymphomas, follicular lymphoma, chronic lymphocytic leukemia, acute lymphoblastic leukemia, hairy cell leukemia, B-cell lymphomas, multiple myeloma, Waldenstrom's macroglobulinemia, Wiskott-Aldrich syndrome, lymphocyte-variant hypereosinophilia, post-transplant lymphoproliferative disorder, and autoimmune lymphoproliferative syndrome. In particular embodiments, lymphoproliferative disorders include lymphoproliferative disease, which is an EBV-related lymphoma that occurs in 1-20% of bone marrow and solid organ transplant recipients.

Symptoms of lymphoproliferative disorders can include adenopathy, splenomegaly, and/or an abnormally high lymphocyte count in a subject's blood sample. In particular embodiments, therapeutically effective amounts provide anti-lymphoproliferative disorder effects. Anti-lymphoproliferative disorder effects include a reduction or elimination of a lymphoproliferative disorder or a symptom of a lymphoproliferative disorder.

In particular embodiments, the term "carcinoma" designates any disease involving unregulated proliferation of epithelial cells, and which may result in unregulated cell growth, lack of differentiation, tumors formation, local tissue invasion, and/or metastasis formation. Nasopharyngeal carcinoma (NPC) is a malignant tumor arising from the epithelial lining of the nasopharynx, which is located behind the nose and above the back of the throat. NPC differs significantly from other cancers of the head and neck, based on its causes, occurrence, clinical behavior, and treatment options. NPC is consistently associated with EBV and is the third most frequent virus-associated malignancy in humans.

Gastric carcinomas include gastric cancer, including intestinal and diffuse gastric adenocarcinoma, gastrointestinal stromal tumor (GIST), gastrointestinal leiomyosarcoma, gastrointestinal carcinoid, gastrointestinal lymphoma, esophagogastric adenocarcinoma (OGA), and colorectal carcinoma.

Leiomyomas are tumors composed of smooth muscle cells which can range from clearly benign leiomyoma (fibroids) to malignant leiomyosarcoma. Intermediate variants have also been identified and are termed "smooth muscle tumors of uncertain malignant potential". These may include cellular leiomyomas. Leiomyomas and leiomyosarcomas are most prevalent in the uterine smooth muscle, however, they can occur in any organ system which possesses smooth muscle. The second highest incidence of occurrence for these tumor types is in the gastrointestinal tract. Leiomyomas represent one of the most common benign tumors of the stomach, while gastric leiomyosarcomas represent 2% of all malignant tumors that occur in the stomach.

In particular embodiments, therapeutically effective amounts provide anti-carcinoma (e.g., anti-NPC; anti-gastric carcinoma) or anti-smooth muscle tumor effects which can include reducing the risk or occurrence of a carcinoma or smooth muscle tumor, limiting the further development of the carcinoma or smooth muscle tumor (e.g., tumor growth and/or metastasis), reversing the severity of the carcinoma or smooth muscle tumor, or other beneficial clinical outcomes, as understood one of ordinary skill in the art. For example, beneficial clinical outcomes include loss of detectable tumor (complete response), decrease in tumor size (partial response, PR), tumor growth or cell number increase arrest (stable disease, SD), enhancement of anti-tumor immune response, and/or relief, to some extent, of one or more symptoms associated with a carcinoma or smooth muscle tumor; increase in the length of survival following treatment; and/or decreased mortality at a given point of time following treatment.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including target, body weight, severity of infection, stage of infection, effects of infection (e.g., IM, lymphoproliferative disorders), previous or concurrent therapeutic interventions, idiopathy of the subject and route of administration.

Useful doses can range from 0.1 to 5 µg/kg or from 0.5 to 1 µg/kg. In other non-limiting examples, a dose can include 1 µg/kg, 15 µg/kg, 30 µg/kg, 50 µg/kg, 55 µg/kg, 70 µg/kg, 90 µg/kg, 150 µg/kg, 350 µg/kg, 500 µg/kg, 750 µg/kg, 1000 µg/kg, 0.1 to 5 mg/kg or from 0.5 to 1 mg/kg. In other non-limiting examples, a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

Useful doses can also include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly).

The pharmaceutical compositions described herein can be administered by, without limitation, injection, inhalation, infusion, perfusion, lavage or ingestion. Routes of administration can include intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual administration and more particularly by intravenous, intradermal, intraarterial, intraparenteral, intranasal, intranodal, intralymphatic, intraperitoneal, intralesional, intraprostatic, intravaginal, intrarectal, topical, intrathecal, intratumoral, intramuscular, intravesicular, oral, subcutaneous, and/or sublingual injection.

X) Exemplary Embodiments

1. An anti-EBV antibody including the CDRs:
   SEQ ID NO: 11, SEQ ID NO: 12, SEQ ID NO: 13, SEQ ID NO: 14, SEQ ID NO: 15, and SEQ ID NO: 16;
   SEQ ID NO: 17, SEQ ID NO: 18, SEQ ID NO: 19, SEQ ID NO: 20, SEQ ID NO: 21, and SEQ ID NO: 22;
   SEQ ID NO: 23, SEQ ID NO: 24, SEQ ID NO: 25, SEQ ID NO: 26, SEQ ID NO: 27, and SEQ ID NO: 28;
   SEQ ID NO: 29, SEQ ID NO: 30, SEQ ID NO: 31, SEQ ID NO: 32, SEQ ID NO: 33, and SEQ ID NO: 34; or
   SEQ ID NO: 35, SEQ ID NO: 36, SEQ ID NO: 37, SEQ ID NO: 38, SEQ ID NO: 39, and SEQ ID NO: 40.
2. An anti-EBV antibody including SEQ ID NO: 41 and SEQ ID NO: 42, but with mutations to SEQ ID NO: 41 selected from one or more of D10E; G76S; S83R; T84S; F91Y; V107T; and P113S and/or mutations to SEQ ID NO: 42 selected from one or more of E3V; Q17K; R18T; T20R; Q49Y; S69N; and G100T.
3. An anti-EBV antibody including SEQ ID NO: 41 and SEQ ID NO: 42, but with mutations to SEQ ID NO: 41 including D10E; G76S; S83R; T84S; F91Y; V107T; and mutations to SEQ ID NO: 42 including E3V; Q17K; R18T; T20R; Q49Y; S69N; and G100T.
4. An anti-EBV antibody including SEQ ID NO: 1 and SEQ ID NO: 2.
5. An anti-EBV antibody including SEQ ID NO: 1 with a Q1N mutation and SEQ ID NO: 2.
6. An anti-EBV antibody including SEQ ID NO: 3 and SEQ ID NO: 4.
7. An anti-EBV antibody including SEQ ID NO: 3 with a Q1N mutation and SEQ ID NO: 4.
8. An anti-EBV antibody including SEQ ID NO: 5 and SEQ ID NO: 6.
9. An anti-EBV antibody including SEQ ID NO: 5 with an E1N mutation and SEQ ID NO: 6.
10. An anti-EBV antibody including SEQ ID NO: 5 and SEQ ID NO: 6 with a Q1N mutation.
11. An anti-EBV antibody including SEQ ID NO: 5 with an E1N mutation and SEQ ID NO: 6 with a Q1N mutation.
12. An anti-EBV antibody including SEQ ID NO: 7 and SEQ ID NO: 8.
13. An anti-EBV antibody including SEQ ID NO: 7 with an Q1N mutation and SEQ ID NO: 8.
14. An anti-EBV antibody including SEQ ID NO: 9 and SEQ ID NO: 10.
15. An anti-EBV antibody including SEQ ID NO: 9 with an E1N mutation and SEQ ID NO: 10.
16. An anti-EBV antibody including SEQ ID NO: 9 and SEQ ID NO: 10 with a E1N mutation.
17. An anti-EBV antibody including SEQ ID NO: 9 with an E1N mutation and SEQ ID NO: 10 with a E1N mutation.
18. An anti-EBV antibody that binds the EBV core fusion machinery: heterodimer envelope glycoprotein H/envelope glycoprotein L (gH/gL) and/or glycoprotein B (gB).
19. An anti-EBV antibody that binds the D-I/D-II groove of the EBV gH/gL heterodimer complex.
20. An anti-EBV antibody that binds at least one of residues 60, 70-81, 211-216, and 234-239 of gH; and/or at least one of residues 123-128 of gL.
21. An anti-EBV antibody that binds residues 60, 70-81, 211-216, and 234-239 of gH; and residues 123-128 of gl
22. An anti-EBV antibody that binds residues 73 and 76 of gH wherein residue 73 is lysine and residue 76 is tyrosine.
23. A human anti-EBV antibody, or an antigen-binding portion thereof (e.g., scFv) that dissociates from EBV gH/gL with a $K_D$ of $1 \times 10^{-10}$ or less and a $k_{off}$ rate constant of $3 \times 10^{-5 \; s^{-1}}$ or less, both determined by surface plasmon resonance or biolayer interferometry.
24. An antibody that binds to Epstein Barr Virus (EBV) gH/gL, wherein the antibody (i) binds an epitope on EBV gH/gL including at least one of residues 60, 70-81, 211-216, and 234-239 of gH; and/or at least one of residues 123-128 of gL, (ii) inhibits EBV envelope fusion with a target cell; and (iii) competes for binding with the antibody CL40.
25. An antibody that binds to Epstein Barr Virus (EBV) gH/gL, wherein the antibody (i) binds an epitope on EBV gH/gL including residues 73 and 76 of gH wherein residue 73 is lysine and residue 76 is tyrosine; (ii) inhibits EBV envelope fusion with a target cell; and and (iii) competes for binding with the antibody CL40.
26. An anti-EBV antibody of any of embodiments 1-25, that neutralizes EBV infection of B cells and/or epithelial cells.
27. An anti-EBV antibody of any of embodiments 1-25, that neutralizes EBV infection of B cells and/or epithelial cells.
28. An anti-EBV antibody of any of embodiments 1-25, that neutralizes EBV infection of B cells and/or epithelial cells with an $IC_{50}$ of $3 \times 10^{-9}$M or less.
29. An anti-EBV antibody of any of embodiments 1-25, wherein the antibody neutralizes EBV infection of B cells and wherein the neutralizing EBV infection includes at least 90% neutralization.
30. An anti-EBV antibody of any of embodiments 1-25, wherein the neutralizing antibody neutralizes EBV infection of epithelial cells and wherein the neutralizing EBV infection includes at least 80% or at least 90% neutralization.
31. An anti-EBV antibody of any of embodiments 1-30, including one or more mutations that increase binding to Fc receptors (e.g., G236A/S239D/A330L/I332E (GASDALIE)) or improve ADCC (e.g., substitutions at positions 298, 333, and/or 334 (EU numbering)).
32. An anti-EBV antibody of any of embodiments 1-31, including one or more mutations that increase protein half-life in serum (e.g., M428L/N434S).
33. An anti-EBV antibody of any of embodiments 1-32, including a thioMab.
34. An anti-EBV antibody of any of embodiments 1-33, wherein the Fc region has a reduced fucose content or lacks fucose.
35. An anti-EBV antibody of any of embodiments 1-34, including one or more polyethylene glycol (PEG)-linkages.
36. An anti-EBV antibody of any of embodiments 1-35, including one or more human serum albumin (HSA)-linkages.
37. An anti-EBV antibody of any of embodiments 1-36, wherein the antibody is derived from a monoclonal antibody and the derivation includes at least one mutation of the monoclonal antibody.
38. An anti-EBV antibody of any of embodiments 1-37, wherein the antibody is an scFV or a Fab.
39. An anti-EBV antibody of any of embodiments 1-38, wherein the antibody was produced by a 293F cell.

40. An EBV vaccine including one or more immunogenic proteins that form (i) an AMMO1 epitope or (ii) an AMMO5 epitope.
41. An EBV vaccine of embodiment 40, wherein the AMMO1 epitope includes (i) gH or a fragment of gH that can bind to gL, and (ii) gL or a fragment of gL that can bind to gH; wherein the gH and gL form a gH/gL heterodimer complex.
42. An EBV vaccine of embodiment 41, wherein the vaccine further includes gp42 or a fragment of gp42 that can bind to the gH/gL heterodimer complex.
43. An EBV vaccine of any of embodiments 40-42, wherein the AMMO5 epitope includes gB or a fragment thereof.
44. An EBV vaccine of any of embodiments 40-43, further including one or more adjuvants.
45. An EBV vaccine of embodiment 44, wherein the one or more adjuvants are selected from alum, a squalene-based adjuvant, a STING agonist, or a liposome-based adjuvant.
46. An EBV vaccine of any of embodiments 40-45, wherein the one or more immunogenic proteins are linked to a multimerization domain.
47. An EBV vaccine of embodiment 46, wherein the multimerization domain is a C4b domain.
48. An EBV vaccine of embodiment 47, wherein the multimerization domain is selected from SEQ ID NOs: 55-59.
49. A cell genetically modified to express an anti-EBV antibody or an EBV vaccine of any of embodiments 1-48.
50. A cell of embodiment 49, wherein the cell is genetically modified ex vivo.
51. A cell of embodiment 49, wherein the cell is genetically modified in vivo.
52. A cell of any of embodiments 49-51, wherein the cell is a B cell.
53. A cell of any of embodiments 49-51, wherein the cell is a cell of hematopoeitic origin that differentiates into a B cell.
54. A cell of any of embodiments 49-51, wherein the cell is a CD34+ hematopoeitic stem cell.
55. A composition formulated for administration to a subject including an anti-EBV antibody, an EBV vaccine, or a cell of any of embodiments 1-50, or 52-54.
56. A method of treating a subject for EBV infection including administering to the subject a therapeutically effective amount of a composition of embodiment 55 thereby treating the subject for EBV infection.
57. A method of embodiment 56, wherein the treating reduces or eliminates infectious mononucleosis (IM) and/or symptoms of IM.
58. A method of embodiment 56 or 57, wherein the treating (i) reduces or eliminates a lymphoproliferative disorder and/or symptoms of the lymphoproliferative disorder (e.g., Hodgkin lymphoma, non-Hodgkin lymphoma, Burkitt lymphoma, T cell lymphoma, lymphoproliferative disease), (ii) reduces the risk or occurrence of a carcinoma (e.g., nasopharyngeal carcinoma, gastric carcinoma), and/or (iii) reduces the risk or occurrence of a smooth muscle tumor.
59. A method of neutralizing EBV infection, including contacting cells or tissue with an antibody of any of embodiments 1-39 or a cell of embodiments 49-54, thereby reducing or inhibiting EBV infection of the cells or the tissue.
60. A method of embodiment 59, wherein the cells are epithelial cells.
61. A method of embodiment 59, wherein the cells are B cells.
62. A method of embodiment 59, wherein the cells are epithelial cells and B cells.
63. A method of embodiment 59, wherein the tissue is epithelial tissue.
64. A method of stimulating an anti-EBV immune response in a subject including administering to the subject a therapeutically effective amount of an EBV vaccine of any of embodiments 41-49, thereby stimulating an EBV immune response in the subject.
65. A method of embodiment 64, wherein the subject is EBV seropositive.
66. A method of embodiment 64, wherein the subject is an EBV seronegative subject, and wherein the therapeutically effective amount reduces the risk of EBV infection.
67. A method of embodiment 64, wherein the EBV seronegative subject is a pediatric patient.
68. A method of any of embodiments 56-67, wherein the administering is prior to treatment with an immunosuppressant.
69. A method of any of embodiments 56-68, wherein the subject is a transplant patient.
70. A method of any of embodiments 56-69, wherein the therapeutically effective amount reduces the risk or severity of infectious mononucleosis (IM).
71. An antibody or vaccine of any of the previous embodiments that is recombinantly produced.
72. An antibody of any of the previous embodiments that is recombinantly produced and includes at least one mutation from the sequences depicted in FIG. 24 wherein the at least one mutation is outside of a CDR region.
73. An antibody of any of the preceding embodiments conjugated to an imaging agent or drug (e.g., alkaline phosphatase, horseradish peroxidase, β-galactosidase; pertussis-toxin, diphtheria toxin, ricin, saporin, pseudomonas exotoxin, calicheamicin, taxoids, maytansinoids, tubulysins, dolastatin, dolastatin analogues (e.g., auristatin E, monomethylauristatin E, auristatin PYE and auristatin PHE); Abiraterone, Adriamycine, Anthracycline (Doxorubicin), Azacitidine, Azathioprine, Beuacizumab, Bortezomib, Bleomycin, Capecitabine, Camptotecine, Carboplatin, Cetuximab, Chlorambucil, Cisplatin, curacin, Cyclophosphamide, Cyclophosphoramide, Cytarabine, Dacarbazine, Daunorubicin, Doxifluridine, Epirubicin, Epothilone, Etoposide, 5-Fluorouracil, Gemeitabine, hydroxyurea, Idarubicin, Irinotecan, Imatinib, Lenalidomide, Leucovorin, Leuprorelin, Mechlorethamine, Mercaptopurine, Methotrexate, Mitoxantrone, oxadiazolines, Oxaliplatin, Paclitaxel, Pemetrexed, retinoic acid, Rituximab, sulfonamides, Taxotere (Docetaxel), Teniposide, Tioguanine, Topotecan, Trastuzumab, Valrubicin, Vinblastin, Vincristine, Vindesine, and Vinorelbine.
74. Use of an antibody of embodiment 73, to target EBV antigen-expressing tumor cells for imaging or destruction.

As indicated previously, variants of the sequences disclosed and referenced herein are included. In particular embodiments, variants of proteins can include those having one or more conservative amino acid substitutions or one or more non-conservative substitutions that do not adversely affect the function of the protein in a measure described in for example, FIGS. 8A, 8B. A "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

In particular embodiments, variants of the protein sequences (e.g., antibodies, vaccine proteins, and/or multimerization domains) disclosed herein include sequences with at least 70% sequence identity, at least 80%, at least 85%, at least 90%, at least 95%, at least 96%, at least 97%, at least 98%, or at least 99% sequence identity to the protein sequences described or disclosed herein.

"% sequence identity" refers to a relationship between two or more sequences, as determined by comparing the sequences. In the art, "identity" also means the degree of sequence relatedness between protein sequences or nucleic acid sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine % sequence identity are designed to give the best match between the sequences tested. Methods to determine % sequence identity and similarity are codified in publicly available computer programs. Sequence alignments and % sequence identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced.

"Default values" will mean any set of values or parameters, which originally load with the software when first initialized.

(XI) Example 1

In particular embodiments, the anti-EBV antibodies have one or more of the following characteristics:
A) bind to recombinant and/or wild-type gH/gL;
B) bind residues 60, 70-81, 211-216, and 234-239 of gH; and residues 123-128 of gL;
C) bind residues 73 and 76 of gH wherein residue 73 is lysine and residue 76 is tyrosine;
D) bind to endogenous gH/gL on the surface of an EBV virion;
E) compete for gH/gL binding with the CL40 antibody;
F) bind to gH D-I/D-II linker region, as well as the gL C-terminus;
G) dissociate from EBV gH/gL with a $K_D$ of $1\times10^{-10}$ or less and a $k_{off}$ rate constant of $3\times10^{-5}$ $s^{-1}$ or less, both determined by surface plasmon resonance or biolayer interferometry;
H) bind to wild-type gH/gL with a $K_A$ of more than $1\times10^7 M^{-1}$, more than $100\times10^7 M^{-1}$, more than $200\times 10^7 M^{-1}$ or more than $500\times10^7 M^{-1}$;
I) bind to recombinant and/or wild-type gB;
J) bind to endogenous gB on the surface of an EBV virion;
K) reduce EBV fusion with a target cell;
L) reduce EBV fusion with an epithelial cell;
M) reduce EBV fusion with a B cell;
N) reduce EBV fusion with an epithelial cell and a B cell;
O) neutralize EBV infection of B cells and/or epithelial cells;
P) neutralize EBV infection of B cells and epithelial cells;
Q) neutralize EBV infection of B cells and/or epithelial cells with an $IC_{50}$ of $3\times10^{-9}M$ or less;
R) include CDRs that include the amino acid sequences SEQ ID NOs: 11-16, SEQ ID NO: 17-22, SEQ ID NOs: 23-28, SEQ ID NOs: 29-34, or SEQ ID NOs: 35-40; and/or
S) are recombinantly produced with mutations outside of the CDR regions described herein.

Example 2

An anti-gH/gL antibody that neutralizes dual-tropic infection defines a site of vulnerability on Epstein-Barr virus. Epstein-Barr virus (EBV) infects the majority of adults worldwide. Although most primary infections are asymptomatic, EBV is a causative agent of infectious mononucleosis in children and young adults, and is associated with numerous hematopoietic and epithelial cell cancers (Cohen et al., 2011; Young and Rickinson, 2004). EBV also causes lymphoproliferative disorders in immunocompromised patients such as those with HIV/AIDS or in patients undergoing immune suppression for organ transplantation (Taylor et al., 2015). Thus, a vaccine that prevents EBV infection would be of major benefit to public health (Cohen et al., 2011). EBV targets B cells and epithelial cells during primary infection. Host cell entry is a complex process mediated by several viral glycoproteins that define tropism and mediate membrane fusion at the plasma membrane during epithelial cell infection or following endocytosis during B-cell infection (Miller and Hutt-Fletcher, 1992). Three virally encoded surface glycoproteins (gH, gL and gB) share a conserved function among herpesviruses and are required for EBV infection of both B cells and epithelial cells (Connolly et al., 2011).

gB is a type III transmembrane fusion protein that promotes the merger of the viral and host membranes (Backovic et al., 2009). gB activity is dependent upon the heterodimeric gH/gL complex, which acts as an adaptor that triggers gB-mediated fusion upon binding a cell-surface receptor on target host cells (Mohl et al., 2016; Stampfer and Heldwein, 2013). The gH/gL complex is anchored to the cell membrane through a C-terminal trans-membrane domain on gH. The expression of gL is critical for the correct folding and cell surface expression of the gH/gL complex (Hutchinson et al., 1992; Li et al., 1997). gH/gL assumes an elongated structure including four distinct domains designated D-I to D-IV. D-I is formed by gL and the N-terminus of gH whereas the rest of gH includes D-II through D-IV (Matsuura et al., 2010). D-I and D-III are separated by a prominent groove and connected by a linker helix (Matsuura et al., 2010). Mutations that affect membrane fusion have been identified throughout gH/gL, but most map to D-I and the DI/D-II interface, including the linker helix and the groove between D-I and D-III (Chen et al., 2013a; Mohl et al., 2014; Omerovic et al., 2005; Plate et al., 2011; Sathiyamoorthy et al., 2016; Wu et al., 2005), indicating that this region of gH/gL is important for the interaction with, or activation of gB.

gH/gL is required for efficient binding to epithelial cells (Molesworth et al., 2000; Oda et al., 2000). $\alpha v\beta 5$, $\alpha v\beta 6$, or $\alpha v\beta 8$ integrins (Chesnokova and Hutt-Fletcher, 2011; Chesnokova et al., 2009), and the ephrin receptor A2 (EphA2) (Chen et al., 2018; Zhang et al., 2018) have been identified as epithelial cell surface receptors that interact directly with gH/gL to trigger gB-mediated fusion. An exposed KGD motif on D-III has been proposed to mediate gH/gL binding to integrins since a D-II-derived peptide containing the KGD motif inhibits binding of soluble gH/gL to epithelial cells and partially blocks EBV infection (Chesnokova and Hutt-Fletcher, 2011; Chesnokova et al., 2009). The binding site of EphA2 on gH/gL is unknown.

B cell infection requires an additional viral glycoprotein, gp42, which forms a 1:1 complex with gH/gL (Kirschner et al., 2006). The N-terminus of gp42 mediates high-affinity interactions with gH/gL and the C-terminus binds to the B chain of human leukocyte antigen (HLA) class II which leads to triggering of gB-mediated fusion through the gH/gL/gp42 complex (Haan et al., 2000; Sathiyamoorthy et al., 2014; Spriggs et al., 1996). Although gp42 is necessary for B cell infection, it inhibits epithelial cell infection (Kirschner et al., 2007; Kirschner et al., 2006; Wang et al., 1998) through a mechanism that is not entirely clear. Residues connecting the N- and C-terminal domains of gp42 make contact with the gH/gL KGD motif suggesting that gp42 could prevent integrin attachment by competing for the same binding site (Sathiyamoorthy et al., 2016).

However, an N-terminal peptide of gp42 that binds distal to the KGD motif is sufficient to inhibit epithelial cell infection (Kirschner et al., 2007; Sathiyamoorthy et al., 2016).

Virions produced in B cells contain lower levels of gp42 than virions produced in epithelial cells. Thus, virions that shed from one cell type preferentially infect the other (Borza and Hutt-Fletcher, 2002).

gp350 is the most abundant glycoprotein on the surface of EBV virions (Edson and Thorley-Lawson, 1981) and it promotes viral attachment to target cells through a high affinity interaction with CD21 (Tanner et al., 1987) or CD35 (Ogembo et al., 2013) without mediating fusion. Although anti-gp350 antibodies can inhibit B cell infection in vitro, some can enhance infection of CD21-negative epithelial cells (Turk et al., 2006).

Sera from EBV-infected individuals can neutralize both B cell and epithelial cell infection in vitro (Miller et al., 1972; Moss and Pope, 1972; Sashihara et al., 2009; Tugizov et al., 2003). However, the antigens and epitope specificities targeted by the corresponding neutralizing antibodies are not known. To date, only a handful of anti-EBV neutralizing monoclonal antibodies (MAbs) have been characterized, and all of them are of murine origin. The 72A1 MAb binds to the CD21/CD35 binding site on gp350 (Ogembo et al., 2013; Tanner et al., 1987) and potently neutralizes B cell infection (Hoffman et al., 1980; Sashihara et al., 2009), but has no effect on infection of CD21-negative epithelial cells (Molesworth et al., 2000; Tugizov et al., 2003). The C1 MAb binds to an unknown epitope on gp350 and inhibits B cell infection but promotes infection of epithelial cells (Thorley-Lawson and Geilinger, 1980; Turk et al., 2006). F-2-1 targets gp42 and inhibits B cell but not epithelial cell infection (Chesnokova and Hutt-Fletcher, 2011; Li et al., 1995; Molesworth et al., 2000; Strnad et al., 1982). CL55 is the only known EBV gB-specific MAb and it is non-neutralizing in both B-cell and epithelial cell infection assays (Chesnokova and Hutt-Fletcher, 2011; Wu et al., 2005).

E1D1, CL59, and CL40 are murine MAbs which bind to gH/gL and neutralize epithelial cell infection but fail to efficiently block infection of B cells (Balachandran et al., 1987; Chesnokova and Hutt-Fletcher, 2011; Li et al., 1995; Molesworth et al., 2000).

Mutagenesis and negative-stain electron microscopy (EM) studies have mapped the CL59 epitope to D-IV of the gH/gL complex (Sathiyamoorthy et al., 2017; Wu et al., 2005). High-resolution structures have recently demonstrated that E1D1 binds exclusively to gL (Sathiyamoorthy et al., 2016), and that CL40 binds to an epitope at the D-II/D-III interface of gH (Sathiyamoorthy et al., 2017), but the mechanisms by which these MAbs neutralize EBV infection have not been elucidated.

The isolation and structural characterization of neutralizing MAbs elicited during natural human infections with human immunodeficiency virus (HIV), influenza virus, respiratory syncytial virus (RSV), human cytomegalovirus (CMV) and dengue virus (DENV) have defined critical epitopes on these pathogens and advanced vaccine design (Rappuoli et al., 2016). To better characterize the human humoral immune response against EBV, antigen-specific memory B cells from EBV-infected individuals were sought. Several anti-gB antibodies were obtained one of which neutralized epithelial cell, but not B cell infection. One anti-gH/gL antibody, called AMMO1 that potently neutralizes both epithelial and B cell infection in vitro (and thus defines an important site of EBV vulnerability) was obtained. Using a combination of cryo-electron microscopy (cyroEM) and X-ray crystallography the structure of the gH/gL/gp42/AMMO1 complex was determined. This analysis demonstrated that AMMO1 binds to a discontinuous epitope on gH/gL at the interface between D-I and D-III, which is implicated in triggering of gB-mediated fusion of the viral and cellular membranes.

The isolation and characterization of AMMO1 described herein paves the way for the design of a gH/gL-based subunit vaccine. The dual-tropic inhibition of EBV entry by AMMO1 indicates that this MAb could also have therapeutic potential in blocking EBV infection, reactivation, and amplification in immunocompromised individuals and transplant recipients.

Material and Methods.

Human Subjects. Peripheral blood mononuclear cells (PBMC) and serum were collected from seven HIV-uninfected, and eight HIV-infected adults recruited at the Seattle HIV Vaccine Trials Unit (Seattle, Wash., USA) as part of the study "Establishing Immunologic Assays for Determining HIV-1 Prevention and Control", also referred to as Seattle Assay Control or SAC. All participants signed informed consent, and the following institutional human subjects review committee approved the protocol prior to study initiation: Fred Hutchinson Cancer Research Center IRB (Seattle, Wash., USA). Donors were selected randomly and no considerations were made for age, or sex.

Plasmids. cDNA encoding to gH (AA 19-679, Genbank AFY97969.1), gp42 (amino acids 33-223, genbank: AFY97939.1), gp350 (AA 1-470, Genbank: AAD51697.1), and gB AA 23-683, Genbank: AFY97983.1) with the residues WY112-113 mutated to HR and WLIW193-196 mutated to RVEA (Backovic et al JIV 2007) were synthesized with an N-terminal TPA leader peptide (MDAMKR-GLCCVLLLCGAVFVSPSAS (SEQ ID NO: 62)) and a C-terminal HIS-Avi Tag (GSGSGHHHHHHGLNDIFEA-QKIEWHE (SEQ ID NO: 63)) and cloned into the EcoRI and NotI sites of the pTT3 plasmid. gL (AA 24-137 Genbank: AFY97944.1), was synthesized with an N-terminal TPA leader peptide (SEQ ID NO: 62) without a C terminal tag and cloned into the EcoRI and NotI sites of the pTT3 plasmid. Site directed mutagenesis was used to introduce stop codons into gH and gp42 between the HIS and Avi tags to produce expression plasmids without the Avi-Tag, and to introduce the T62A and T175A mutations into gH and gp42, respectively. The murine CD40L sequence flanked by an XbaI-Kozak sequence on the 5' end and a Not I site on the 3' end was synthesized by Genscript and cloned into the XbaI and NotI sites of pCDH-EF-MCS-IRES-RFP vector (Systembio) to create pCDH-muCD40L-RFP.

pCAGGS expression plasmids for gH, gL, gB, and pT7EMCLuc (which carries a luciferase-containing reporter plasmid under the control of the T7 promoter) were kindly provided by Dr. R. Longnecker (Haan et al., 2001; Okuma et al., 1999; Plate et al., 2011). Plasmids for the expression of humanized, recombinant 72A1 were provided by Dr. F. Wang (Herrman et al., 2015). p509, an expression plasmid encoding BZLF1, was provided by Dr. W. Hammerschmidt (Delecluse et al., 1998). p2670, an expression plasmid encoding BALF4, was provided by Dr. H. Delecluse (Neuhierl et al., 2002).

Recombinant Antibody Cloning. Codon optimized cDNAs encoding a murine leader sequence MGWSCIIL-FLVATATGVHS (SEQ ID NO: 64) followed by the human IgG1, IgL or IgK constant regions were synthesized by IDT and cloned into the EcoRI and BamHI sites of pTT3. VH and VL sequences recovered from sorted B cells using RT PCR (see below) were amplified with gene-specific primers or synthesized by IDT and assembled in frame into the appropriate linearized IgG IgK or IgL plasmid using InFusion cloning (Clontech) according to the manufacturer's instructions. The sequences of the recombinant antibody plasmids were verified by Sanger sequencing (Genewiz).

Cell lines. All cell lines were incubated at 37° C. in the presence of 5% $CO_2$ and were not tested for mycoplasma contamination. 293T (ATCC: CRL-3216) cells were grown in DMEM containing 10% FBS, 2 mM L-glutamine, 100 U/ml penicillin, and 100 µg/ml streptomycin (cDMEM).

CHO K-1 (ATCC: CCL-61), and AGS (ATCC:CRL-1739) cells were maintained in Ham's F-12+10% FBS, 2 mM L-glutamine, 100 U/ml penicillin, and 100 µg/ml streptomycin (cF-12). Raji cells, as well as the 72A1 (ATCC: HB-168), CL55 (Wu et al., 2005), F-2-1 (Strnad et al., 1982), CL40, CL59 (Molesworth et al., 2000), and E1D1 (Balachandran et al., 1987) hybridomas, were maintained in RMPI+10% FBS, 2 mM L-glutamine, 100 U/ml penicillin, and 100 µg/ml streptomycin (cRPMI). 293-2089 cells (Delecluse et al., 1998) were grown in cRPMI containing 100 µg/ml hygromycin. AKATA B cells harboring EBV in which the thymidine kinase gene has been replaced with a neomycin and GFP cassette virus (AKTA-GFP) (Molesworth et al., 2000), were grown in cRMPI containing 350 µg/ml G418. SVKCR2 cells (Li et al., 1992) were grown in DMEM containing 10% cosmic calf serum, 2 mM L-glutamine, 100 U/ml penicillin, and 100 µg/ml streptomycin, 10 ng/ml cholera toxin and 400 µg/ml G418. 293-T7 cells (Omerovic et al., 2005) were maintained in cDMEM containing 100 µg/ml Zeocin. 293F cells (ThermoFisher) were maintained in Freestyle 293 media with gentle shaking.

Recombinant Protein Expression. Plasmids encoding EBV proteins, or antibody heavy and light chains were transfected into 293F cells at a density of $10^6$ cells/ml in Freestyle 293 media (ThermoFisher) using the 293Free transfection reagent (EMD Millipore) according to the manufacturer's instructions. Expression was carried out in Freestyle 293 media for 6 days after which cells and cellular debris were removed by centrifugation at 4,000×g followed by filtration through a 0.22 µm filter. Clarified cell supernatant containing EBV proteins was passed over Ni-NTA resin (Qiagen), pre-equilibrated with Ni-NTA binding buffer (0.3 M NaCl, 20 mM Tris, 10 mM imidazole, pH 8.0), followed by extensive washing with Ni-NTA binding buffer, and then eluted with 250 mM imidazole, 0.3 M NaCl, 20 mM Tris, pH 8.0 (Ni-NTA elution buffer). Purified proteins were then dialyzed overnight into PBS. AVI-tagged gB, gp350, and gp42 were biotinylated in vitro using the In Vitro Biotin Ligase Kit (Avidity) according to the manufacturer's instructions.

Proteins were further purified by SEC using a 10/300 S 200 column (GE Healthcare) equilibrated into HBSE (10 mM HEPES, 150 mM NaCl, 2 mM EDTA pH 7.4), which also served to remove un-ligated biotin and BirA enzyme. Biotinylated proteins were flash frozen and stored at −20° C. until use.

Clarified cell supernatant containing recombinant antibodies was passed over Protein A Agarose (Pierce, cat #20333), followed by extensive washing with PBS, and then eluted with 1 ml of Pierce IgG Elution Buffer, pH 2.0 (cat. #21028) into 0.1 ml of Tris HCl, pH 8.0. Purified antibodies were then dialyzed overnight into PBS.

Recombinant monomeric DRB1*01:1 complexed with the Human CLIP peptide was obtained from the NIH Tetramer Core Facility. αvβ5 (Cat #2528-AV-050), αvβ6 (Cat #3817-AV-050) and αvβ8 (Cat #4135-AV-050) integrins, and the Ephrin receptor A2 (Cat #3035-A2-100) were purchased from R&D systems.

Recombinant Protein Biotinylation. AMMO1, E1D1, CL40, CL59, and gH/gL were biotinylated at a theoretical 1.5:1 biotin/protein with the EZ-Link Sulfo-NHS-Biotin Kit (ThermoFisher Scientific) according to the manufacturer's instructions. Free biotin was removed by 3 successive rounds of dilution with PBS and concentration with a 30,000 MCOW concentrator (Amicon).

Antigen Binding Fragment (Fab) preparation. AMMO1 Fab was produced by digesting AMMO1 IgG with Endoproteinase Lys-C(Roche) overnight at 37° C. (10 µg IgG: Ing Lys C). Fab fragments were separated from Fc fragments with protein A agarose (Pierce), then further purified with SEC (Superdex 200). CL40 Fab was produced by digesting CL40 IgG with activated immobilized ficin (Thermo Fisher) at 37° C. for 48 hrs. Fab fragments were separated from Fc fragments with protein A agarose (Pierce), then further purified with SEC (Superdex 200).

3T3-CD40L cell line generation. Lentiviruses were produced by co-transfecting the pCDH-muCD40L-RFP, psPAX2 (Addgene #12260) and pMD2.G (Addgene #12259) plasmids at a 4:2:1 ratio (6, 3, and 1.5 µg, respectively) into 293T cells using the GeneJuice Transfection reagent according to the manufacturer's instructions. 48 hours later the supernatant was collected and passed through a 0.22 µm filter. Supernatant was then transferred to 3T3 cells followed by the addition of 4 µg/ml polybrene (ATCC # CRL-1658) and incubated overnight in cDMEM. Cells were then passaged for 7 days. CD40L-expressing cells were identified with a PE-labeled CD154 antibody (Biolegend Cat #106505) and sorted by FACS on a Beckman FACS Ariall. Sorted cells were expanded and cultured indefinitely.

Biolayer Interferometry (BLI). BLI assays were performed on the Octet Red instrument (ForteBio, Inc.) at 30° C. with shaking at 1,000 RPM.

Validation of EBV glycoprotein antigenicity using murine hybridomas: Anti-EBV antibodies were captured using Anti-Mouse IgG Fc capture (AMC) biosensors (Fortebio) by immersing sensors directly into hybridoma culture supernatants for 600 s. A baseline signal (nm shift) was recorded for 1 min in kinetics buffer (KB: 1×PBS, 0.01% BSA, 0.02% Tween 20, and 0.005% NaN3) at pH 7.4 or pH 5.0 as indicated. Sensors were then immersed into solutions containing a 0.5 µM concentration of each EBV glycoprotein for 250 s to measure association, followed by immersion in KB for 500 s to measure dissociation. All measurements of antibody binding were corrected by subtracting the signal obtained from simultaneous traces performed with the corresponding envelopes in the absence of antibody, using PBS only.

Kinetic analysis: Anti-Human IgG Fc capture (AHC) sensors (for human antibodies), AMC (for murine antibodies), or streptavidin sensors (for biotinylated antibodies or biotinylated gH/gL or gH T62A/gL) were immersed in KB containing 10 µg/ml of purified antibody or biotinylated protein for 200 s. After loading, the baseline signal was then recorded for 1 min in KB. The sensors were immersed into wells containing serial dilutions of purified recombinant gH/gL or gH-T62A/gL in KB for 250 s (association phase), followed by immersion in KB for an additional 750 s (dissociation phase). The background signal from each analyte-containing well was measured using empty reference sensors, and subtracted from the signal obtained with each corresponding ligand-coupled sensor. The background signal of ligand-coupled sensors in KB was subtracted from each sensor at each time-point using the data analysis software (ForteBio). Kinetic analyses were performed at least twice with an independently prepared analyte dilution series. Curve fitting was performed using a 1:1 binding model and the data analysis software (ForteBio). Mean $k_{on}$, $k_{off}$ values were determined by averaging all binding curves that matched the theoretical fit with an $R^2$ value of >0.99. Binding analyses at pH 5.0 were carried out as above using biotinylated antibodies and Streptavidin sensors.

Antibody competition binding assays: Biotinylated antibodies were diluted to 10 µg/ml and captured onto streptavidin sensors for 120 s. The baseline interference was then read for 60 s in KB buffer, followed by immersion for 250 s (association phase) in a 250 nM solution of gH/gL alone, or gH/gL that had been pre-incubated with 500 nM of non-biotinylated Abs for 20 min in KB. Sensors were then immersed in KB for 750 s (dissociation phase).

gH/gL/gp42-HLA-DR binding assays: Biotinylated gH/gL was immobilized on streptavidin biosensors, and then immersed into KB buffer for 60 seconds followed by into a 1 µM solution of gp42 for 200 seconds. One biosensor was then immersed into a 1 µM solution of the AMMO1 Fab, while the other was immersed in KB for 200 seconds. The biosensors were then immersed into a 500 nM solution of HLA-DR for 300 seconds (association phase) and then into KB for 300 seconds (dissociation phase). One gH/gL-gp42 loaded sensor was immersed in buffer as a reference during the association and dissociation steps and used to subtract the background signal.

gH/gL-integrin binding assays: Biotinylated gH/gL was diluted to 10 µg/ml and captured onto streptavidin sensors for 120 s. The baseline interference was then read for 60 s in KB buffer containing followed by immersion for 200 s (association phase) into KB buffer containing 1 µM of $\alpha v \beta 5$, $\alpha v \beta 6$, $\alpha v \beta 8$, gp42, or an HIV-1 Envelope protein (426c TM4 ΔV1-3(McGuire et al., 2016)). Sensors were then immersed in KB containing for 400 s (dissociation phase).

gH/gL EphA2 binding assays: Biotinylated gH/gL was diluted to 30 µg/ml and immobilized on streptavidin biosensors for 120 s, and then immersed in KB buffer for 60 seconds.

Biosensors were then immersed into either KB buffer or into a 1.5 µM solution of AMMO1 for 60 seconds. The biosensors were then immersed into a 3.5 µM solution of EphA2 for 250 seconds (association phase) and then into KB for 250 seconds (dissociation phase). To control for non-specific binding due to the high analyte concentration, the binding signal to biotinylated gp42 immobilized on biosensors assayed under identical conditions was subtracted.

Serum ELISA. 50 ng/well of gp350, gp42 or gB, were adsorbed onto 96 well Immulon 2HB ELISA plates at either 37° C. for 1 hour or room temperature overnight in a solution of 0.1 M NaHCO$_3$ pH 9.4-9.6. Plates were then washed 4 times with ELISA washing buffer (1×PBS, 0.02% Tween 20) prior to blocking at 37° C. for 1 hour or 4° C. overnight with 250 µl per well of PBS containing 10% Non-Fat Milk and 0.02% Tween 20 (blocking buffer). After blocking, plates were washed 4× with ELISA washing buffer. Serum was diluted in blocking buffer and three-fold serial dilutions were performed in duplicate followed by a 1 hour incubation at 37° C. Following 4 additional washes with ELISA washing buffer, a 1:3000 dilution of goat anti-human Ig HRP (Southern Biotech 2010-05) in blocking buffer was added to each well and incubated at 37° C. for 1 hour followed by 4 washes with wash buffer. 50 µl/well of SureBlue Reserve TMB Microwell Peroxidase substrate (KPL 53-00-00) was added. After 3 min, 50 µl/well of 1N Sulfuric Acid was added and the A450 of each well was read on a Molecular Devices SpectraMax M2. Analysis was performed using the Prism 6 package (Graphpad Software).

ELISAs against gH/gL were performed essentially the same as above except for the following changes. 100 µl/well of a 1 µg/ml solution of His-tagged gH/gL was immobilized on Nickel Coated Plates (Pierce Cat #15442) in 1×PBS and 0.5% Tween 20 overnight at 4° C. The blocking buffer consisted of PBS containing 10% Non-Fat Milk, 0.02% Tween20, and 10 mM imidazole. The background of serum reactivity with the nickel-coated plates of each donor's sera was subtracted from that of gH/gL at each serum dilution.

Conjugation of antigens to fluorescently labeled streptavidin. Biotinylated EBV glycoproteins were mixed with streptavidin-phycoerythrin (SA-PE, Prozyme Cat # PJRS25) at a 4:1 biotin to streptavidin ratio.

B cell sorting. Cryopreserved PBMC were thawed into cRMPI, at a concentration of 4 million PBMC/ml, followed by centrifugation at 300×g for 5 min. Cells were suspended in 100 µl cRPMI and incubated with an irrelevant, Avi-tagged recombinant decoy protein from *Plasmodium yoelii* (PY-gamma, a kind gift from Dr. D. N. Sather) conjugated to streptavidin PE labeled with Dylite 650 (SA-PE-DL650) to a final concentration of 10 nM of PE-DL650 for 10 min at 4° C.

Antigen (gB, gH/gL, gp42, or gp350) conjugated to streptavidin-phycoerythrin (SA-PE) was then added to a final concentration of 10 nM and incubated for 20 min at 4° C. 25 µl of Anti-PE MicroBeads (Miltenyi Biotech) were added and incubated for an additional 30 min at 4° C. The cell/bead mixture was then passed over a LS MACS separation column (Miltenyi Biotec #130-042-401) on a MACS separator and washed with 6 ml of FACS buffer (PBS+1% FBS). The column was removed from the MACS separator and eluted two times with 5 ml of FACS buffer. PE-enriched PBMC were then pelleted by centrifugation at 300×g for 5 min, and then re-suspended in 100 µl of FACS buffer. Enriched PBMC were then stained with the following antibodies: IgM-FITC (BD #555782) at a 1:20 dilution, IgD-PerCP-Cy5.5 (BD #561316) at a 1:100 dilution, CD27-PE-Cy7 (eBioscience #25-0271-82) at a 1:200 dilution, CD20-eF450 (eBioscience 48-0209-42) at a 1:100 dilution, CD3-BV711 (BD #563725) at a 1:100 dilution, CD14-BV711 (BD #563372) at a 1:100 dilution, CD16-BV711 (BD 563127) at a 1:100 dilution, CD19-BV786 (BD 563325) at a 1:100 dilution, and a fixable viability dye eFluor 506 (eBioscience #65-0866-14) at a 1:200 dilution for 25 min at 4° C. Stained cells were diluted to 5 ml with FACS buffer, pelleted by centrifugation at 300×g for 5 min and then suspended in 0.5 ml of FACS buffer and subjected to FACS on a BD FACS Aria II.

Live, antigen-positive class-switched B cells (Live/dead-, CD3-, CD14-, CD16-, CD19+CD20+ IgM-, IgD-, PE-DL650-, PE+) were sorted individually into 96 well plates containing $2.86 \times 10^4$ irradiated 3T3-CD40L cells in 100 µl/well IMDM containing 10% FBS, 1× glutamax, 100 U/ml penicillin, 100 µg/ml streptomycin, 100 U/ml IL2 (Roche, cat. no. 11147528001) and 50 ng/ml IL21 (Invitrogen, cat. no. PHC0215) (Huang et al., 2013). Cells were cultured at 37° C., 5% $CO_2$. 13 days later the 80 µl of supernatant was transferred into 96 well round-bottom plates. 20 µl of lysis buffer (15 mM Tris pH 8.0, containing RNAse inhibitor) was added to the wells containing cells. The cells were then frozen on dry ice and stored at −80° C.

Sorted Cell Supernatant Screening. Nunc 384 well MaxiSorp plates were coated overnight at room temperature with 50 µl of a 0.5 µg/ml solution of unlabeled goat anti human IgG or gB, in 0.1 M $NaHCO_3$ pH 9.4-9.6. 100 µl/well of a 1 µg/ml solution of His-tagged gH/gL was immobilized 96 well nickel coated plates in 1×PBS and 0.5% Tween 20 overnight at 4° C. ELISA plates were then washed 4× with ELISA wash buffer, and cell supernatant diluted 1:1 with blocking buffer was then added to the appropriate wells (one well per antigen). ELISA was performed as described under "Serum ELISA", except that all volumes were halved in the 384 well plates. Wells were scored as positive if the A450 was >2 standard deviations of the A450 recorded with the feeder cell only control supernatants (n=4 wells).

VH/VL Recovery from Sorted Cells. Wells containing sorted cells that were antigen positive by ELISA were thawed and 15 µl of cell lysate was transferred to a thin wall PCR tube and mixed with 10 µl of RT mix containing 5 µl of first strand buffer, 1.25 µl of 100 mM DTT, 0.06 µl of IGEPAL (Sigma Aldrich Cat. #68987-90-6), 125 ng of random hexamers (Invitrogen Cat. #N8080127), 2 µl of 10 mM dNTP mix, 0.5 µl of RNAse inhibitor (Invitrogen Cat #100000840), and 1 µl of superscript III reverse transcriptase (Invitrogen Cat #56575). RT was carried out at 42° C. for 10 min, 25° C. for 10 min, 50° C. for 60 min, and 94° C. for 5 min, followed by a hold at 4° C.

3 µl of cDNA was used as a template for a two-step nested VH, VK, or VL amplification using the primer set and protocol developed by Doria-Rose and colleagues (Doria-Rose et al., 2015). VH and VL amplicons were Sanger sequenced and then cloned into recombinant expression vectors and expressed as recombinant IgG1 proteins.

Virus Production. To produce B-cell tropic GFP reporter viruses (B95-8/F), $9 \times 10^6$ 293-2089 cells were seeded on a 15 cm tissue culture plate in cRPMI containing 100 µg/ml hygromycin. 24 hours later the cells were washed 2× with PBS, media was replaced with cRMPI without hygromycin, and the cells were and transfected with 15 µg of each of p509 (Delecluse et al., 1998) and p2670 (Neuhierl et al., 2002) expressing BZLF1 and BALF4, respectively, using GeneJuice transfection reagent (EMD Millipore Cat #70967) according to the manufacturer's instructions. 72 hours later the cell supernatant was collected, cell debris removed by centrifugation at 300×g for 5 min and then passed through a 0.8 µm filter. To produce epithelial cell tropic virus, B cells harboring AKATA-GFP EBV were suspended at $4 \times 10^6$ cells/ml in RPMI containing 1% FBS. Anti-human IgG was added to a final concentration 100 µg/ml and incubated at 37° C. for 4 hours. Cells were then diluted to $2 \times 10^6$ cells/ml in RPMI containing 1% FBS and incubated for 72 hours. Cells were pelleted by centrifugation at 300×g for 10 min and then the supernatant was passed through a 0.8 µm filter. Bacitracin was added to a final concentration of 100 µg/ml.

Virions were concentrated 25× by centrifugation at 25000×g for 2 hours and re-suspended in RPMI containing 100 µg/ml bacitracin. Virus was stored at 4° C. for up to 2 weeks.

B cell Neutralization Assay. B cell neutralization assays were carried out in Raji cells essentially as described (Sashihara et al., 2009). Monoclonal antibodies were serially diluted in duplicate wells of 96 well round-bottom plates containing 25 µl of cRPMI in duplicate. 12.5 µl of B95-8/F virus (diluted to achieve an infection frequency of 1-5% at the final dilution) was added and incubated at 37° C. for 1 hour. 12.5 µl of cRMPI containing $4 \times 10^6$ Raji cells/ml was added to each well and incubated for another hour at 37° C. The cells were then pelleted, washed once with cRMPI, and re-suspended in cRMPI. Antibody concentration is reported relative to the final infection volume (50 µl). After 3 days at 37° C., cells were fixed in 2% paraformaldehyde. The percentage of GFP+ Raji cells as determined on a BD LSRII cytometer.

To account for any false positive cells due to autofluorescence in the GFP channel, the % GFP+ cells in negative control wells (no virus, n=5) was subtracted from each well. % neutralization in each well was defined as: [% GFP+ cells in the positive control wells containing virus alone (n=5 wells)−% GFP+ cells in the antibody containing well]/% GFP+ cells in the positive control wells×100.

The % neutralization for each well was plotted as a function of the log 10 of the MAb concentration. The neutralization curve was fit using the log(inhibitor) vs response-variable slope (four parameters) analysis in Graphpad Prism 6 software.

Epithelial Cell Neutralization Assay. $1.5 \times 10^4$ SVKCR2 cells per well were seeded into a 96 well tissue culture plate. The following day antibodies were serially diluted in duplicate wells containing 20 µl of media in a 96 well round bottom plate followed by the addition of 20 µl of 25× concentrated epithelial cell-tropic virus and incubated for 15 min. Media was aspirated from the SVKCR2 cells and replaced by the antibody-virus mixture followed by a 3 hour incubation at 37° C. The antibody-virus mixture was then aspirated and replaced with media. 48 hours later the cells were trypsinized and the percentage of GFP positive cells were determined on an BD LSRII cytometer. Percent neutralization was determined as in the B cell neutralization assay.

Cell Surface Binding Assays. Streptavidin-PE conjugated to 0.5 µg of gH/gL biotin (gH/gL-PE), or to 0.5 µg of gB (gB-PE) was diluted in 10 µl of PBS to individual wells of a 96 well plate. An equimolar amount of gp42 was added to select wells containing gH/gL-PE. 7 µg of monoclonal antibodies, AMMO1, AMMO4, or CL40 were added to select wells containing gH/gL±gp42 and incubated for 1.5 hours at room temperature. Meanwhile, adherent AGS cells were trypsinized, washed with cF-12 and then allowed to recover at 37° C. 5% $CO_2$ for 30 min. The cells were gently agitated and then returned to 37° C. 5% $CO_2$ for an additional 30 min. Recovered AGS, and Raji cells were pelleted by centrifugation at 300×g for 3 min and then resuspended at a density of $1 \times 10^6$ cells/ml in ice-cold 0.5% bovine serum albumin (BSA) in PBS. 100 µl of AGS or Raji cells were added to wells containing SA-PE, SA-gB, SA-PE gH/gL±gp42 and ±antibodies in quadruplicate, and incubated on ice for 1 h. Cells were pelleted by centrifugation at 300×g for 3 min, washed with 200 µl of ice cold 0.5% BSA in PBS, pelleted again and resuspended in 10% phosphate buffered formalin. The amount of PE staining was determined on a BD LSRII cytometer.

Virus Free Fusion Assay. CHO-K1 cells were seeded onto six-well plates at a density of $3 \times 10^5$ cells/well. 24 hours later, the cells were transfected with 0.5 µg each of pCAGGS-gH, pCAGGS-gL, pCAGGS-gB (Haan et al., 2001) and 0.8 µg of pT7EMCLuc, which carries a luciferase-containing reporter plasmid under the control of the T7 promoter (Okuma et al., 1999), using GeneJuice, according to the manufacturer's instructions.

Meanwhile, 293-T7 cells were seeded into a 96 well plate at a density of $1 \times 10^4$ cells per well in a volume of 100 µl/well of cF-12 without Zeocin selection. 8 hours later, the transfected CHO cells were trypsinized, washed once with cF-12, and re-suspended at a density of $1 \times 10^5$ cells/ml in F-12 media. 100 µl/well of CHO-K1 suspension was added to the plate containing 293-T7 cells. Immediately after the addition of CHO-K1 cells, 2 µg of AMMO1, AMMO3, AMMO5, or CL40 were added to 6 wells in parallel. 24 hours later, the media was aspirated and the cells were lysed in 100 µl of Steady-Glo luciferase reagent (Promega). 75 µl of cell lysate was transferred to a white bottom assay plate and luciferase activity was read on a Fluroskan Ascent FL fluorimeter.

Crystallization of the AMMO1 FAb and data collection. Crystals of AMMO1 Fab were obtained using a NT8 dispensing robot and screening was done with Rigaku Wizard Precipitant Synergy block #2, Molecular Dimensions Proplex screen HT-96, Hampton Research Crystal Screen HT by the vapor diffusion method. Crystals used for diffraction data were grown in 16.75% PEG 400, 13.4% PEG 3350, 0.1M MgCl2, 0.1M Tris pH 8.5. Crystals were cryoprotected in solutions containing 30% molar excess of their original reagents and 20% Glycerol. Crystal diffracted to 1.6 Å (FIG. 1). Data was collected at ALS 5.1 and 5.2 and processed using HKL2000 (Otwinowski and Minor, 1997).

Structure solution and refinement. The structure of AMMO1 Fab was solved by molecular replacement using Phaser in CCP4 (Collaborative Computational Project, 1994) and PDB ID 4FQQ_L (light chain) and 4JPK_H (heavy chain) as search model. COOT (Emsley et al., 2010) and PHENIX (Adams et al., 2010) were used for model building and refinement of the structure, which included TLS parameters. A cross validation (Rfree) test set consisting of 5% of the data was used throughout the refinement process. The refinement statistics are summarized in FIG. 2. Structural figures were made with Pymol (DeLano, 2002), or USCF Chimera (Pettersen et al., 2004).

Negative stain electron microscopy. Stock solution of gH/gL, gp42, AMMO1 and CL40 were diluted to an estimated concentration of 25 nM of each component in 50 mM HEPES pH 7.5, 150 mM NaCl. Carbon-coated Ted Pella G400 copper grids, glow discharged immediately before use were used. A volume of 3.5 µL of sample was deposited on the grid for 20-30 s before excess solution was blotted away using Whatman No. 1 filter paper. This was immediately followed by two rounds of staining in 3.5 µL of 2% (w/v) of uranyl formate. Data was collected on an FEI Tecnai Spirit transmission electron microscope equipped with a US4000 CCD camera. Images were acquired at a nominal magnification of 67,000× at a defocus range between −1 µm and −4 µm.

CTF parameters were estimated using GCTF (Zhang, 2016). Particles were picked using DoG Picker (Voss et al., 2009). Particle images were extracted using a box size of 192 pixels binned by a factor of 2 to an effective pixel size of 3.2 Å/pixel and analyzed using RELION 2.0 (Kimanius et al., 2016).

Cryo Electron Microscopy Sample Preparation and Data Collection. Stock solutions of gH/gL, gp42 and AMMO1 were diluted to an estimated concentration of 3 µM of each component in 50 mM HEPES pH 7.5, 150 mM NaCl and 0.01% (v/v) NP40. Protochips C-flat 1.2/1.3-4C-T carbon-coated copper grids, glow discharged immediately before use were used. Particles showed a preferred orientation in ice in the absence of NP40, limiting the overall resolution of the reconstructions. Addition of NP40 resulted in more diverse particle orientations, but resulted in significantly fewer particles in ice. To overcome this issue, a multiple blotting strategy was employed, as previously described (Snijder et al., 2017). After two rounds of sample application and blotting on the lab bench using Whatman No. 1 filter paper, a third volume of sample was applied to the grids, which were then mounted in an FEI Mark I Vitrobot for a final round of blotting and plunge-freezing in liquid ethane, using a 9 s blotting time with −3 mm offset at room temperature and 80-90% relative humidity.

Data were collected using the Leginon software (Suloway et al., 2005) on an FEI Titan Krios electron microscope, equipped with a Gatan Quantum GIF energy filter, operated in zero-loss mode with a slit-width of 20 eV, and a Gatan K2 Summit direct electron detector. The dose rate was adjusted to 8 counts/pixel/s, and each movie was acquired in counting mode fractionated in 75 frames of 200 ms. 2300 micrographs were collected in a single session with a defocus range included between 2.0 μm and 4.0 μm.

CryoEM data processing. Movie frames were aligned with MotionCor2 (Zheng et al., 2017), with the use of dose weighting. CTF parameters were estimated from the aligned micrographs without applied dose weighting, using GCTF (Zhang, 2016). Particles were picked from aligned dose-weighted micrographs using DoG Picker (Voss et al., 2009). Particle images were extracted using a box size of 224 pixels binned by a factor of 2 to an effective pixel size of 2.72 Å/pixel and analyzed with RELION 2.0 (Kimanius et al., 2016). After 2 rounds of reference-free 2D classification, 137,000 particles were selected for 3D classification in 5 classes, starting with an initial model was generated from 2D class averages using the e2initialmodel.py function in EMAN2 (Tang et al., 2007). One predominant class of 104,000 particles was selected for further classification and refinement using the re-extracted particles with original pixel size of 1.36 Å. In addition, one minor class of 15,000 particles with the displaced gp42 CTD was refined using the 2× binned images to a resolution of 10.5 Å. The major class of gH/gL-gp42-AMMO1 was further classified in 3 classes with a finer angular sampling (HEALPix order 3 with oversampling) and local searches. One dominant class of 72,000 particles was selected to generate the final map, at Å resolution, using a solvent mask and the solvent fcs flag in RELION 2.0. A B-factor of −400 Å$^2$ was applied to sharpen the map. Reported resolutions are based on the gold-standard FSC=0.143 criterion (Rosenthal and Henderson, 2003; Scheres and Chen, 2012) and Fourier shell correlation curves were corrected for the effects of soft masking by high-resolution noise substitution (Chen et al., 2013b).

Model building. UCSF Chimera (Goddard et al., 2007) and Coot (Brown et al., 2015) were used to fit the crystal structures of gH/gL/gp42 (PDB 5T1D) and of AMMO1 into the cryoEM map. The quality of the reconstruction is highest for the density corresponding to the gH core, for which several amino acid side chains are resolved. The quality of the reconstruction is lower for the regions corresponding to gL, gp42 and AMMO1. Refinement of the model was carried out using Rosetta density-guided iterative refinement (DiMaio et al., 2015) and Rosetta Relax (DiMaio et al., 2009). Deviations from the input structures were allowed only if supported by density or to resolve stereochemical issues. Glycans were initially docked into the density and their geometry was then refined using Rosetta, optimizing the fit-to-density as well as the energetics of protein/glycan contacts. The model of the gH/gL/gp/42/AMMO1 complex showing the displacement of gp42 was obtained by rigid-body docking the gp42 C-terminal domain into the corresponding density. The quality of the final model was validated using Molprobity (Chen et al., 2010) and Privateer (Agirre et al., 2015). Structure analysis was assisted by the PISA server (Krissinel and Henrick, 2007).

gH/gL mutant binding analysis. Targeted mutations were introduced into pCAGGS-gH or pCAGGS-gL using the Quickchange XL site-directed mutagenesis kit (Agilent Genomics) using the manufacturer's instructions. All mutations were confirmed by Sanger sequencing. Wildtype and mutant gH or gL plasmids were co-transfected into 4 ml of 293F cells at a density of 10$^6$ cells/ml in Freestyle 293 media (ThermoFisher) using the 293Free transfection reagent (EMD Millipore) according to the manufacturer's instructions. 24 h later, cells expressing wildtype gH/gL, each gH/gL mutant, or mock transfected cells were pelleted by centrifugation at 300×g for 3 min and then re-suspended in 200 μl of PBS containing 0.5% BSA and 2 μg of the CL59 MAb and incubated on ice for 1 h. Meanwhile 3-fold serial dilutions of AMMO1 labeled with Dylite 650 (ThermoFisher Cat #62265, according to the manufacturer's instructions) were prepared in 50 μl of PBS containing 0.5% BSA in 96 well plates. 20 μl of PBS containing 0.5% BSA and 0.5 μl of PE-anti-mouse IgG (ThermoFisher Cat # P852) was added to each well. Cells expressing gH/gL variants, as well as mock-transfected cells were washed with 3 ml of PBS containing 0.5% BSA and resuspended in 650 μl of PBS containing 0.5% BSA. 30 μl of cell suspension was added to wells containing serially diluted AMMO1 and anti-mouse PE in duplicate, followed by a 1 h incubation on ice. Each well was washed twice with 200 μl of PBS containing 0.5% BSA and then resuspended in 100 μl of 10% phosphate buffered formalin. gH/gL positive cells were determined by PE (CL59) staining, using mock-transfected cells as a reference. The level of AMMO1 binding to gH/gL was determined by measuring the mean fluorescence intensity (MFI) of DL650 staining of PE+ cells. To account for differences in gH/gL expression the MFI of PE staining for each gH/gL variant (16 wells total) was averaged and used to normalize the DL650 staining of each well. The normalized MFI of DL650 was plotted against the concentration of AMMO1 for each well and fit to a sigmoidal dose response curve using GraphPad Prism software.

Mass spectrometry to identify glycopeptides. 250 μmol of gH/gL and gp42 were separately prepared for mass spectrometry analysis of glycopeptides. Stock solutions were denatured, reduced and alkylated by dilution to 5 μM in 50 μL of buffer containing 100 mM Tris pH 8.5, 10 mM TCEP, 40 mM iodoacetamide and 2% (w/v) sodium deoxycholate. Samples were first heated to 95° C. for 10 min and then incubated for an additional 20-30 min at room temperature in the dark. The samples were split in two for digestion with trypsin and chymotrypsin (Sigma Aldrich) in parallel, by diluting 20 μL of sample for each protease in a total volume of 100 μL 50 mM ammonium bicarbonate pH 8.5. Protease was added to the samples in a ratio of 1:75 by weight and left to incubate at 37° C. overnight. After digestion, 2 μL of formic acid was added to the samples to precipitate the sodium deoxycholate from solution. After centrifugation for 20 min at maximum speed in a bench top centrifuge, 80 μL of the supernatant was collected. For each sample 8 μL was injected on a Thermo Scientific Orbitrap Fusion Tribrid mass spectrometer. A 35-cm analytical column and a 3-cm trap column filled with ReproSil-Pur C18AQ 5 μm beads (Dr. Maisch) were used. Nanospray LC-MS/MS was used to separate peptides over a 110-min gradient from 5% to 30% acetonitrile with 0.1% formic acid. A positive spray voltage of 2,100 V was used with an ion-transfer-tube temperature of 350° C. An electron-transfer/higher-energy collision dissociation ion-fragmentation scheme (Frese et al., 2013) was used with calibrated charge-dependent ETD parameters and supplemental higher-energy collision dissociation energy of 0.15. A resolution setting of 120,000 with an AGC target of 2×10$^5$ was used for MS1, and a resolution setting of 30,000 with an AGC target of 1×10$^5$ was used for MS2. Data was searched with Protein Metrics Byonic software (Bern et al., 2012), using a small custom database of recombinant protein sequences including gH, gL, gp42, other viral glycoproteins and the proteases used to prepare the glycopeptides. Reverse decoy sequences were also included in the search. Specificity of the search was set to C-terminal cleavage at R/K (trypsin) or F/W/Y/M/L (chymotrypsin), allowing up to two missed cleavages, with EThcD fragmentation (b/y- and c/z-type ions). A precursor mass and product mass tolerance of 12 ppm and 24 ppm respectively were used. Carbamidomethylation of cysteines was set as fixed modification, methionine oxidation as variable modification, and all four software-provided N-linked glycan databases were used to identify glycopeptides. All glycopeptide hits were manually inspected and only those with quality peptide sequence information are reported here.

Figure 3A:
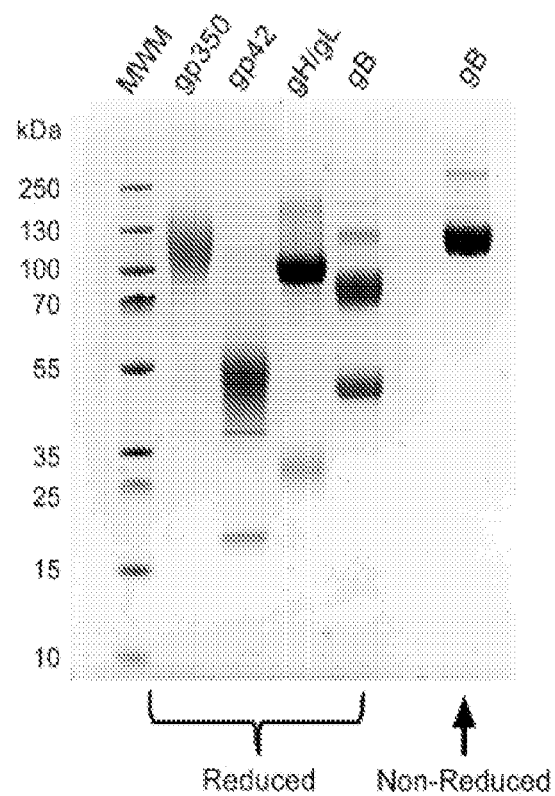
FIGS. 3A-3C. Biochemical and antigenic characterization of EBV glycoprotein ectodomains.
Figure 3B:
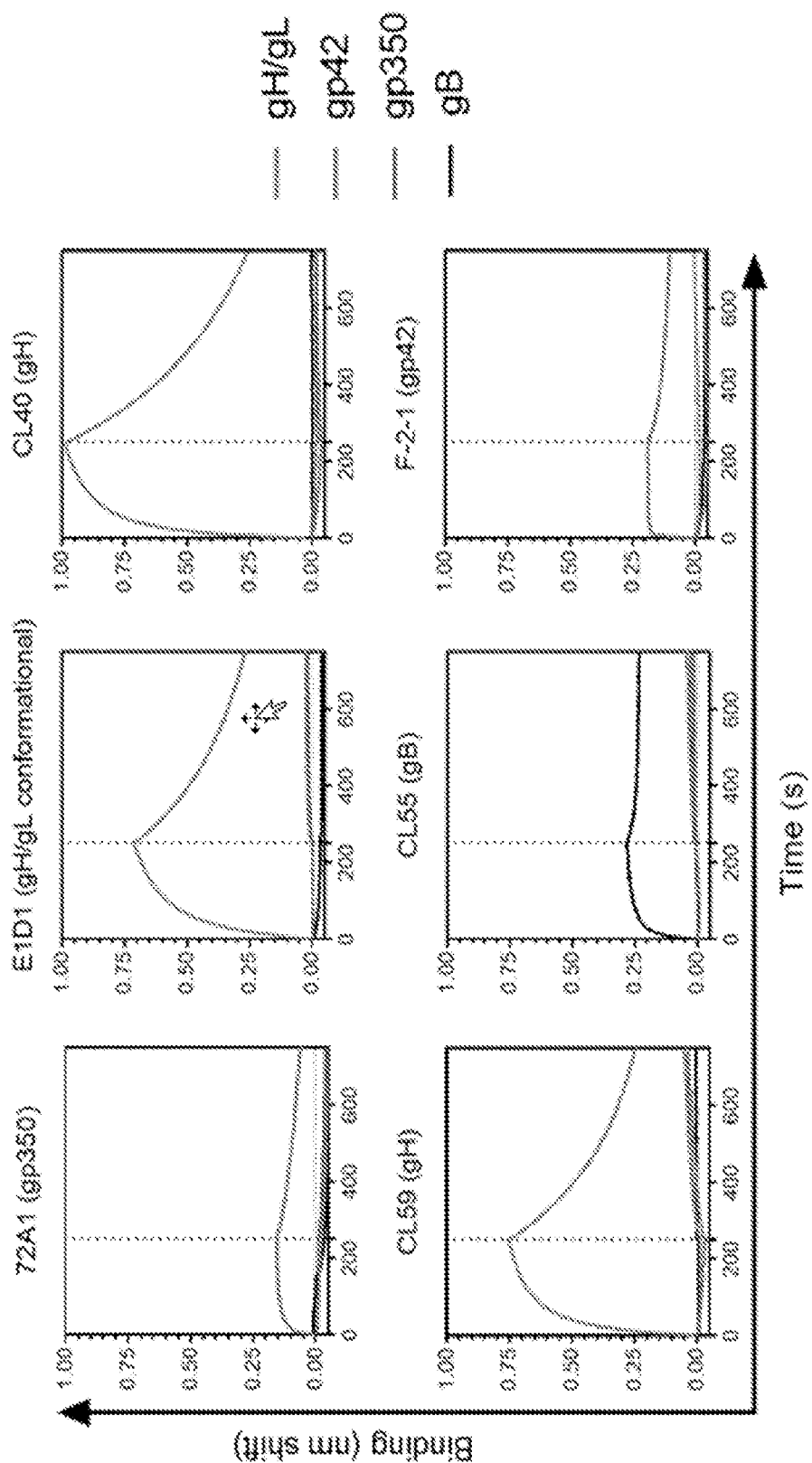
Figure 3C:
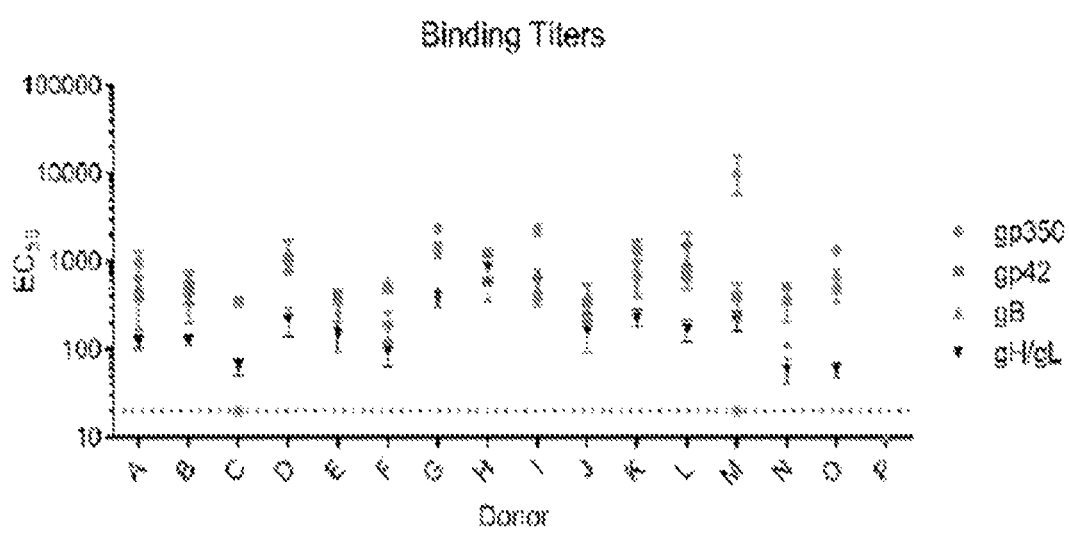

Results. Isolation of anti-EBV human monoclonal antibodies from infected individuals. To understand the humoral immune response elicited during natural EBV infection, isolation of antigen-specific memory B cells against gp42, gp350, gH/gL and gB were sought using recombinant bait ectodomains produced in HEK 293 cells (FIG. 3A). All glycoproteins were recognized by known anti-EBV MAbs (FIG. 3B) and serum antibodies from 15 out of 16 donors, as tested by ELISA (FIG. 3C), indicating that the purified ectodomains were properly folded and exhibited native antigenicity. Although a range of binding specificities across donors was observed, most sera displayed the highest antibody titers against gp350 and the lowest against gH/gL.

EBV glycoproteins conjugated to streptavidin-PE were used to identify antigen-specific class-switched B cells. The majority of B cells stained positive with gp350 or gp42 (FIG. 4A) due to their ability to bind CD21 (Tanner et al., 1987) and CD35 (Ogembo et al., 2013) or MHCII (Haan et al., 2000; Spriggs et al., 1996), respectively. Attempts to completely block gp350 and gp42 binding to these cellular receptors with commercially available antibodies were unsuccessful and efforts to sort these B cells were not pursued further.

Figure 4A:
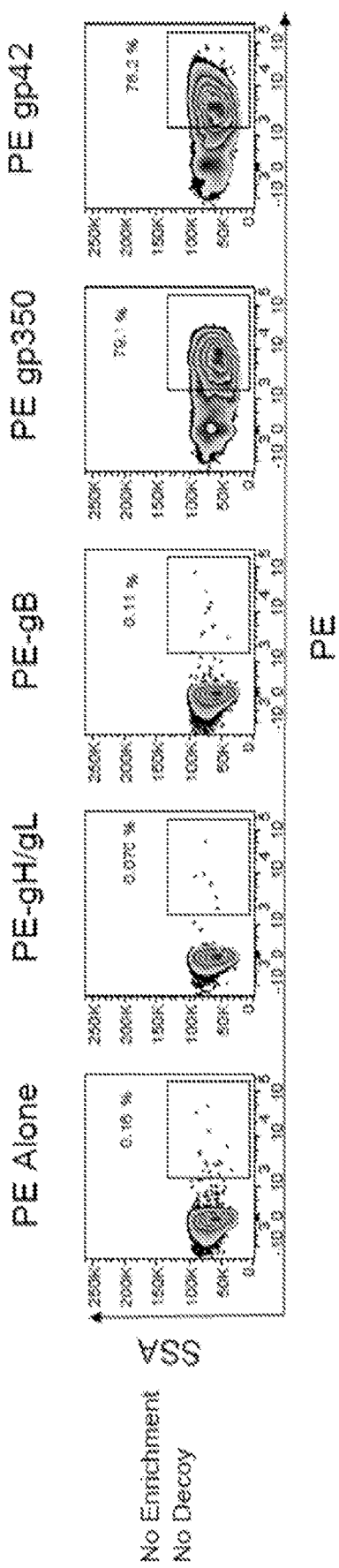
Figure 4B:
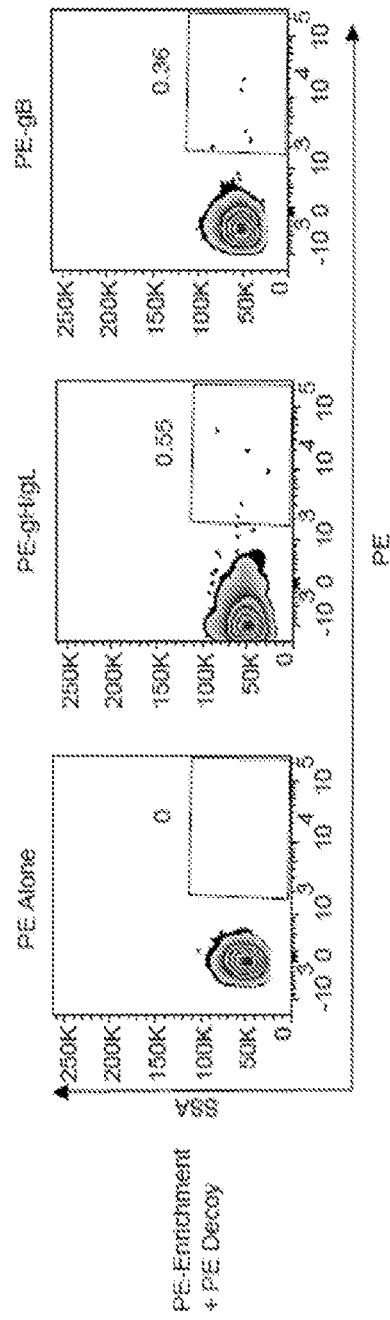
Figure 5A:
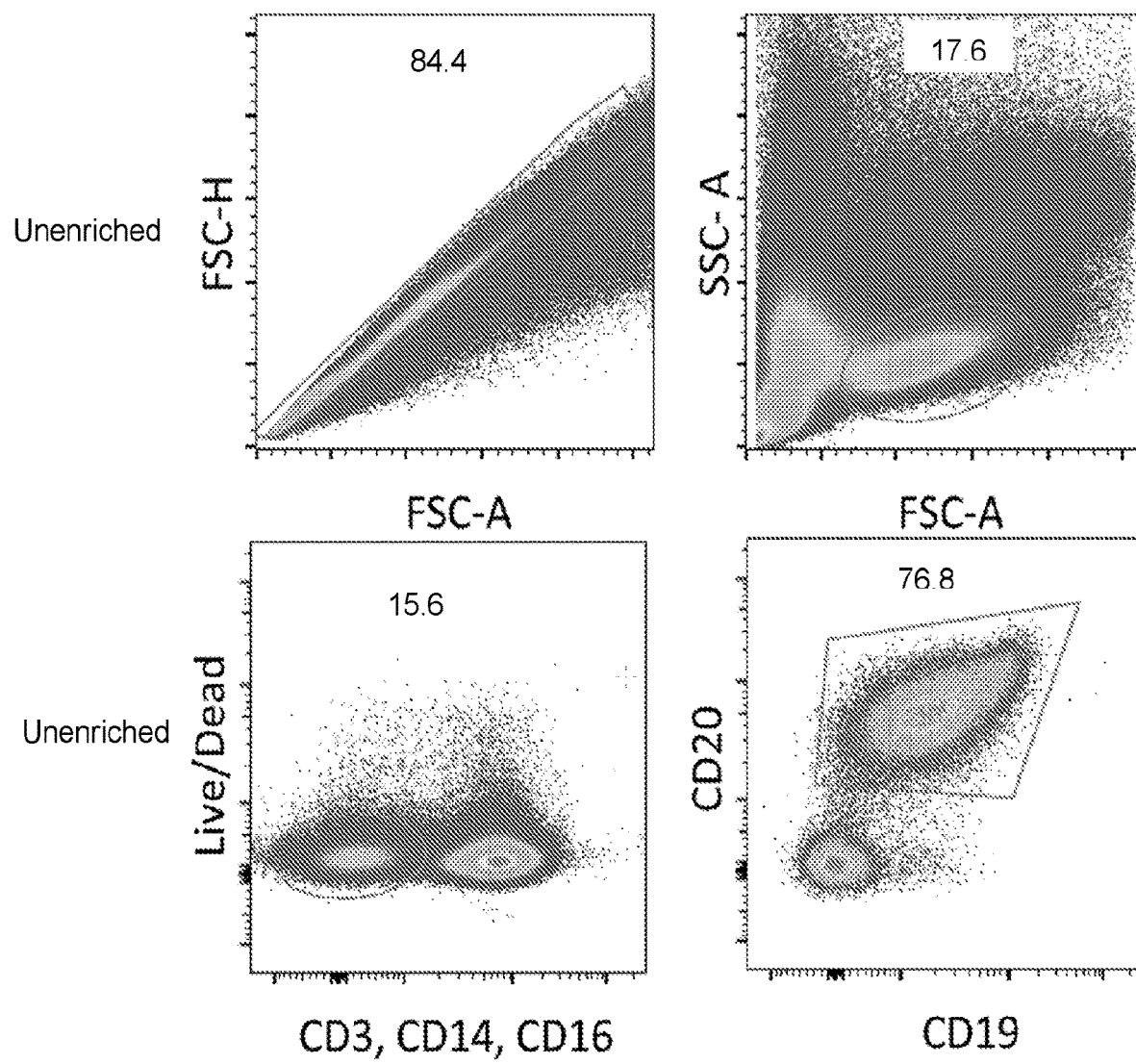
Figure 5A:
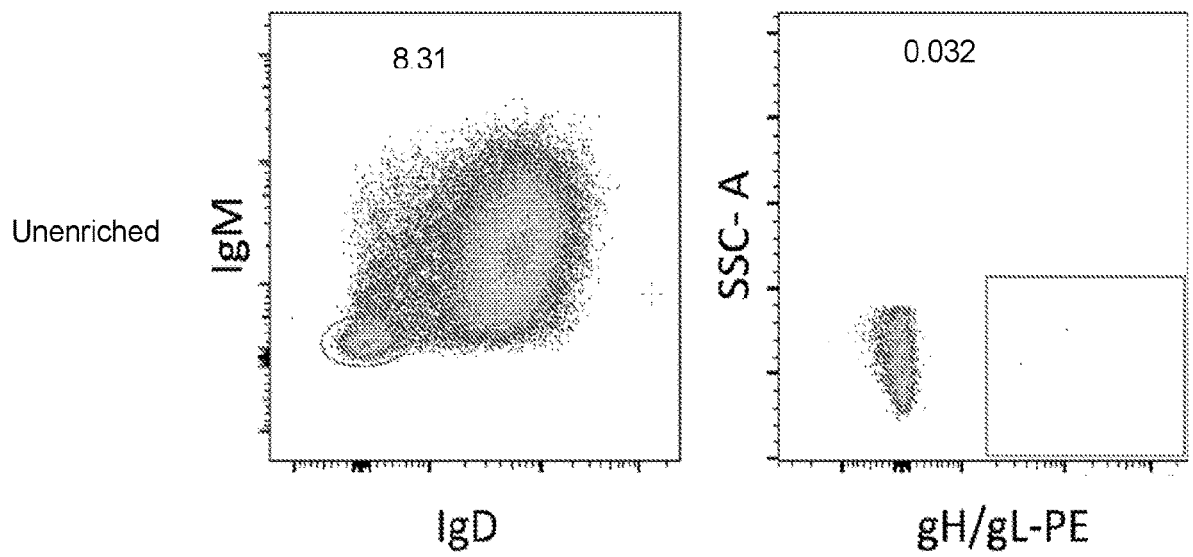
Figures 5C, 6:
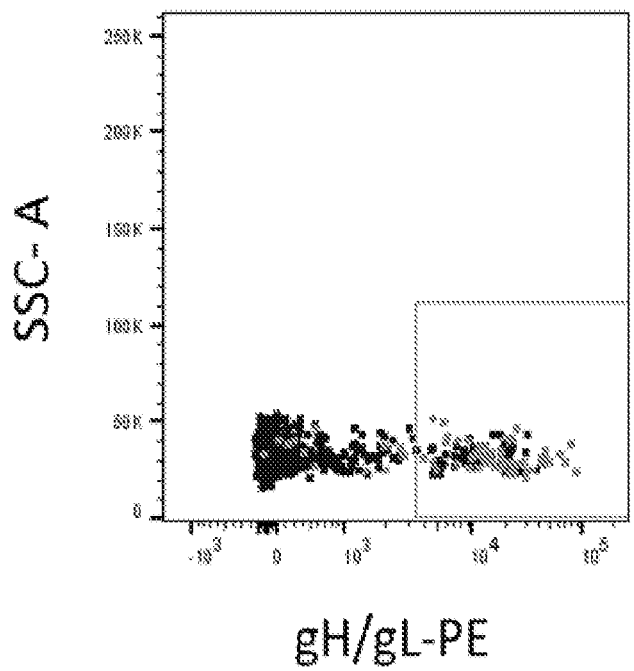

The number of B cells that stained with gH/gL or gB was comparable to the number of B cells that stained positive with the unconjugated PE control (FIG. 4A). This observation indicated that gH/gL- or gB-specific B cells are quite rare, and led us to use complimentary approaches to isolate them. A magnetic bead-based strategy coupled with an antigen decoy to enrich for, and identify rare, antigen-specific B cells (Taylor et al., 2012) was employed. This enrichment strategy reduced the number of background B cells and allowed us to more confidently identify gH/gL- and gB-specific B cells (FIG. 4A). Based on the number of cells that were excluded using this approach, it was estimated that a 2.5 fold enrichment of antigen specific B cells was achieved (FIG. 5). Sorting was carried out starting with a total of $8\times10^8$ cryopreserved peripheral blood mononuclear cells from three separate donors using PE-conjugated gH/gL, gB, or gH/gL and gB concurrently (FIG. 6). B cells were individually sorted into irradiated feeder cell cultures in the presence of recombinant cytokines. To verify isolation of antigen-specific B cells, the supernatants were screened for antigen reactivity by ELISA. Despite the implementation of an enrichment step, most of the sorted cells were false positives and only two gH/gL- and seven gB-specific B cells could be identified (FIG. 6). From these, paired variable heavy (VH) and variable light (VL) chain transcripts for one gH/gL antibody (AMMO1) and four gB-specific antibodies (AMMO2-AMMO5) were successfully recovered. All of these antibodies are derived from distinct heavy and light chain genes, and displayed VH mutation frequencies ranging from 8-10% and VK/VL frequencies ranging from 5-8% at the nucleotide level (FIG. 7). The VH/VL sequences were cloned into recombinant expression vectors and that AMMO1 specifically bound to gH/gL, and that AMMO2-AMMO5 specifically bound to gB using biolayer interferometry (BLI, FIG. 4C) was verified.

AMMO1 inhibits EBV infection of both epithelial cells and B cells. The ability of AMMO1-AMMO5 to neutralize EBV infection of epithelial cells (FIG. 8A) and B cells (FIG. 8B) was assessed. For comparison, the murine anti-gH/gL MAbs CL40, CL59 and E1D1, which have been reported to completely block epithelial cell infection but poorly inhibit B-cell infection (Chesnokova and Hutt-Fletcher, 2011; Wu et al., 2005) were also included.

Figure 8A:
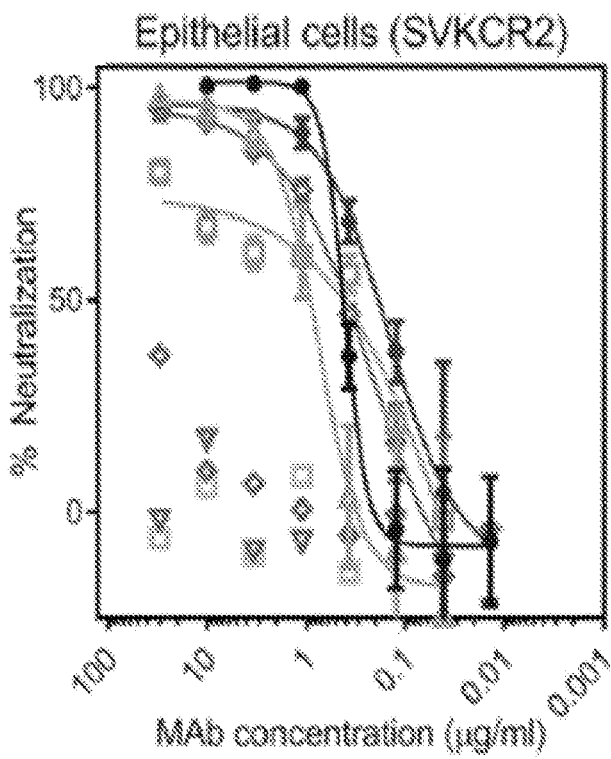
FIGS. 8A, 8B. Neutralization of EBV infection in epithelial cells and B cells by newly isolated MAbs. Serial dilutions of the indicated antibodies were evaluated for their ability to neutralize (FIG. 8A) AKTA-GFP EBV infection of epithelial (SVKCR2) cells or (FIG. 8B) B95.8/F EBV infection of B (Raji) cells. Anti-gH/gL antibodies are AMMO1, CL40, CL59, AND E1D1, anti-gB antibodies are AMM02, AMMO3, AMM04, and AMM05, and the anti-gp350 antibody is 72A1. The human or murine origins of the antibodies are indicated in the legend.

In an epithelial cell infection assay, the anti-gH/gL MAbs AMMO1, CL40 and CL59 had comparable potency. AMMO1 IC50=0.42±0.02 µg/ml (n=6), CL40 IC50=0.89±0.21 µg/ml (n=4), and CL59 IC50=0.52±0.25 µg/ml (n=3). The anti-gH/gL E1D1 antibody displayed incomplete neutralization at the highest concentration tested. The anti-gB MAb AMMO5 also neutralized EBV infection of epithelial cells infection with an IC50 of 0.16±0.09 µg/ml (n=3). The other anti-gB MAbs (AMMO2-AMMO4) were non-neutralizing (FIG. 8A).

Figure 8B:
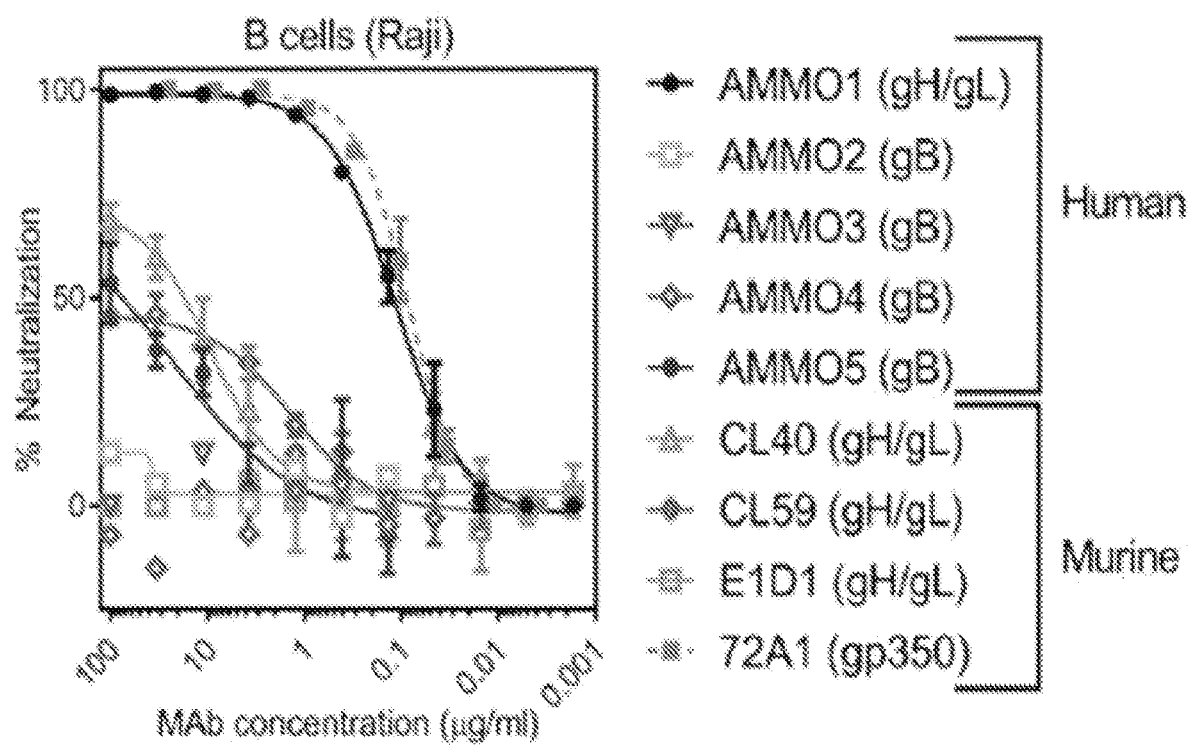

AMMO1 was the only anti-gH/gL Mab that was completely neutralizing in the B cell infection assay (FIG. 8B, IC50=0.16±0.06 µg/ml, n=5). In agreement with previous reports, CL40, CL59 and E1D1 failed to completely neutralize EBV infection of B cells, (Chesnokova and Hutt-Fletcher, 2011; Molesworth et al., 2000) (FIG. 8B).

Despite not being completely neutralizing, CL40 was able to reduce B cell infection to 50% at a concentration of 14.6±2.44 µg/ml (n=3), which is 100 times less potent than AMMO1. An IC50 for CL59 was not measured because it did not reproducibly achieve 50% neutralization. E1D1 was completely ineffective at neutralizing B cell infection (FIG. 8B). AMMO1 displayed comparable potency to the anti-gp350 MAb 72A1 in this assay (FIG. 8B, IC50 0.08±0.003 µg/ml, n=2).

Figure 13A:
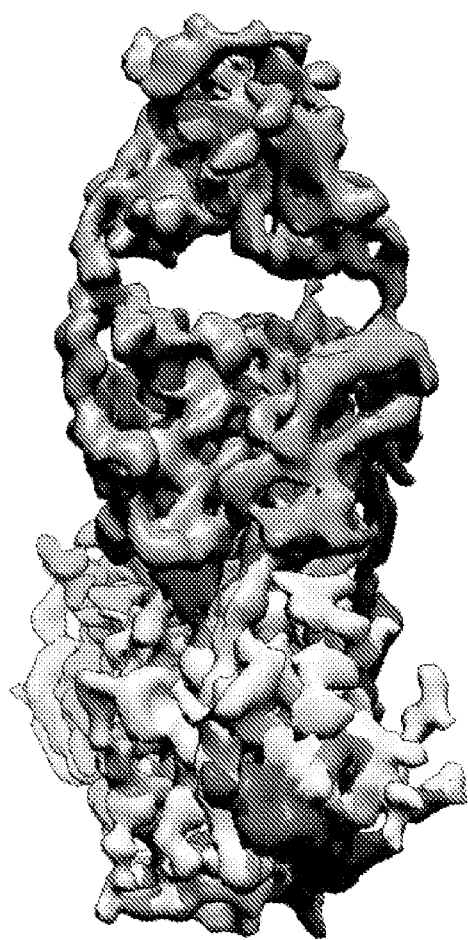
Figure 13B:
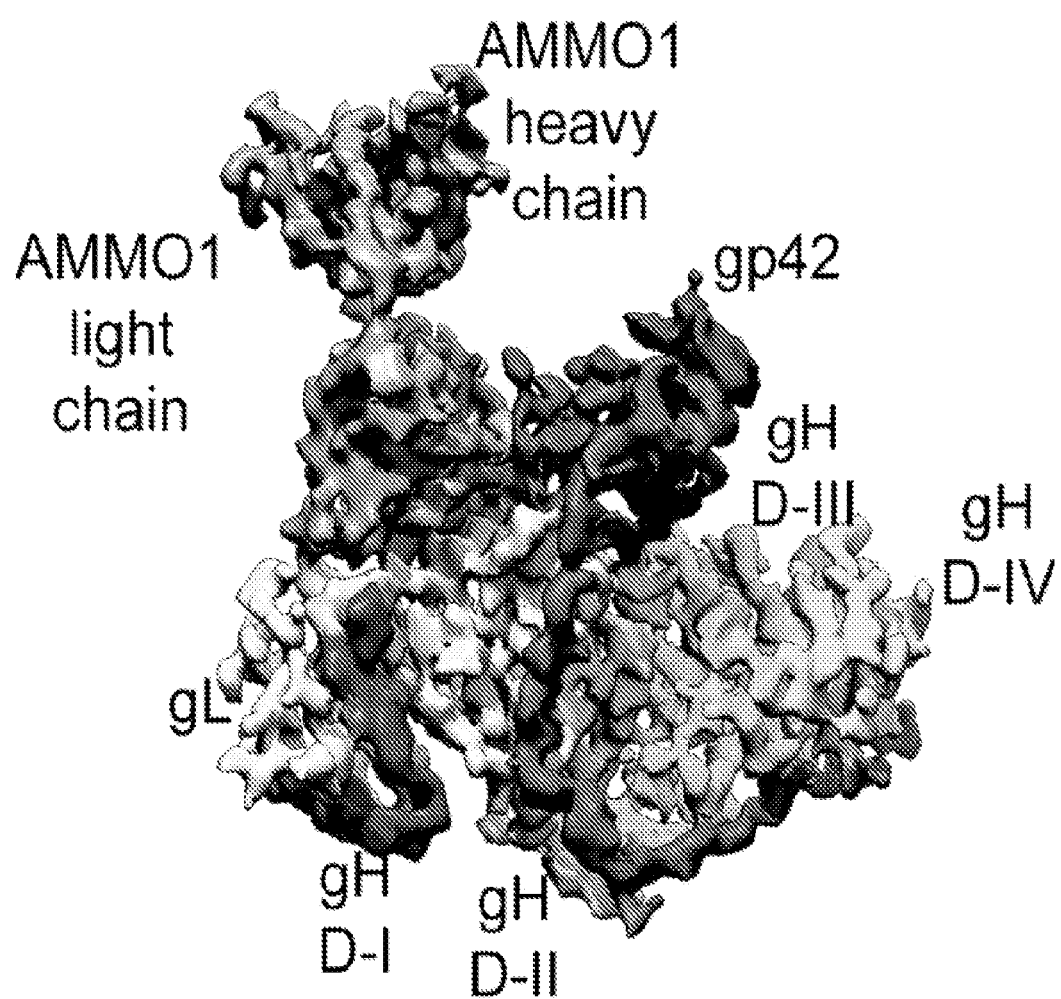
Figure 13C:
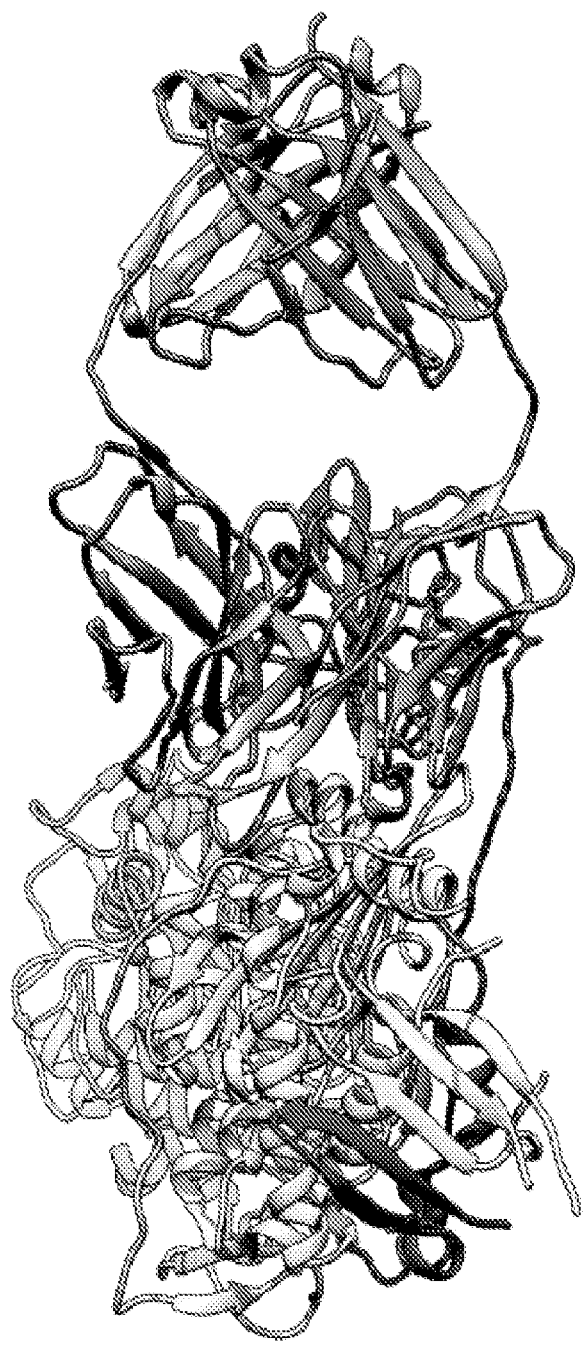
Figure 13D:
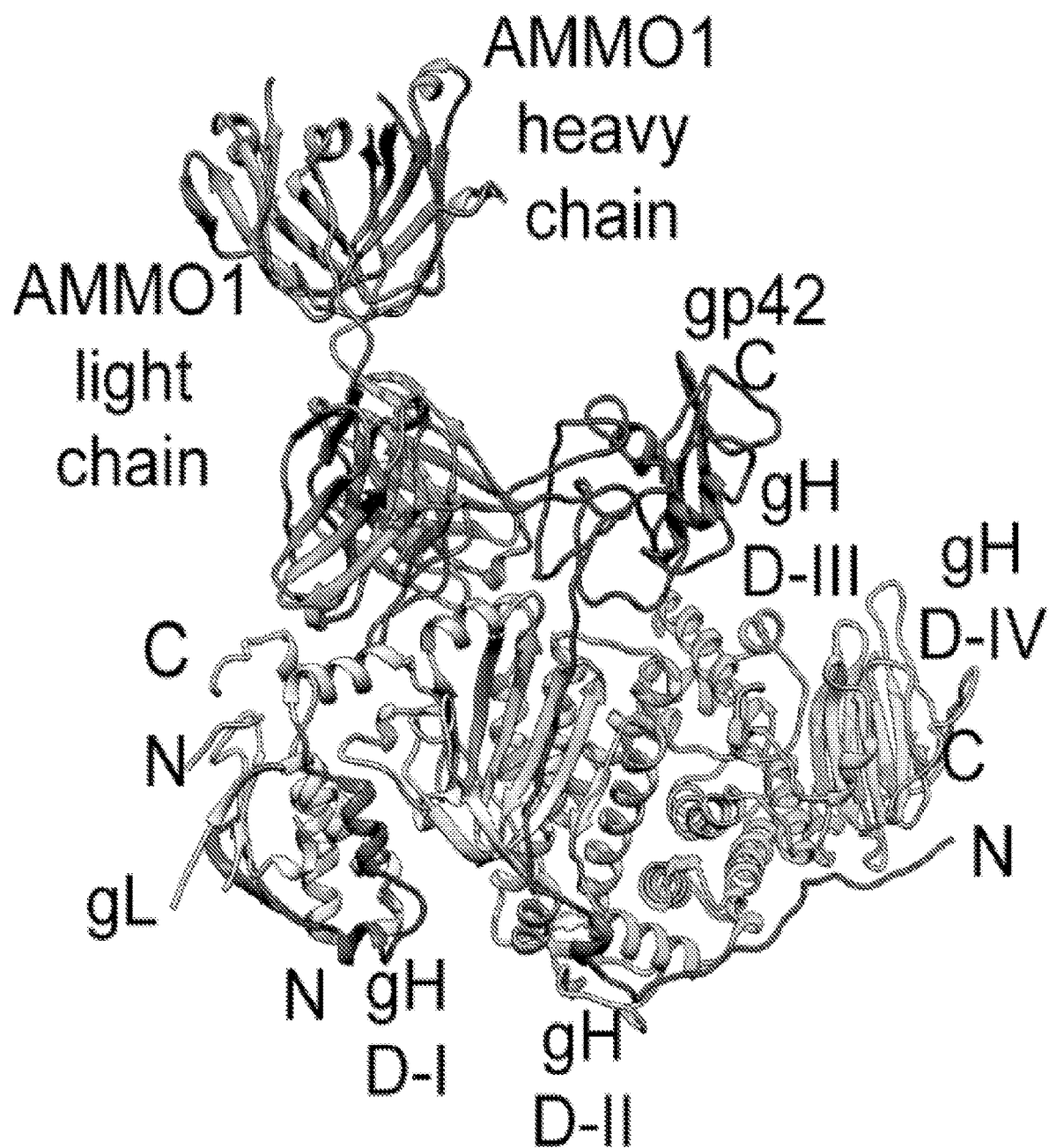

Mapping the Epitope of the AMMO1 Neutralizing MAb using CryoEM. To understand observed differences in the neutralization potency of AMMO1 and other anti-gH/gL MAbs, their binding affinities for gH/gL were determined. AMMO1 bound 1-2 orders of magnitude more tightly to gH/gL than other MAbs tested, due to a much slower off-rate (FIG. 9). Although membrane fusion with Raji B cells can occur independently of endocytosis (Miller and Hutt-Fletcher, 1992), binding assays at pH 5.0 were also carried out to assess whether differences in the neutralization potency of B cell infection might be due to the acidic pH of the endosomal compartment which could affect antibody binding. Only E1 D1 binding was affected by pH (FIGS. 9 and 10). Therefore, the higher potency of AMMO1 could not be attributed to dissociation of the other MAbs from gH/gL due to exposure to the low pH of the endosomes upon virion internalization. Based on these results, it was surmised that epitope differences between the gH/gL MAbs may explain why AMMO1 is the only MAb that completely neutralized infection of both B cells and epithelial cells. To delineate the epitope recognized by AMMO1, the gH/gL/gp42/AMMO1 complex was analyzed by cryoEM (FIGS. 13A, 13B, 14, and 2). A reconstruction of the complex at a resolution of 4.8 Å, which resolves secondary structural elements and several amino acid side chains as well as densities corresponding to N-linked glycans on gH, gL and gp42 was determined. The local resolution varies between 4 Å in the region of the map corresponding to the gH core and 4.5-6.0 Å for gL, gp42 and AMMO1 (FIG. 14). A 1.6 Å crystal structure of the unliganded AMMO1 antigen binding fragment (Fab, FIG. 1) was determined and a model of the gH/gL/gp42/AMMO1 complex was generated using Rosetta (DiMaio et al., 2015) and available EBV glycoprotein structures (Matsuura et al., 2010; Sathiyamoorthy et al., 2016) (FIGS. 13C, 13D, 2). The architecture of gH/gL/gp42 in the complex is in good agreement with the recently reported gH/gL/gp42/E1D1 crystal structure (Cα root mean square deviation of 1.1 Å over 915 aligned residues of gH/gL/gp42) (Sathiyamoorthy et al., 2016). AMMO1 binds to a discontinuous epitope spanning gH/gL D-I and D-II, which includes residues of both gH and gL, and burying a surface area of 1160 Å$^2$ on gH/gL and on AMMO1 (FIGS. 13E, 13F).

Figure 13E:
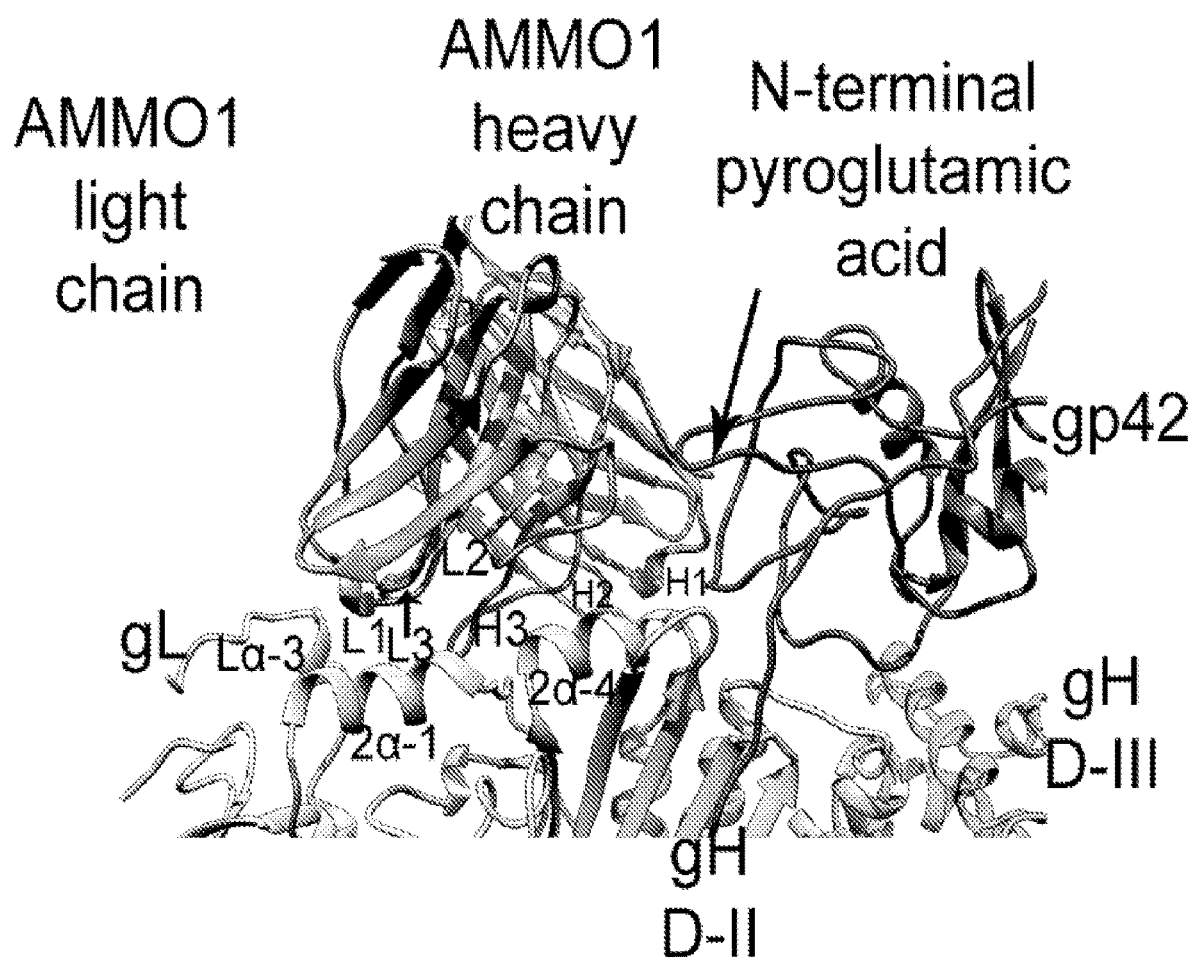
Figure 13F:
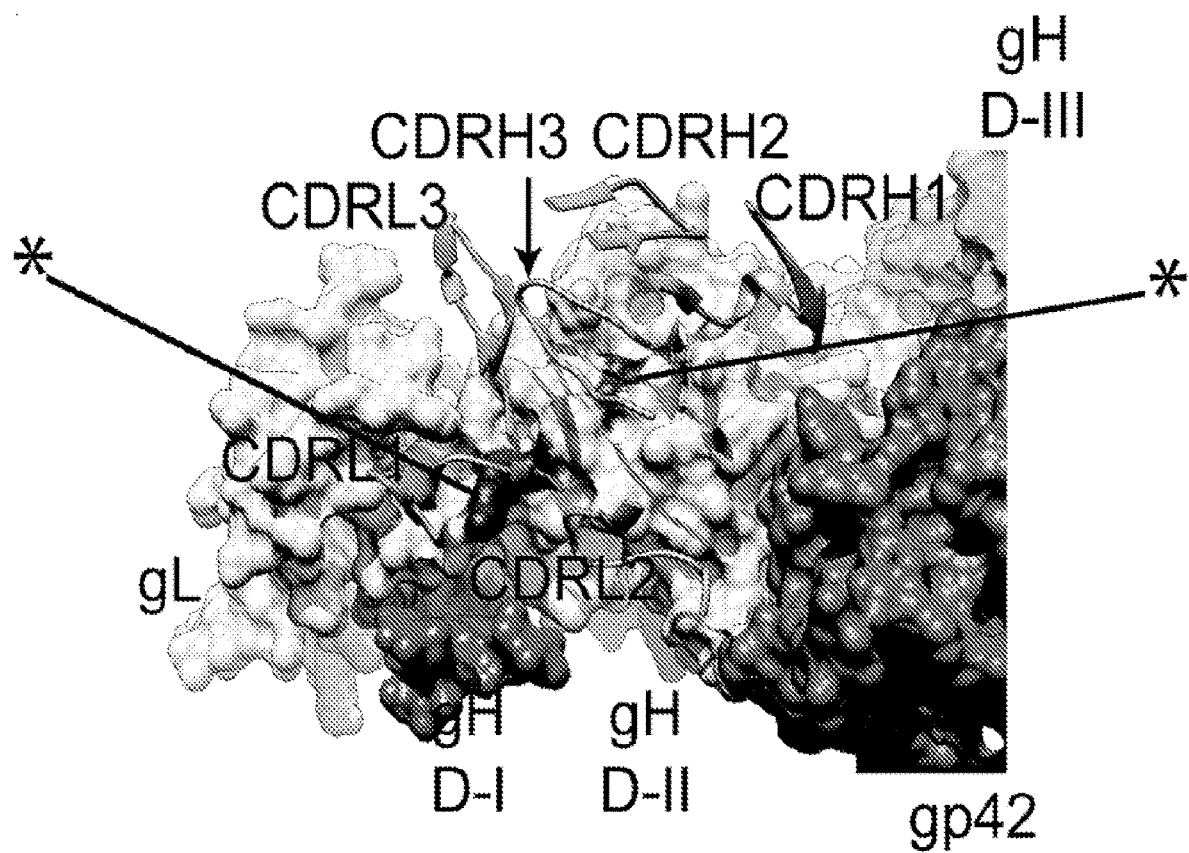
Figure 14A:
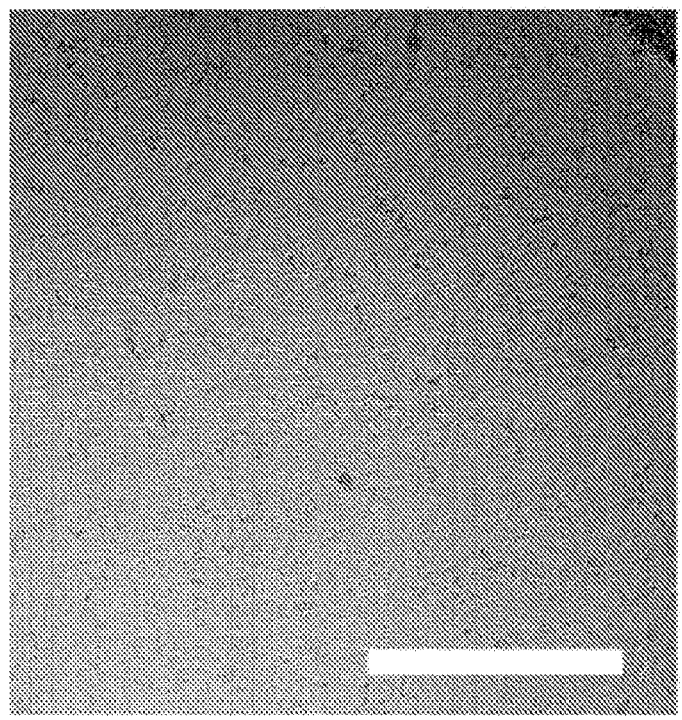
Figure 14B:
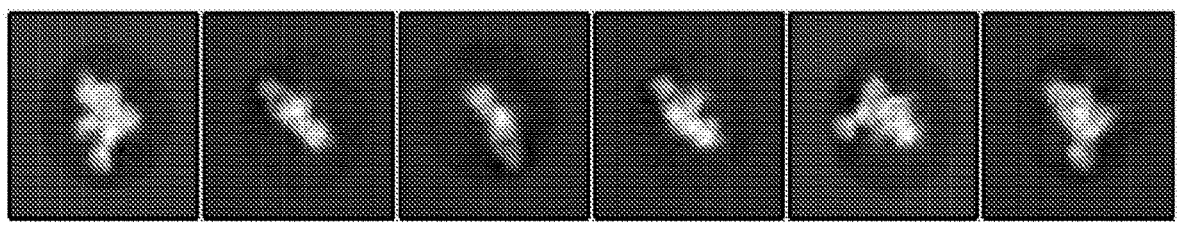
Figure 14C:
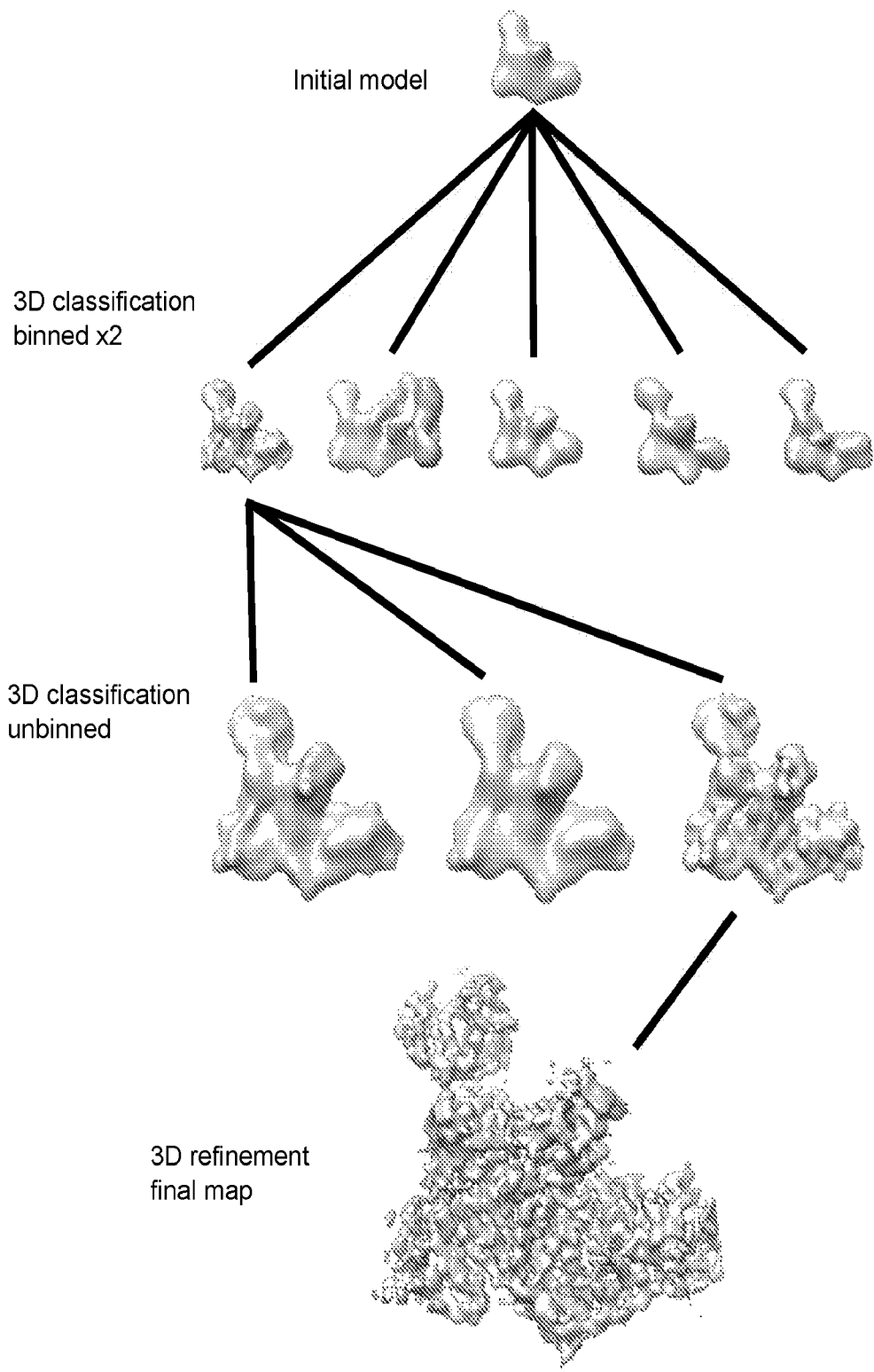
Figure 14D:
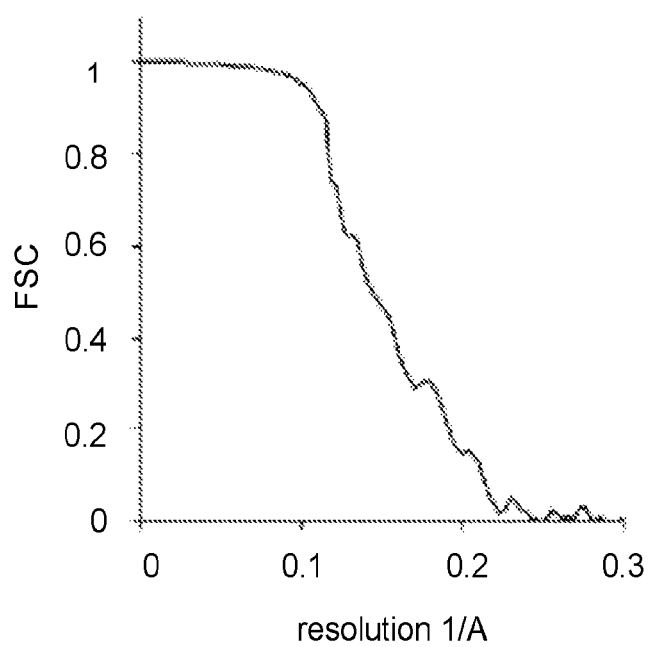
Figure 14E:
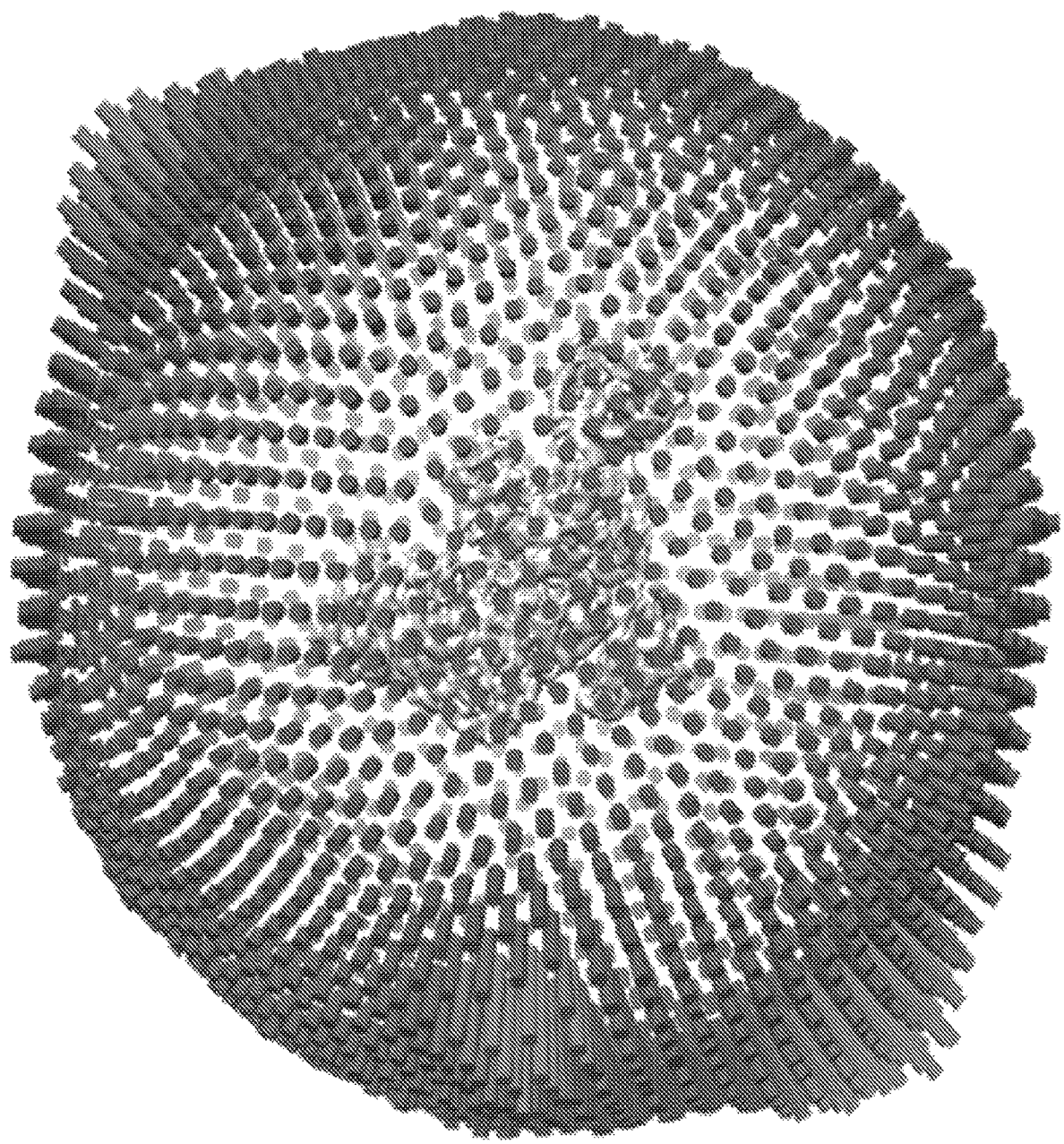
Figure 14F:
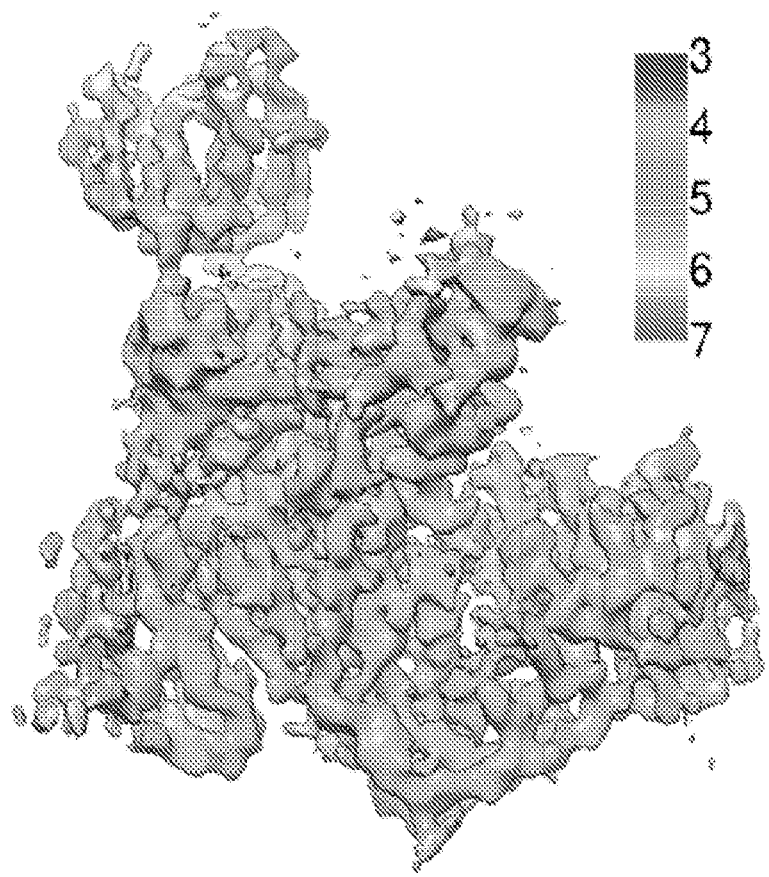

CDRL2, CDRH1 and CDRH3 contact the 2α-4 helix (FIGS. 13E, 13F). CDRH3 also binds the short helix between the 213-7 and 213-8 strands, and the loop between 2α-1 and 213-1. CDRL1 binds to the gH/gL interface, contacting the gH 2α-1 linker helix between D-I/D-II, and the gL C-terminal Lα-3 helix (FIGS. 13E, 13F).

Using site-directed mutagenesis, several mutations were introduced in gH and gL at residues which are predicted to contact AMMO1 based on the cryoEM structure, and binding of the Mab to cell surface expressed gH/gL was assessed (FIG. 15). Among the mutants tested, two residues, K73 and Y76 in the 2α-1 linker helix that led to a reduction in AMMO1 binding when mutated to alanine were identified (FIGS. 15D, 13F). Substitution of K73 with a bulkier tryptophan residue virtually abrogated AMMO1 binding (FIG. 15D), as predicted by the atomic model.

Figure 13G:
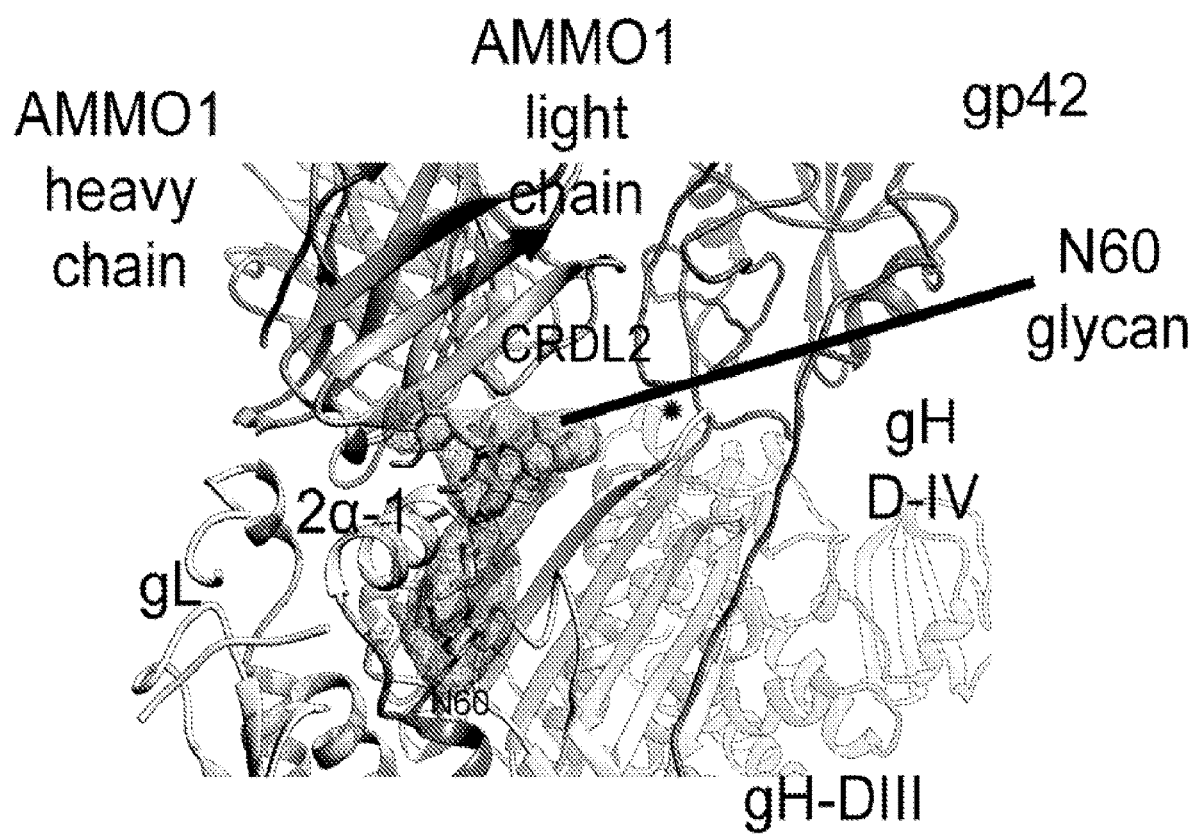
Figure 14G:
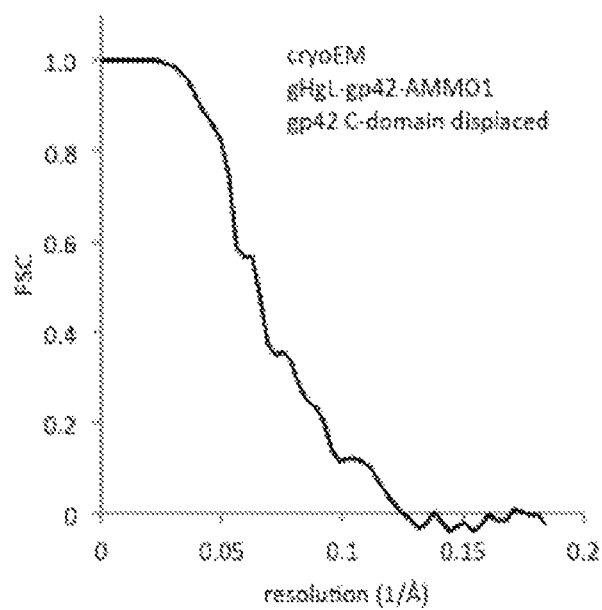
Figure 14H:
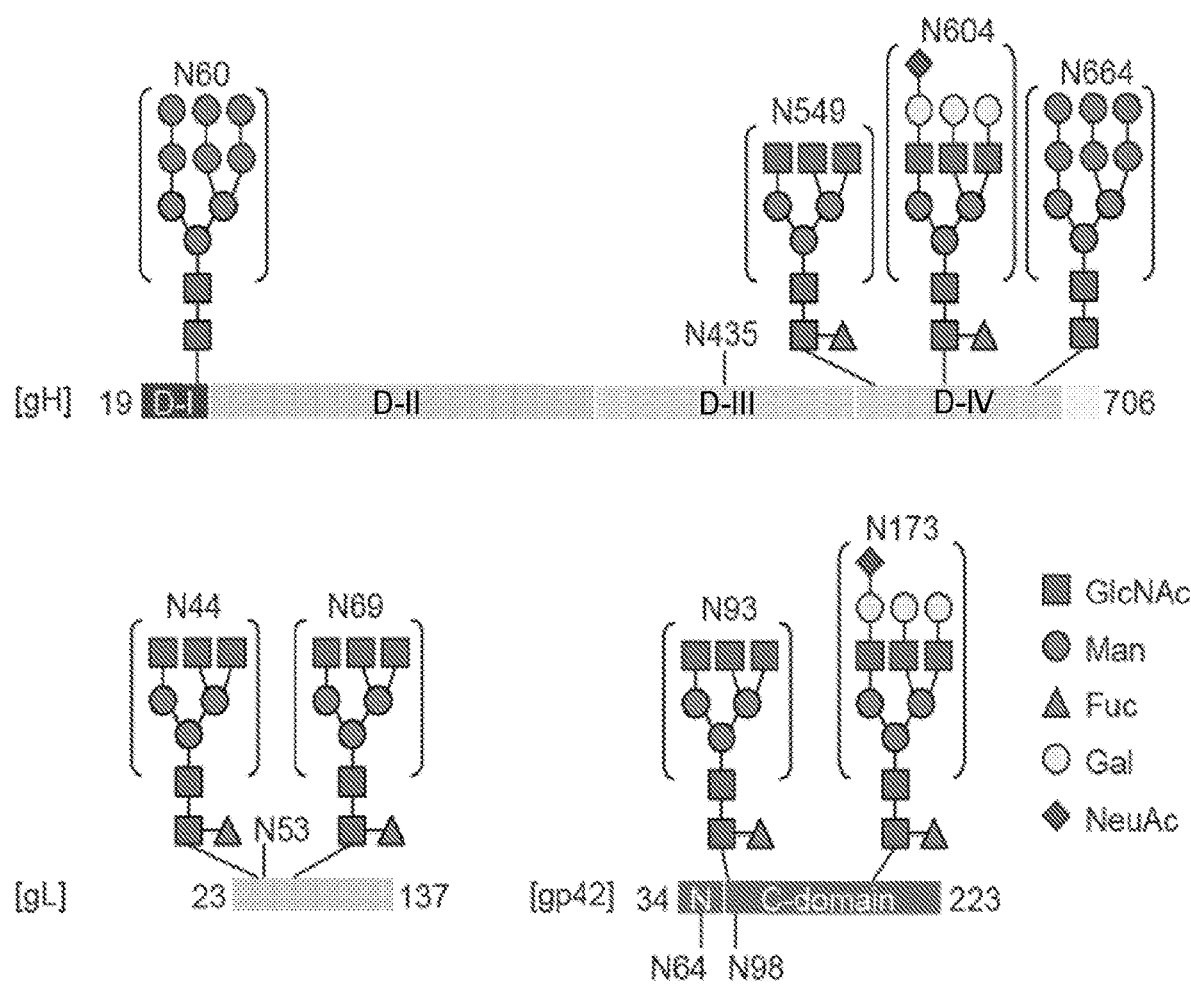
Figure 15A:
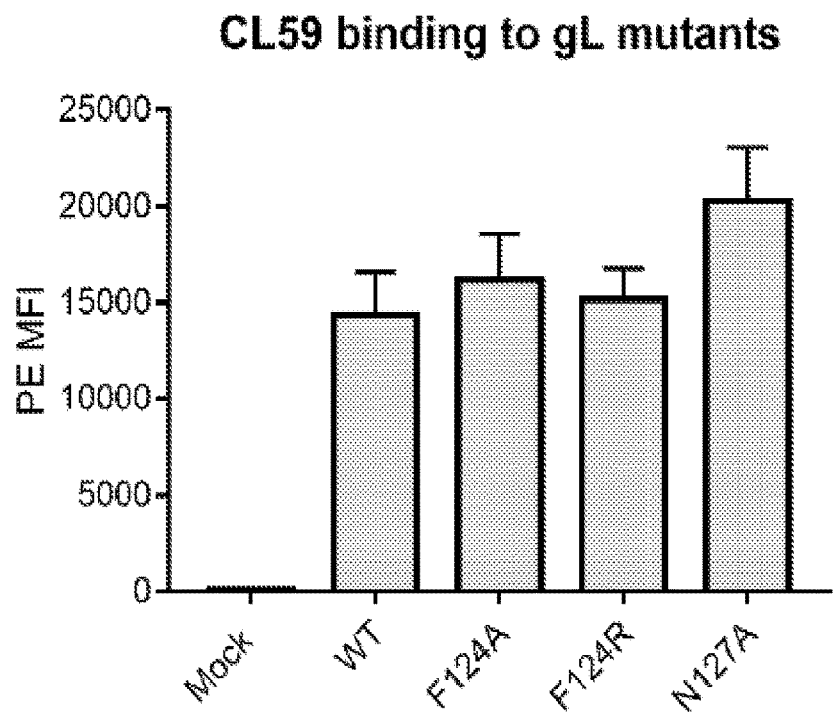
Figure 15B:
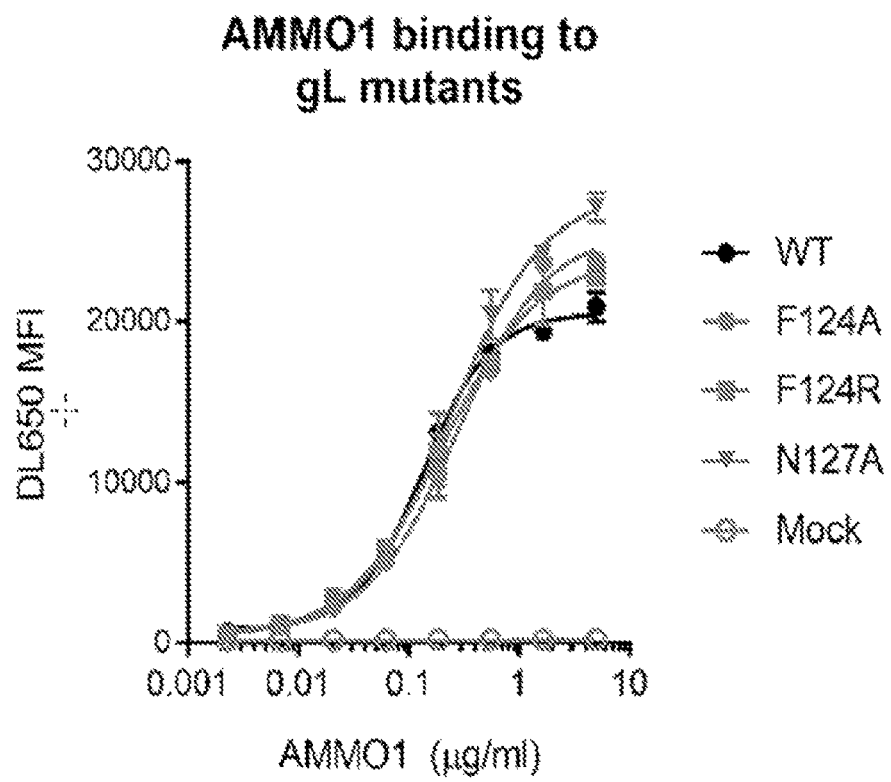
Figure 15C:
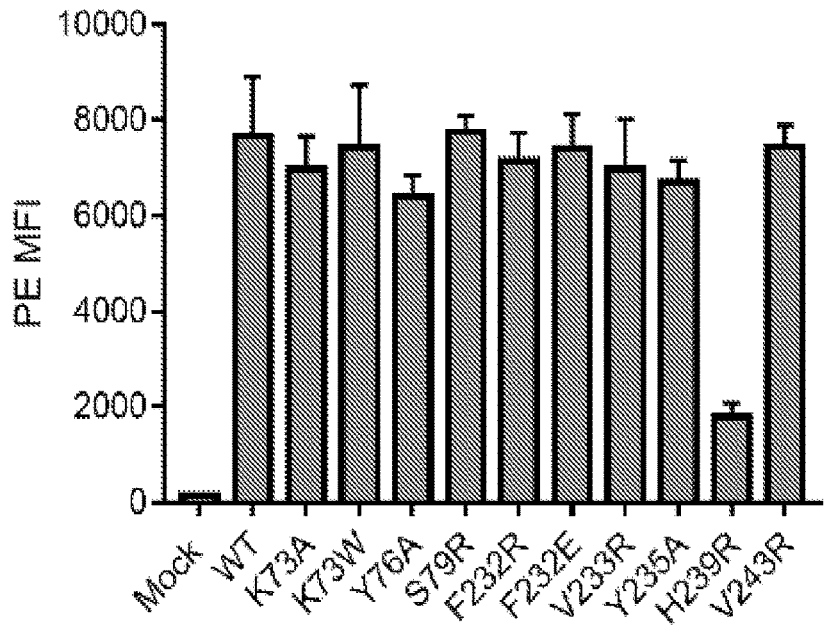
Figure 15D:
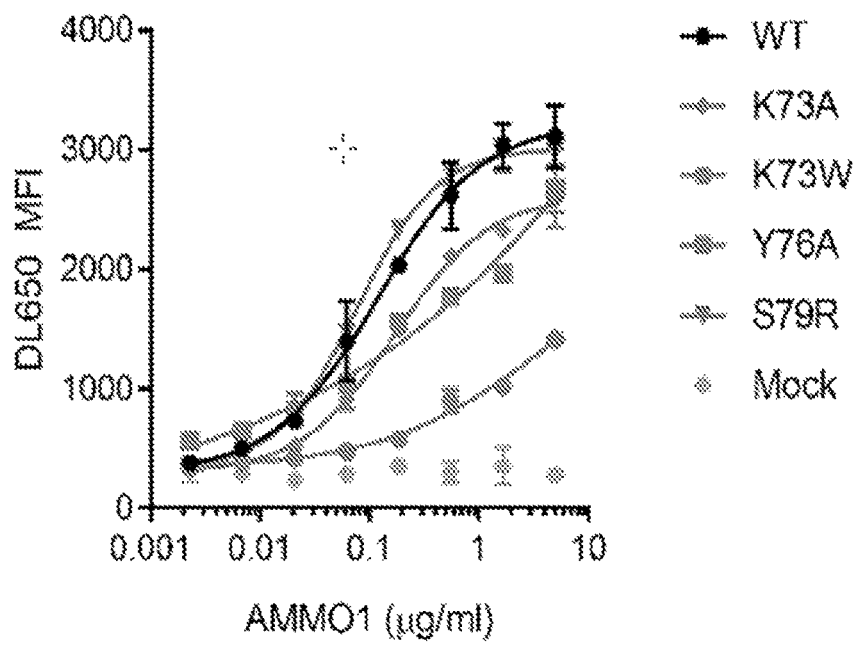
Figure 15E:
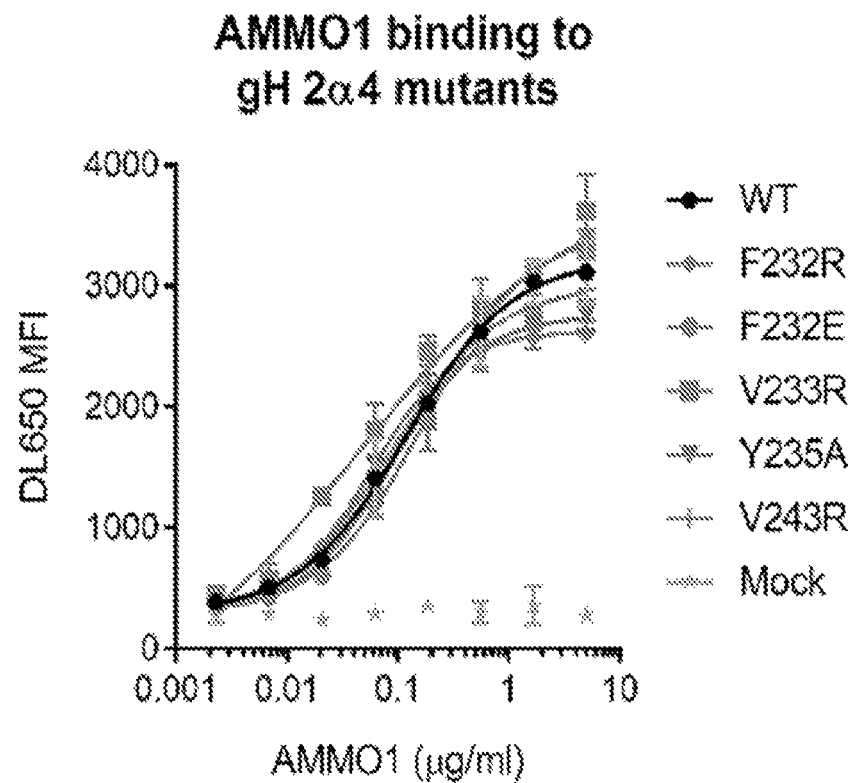

The N-linked glycan on gH-N60 is oriented such that it appears to form interactions with the AMMO1 framework region and could putatively contact the CDRL2 (FIG. 13G). N-linked glycosylation in gH, gL and gp42 was profiled by on-line reversed-phase liquid chromatography with electron transfer/high-energy collision-dissociation tandem mass-spectrometry which verified the presence of several high-mannose and hybrid glycans at the gH-N60 position (FIGS. 14H, 6).

Disruption of the gH-N60 glycosylation sequon, by introducing a T62A substitution in gH, altered AMMO1 binding kinetics, supporting that the glycan could interact with the antibody (FIG. 9). Additionally, the first residue of the AMMO1 heavy chain, a pyroglutamic acid, appears to directly interact with the gp42 C-domain. Substitution of this residue by an asparagine (AMMO1Q1NHC), however, did not significantly affect the AMMO binding affinity for gH/gL (FIG. 9), and had no significant effect on its ability to neutralize EBV infection of B cells, or epithelial cells (FIG. 16).

The cryoEM structure indicates that the AMMO1 epitope is distinct from that of E1D1 and CL59, which bind exclusively to gL and to D-IV, respectively (Sathiyamoorthy et al., 2016; Sathiyamoorthy et al., 2017). Comparison of the gH/gL/gp42/AMMO1 cryoEM structure with the recently described gH/gL/gp42 N-terminal domain/CL40 crystal structure (Sathiyamoorthy et al., 2017), showed not only that the epitopes of the two antibodies overlap at the 2α-4 helix, but also that their FAb fragments would clash with each other upon binding to gH/gL (FIGS. 17A-17C), suggesting that they would compete for binding via steric hindrance. To confirm this observation and assess whether AMMO1 affects the binding of other anti-gH/gL MAbs, reciprocal competitive binding experiments were performed. Biotinylated anti-gH/gL MAbs were immobilized on streptavidin biosensors and used to measure binding to gH/gL which had been preincubated with a two-fold excess of non-biotinylated competing MAb (FIGS. 17D-17G).

Figure 17E:
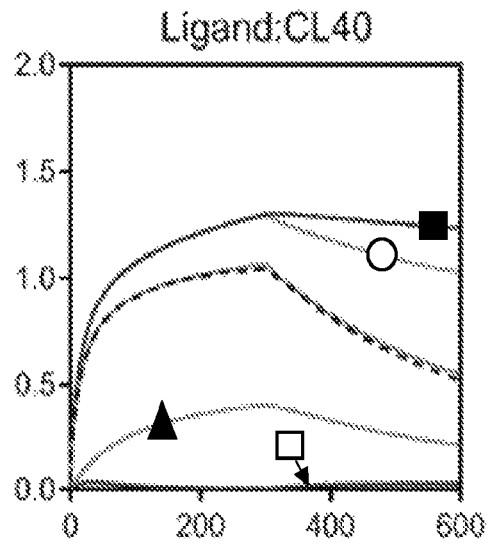
Figure 17F:
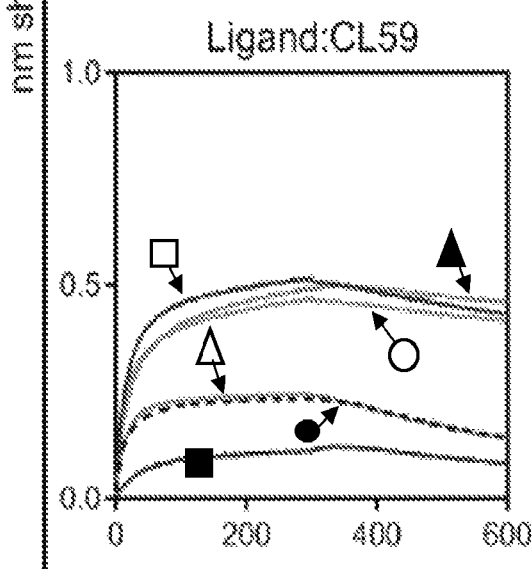
Figure 17G:
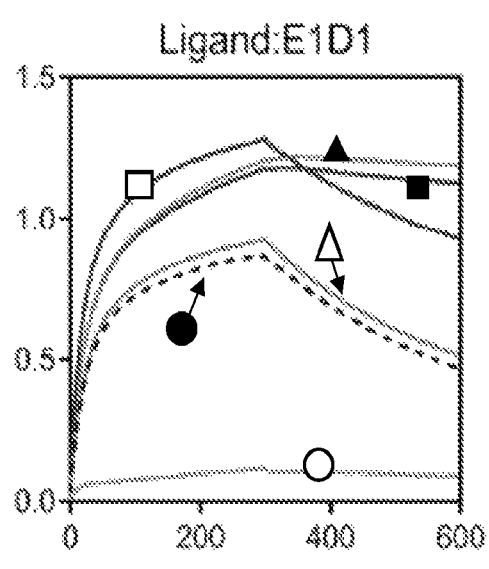

The binding of each antibody to gH/gL was inhibited when incubated with an excess of the same unlabeled antibody, as indicated by a decrease in the nm shift of the binding trace (FIGS. 17D-17G). In agreement with the structural data, reduced binding of AMMO1 to gH/gL when an excess of CL40 was present (FIG. 17D) and a complete inhibition of CL40 binding to gH/gL in the presence of an excess of AMMO1 was observed (FIG. 17E). Consistent with the formation of higher-molecular weight complexes, an increase in the nm shift, for the other combinations of gH/gL/MAbs was detected (FIG. 17F, or FIG. 17G). These results confirmed that the AMMO1 epitope is distinct from that of CL59 and E1D1 but partially overlaps with the CL40 epitope.

Figure 18A:
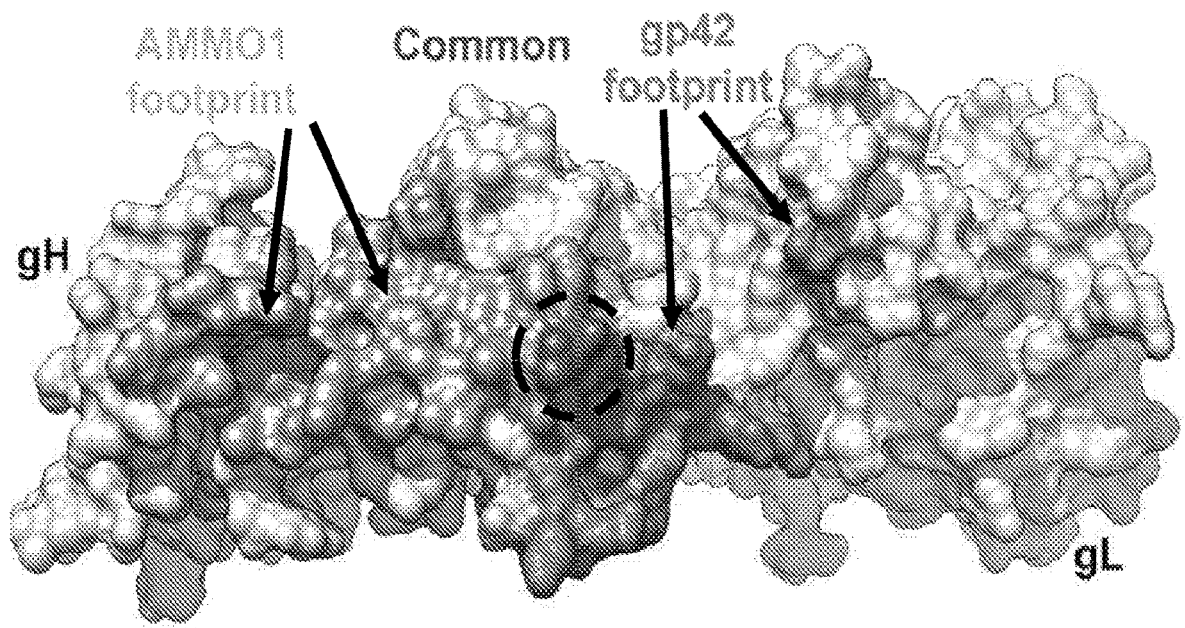
Figure 18B:
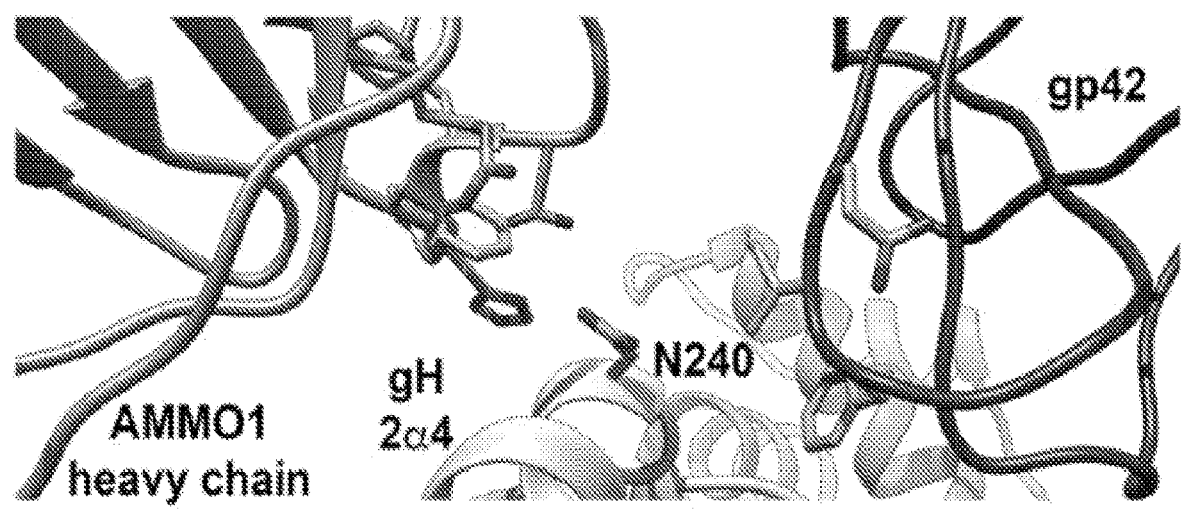

CL40 was reported to displace the gp42 CTD upon binding to the gH/gL/gp42 complex as a consequence of the overlap of their interaction sites on gH/gL (Sathiyamoorthy et al., 2017). Although the footprints of AMMO1 and gp42 are distinct, gH residue N240 experiences a change of accessible surface area upon binding to either of these two proteins (FIG. 18A). Since AMMO1 and gp42 are located on opposite sides of this residue, AMMO1 and gp42 interactions with N240 do not appear mutually exclusive (FIG. 18B). Using a distinct subset of particles identified by three-dimensional classification of the cryoEM dataset, a second reconstruction of the gH/gL/gp42/AMMO1 complex at 10 Å resolution in which the gp42 C-domain density is displaced relative to gH/gL was obtained (FIGS. 18C, 18D 14G).

Two-dimensional classification of negatively stained gH/gL/gp42 (FIG. 19A) and gH/gL/gp42/AMMO1 complexes (FIGS. 19B, 19C) also unambiguously showed that a small fraction of AMMO1-bound complexes had a displaced gp42 CTD (FIG. 19C). In contrast, gp42 was displaced from all gH/gL/gp42/CL40 complexes under the same conditions (FIG. 19D).

Figure 18F:
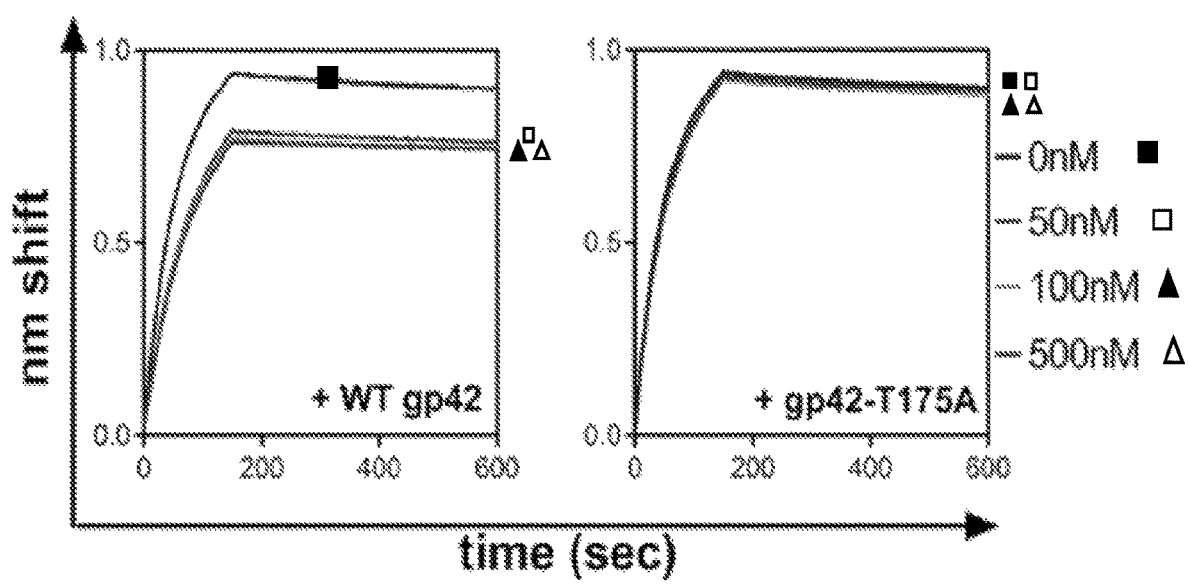

The cryoEM map at 4.8 Å resolution shows that the gp42-N173 glycan points toward the framework region of the AMMO1 light chain, indicating that it might interfere with AMMO1 binding (FIG. 18E). Using mass spectrometry, the presence of various glycans at this position was verified (FIGS. 14H, 9). In line with these observations, binding experiments revealed partial competition between AMMO1 and gp42 for binding to gH/gL (FIG. 18F, left panel). This competition was fully abrogated by the introduction of a T175A mutation, which disrupts the N173 glycosylation sequon (FIG. 18F, right panel), while retaining nanomolar binding affinity between gp42 and gH/gL (FIG. 9). These data reveal that AMMO1 can sterically displace the gp42 CTD from gH/gL through the gp42 N173 glycan. This mechanism is distinct from that of CL40-mediated gp42 CTD displacement, which results from a direct overlap between the Mab epitope and the gp42 CTD-binding site on gH/gL (Sathiyamoorthy et al., 2017).

Figure 20A:
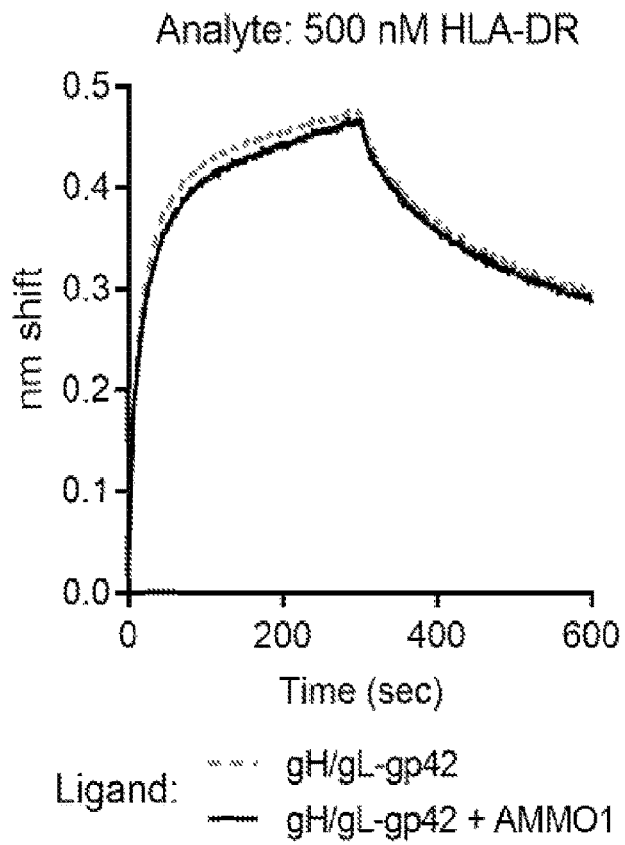
Figure 20B:
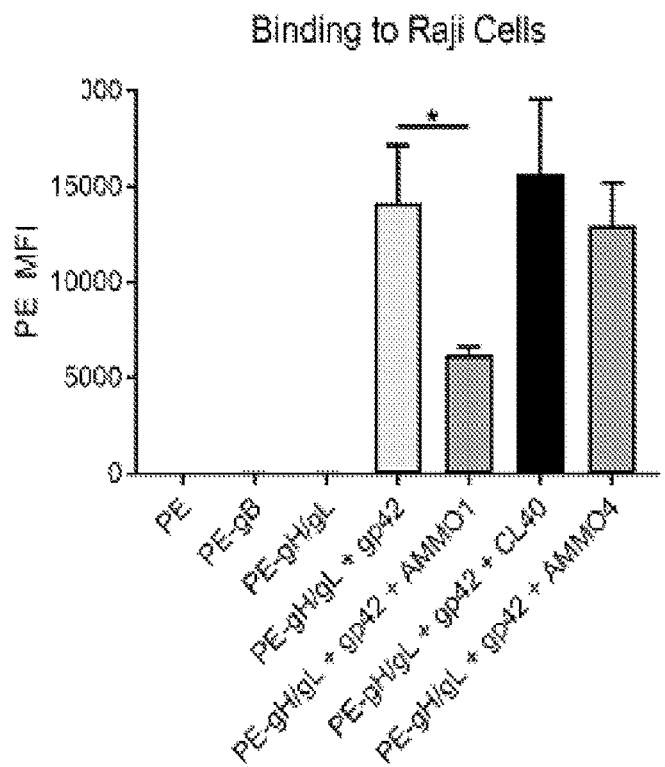
Figure 20C:
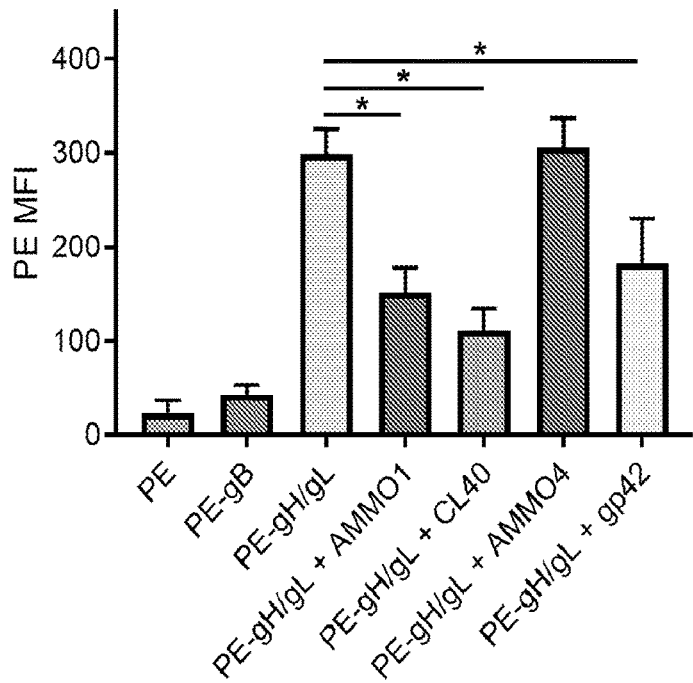
Figure 20D:
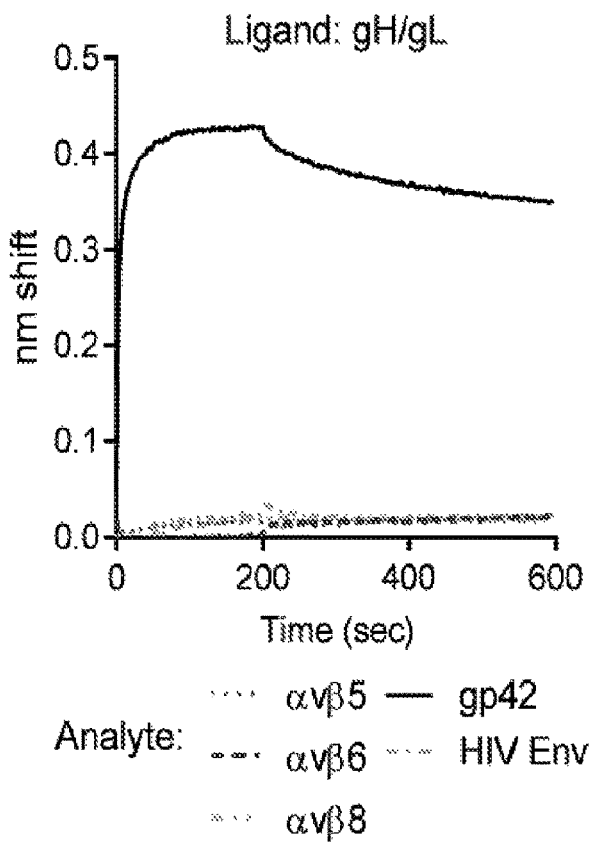

AMMO1 Neutralization Mechanism. Since AMMO1 can alter the conformation of gp42 in the complex, it was assessed whether it also affected the ability of gH/gL/gp42 to bind to HLA class II and did not observe difference in the binding irrespective of the presence of the AMMO1 FAb (FIG. 20A). It was also assessed whether AMMO1 binding to gH/gL/gp42 could affect the ability of the complex to bind to B cells. As expected, PE-labeled gH/gL bound to Raji cells in the presence, but not in the absence of gp42 (FIG. 20B). Pre-incubation of PE-labeled gH/gL with an excess of AMMO1, but not CL40 or the control MAb AMMO4 reduced, but did not completely inhibit gH/gL/gp42 binding to B cells (FIG. 20B). During epithelial cell infection, gH/gL binds directly to receptors on the surface of epithelial cells that presumably trigger gH/gL and lead to the subsequent activation of gB (Borza et al., 2004; Chen et al., 2012). Weak binding of PE-labeled gH/gL to the surface of the AGS epithelial cell line was observed (FIG. 20C). This binding was specific as direct binding of gH/gL to Raji cells under the same conditions was not detected (FIG. 20B), nor was binding of PE-labeled gB to either cell type (FIGS. 20B, 20C). Pre-incubation with AMMO1, CL40, or gp42 reduced, but did not abrogate gH/gL binding to AGS cells (FIG. 20C), whereas the anti-gB Mab AMMO4 had no effect.

gH/gL is thought to interact directly with αvβ5, αvβ6, or αvβ8 integrins present at the surface of epithelial cells through the KGD motif on gH D-III (Chen et al., 2012; Chesnokova and Hutt-Fletcher, 2011; Chesnokova et al., 2009). The results suggest that AMMO1 binding could restrict integrin access to the KGD motif due to the proximity of its epitope (FIG. 13G). Binding of gH/gL to αvβ5, αvβ6 or αvβ8 integrins was not detected (FIG. 20D). These observations are in line with a recent report (Sathiyamoorthy et al., 2017), but contrast with previous studies (Chesnokova and Hutt-Fletcher, 2011; Chesnokova et al., 2009).

Recently, a direct interaction between gH/gL and EphA2 has also been shown to be important for EBV viral entry (Chen et al., 2018; Zhang et al., 2018). A very weak binding signal between EphA2 and gH/gL that was unaltered by pre-incubation of AMMO1 (FIG. 20E) was observed suggesting that AMMO1 does not prevent a gH/gL-EphA2 interaction.

Figure 20E:
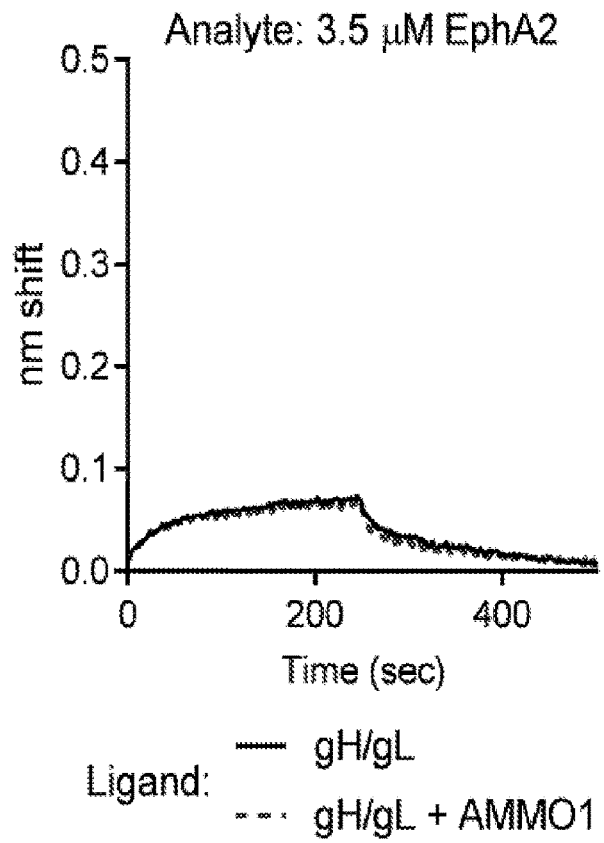
Figure 20F:
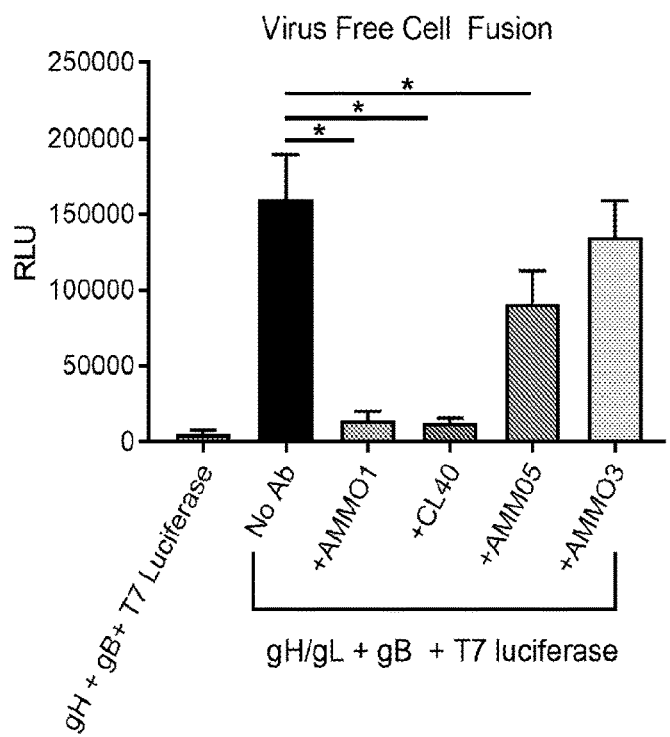

The observation that AMMO1 potently neutralizes EBV infection of both B cells and epithelial cells points to a common mechanism of viral inhibition. Since AMMO1 fails to completely block binding of gH/gL to epithelial cells, or gH/gL/gp42 to B cells it was hypothesized that AMMO1 is likely interfering with gB activation and membrane fusion. Using a virus-free cell fusion assay (McShane and Longnecker, 2005), it was observed that the anti-gH/gL MAbs AMMO1 and CL40, and the anti-gB MAb AMMO5 significantly reduced cell fusion whereas the non-neutralizing MAb AMMO3 had no effect (FIG. 20E).

Sequences for the VHNL regions of the antibodies reported here can be found at genbank under the accession numbers: KY631779-KY631788. Glycopeptide LC-MS/MS raw data and Byonic search results have been deposited in proteomics identification (PRIDE) database under PXD006403. The cryoEM maps have been deposited in the Electron Microscopy Data Bank with accession code EMD-7344 (4.8 Å) and EMD-7345 (10 Å). The atomic models of AMMO1 (PDB ID: 6BLA) and gH/gL-gp42-AMMO1 (PDB ID: 6C5V) have been deposited in the Protein Data Bank.

Discussion Orally transmitted EBV establishes lytic infection in permissive cells in the oral mucosa such as epithelial cells or infiltrating B cells (Rickinson et al., 2014; Taylor et al., 2015). EBV has tropism for both cell types and it is not clear which one is preferentially infected during primary infection (Tangye et al., 2017). The virus could first infect epithelial cells and lytic viral replication would subsequently seed B cell infections.

Alternatively, the virus may initially infect infiltrating B cells, which would lead to subsequent targeting of epithelial cells. Neither scenario is mutually exclusive, thus a combination of epithelial and B cell neutralizing antibodies may be required to most effectively block incoming virus at the oral mucosa (Herrman et al., 2015).

Serum antibodies from natural infection can neutralize EBV entry in both B cells and epithelial cells in vitro but the epitopes targeted by these MAbs are unknown.

Previously isolated anti-gp350 MAbs can inhibit infection of B cells but not CD21 negative epithelial cells. Conversely, known anti-gH/gL antibodies are effective at preventing epithelial cell infection but fail to prevent B cell infection. These observations suggest that gp350 or gH/gL antibodies alone might not be sufficient to prevent EBV infection, and that an effective EBV subunit vaccine might need to elicit both types of MAbs to prevent an initial infection event.

Previous EBV subunit vaccine studies in humans have focused on gp350. Recombinant gp350 elicits antibodies that can neutralize B cell infection in vitro (Moutschen et al., 2007) and compete for binding with the 72A1 MAb, which is used as a surrogate marker for B cell neutralizing antibodies (Sokal et al., 2007). Although a gp350 subunit vaccine showed clinical benefit by reducing the incidence of infectious mononucleosis, it failed to protect from EBV infection in a phase II clinical trial in humans (Sokal et al., 2007). From these results emerged the idea that the efficacy of EBV subunit vaccines could be improved if they were formulated with additional glycoproteins (Cohen et al., 2013). The potent in vitro neutralizing activity of AMMO1 suggests that a gH/gL-based vaccine capable of eliciting AMMO1-like antibodies could be as effective as gp350 at eliciting a humoral immune response blocking EBV entry into B cells, while also preventing epithelial cell infection. Moreover a gH/gL vaccine would avoid the potential enhancement of epithelial cell infection reported for anti-gp350 antibodies (Turk et al., 2006). In support of this notion, rabbit immunization with gH/gL elicited higher antibody titers blocking B cell infection than gp350 (Cui et al., 2016). However, the epitope specificities of these serum antibodies have not been mapped and the efficacy with which they neutralize epithelial cell infection is not known.

AMMO1 has utility as a therapeutic agent as well. Passive administration of the 72A1 MAb demonstrated capacity to prevent EBV infection during the early post-transplant period in high-risk EBV-seronegative transplant recipients. However, administration of 72A1 led to the production of anti-drug antibodies, which were attributed to its murine origin (Haque et al., 2006). Since AMMO1 can neutralize infection of the two main cell types targeted by EBV, and is human-derived, this antibody presents a more effective and safer alternative than 72A1.

EBV infection of B cells and epithelial cells requires gH/gL to engage distinct cell-surface receptors, which lead to triggering of gB-mediated fusion. The unique ability of AMMO1 among anti-gH/gL MAbs to neutralize both epithelial and B cell infection points to a common mechanism of neutralization, without being bound by theory, most likely by interfering with gB triggering. This is supported by the observation that AMMO1 blocks cell-cell fusion in a virus-free assay. Mutagenesis data identified that the D-I/D-II linker region is key for activation of membrane fusion during B cell and epithelial cell infection (Matsuura et al., 2010; Omerovic et al., 2005). Several of these critical residues are buried by AMMO1 which suggests that this antibody inhibits fusion activation by preventing a direct interaction between gB and the linker-helix on gH/gL (FIG. 7A). Residues within the D-I/D-II groove have been shown to mediate membrane fusion as well (Chen et al., 2013a; Matsuura et al., 2010; Plate et al., 2009). It has been proposed that conformational changes within the D-1/D-II groove induced by from receptor binding might be required for triggering of (or interaction with) gB (Chen et al., 2013a; Chesnokova and Hutt-Fletcher, 2011). Since AMMO1 binds to elements of D-1 (including gL), D-II, and the linker helix bridging D-1 and D-II, it could also inhibit gB activation by acting as a molecular clamp which prevents movements within and across D-1 and D-II that are necessary for gB triggering (FIG. 7B).

The architecture of CMVgH/gL resembles that of EBVgH/gL, including a groove between D-1 and D-II that is connected by a linker helix (Chandramouli and Malito, 2017). It has been proposed that binding of the CMVgH/gL/UL128/UL130/UL131 pentamer to a cell surface receptor induces a D-1 rearrangement around the linker helix which leads to a widening of the D-I/D-II groove and gB triggering (Chandramouli and Malito, 2017). Thus, antibodies that target the linker helix are important for CMV vaccine design as well. In line with this notion, the human MAb 13H11, which neutralizes CMV infection of both epithelial cells and fibroblasts binds in proximity of the linker helix of CMVgH/gL.

The fusion inhibition activity of AMMO1 is further supported by studies of neutralizing MAbs against gH/gL from other herpesviruses. MAbs that inhibit gB-mediated fusion of varicella zoster virus (VZV) bind to epitopes bridging the first two domains of VZVgH/gL (FIG. 22A, 22B) (Xing et al., 2015). Escape mutations from the LP11 antibody, which blocks the herpes simplex virus (HSV) gH/gL-gB interaction, also map to a similar epitope region on HSVgH/gL (Chowdary et al., 2010).

CL40 weakly neutralizes B-cell infection compared to AMMO1, and binds exclusively to gH D-II/D-III. Previous studies suggested that displacement of the gp42 CTD by CL40 prohibits a conformation of the gH/gL/gp42/HLA class II complex necessary for triggering gB-mediated fusion during B cell infection (Sathiyamoorthy et al., 2017). The observation that CL40 more readily displaces gp42 than AMMO1 but fails to potently neutralize B-cell infection, suggests that this is not the primary mechanism of B-cell neutralization by AMMO1.

The data also indicate that AMMO1 could contribute to neutralization by restricting access of gH/gL or gH/gL/gp42 to cell surface receptors during epithelial and B cell infection, respectively (FIG. 7 C-D). Despite having no effect on the ability of the gH/gL/gp42 complex to bind to soluble HLA class II, AMMO1 reduced binding of gH/gL/gp42 to the surface of B cells. In contrast, CL40 which binds to gH near the AMMO1 epitope has no effect on the binding of gH/gL/gp42 to B cells. This result could explain the difference in B cell neutralization potency between these two MAbs.

AMMO1 also reduced binding of gH/gL to the surface of epithelial cells. αVβ5 αVβ6, and αVβ8 integrins (Chesnokova and Hutt-Fletcher, 2011; Chesnokova et al., 2009), and EphA2 (Chen et al., 2018; Zhang et al., 2018) have been implicated as cell surface EBV receptors during epithelial cell infection. Since a weak interaction between gH/gL and EphA2 was detected, which was unaffected by AMMO1, it is unlikely that AMMO1 inhibits EBV infection of epithelial cells by blocking this interaction.

The KGD motif on D-II of gH/gL is believed to mediate direct binding to integrins (Chesnokova and Hutt-Fletcher, 2011; Chesnokova et al., 2009; Sathiyamoorthy et al., 2016; Sathiyamoorthy et al., 2017). Although the KGD motif remains exposed when AMMO1 is bound (FIG. 3G), its presence would greatly reduce accessibility to integrin. An interaction between gH/gL and soluble αVβ5 αVβ6 or αVβ8 integrins was not detected by BLI (FIG. 6D), but the reduced binding of gH/gL to the epithelial cell surface observed in the presence of AMMO1 indicates that the MAb may restrict binding to cell-surface anchored integrins, to membrane anchored EphA2, or to an alternative receptor (FIG. 7D).

In this Example, the AMMO5 Mab was also characterized. AMMO5 is the first reported anti-gB antibody with neutralizing activity against EBV, although it only inhibits entry into epithelial cells. The observed potency of AMMO1 towards EBV infection of epithelial cells and B cells suggests that the mechanism of gB activation by gH/gL is similar in both cases. The inability of AMMO5 to antagonize B cell infection, however, points to putative differences in gB triggering and/or fusion during EBV entry into the two cell types. This latter point is supported by mutagenesis studies of gH/gL, which revealed distinct effects on fusion with B cells and with epithelial cells (Chen et al., 2013a; Mohl et al., 2014; Sathiyamoorthy et al., 2016; Wu et al., 2005).

Most of the anti-gB MAbs characterized in this Example are non-neutralizing. It is emphasized that the gB protein used to sort B cells is most likely in the post-fusion conformation (Backovic et al., 2009) and might fail to bait out neutralizing antibodies recognizing the pre-fusion state, as was reported for the RSV fusion protein (Magro et al., 2012; McLellan et al., 2013).

In summary, AMMO1 is currently the only known anti-gH/gL antibody that potently neutralizes both epithelial and B-cell infections. The near-atomic resolution cryoEM structure of the gH/gL/gp42/AMMO1 complex presented here defines a key site of EBV vulnerability and paves the way for the design of next-generation subunit vaccines. The moderate level of somatic mutation in AMMO1 is within the range that could be elicited with current human vaccine regimens implemented for influenza or HIV (Easterhoff and Moody, 2017; Joyce et al., 2016; Moody et al., 2011; Wrammert et al., 2008). AMMO1 can be used to treat and/or prevent EBV-related complications such as lymphoproliferative diseases in organ transplant recipients and immunocompromised individuals.

Example 3

Human hematopoietic progenitor stem cells engrafted in immunocompromised mice develop into human B cells that can be infected with EBV. A low EBV dose results in persistent latent infection that mimics natural human infection, while a higher dose results in a lymphoproliferative disease state. As a proof of concept that disclosed antibodies protect from infection, B cells were harvested from these mice and challenged with a low-dose EBV reporter virus that induces GFP expression upon infection. The absence of antibody could readily be detected (FIG. 23A, left), yet there was no evidence of infection in the presence of AMMO1 (FIG. 233A, right).

Next, the ability of AMMO1 to protect against EBV in vivo was assessed. 0.5 mg AMMO1 or an irrelevant anti-HIV MAb was administered to humanized mice 2 days prior to a high dose ($5 \times IC_{50}$) intravenous EBV challenge. 6 weeks later, nearly all of the human B cells (hCD45+,hCD19+) in the blood had died in mice that received the control antibody (FIG. 23B), while B cells survived in mice that received AMMO1 (FIG. 23B). Similar results were observed in the spleen at week 7 (FIG. 23C). This data indicates that AMMO1 has protective benefit at the tested physiological dose and route (i.e. low levels of incoming virions in the nasopharynx vs high level of virions injected intravenously).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. In particular embodiments, a material effect would cause a statistically-significant reduction in the ability of an anti-EBV antibody to neutralize EBV in the assay described in relation to FIGS. 8A, 8B. In particular embodiments, a material effect would cause a statistically-significant reduction in a primary antibody response to an EBV vaccine.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; +19% of the stated value; +18% of the stated value; +17% of the stated value; +16% of the stated value; +15% of the stated value; +14% of the stated value; ±13% of the stated value; ±12% of the stated value; +11% of the stated value; +10% of the stated value; ±9% of the stated value; +8% of the stated value; +7% of the stated value; +6% of the stated value; +5% of the stated value; +4% of the stated value; +3% of the stated value; +2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

Example 2 References

Adams, et al. (2010). Acta Crystallogr D Biol Crystallogr 66, 213-221.

Agirre, et al. (2015). Nature structural & molecular biology 22, 833-834.
Backovic, et al. (2009). Proceedings of the National Academy of Sciences of the United States of America 106, 2880-2885.
Balachandran, et al. (1987). Journal of virology 61, 1125-1135.
Bern, et al. (2012). Byonic: advanced peptide and protein identification software. Current protocols in bioinformatics Chapter 13, Unit 13 20.
Borza & Hutt-Fletcher (2002). Nature medicine 8, 594-599.
Borza, et al. (2004). Journal of virology 78, 5007-5014.
Brown, et al. (2015). Acta crystallographica Section D, Biological crystallography 71, 136-153.
Chandramouli & Malito (2017). Structural basis for potent antibody-mediated neutralization of human cytomegalovirus. 2.
Chen, et al. (2013a). Journal of virology 87, 3620-3627.
Chen, et al. (2012). The KGD motif of Epstein-Barr virus gH/gL is bifunctional, orchestrating infection of B cells and epithelial cells. mBio 3.
Chen, et al. (2018). Ephrin receptor A2 is a functional entry receptor for Epstein-Barr virus. Nature Microbiology.
Chen, et al. (2013b). Ultramicroscopy 135, 24-35.
Chen, et al. (2010). Acta crystallographica Section D, Biological crystallography 66, 12-21.
Chesnokova, et al. (2011). Journal of virology 85, 13214-13223.
Chesnokova, et al. (2009). PNAS USA 106, 20464-20469.
Chowdary, et al. (2010). Nature structural & molecular biology 17, 882-888.
Ciferri, et al. (2015). PLoS pathogens 11, e1005230.
Cohen, et al. (2011). Science translational medicine 3, 107fs107.
Cohen, et al. (2013). Vaccine 31 Suppl 2, B194-196.
Collaborative Computational Project, N. (1994). Acta Crystallogr D Biol Crystallogr 50, 760-763.
Connolly, et al. (2011). Nature reviews Microbiology 9, 369-381.
Cui, et al. (2016). Vaccine 34, 4050-4055.
DeLano (2002). The PyMOL Molecular Graphics System (San Carlos, Calif.: DeLano Scientific).
Delecluse, et al. (1998). PNAS USA 95, 8245-8250.
DiMaio, et al. (2015). Nature methods 12, 361-365.
DiMaio, et al. (2009). Journal of molecular biology 392, 181-190.
Doria-Rose, et al. (2015). Journal of virology 90, 76-91.
Easterhoff & Moody (2017). Boosting of HIV envelope CD4 binding site antibodies with long variable heavy third complementarity determining region in the randomized double blind RV305 HIV-1 vaccine trial. 13, e1006182.
Edson & Thorley-Lawson (1981). Journal of virology 39, 172-184.
Emsley, et al. (2010). Acta crystallographica Section D, Biological crystallography 66, 486-501.
Frese, et al. (2013). Journal of proteome research 12, 1520-1525.
Goddard, et al. (2007). Journal of structural biology 157, 281-287.
Haan, et al. (2000). Journal of virology 74, 2451-2454.
Haan, et al. (2001). Virology 290, 106-114.
Haque, et al. (2006). The Journal of infectious diseases 194, 584-587.
Herrman, et al. (2015). Journal of virology 90, 1222-1230.
Hoffman, et al. (1980). PNAS USA 77, 2979-2983.
Huang, et al. (2013). Nature protocols 8, 1907-1915.
Hutchinson, et al. (1992). Journal of virology 66, 2240-2250.
Joyce, et al. (2016). Cell 166, 609-623.
Kimanius, et al. (2016). Accelerated cryo-EM structure determination with parallelisation using GPUs in RELION-2. eLife 5.
Kirschner, et al. (2007). Journal of virology 81, 9216-9229.
Kirschner, et al. (2006). Journal of virology 80, 9444-9454.
Krissinel & Henrick (2007). Journal of molecular biology 372, 774-797.
Li, et al. (1997). Journal of virology 71, 1667-1670.
Li, et al. (1995). Journal of virology 69, 3987-3994.
Li, et al. (1992). Nature 356, 347-350.
Macagno, et al. (2010). Journal of virology 84, 1005-1013.
Magro, et al. (2012). PNAS USA 109, 3089-3094.
Matsuura, et al. (2010). PNAS USA 107, 22641-22646.
McGuire, et al. (2016). Nature communications 7, 10618.
McLellan, et al. (2013). Science 340, 1113-1117.
McShane & Longnecker (2005). Methods Mol Biol 292, 187-196.
Miller, et al. (1972). The Journal of infectious diseases 125, 403-406.
Miller & Hutt-Fletcher (1992). Journal of virology 66, 3409-3414.
Mohl, et al. (2016). Molecules and cells 39, 286-291.
Mohl, et al. (2014). Journal of virology 88, 13570-13579.
Molesworth, et al. (2000). Journal of virology 74, 6324-6332.
Moody, et al. (2011). PloS one 6, e25797.
Moss & Pope, (1972). The Journal of general virology 17, 233-236.
Moutschen, et al. (2007). Vaccine 25, 4697-4705.
Neuhierl, et al. (2002). PNAS USA 99, 15036-15041.
Oda, et al. (2000). Virology 276, 52-58.
Ogembo, et al. (2013). Cell reports 3, 371-385.
Okuma, et al. (1999). Virology 254, 235-244.
Omerovic, et al. (2005). Journal of virology 79, 12408-12415.
Otwinowski & Minor (1997). Methods in enzymology 276, 307-326.
Pettersen, et al. (2004). Journal of computational chemistry 25, 1605-1612.
Plate, et al. (2011). Virology 413, 26-38.
Plate, et al. (2009). Journal of virology 83, 7678-7689.
Rappuoli, et al. (2016). The Journal of experimental medicine 213, 469-481.
Rickinson, et al. (2014). Trends in immunology 35, 159-169.
Rosenthal & Henderson (2003). Journal of molecular biology 333, 721-745.
Sashihara, et al. (2009). Virology 391, 249-256.
Sathiyamoorthy, et al. (2016). Nature communications 7, 13557.
Sathiyamoorthy, et al. (2014). PLoS pathogens 10, e1004309.
Sathiyamoorthy, et al. (2017). PNAS USA 114, E8703-e8710.
Scheres & Chen (2012). Nature methods 9, 853-854.
Snijder, et al. (2017). Vitrification after multiple rounds of sample application and blotting improves particle density on cryo-electron microscopy grids. Journal of structural biology.
Sokal, et al. (2007). The Journal of Infectious Diseases 196, 1749-1753.
Spriggs, et al. (1996). Journal of Virology 70, 5557-5563.
Stampfer & Heldwein (2013). Current Opinion in Virology 3, 13-19.
Strnad, et al. (1982). Journal of virology 41, 258-264.

Suloway, et al. (2005). Journal of structural biology 151, 41-60.
Tang, et al. (2007). Journal of structural biology 157, 38-46.
Tangye, et al. (2017). The Journal of experimental medicine 214, 269-283.
Tanner, et al. (1987). Cell 50, 203-213.
Taylor, et al. (2015). Annual review of immunology 33, 787-821.
Taylor, et al. (2012). The Journal of experimental medicine 209, 2065-2077.
Thorley-Lawson & Geilinger (1980). PNAS USA 77, 5307-5311.
Tugizov, et al. (2003). Nature medicine 9, 307-314.
Turk, et al. (2006). Journal of virology 80, 9628-9633.
Voss, et al. (2009). Journal of structural biology 166, 205-213.
Wang, et al. (1998). Journal of virology 72, 5552-5558.
Wrammert, et al. (2008). Nature 453, 667-671.
Wu, et al. (2005). Journal of virology 79, 10923-10930.
Xing, et al. (2015). PNAS USA 112, 6056-6061.
Young & Rickinson (2004). Nature Reviews Cancer 4, 757-768.
Zhang, et al. (2018). Ephrin receptor A2 is an epithelial cell receptor for Epstein-Barr virus entry. Nature Microbiology.
Zhang, (2016). Journal of structural biology 193, 1-12.
Zheng, et al. (2017). Nature methods 14, 331-332.

What is claimed is:

1. An anti-EBV antibody comprising:
   (i) variable light chain complementary determining regions (CDRs) having the sequences as set forth in SEQ ID NO: 11 for CDRL1, SEQ ID NO: 12 for CDRL2, SEQ ID NO: 13 for CDRL3, and variable heavy chain CDRs having the sequences as set forth in SEQ ID NO: 14 for CDRH1, SEQ ID NO: 15 for CDRH2, and SEQ ID NO: 16 for CDRH3;
   (ii) variable light chain CDRs having the sequences as set forth in SEQ ID NO: 17 for CDRL1, SEQ ID NO: 18 for CDRL2, SEQ ID NO: 19 for CDRL3, and variable heavy chain CDRs having the sequences as set forth in SEQ ID NO: 20 for CDRH1, SEQ ID NO: 21 for CDRH2, and SEQ ID NO: 22 for CDRH3;
   (iii) variable light chain CDRs having the sequences as set forth in SEQ ID NO: 23 for CDRL1, SEQ ID NO: 24 for CDRL2, SEQ ID NO: 25 for CDRL3, and variable heavy chain CDRs having the sequences as set forth in SEQ ID NO: 26 for CDRH1, SEQ ID NO: 27 for CDRH2, and SEQ ID NO: 28 for CDRH3;
   (iv) variable light chain CDRs having the sequences as set forth in SEQ ID NO: 29 for CDRL1, SEQ ID NO: 30 for CDRL2, SEQ ID NO: 31 for CDRL3, and variable heavy chain CDRs having the sequences as set forth in SEQ ID NO: 32 for CDRH1, SEQ ID NO: 33 for CDRH2, and SEQ ID NO: 34 for CDRH3; or
   (v) variable light chain CDRs having the sequences as set forth in SEQ ID NO: 35 for CDRL1, SEQ ID NO: 36 for CDRL2, SEQ ID NO: 37 for CDRL3, and variable heavy chain CDRs having the sequences as set forth in SEQ ID NO: 38 for CDRH1, SEQ ID NO: 39 for CDRH2, and SEQ ID NO: 40 for CDRH3, according to Kabat numbering,
wherein the anti-EBV antibody is conjugated to a drug, an imaging agent, an enzyme label, or biotin.

2. The anti-EBV antibody of claim 1, comprising a human IgG1 Fc comprising mutations: G236A; S239D; A330L; and I332E, according to EU numbering.

3. The anti-EBV antibody of claim 1, comprising a human IgG1 Fc comprising mutations M428L and N434S, according to EU numbering.

4. The anti-EBV antibody of claim 1, comprising a thioMab.

5. The anti-EBV antibody of claim 1, comprising an Fc region having a reduced fucose content or lackinq fucose.

6. The anti-EBV antibody of claim 1, comprising a polyethylene glycol (PEG)-linkage and/or a human serum albumin (HSA)-linkage.

7. The anti-EBV antibody of claim 1, wherein the anti-EBV antibody is conjugated to an enzyme label comprising alkaline phosphatase, horseradish peroxidase, or β-galactosidase.

8. An antibody-based binding domain comprising:
   (i) a variable light chain having at least 95% sequence identity to the sequence as set forth in SEQ ID NO: 2 and a variable heavy chain having at least 95% sequence identity to the sequence as set forth in SEQ ID NO: 1;
   (ii) a variable light chain having at least 95% sequence identity to the sequence as set forth in SEQ ID NO: 4 and a variable heavy chain having at least 95% sequence identity to the sequence as set forth in SEQ ID NO: 3;
   (iii) a variable light chain having at least 95% sequence identity to the sequence as set forth in SEQ ID NO: 6 and a variable heavy chain having at least 95% sequence identity to the sequence as set forth in SEQ ID NO: 5;
   (iv) a variable light chain having at least 95% sequence identity to the sequence as set forth in SEQ ID NO: 8 and a variable heavy chain having at least 95% sequence identity to the sequence as set forth in SEQ ID NO: 7; or
   (v) a variable light chain having at least 95% sequence identity to the sequence as set forth in SEQ ID NO: 10 and a variable heavy chain having at least 95% sequence identity to the sequence as set forth in SEQ ID NO: 9;
wherein the antibody-based binding domain is
   (a) a single chain variable fragment (scFv); and/or
   (b) conjugated to a drug, an imaging agent, an enzyme label, or biotin.

9. The antibody-based binding domain of claim 8 wherein:
   (i) the variable light chain has at least 98% sequence identity to the sequence as set forth in SEQ ID NO: 2 and the variable heavy chain has at least 98% sequence identity to the sequence as set forth in SEQ ID NO: 1;
   (ii) the variable light chain has at least 98% sequence identity to the sequence as set forth in SEQ ID NO: 4 and the variable heavy chain has at least 98% sequence identity to the sequence as set forth in SEQ ID NO: 3;
   (iii) the variable light chain has at least 98% sequence identity to the sequence as set forth in SEQ ID NO: 6 and the variable heavy chain has at least 98% sequence identity to the sequence as set forth in SEQ ID NO: 5;
   (iv) the variable light chain has at least 98% sequence identity to the sequence as set forth in SEQ ID NO: 8 and the variable heavy chain has at least 98% sequence identity to the sequence as set forth in SEQ ID NO: 7; or
   (v) the variable light chain has at least 98% sequence identity to the sequence as set forth in SEQ ID NO: 10 and the variable heavy chain has at least 98% sequence identity to the sequence as set forth in SEQ ID NO: 9.

10. The antibody-based binding domain of claim 9, wherein
   (i) the variable heavy chain having at least 98% sequence identity to the sequence as set forth in SEQ ID NO: 1 comprises a Q1N mutation;
   (ii) the variable heavy chain having at least 98% sequence identity to the sequence as set forth in SEQ ID NO: 3 comprises a Q1N mutation;
   (iii) the variable heavy chain having at least 98% sequence identity to the sequence as set forth in SEQ ID NO: 5 comprises a E1N mutation;
   (iv) the variable light chain having at least 98% sequence identity to the sequence as set forth in SEQ ID NO: 6 comprises a Q1N mutation;
   (v) the variable heavy chain having at least 98% sequence identity to the sequence as set forth in SEQ ID NO: 7 comprises a Q1N mutation;
   (vi) the variable heavy chain having at least 98% sequence identity to the sequence as set forth in SEQ ID NO: 9 comprises a E1N mutation; and/or
   (vii) the variable light chain having at least 98% sequence identity to the sequence as set forth in SEQ ID NO: 10 comprises a E1N mutation.

11. The antibody-based binding domain of claim 8 wherein:
   (i) the variable light chain has the sequence as set forth in SEQ ID NO: 2 and the variable heavy chain has the sequence as set forth in SEQ ID NO: 1;
   (ii) the variable light chain has the sequence as set forth in SEQ ID NO: 4 and the variable heavy chain has the sequence as set forth in SEQ ID NO: 3;
   (iii) the variable light chain has the sequence as set forth in SEQ ID NO: 6 and the variable heavy chain has the sequence as set forth in SEQ ID NO: 5;
   (iv) the variable light chain has the sequence as set forth in SEQ ID NO: 8 and the variable heavy chain has the sequence as set forth in SEQ ID NO: 7; or
   (v) the variable light chain has the sequence as set forth in SEQ ID NO: 10 and the variable heavy chain has the sequence as set forth in SEQ ID NO: 9.

12. The antibody-based binding domain of claim 8, comprising a thioMab.

13. The antibody-based binding domain of claim 8, comprising a polyethylene glycol (PEG)-linkage and/or a human serum albumin (HSA)-linkage.

14. The antibody-based binding domain of claim 8, wherein the antibody-based binding domain is conjugated to an enzyme label comprising alkaline phosphatase, horseradish peroxidase, or β-galactosidase.

15. An isolated cell transfected with a heterologous nucleic acid encoding
   an anti-EBV antibody comprising:
   (i) variable light chain complementary determining regions (CDRs) having the sequences as set forth in SEQ ID NO: 11 for CDRL1, SEQ ID NO: 12 for CDRL2, SEQ ID NO: 13 for CDRL3, and variable heavy chain CDRs having the sequences as set forth in SEQ ID NO: 14 for CDRH1, SEQ ID NO: 15 for CDRH2, and SEQ ID NO: 16 for CDRH3, according to Kabat numbering; and/or a variable light chain having at least 95% sequence identity to the sequence as set forth in SEQ ID NO: 2 and a variable heavy chain having at least 95% sequence identity to the sequence as set forth in SEQ ID NO: 1;
(ii) variable light chain CDRs having the sequences as set forth in SEQ ID NO: 17 for CDRL1, SEQ ID NO: 18 for CDRL2, SEQ ID NO: 19 for CDRL3, and variable heavy chain CDRs having the sequences as set forth in SEQ ID NO: 20 for CDRH1, SEQ ID NO: 21 for CDRH2, and SEQ ID NO: 22 for CDRH3, according to Kabat numbering; and/or
a variable light chain having at least 95% sequence identity to the sequence as set forth in SEQ ID NO: 4 and a variable heavy chain having at least 95% sequence identity to the sequence as set forth in SEQ ID NO: 3;
(iii) variable light chain CDRs having the sequences as set forth in SEQ ID NO: 23 for CDRL1, SEQ ID NO: 24 for CDRL2, SEQ ID NO: 25 for CDRL3, and variable heavy chain CDRs having the sequences as set forth in SEQ ID NO: 26 for CDRH1, SEQ ID NO: 27 for CDRH2, and SEQ ID NO: 28 for CDRH3, according to Kabat numbering; and/or
a variable light chain having at least 95% sequence identity to the sequence as set forth in SEQ ID NO: 6 and a variable heavy chain having at least 95% sequence identity to the sequence as set forth in SEQ ID NO: 5;
(iv) variable light chain CDRs having the sequences as set forth in SEQ ID NO: 29 for CDRL1, SEQ ID NO: 30 for CDRL2, SEQ ID NO: 31 for CDRL3, and variable heavy chain CDRs having the sequences as set forth in SEQ ID NO: 32 for CDRH1, SEQ ID NO: 33 for CDRH2, and SEQ ID NO: 34 for CDRH3, according to Kabat numbering; and/or
a variable light chain having at least 95% sequence identity to the sequence as set forth in SEQ ID NO: 8 and a variable heavy chain having at least 95% sequence identity to the sequence as set forth in SEQ ID NO: 7;
or
(v) variable light chain CDRs having the sequences as set forth in SEQ ID NO: 35 for CDRL1, SEQ ID NO: 36 for CDRL2, SEQ ID NO: 37 for CDRL3, and variable heavy chain CDRs having the sequences as set forth in SEQ ID NO: 38 for CDRH1, SEQ ID NO: 39 for CDRH2, and SEQ ID NO: 40 for CDRH3, according to Kabat numbering; and/or
a variable light chain having at least 95% sequence identity to the sequence as set forth in SEQ ID NO: 10 and a variable heavy chain having at least 95% sequence identity to the sequence as set forth in SEQ ID NO: 9.

16. The cell of claim 15, wherein
(i) the variable light chain has at least 98% sequence identity to the sequence as set forth in SEQ ID NO: 2 and the variable heavy chain has at least 98% sequence identity to the sequence as set forth in SEQ ID NO: 1;
(ii) the variable light chain has at least 98% sequence identity to the sequence as set forth in SEQ ID NO: 4 and the variable heavy chain has at least 98% sequence identity to the sequence as set forth in SEQ ID NO: 3;
(iii) the variable light chain has at least 98% sequence identity to the sequence as set forth in SEQ ID NO: 6 and the variable heavy chain has at least 98% sequence identity to the sequence as set forth in SEQ ID NO: 5;
(iv) the variable light chain has at least 98% sequence identity to the sequence as set forth in SEQ ID NO: 8 and the variable heavy chain has at least 98% sequence identity to the sequence as set forth in SEQ ID NO: 7; or
(v) the variable light chain has at least 98% sequence identity to the sequence as set forth in SEQ ID NO: 10 and the variable heavy chain has at least 98% sequence identity to the sequence as set forth in SEQ ID NO: 9.

17. The cell of claim 16, wherein
(i) the variable heavy chain having at least 98% sequence identity to the sequence as set forth in SEQ ID NO: 1 comprises a Q1N mutation;
(ii) the variable heavy chain having at least 98% sequence identity to the sequence as set forth in SEQ ID NO: 3 comprises a Q1N mutation;
(iii) the variable heavy chain having at least 98% sequence identity to the sequence as set forth in SEQ ID NO: 5 comprises a E1N mutation;
(iv) the variable light chain having at least 98% sequence identity to the sequence as set forth in SEQ ID NO: 6 comprises a Q1N mutation;
(v) the variable heavy chain having at least 98% sequence identity to the sequence as set forth in SEQ ID NO: 7 comprises a Q1N mutation;
(vi) the variable heavy chain having at least 98% sequence identity to the sequence as set forth in SEQ ID NO: 9 comprises a E1N mutation; and/or
(vii) the variable light chain having at least 98% sequence identity to the sequence as set forth in SEQ ID NO: 10 comprises a E1N mutation.

18. The cell of claim 15, wherein
(i) the variable light chain has the sequence as set forth in SEQ ID NO: 2 and the variable heavy chain has the sequence as set forth in SEQ ID NO: 1;
(ii) the variable light chain has the sequence as set forth in SEQ ID NO: 4 and the variable heavy chain has the sequence as set forth in SEQ ID NO: 3;
(iii) the variable light chain has the sequence as set forth in SEQ ID NO: 6 and the variable heavy chain has the sequence as set forth in SEQ ID NO: 5;
(iv) the variable light chain has the sequence as set forth in SEQ ID NO: 8 and the variable heavy chain has the sequence as set forth in SEQ ID NO: 7; or
(v) the variable light chain has the sequence as set forth in SEQ ID NO: 10 and the variable heavy chain has the sequence as set forth in SEQ ID NO: 9.

19. The cell of claim 16, wherein the cell is a B cell, a bacterial cell, a mammalian cell, or an insect cell.

20. The cell of claim 16, further comprising a gene editing nuclease and/or viral vector.

* * * * *